United States Patent
Ferrara Koller et al.

(10) Patent No.: US 12,065,478 B2
(45) Date of Patent: Aug. 20, 2024

(54) HER2-TARGETING ANTIGEN BINDING MOLECULES COMPRISING 4-1BBL

(71) Applicant: Hoffmann-La Roche Inc., Little Falls, NJ (US)

(72) Inventors: Claudia Ferrara Koller, Zug (CH); Teemu Tapani Junttila, San Mateo, CA (US); Christian Klein, Bonstetten (CH); Pablo Umana, Wollerau (CH); Christina Claus, Ennetbaden (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 75 days.

(21) Appl. No.: 17/066,711

(22) Filed: Oct. 9, 2020

(65) Prior Publication Data

US 2021/0024610 A1    Jan. 28, 2021

Related U.S. Application Data

(63) Continuation of application No. PCT/EP2019/059391, filed on Apr. 12, 2019.

(30) Foreign Application Priority Data

Apr. 13, 2018   (EP) .................................... 18167147

(51) Int. Cl.
| | | |
|---|---|---|
| A61P 35/00 | (2006.01) | |
| A61K 38/17 | (2006.01) | |
| A61K 39/00 | (2006.01) | |
| A61K 39/395 | (2006.01) | |
| C07K 14/705 | (2006.01) | |
| C07K 16/28 | (2006.01) | |
| C07K 16/32 | (2006.01) | |

(52) U.S. Cl.
CPC ...... *C07K 14/70575* (2013.01); *A61K 38/177* (2013.01); *A61K 39/39541* (2013.01); *A61K 39/39558* (2013.01); *A61P 35/00* (2018.01); *C07K 16/2809* (2013.01); *C07K 16/32* (2013.01); A61K 2039/505 (2013.01); C07K 2317/31 (2013.01); C07K 2317/52 (2013.01); C07K 2317/522 (2013.01); C07K 2317/66 (2013.01); C07K 2317/92 (2013.01); C07K 2319/30 (2013.01)

(58) Field of Classification Search
None
See application file for complete search history.

(56) References Cited

U.S. PATENT DOCUMENTS

| | | | |
|---|---|---|---|
| 5,500,362 A | 3/1996 | Robinson et al. | |
| 5,565,332 A | 10/1996 | Hoogenboom et al. | |
| 5,571,894 A | 11/1996 | Wels et al. | |
| 5,587,458 A | 12/1996 | Richter et al. | |
| 5,677,171 A | 10/1997 | Hudziak et al. | |
| 5,731,168 A * | 3/1998 | Carter ................ | C07K 16/2809 435/71.1 |
| 5,821,333 A | 10/1998 | Carter et al. | |
| 5,821,337 A | 10/1998 | Carter et al. | |
| 5,869,046 A | 2/1999 | Presta et al. | |
| 5,959,177 A | 9/1999 | Hein et al. | |
| 5,969,108 A | 10/1999 | McCafferty et al. | |
| 6,040,498 A | 3/2000 | Stomp et al. | |
| 6,054,297 A | 4/2000 | Carter et al. | |
| 6,165,464 A | 12/2000 | Hudziak et al. | |
| 6,171,586 B1 | 1/2001 | Lam et al. | |
| 6,248,516 B1 | 6/2001 | Winter et al. | |
| 6,267,958 B1 | 7/2001 | Andya et al. | |
| 6,310,082 B1 | 10/2001 | Griffin et al. | |
| 6,339,142 B1 | 1/2002 | Basey et al. | |
| 6,407,213 B1 | 6/2002 | Carter et al. | |
| 6,417,429 B1 | 7/2002 | Hein et al. | |
| 6,420,548 B1 | 7/2002 | Vezina et al. | |
| 6,602,684 B1 | 8/2003 | Umana et al. | |
| 6,639,055 B1 | 10/2003 | Carter et al. | |
| 6,719,971 B1 | 4/2004 | Carter et al. | |
| 6,737,056 B1 | 5/2004 | Presta | |
| 6,800,738 B1 | 10/2004 | Carter et al. | |
| 6,818,418 B1 | 11/2004 | Lipovsek et al. | |
| 6,982,321 B2 | 1/2006 | Winter | |
| 7,074,404 B2 | 7/2006 | Basey et al. | |
| 7,087,409 B2 | 8/2006 | Barbas et al. | |
| 7,125,978 B1 | 10/2006 | Vezina et al. | |
| 7,166,697 B1 | 1/2007 | Galanis et al. | |
| 7,250,297 B1 | 7/2007 | Beste et al. | |
| 7,332,581 B2 | 2/2008 | Presta | |

(Continued)

FOREIGN PATENT DOCUMENTS

| | | |
|---|---|---|
| EP | 0404097 B1 | 12/1990 |
| EP | 1641818 B1 | 12/2008 |

(Continued)

OTHER PUBLICATIONS

TNFSF9 Genecard—Accessed 2022 (Year: 2022).*
Wermke et al.(2016) (A Phase 1 Study of the Bispecific Antibody T Cell Engager, Glenmark Pharmaceuticals, presented in 2016) (Year: 2016).*
Hinner, M. et al., "Costimulatory T cell engagement via a novel bispecific anti-CD137/anti-HER2 protein based on Anticalin® technology" J Immunother Cancer 3( Suppl 2):P187 (Sep. 18, 2015).

(Continued)

*Primary Examiner* — Laura B Goddard
*Assistant Examiner* — Sarah A Alsomairy
(74) *Attorney, Agent, or Firm* — Lawrence S. Graham

(57) ABSTRACT

The invention relates to Her2 targeting 4-1BB agonists, in particular 4-1BBL trimer-containing antigen binding molecules comprising at least one antigen binding domain capable of specific binding to Her2 and their use in the treatment of cancer as well as their use in combination with T-cell activating anti-CD3 bispecific antibodies.

11 Claims, 16 Drawing Sheets
Specification includes a Sequence Listing.

(56) References Cited

U.S. PATENT DOCUMENTS

| | | | |
|---|---|---|---|
| 7,521,541 B2 | 4/2009 | Eigenbrot et al. | |
| 7,527,791 B2 | 5/2009 | Adams et al. | |
| 7,560,111 B2 | 7/2009 | Kao et al. | |
| 7,659,384 B2 | 2/2010 | Jure-Kunkel et al. | |
| 7,695,936 B2 * | 4/2010 | Carter | C07K 16/2809 |
| | | | 435/71.1 |
| 9,758,582 B2 | 9/2017 | Govindappa et al. | |
| 10,155,815 B2 | 12/2018 | Bacac et al. | |
| 10,377,833 B2 * | 8/2019 | Li | A61P 35/00 |
| 10,392,445 B2 * | 8/2019 | Amann | C07K 16/46 |
| 10,464,981 B2 | 11/2019 | Amann et al. | |
| 10,519,248 B2 * | 12/2019 | Cheung | A61P 35/02 |
| 10,526,413 B2 | 1/2020 | Amann et al. | |
| 10,584,178 B2 * | 3/2020 | Croasdale-Wood | A61P 43/00 |
| 10,781,262 B2 | 9/2020 | Klien et al. | |
| 11,149,083 B2 | 10/2021 | Amann et al. | |
| 11,267,903 B2 | 3/2022 | Amann et al. | |
| 11,285,207 B2 | 3/2022 | Codarri-Deak et al. | |
| 11,306,154 B2 | 4/2022 | Amann et al. | |
| 2003/0157108 A1 | 8/2003 | Presta et al. | |
| 2004/0093621 A1 | 5/2004 | Shitara et al. | |
| 2004/0132028 A1 | 7/2004 | Stumpp et al. | |
| 2004/0132066 A1 | 7/2004 | Balint et al. | |
| 2005/0123546 A1 | 6/2005 | Umana et al. | |
| 2005/0260186 A1 | 11/2005 | Bookbinder et al. | |
| 2006/0104968 A1 | 5/2006 | Bookbinder et al. | |
| 2006/0235201 A1 | 10/2006 | Kischel et al. | |
| 2007/0224633 A1 | 9/2007 | Skerra et al. | |
| 2008/0139791 A1 | 6/2008 | Lipovsek et al. | |
| 2012/0039990 A1 | 2/2012 | Reshetnyak et al. | |
| 2014/0242079 A1 | 8/2014 | Bacac et al. | |
| 2014/0242080 A1 | 8/2014 | Jaeger et al. | |
| 2016/0000842 A1 * | 1/2016 | Song | A61K 45/06 |
| | | | 435/235.1 |
| 2016/0200833 A1 | 7/2016 | Amann et al. | |
| 2017/0029529 A1 | 2/2017 | Coarsdale-Wood et al. | |
| 2017/0247467 A1 | 8/2017 | Amann et al. | |
| 2019/0016771 A1 | 1/2019 | Amann et al. | |
| 2019/0185566 A1 | 6/2019 | Koller et al. | |
| 2019/0194291 A1 | 6/2019 | Bruenker et al. | |
| 2019/0211113 A1 | 7/2019 | Amann et al. | |
| 2020/0071411 A1 | 3/2020 | Amann et al. | |
| 2020/0190206 A1 | 6/2020 | Koller et al. | |
| 2020/0199234 A1 | 6/2020 | Georges et al. | |
| 2020/0270321 A1 | 8/2020 | Amann et al. | |
| 2020/0325225 A1 | 10/2020 | Bacac et al. | |
| 2020/0325238 A1 | 10/2020 | Bacac et al. | |
| 2020/0347115 A1 | 11/2020 | Duerr et al. | |
| 2020/0377608 A1 * | 12/2020 | Luo | C07K 16/2878 |
| 2020/0392237 A1 | 12/2020 | Bacac et al. | |
| 2021/0087291 A1 | 3/2021 | Klein et al. | |
| 2021/0095002 A1 | 4/2021 | Claus et al. | |
| 2021/0163617 A1 | 6/2021 | Ferrara et al. | |
| 2021/0253724 A1 | 8/2021 | Claus et al. | |
| 2021/0324108 A1 | 10/2021 | Amann et al. | |
| 2022/0017637 A1 | 1/2022 | Gasser et al. | |
| 2022/0025069 A1 | 1/2022 | Claus et al. | |
| 2022/0073646 A1 | 3/2022 | Amann et al. | |
| 2022/0267395 A1 | 8/2022 | Amann et al. | |

FOREIGN PATENT DOCUMENTS

| | | | | |
|---|---|---|---|---|
| EP | 2101823 B1 | 11/2016 | | |
| EP | 3 178 848 A1 | 6/2017 | | |
| WO | 93/01161 A1 | 1/1993 | | |
| WO | 93/16185 A2 | 8/1993 | | |
| WO | 97/30087 A1 | 8/1997 | | |
| WO | 98/58964 A1 | 12/1998 | | |
| WO | 99/22764 A1 | 5/1999 | | |
| WO | 03/011878 A2 | 2/2003 | | |
| WO | 03/011878 A3 | 2/2003 | | |
| WO | 2005/056764 A2 | 6/2005 | | |
| WO | 2005/100402 A1 | 10/2005 | | |
| WO | 2006/029879 A2 | 3/2006 | | |
| WO | 2006/044908 A2 | 4/2006 | | |
| WO | 2007/000675 A2 | 1/2007 | | |
| WO | 2008/098796 A1 | 8/2008 | | |
| WO | 2009/089004 A1 | 7/2009 | | |
| WO | 2012/020006 A2 | 2/2012 | | |
| WO | 2012/032433 A1 | 3/2012 | | |
| WO | 2012/130831 A1 | 10/2012 | | |
| WO | 2012/143523 A1 | 10/2012 | | |
| WO | 2015/091738 A1 | 6/2015 | | |
| WO | 2015/095392 A1 | 6/2015 | | |
| WO | 2015/095404 A2 | 6/2015 | | |
| WO | 2015/150447 A1 | 10/2015 | | |
| WO | 2016/030350 A1 | 3/2016 | | |
| WO | 2016/075278 A1 | 5/2016 | | |
| WO | 2016/177802 A1 | 11/2016 | | |
| WO | WO-2016177802 A1 * | 11/2016 | | A61K 39/395 |
| WO | 2016/207091 A1 | 12/2016 | | |
| WO | 2017/167672 A1 | 10/2017 | | |
| WO | 2017/194438 A1 | 11/2017 | | |
| WO | 2017/194442 A1 | 11/2017 | | |
| WO | 2017/194641 A1 | 11/2017 | | |
| WO | 2018/060301 A1 | 4/2018 | | |
| WO | 2018/114754 A1 | 6/2018 | | |
| WO | 2018/127473 A1 | 7/2018 | | |

OTHER PUBLICATIONS

Adams et al., "Humanization of a recombinant monoclonal antibody to produce a therapeutic HER dimerization inhibitor, pertuzumab" Cancer Immunol Immunother 55(6):717-727 ( 2006).

Aggarwal, B., et al., "Signalling pathways of the TNF superfamily: a double-edged sword" Nat Rev Immunol 3(9):745-756 (Sep. 1, 2003).

Ali, S., et al., "Transferrin Trojan Horses as a Rational Approach for the Biological Delivery of Therapeutic Peptide Domains" J Biol Chem 274(34):24066-24073 (Aug. 20, 1999).

Almagro, J., et al., "Humanization of antibodies" Front Biosci 13:1619-1633 (Jan. 1, 2008).

Ascierto, P et al., "Clinical Experiences With Anti-CD137 and Anti-PD1 Therapeutic Antibodies" Semin Oncol 27(5):508-516 (Oct. 1, 2010).

Banner, D., et al., "Crystal Structure of the Soluble Human 55 kd TNF Receptor-Human TNFB Complex: Implications for TNF Receptor Activation" Cell 73(3):431-445 (May 7, 1993).

Bartkowiak, T., et al., "4-1BB Agonists: Multi-Potent Potentiators of Tumor Immunity" Front Oncol 5(117):1-16 (Jun. 8, 2015).

Baselga et al., "Recombinant Humanized Anti-HER2 Antibody (Herceptin™) Enhances the Antitumor Activity of Paclitaxel and Doxorubicin against HER2/neu Overexpressing Human Breast Cancer Xenografts" Cancer Res. 58:2825-2831 (Jul. 1, 1998).

Baselga, J., et al., "Phase II study of weekly intravenous recombinant humanized anti-p185HER2 monoclonal antibody in patients with HER2/neu-overexpressing metastatic breast cancer" J Clin Oncol 14(3):737-744 (Mar. 1, 1996).

Baudino, L., et al., "Crucial Role of Aspartic Acid at Position 265 in the CH2 Domain for Murine IgG2a and IgG2b Fc-Associated Effector Functions" J. Immunol 181(9):6664-6669 (Nov. 1, 2008).

Binz, H., et al., "Designing Repeat Proteins: Well-expressed, Soluble and Stable Proteins from Combinatorial Libraries of Consensus Ankyrin Repeat Proteins" J Mol Biol 332(2):489-503 (Sep. 12, 2003).

Bodmer et al., "The molecular architecture of the TNF superfamily" Trends Biochem Sci 27:19-26 ( 2002).

Borghouts, C., et al., "Peptide aptamers: recent developments for cancer therapy" Expert Opin Biol Th 5(6):783-797 (Nov. 24, 2005).

Bowie, J. et al., "Deciphering the message in protein sequences: tolerance to amino acid substitutions" Science 247(4948):1306-1310 (Mar. 16, 1990).

Braddock, M., "11th Annual Inflammatory and Immune Diseases Drug Discovery and Development Summit" Expert Opin Inv Drug 16(6):909-917 (Jun. 1, 2007).

Brodeur, B. et al., "Mouse-human myeloma partners for the production of heterohybridomas" Monoclonal Antibody Production Techniques and Applications (New York: Marcel Dekker, Inc.),:51-63 ( 1987).

(56) References Cited

OTHER PUBLICATIONS

Broll, K., et al., "CD137 Expression in Tumor Vessel Walls High Correlation With Malignant Tumors" Am J Clin Pathol 115(4):543-549 (Apr. 1, 2001).
Bruggemann, M., et al., "Comparison of the Effector Functions of Human Immunogobulins Using a Matched set of Chimeric Antibodies" J Exp Med 166(5):1351-1361 (Oct. 1, 1987).
Buechele, C., et al., "4-1BB ligand modulates direct and Rituximab-induced NK-cell reactivity in chronic lymphocytic leukemia" Eur J Immunol 42(3):737-748 (Mar. 1, 2012).
Carter, Paul, "Bispecific human IgG by design" J Immunol Methods 248(1-2):7-15 (Feb. 1, 2001).
CAS Registry Database, 180288-69-1, (CAS Registry ID: 180288-69-1: Immunoglobulin G1: Herceptin/Trastuzumab), pp. 1-2Creation Date Aug. 29, 1996.
Chen, S., et al., "Combination of 4-1BB Agonist and PD-1 Antagonist Promotes Antitumor Effector/Memory CD8 T Cells in a Poorly Immunogenic Tumor Model" Cancer Immunol Res 3(2):149-160 (Feb. 1, 2015).
Cho, H.S., et al., "Structure of the extracellular region of HER2 alone and in complex with the Herceptin Fab" Nature 421(6924):756-760 (Feb. 13, 2003).
Choi, B., et al., "4-1BB Functions As a Survival Factor in Dendritic Cells" J Immunol 182(7):4107-4115 (Apr. 1, 2009).
Clynes, R., et al., "Fc receptors are required in passive and active immunity to melanoma" PNAS USA 95(2):652-656 (Jan. 1, 1998).
Coussens et al., "Tyrosine Kinase Receptor with Extensive Homology to EGF Receptor Shares Chromosomal Location with neu Oncogene" Science 230:1132-1139 ( 1985).
Cragg, M., et al., "Antibody Specificity Controls in Vivo Effector Mechanisms of Anti-CD20 Regents" Blood 103(7):2738-2743 (Apr. 1, 2004).
Cuadros, C., et al., "Vaccination with dendritic cells pulsed with apoptotic tumors in combination with anti-OX40 and anti-4-1BB monoclonal antibodies induces T cell-mediated protective immunity in Her-2/neu transgenic mice." Int J Cancer 116(6):934-943 (Oct. 10, 2005).
Curran, M., et al., "Combination CTLA-4 blockade and 4-1BB activation enhances tumor rejection by increasing T-cell infiltration, proliferation, and cytokine production" Plos One 6(4):e19499, 1-11 (Apr. 29, 2011).
Dall'Acqua, W., et al., "Antibody humanization by framework shuffling" Methods 36(1):43-60 (Jan. 17, 2005).
Diehl, L., et al., "In Vivo Triggering Through 4-1BB Enables Th-Independent Priming of CTL in the Presence of an Intact CD28 Costimulatory Pathway" J Immunol 168(8):3755-3762 (Apr. 15, 2002).
Dubrot, J., et al., "Treatment with anti-CD137 mAbs causes intense accumulations of liver T cells without selective antitumor immunotherapeutic effects in this organ" Cancer Immunol Immun 59(8):1223-1233 (Aug. 1, 2010).
Franklin et al., "Insights into ErbB signaling from the structure of the ErbB2-pertuzumab complex" Cancer Cell 5:317-328 (Apr. 2004).
Futagawa, T., et al., "Expression and function of 4-1 BB and 4-1BB ligand on murine dendritic cells" Int Immunol 14(3):275-286 (Mar. 1, 2002).
Gazzano-Santoro, H., et al., "A non-radioactive complement-dependent cytotoxicity assay for anti-CD20 monoclonal antibody" J Immunol Methods 202(2):163-171 (Mar. 28, 1997).
Gebauer, M., et al., "Engineered protein scaffolds as next-generation antibody therapeutics" Curr Opin Chem Biol 13(3):245-255 (Jun. 6, 2009).
Gerngross, T., "Advances in the Production of Human Therapeutic Proteins in Yeasts and Filamentous Fungi" Nat Biotechnol 22(11):1409-1414 (Nov. 22, 2004).
Goodwin, R., et al., "Molecular cloning of a ligand for the inducible T cell gene 4-1BB: a member of an emerging family of cytokines with homology to tumor necrosis factor" Eur J Immunol 23(10):2631-2641 (Oct. 1, 1993).

Graham, F., et al., "Characteristics of a Human Cell Line Transformed by DNA form Human Adenovirus Type 5" J Gen Virol 36(1):59 (Jul. 1, 1977).
Gunasekaran, K. et al., "Enhancing Antibody Fc Heterodimer Formation through Electrostatic Steering Effects: Applications to Bi-Specific Molecules and Monovalent IgG" J Biol Chem 285(25):19637-19646 (Jun. 18, 2010).
Guo, Z., et al., "Combined TIM-3 blockade and CD137 activation affords the long-term protection in a murine model of ovarian cancer." J Transl Med 11(215):1-11 (Sep. 17, 2013).
Harari and Yarden et al., "Molecular mechanisms underlying ErbB2/HER2 action in breast cancer" Oncogene 19(53):6102-14 (Dec. 2000).
Harris, R. et al. Mass Spectrometry in the Biological Sciences "Identifying Unexpected Protein Modifications" (Mass Spectrometry in the Biological Sciences. Humana Press, Totowa, NJ.), Carr S.A., Burlingame::333-350 (Jan. 1996).
Heeley, R. et al., "Mutations Flanking the Polyglutamine Repeat in the Modulatory Domain of Rat Glucocorticoid Receptor Lead to an Increase in Affinity for Hormone" Endocr Res 28(3):217-229 (Aug. 1, 2002).
Heinisch, I., et al., "CD137 activation abrogates granulocytemacrophage colony-stimulating factor-mediated anti-apoptosis in neutrophils" Eur J Immunol 30(12):3441-3446 (Dec 1, 2000).
Hellstrom et al., "Antitumor effects of L6, an IgG2a antibody that reacts with most human carcinomas" P Natl Acad Sci USA 83:7059-7063 (Sep. 1986).
Hellstrom, I et al., "Strong antitumor activities of IgG3 antibodies to a human melanoma-associated ganglioside" PNAS USA 82(5):1499-1502 (Mar. 1, 1985).
Holliger, P., et al., "Diabodies: Small Bivalent and Bispecific Antibody Fragments" PNAS 90(14):6444-6448 (Jul. 15, 1993).
Hoogenboom, H., et al., "Overview of antibody phage-display technology and its applications" Methods Mol Biol 178:1-37 ( 2002).
Hornig, N., et al., "Combination of a Bispecific Antibody and Costimulatory Antibody-Ligand Fusion Proteins for Targeted Cancer Immunotherapy" J Immunother 35(5):418-429 (Jun. 1, 2012).
Hotaling et al., "The humanized anti-HER2 antibody rhuMAb HER2 mediates antibody dependent cell-mediated cytotoxicity via FcγR III" Proceedings of the American Association for Cancer Research (Abstract #3215), 37:471 (Mar. 1996).
Hudson, P., et al., "Engineered antibodies" Nat Med 9(1):129-134 (Jan. 1, 2003).
Hudziak et al., "p185$^{HER2}$Monoclonal Antibody Has Antiproliferation Effects In Vitro and Sensitizes Human Breast Tumor Cells to Tumor Necrosis Factor" Mol Cell Biol 9(3):1165-1172 (Mar. 1989).
International Preliminary Report on Patentability—PCT/EP2019/059391 dated Oct. 13, 2020.
International Search Report—PCT/EP2019/059391dated Jul. 1, 2019.
Irving, R., et al., "Ribosome display and affinity maturation: from antibodies to single V-domains and steps towards cancer therapeutics" J Immunol Methods 248(1-2):31-45 (Feb. 1, 2001).
Johnson and Wu et al., "Kabat Database and its applications: 30 years after the first variability plot" Nucleic Acids Res 28(1):214-218 ( 2000).
Jones, P.T., et al., "Replacing the Complementarity-Determining Regions in a Human Antibody with Those From a Mouse" Nature 321(6069):522-525 (May 29, 1986).
Ju, S., et al., "Eradication of established renal cell carcinoma by a combination of 5-fluorouracil and anti-4-1BB monoclonal antibody in mice." Int J Cancer 122(12):2784- 2790 (Jun. 15, 2008)
Junttila et al., "Antitumor Efficacy of a Bispecific Antibody That Targets HER2 and Activates T Cells" Cancer Res. 74(19):5561-5571 (2014).
Kabat et al., "Evolutionary and structural influences on light chain constant (C/subL/nor) region of human and mouse immunoglobulins" Proc Natl Acad Sci U S A. 72(7):2785-2788 (Jul. 1975).
Kam, N., et al., "Carbon nanotubes as multifunctional biological transporters and near-infrared agents for selective cancer cell destruction" PNAS 102(33):11600-11605 (Aug. 16, 2005).
Kashmiri, S., et al., "SDR grafting-a new approach to antibody humanization" METHODS 36:25-34 (Jan. 1, 2005).

(56) References Cited

OTHER PUBLICATIONS

Kienzle, G., et al., "CD137 (ILA/4-1BB), expressed by primary human monocytes, induces monocyte activation and apoptosis of B lymphocytes" Int Immunol 12(1):73-82 (Jan. 1, 2000).
Kim, D., et al., "4-1BB Engagement Costimulates NKT Cell Activation and Exacerbates NKT Cell Ligand-Induced Airway Hyperresponsiveness and Inflammation" J Immunol 180(4):2062-2068 (Feb. 1, 2008).
Kim, Y. H., et al., "Mechanisms involved in synergistic anticancer effects of anti-4-1BB and cyclophosphamide therapy." Mol Cancer Ther 8(2):469-478 (Feb. 1, 2009).
Klimka, A et al., "Human anti-CD30 recombinant antibodies by guided phage antibody selection using cell panning" Brit J Cancer 83(2):252-260 (Jun. 15, 2000).
Kohl, A., et al., "Designed to be stable: Crystal structure of a consensus ankyrin repeat protein" PNAS 100(4):1700-1705 (Feb. 18, 2003).
Kwon, B., et al., "cDNA sequences of two inducible T-cell genes" Pnas USA 86(6):1963-1967 (Mar. 1, 1989).
Lee, H., et al., "Combinatorial therapy for liver metastatic colon cancer: dendritic cell vaccine and low-dose agonistic anti-4-1BB antibody costimulatory signal" J Surg Res 169(1):e43-50 (Jul. 1, 2011).
Leo et al., "Identification of a monoclonal antibody specific for a murine T3 polypeptide" Proc. Natl. Acad. Sci. USA 84:1374-1378 (1987).
Levitsky, V., et al., "The clonal composition of a peptide-specific oligoclonal CTL repertoire selected in response to persistent EBV infection is stable over time." J Immunol 161(2):594-601 (Jun. 30, 1998).
Lewis et al., "Differential Responses of Human Tumor Cell Lines to Anti-p185 HER2 Monoclonal Antibodies" Cancer Immunol Immunother 37:255-263 (1993).
Li, F., et al., "Inhibitory Fcγ Receptor Engagement Drives Adjuvant and Anti-Tumor Activities of Agonistic CD40 Antibodies" SCIENCE 333(6045):1030-1034 (Aug. 19, 2011).
Li, H., et al., "Optimization of humanized IgGs in glycoengineered Pichia pastoris" Nat Biotechnol 24(2):210-215 (Feb. 1, 2006).
Li, J et al., "IFNγ-induced Chemokines Are Required for CXCR3-mediated T-Cell Recruitment and Antitumor Efficacy of Anti-HER2/CD3 Bispecific Antibody" Clin Cancer Res 24:6447-6458 (2018).
Liljeblad, M., et al., "Analysis of agalacto-IgG in rheumatoid arthritis using surface plasmon resonance" Glycoconjugate J 17:323-329 (Jul. 14, 2000).
Lin, W., et al., "Fc-dependent expression of CD137 on human NK cells: insights into agonistic effects of anti-CD137 monoclonal antibodies" BLOOD 112(3):699-707 (Aug. 1, 2008).
Lonberg, N., "Fully human antibodies from transgenic mouse and phage display platforms" Curr Opin Immunol 20(4):450-459 (Aug. 1, 2008).
Lonberg, N., "Human antibodies from transgenic animals" Nat Biotechnol 23(9):1117-1125 (Sep. 7, 2005).
MacCallum, R., et al., "Antibody-antigen Interactions: Contact Analysis and Binding Site Topography" J Mol Biol 262:732-745 (Oct. 11, 1996).
Malik et al., "Dose-Response Studies of Recombinant Humanized Monoclonal Antibody 2C4 in Tumor Xenograft Models" Pro Am Soc Cancer Res 44: Abstract No. 773 (2003).
Mather, J., "Establishment and characterization of two distinct mouse testicular epithelial cell lines" Biol Reprod 23(1):243-252 (Aug. 1, 1980).
Mather, J., et al., "Culture of Testicular Cells in Hormone-Supplemented Serum-Free Medium" Ann NY Acad Sci 383:44-68 (Jan. 1, 1982).
McCafferty, J., et al., "Phage Antibodies: Filamentous Phage Displaying Antibody Variable Domains" Nature 348(6301):552-554 (Dec. 6, 1990).
Melero, I. et al., "Monoclonal Antibodies Against the 4-1BB T-cell Activation Molecule Eradicate Established Tumors" Nat Med 3(6):682-685 (Jun. 1, 1997).
Melero, I. et al., "NK1.1 Cells Express 4-1BB (CDw137) Costimulatory Molecule and Are Required for Tumor Immunity Elicited by Anti-4-1BB Monoclonal Antibodies" Cell Immunol 190(2 Suppl CI981396):167-172 (Dec. 15, 1998).
Merchant et al., "An efficient route to human bispecific IgG" Nat Biotechnol 16(7):677-681 (Jul. 1, 1998).
Morales-Kastresana, A., et al., "Combined immunostimulatory monocolonal antibodies extend survival in an aggressive transgenic heptocellular carcinoma mouse model" Clin Cancer Res 19(22):6151-6162 (Nov. 1, 2013).
Morrison, S., et al., "Chimeric human antibody molecules: Mouse antigen-binding domains with human constant region domains" PNAS 81(21):6851-6855 (Nov. 1, 1984).
Morrison, S., et al., "Genetically Engineered Antibody Molecules" Adv Immunol 44:65-92 (1989).
Mueller, D. et al., "A Novel Antibody-4-1BBL Fusion Protein for Targeted Costimulation in Cancer Immunotherapy" J Immunother 31(8):714-722 (Oct. 1, 2008).
Murillo, O., et al., "In vivo depletion of DC impairs the anti-tumor effect of agonistic anti-CD137 mAb" Eur J Immunol 39(9):2424-2436 (Sep. 1, 2009).
Narazaki, H., et al., "CD137 agonist antibody prevents cancer recurrence: contribution of CD137 on both hematopoietic and nonhematopoietic cells" Blood 115(10):1941-1948 (Mar. 11, 2010).
Nishimoto, H., et al., "Costimulation of mast cells by 4-1BB, a member of the tumor necrosis factor receptor superfamily, with the high-affinity IgE receptor" Blood 106(13):4241-4248 (Dec. 15, 2005).
Olofsson, P., et al., "CD137 Is Expressed in Human Atherosclerosis and Promotes Development of Plaque Inflammation in Hypercholesterolemic Mice" Circulation 117(10):1292-1301 (Mar. 11, 2008).
Osbourn, J. et al., "From rodent reagents to human therapeutics using antibody guided selection" Methods 36(1):61-68 (May 1, 2005).
Padlan, E., "A possible procedure for reducing the immunogenicity of antibody variable domains while preserving their ligand-binding properties" Mol Immunol 28(4-5):489-498 (Apr. 30, 1991).
Padlan, E., "Anatomy of the Antibody Molecule" Mol Immunol 31(3):169-217 (Feb. 1, 1994).
Palazon, A., et al., "Agonist Anti-CD137 mAb Act on Tumor Endothelial Cells to Enhance Recruitment of Activated T Lymphocytes" Cancer Res 71:801-811 (Feb. 1, 2011).
Parker, M.H., et al., "Antibody mimics based on human fibronectin type three domain engineered for thermostability and high-affinity binding to vascular endothelial growth factor receptor two" Protein Eng Des Sel 18(9):435-444 (Aug. 8, 2005).
Pegram et al., "Antibody dependent cell-mediated cytotoxicity in breast cancer patients in Phase III clinical trials of a humanized anti-HER2 antibody" P Am Assoc Canc Res (Abstract No. 4044), 38:602 (Mar. 1997).
Pieris Pharmaceuticals, Inc. et al., "Pieris Pharmaceuticals Presents Positive Data for Its Lead Bispecific Drug Candidate, PRS-343, at the 2016 CRI-CIMT-EATI-AACR International Cancer Immunotherapy Conference: Novel 4-1 BB/HER2 Bispecific Demonstrates Differentiation Over Conventional 4-1 BB mAb and HER2 mAb Approaches" Corporate Communications: 1-3 (Sep. 26, 2016) https://ir.pieris.com/press-releases/detail/543/pieris-pharmaceuticals-presents-positive-data-for-its-lead.
Pluckthun, A. et al. The Pharmacology of Monoclonal Antibodies "Antibodies from *Escherichia coli*" (Antibodies from *Escherichia coli*), Rosenberg & Moore, vol. 113:269-315 (1994).
Queen, C., et al., "A humanized antibody that binds to the interleukin 2 receptor" PNAS USA 86(24):10029-10033 (Dec. 1, 1989).
Ridgway, J., et al., "Knobs-into-holes' engineering of antibody CH3 domains for heavy chain heterodimerization" Protein Eng 9(7):617-621 (Jul. 1, 1996).
Riechmann, L., et al., "Reshaping human antibodies for therapy" Nature 332(6162):323-327 (Mar. 24, 1988).
Schlehuber and Skerra et al., "Anticalins in Drug Development" Biodrugs 19(5):279-288 (2005).

(56) References Cited

OTHER PUBLICATIONS

Schwarz, H., et al., "ILA, the Human 4-1BB Homologue, Is Inducible in Lymphoid and Other Cell Lineages" Blood 85(4):1043-1052 (Feb. 15, 1995).
Shao, Z., et al., "Mini-Review: CD137 ligand, a member of the tumor necrosis factor family, regulates immune responses via reverse signal transduction" J Leukocyte Biol 89(1):21-29 (Jan. 1, 2011).
Shi, W., et al., "Augmented antitumor effects of radiation therapy by 4-1BB antibody (BMS-469492) treatment." Anticancer Res 26(5A):3445-3453 (Sep. 2006).
Shindo, Y., et al., "Combination Immunotherapy with 4-1BB activation and PD-1 blockade enhances antitumor efficacy in a mouse model of subcutaneous tumor" Anticancer Res 35(1):129-136 (Jan. 1, 2015).
Silverman, J. et al., "Multivalent avimer proteins evolved by exon shuffling of a family of human receptor domains" Nat Biotechnol 23(12):1556-1561 (Dec. 1, 2005).
Simeone, E. et al., "Immunomodulating antibodies in the treatment of metastatic melanoma: The experience with anti-CTLA-4, anti-CD137, and anti-PD1" J Immunotoxcity 9(3):241-247 (Jul. 1, 2012).
Skerra, A. et al., "Review: Lipocalins as a scaffold" Biochim Biophys Acta 1482(1-2):337-350 (Oct. 18, 2000).
Slamon et al., "Human breast cancer: correlation of relapse and survival with amplification of the HER-2/neu oncogene" Science 235(4785):177-182 ( 1987).
Slamon, D., et al., "Use of chemotherapy plus a monoclonal antibody against HER2 for metastatic breast cancer that overexpresses HER2" New Engl J Med 344(11):783-792 (Mar. 15, 2001).
Slamon, D.J. et al., "Studies of the HER-2/neu proto-oncogene in human breast and ovarian cancer" Science 244:707-712 ( 1989).
Sliwkowski et al., "Nonclinical studies addressing the mechanism of action of trastuzumab (Herceptin)" Semin Oncol 26:60-70 ( 1999).
Sliwkowski et al., "Ready to partner" Nat Struct Biol 10(3):158-159 (Mar. 2003).
Snell, L., et al., "T-cell intrinsic effects of GITR and 4-1BB during viral infection and cancer immunotherapy" Immunol Rev 244(1):197-217 (Nov. 1, 2011).
Stagg, J., et al., "Anti-ErbB-2 mAb therapy requires type I and II interferons and synergizes with anti-PD-1 or anti-CD137 mAb therapy" PNAS USA 108(17):7142-7147 (Apr. 26, 2011).
Stumpp, M., et al., "DARPins: A new generation of protein therapeutics" Drug Discov Today 13(15-16):695-701 (Aug. 1, 2008).
Taraban et al., "Expression and costimulatory effects of 5 the TNF receptor superfamily members CD134 (OX40) and CD137 (4-1BB), and their role in the generation of anti-tumor immune responses" Eur. J. Immunol. 32:3617-3627 ( 2002).
Teng, M., et al., "CD1d-Based Combination Therapy Eradicates Established Tumors in Mice" J Immunol 183(3):1911-1920 (Aug. 1, 2009).
Tim Clarkson et al., "Making antibody fragments using phage display libraries" Nature 352:624-628 (Aug. 15, 1991).
Urlaub, G., et al., "Isolation of Chinese hamster cell mutants deficient in dihydrofolate reductase activity" PNAS US 77(7):4216-4220 (Jul. 1, 1980).
Van Dijk and Van De Winkel et al., "Human antibodies as next generation therapeutics" Curr Opin Chem Biol 5(4):368-374 (Aug. 2001).
Vazquez-Lombardi et al., "Challenges and opportunities for non-antibody scaffold drugs" Drug Discov Today 20(10):1271-1283 ( 2015).
Verhoeyen, M., et al., "Reshaping human antibodies: Grafting an antilysozyme activity" Science 239(4847):1534-1536 (Mar. 25, 1988).
Vinay, D. et al., "4-1BB signaling beyond T cells" Cell Mol Immunol 8(4):281-284 (Jul. 1, 2011).
Von Kempis, J., et al., "Differentiation-dependent and stimulus-specific expression of ILA, the human 4-1BB-homologue, in cells of mesenchymal origin" Steoarthr Cartilage 5(6):394-406 (Nov. 1, 1997).
Wei, H et al., "Dual targeting of CD137 co-stimulatory and PD-1 co-inhibitory molecules for ovarian cancer immunotherapy" Oncoimmunology 3(4):e28248, 1-3 (Mar. 28, 2014).
Wei, H., et al., "Combinatorial PD-1 blockade and CD137 activation has therapeutic efficacy in murine cancer models and synergizes with cisplatin" Plos One 8(12):e84927, 1-11 (Dec. 19, 2013).
Wikman, M., et al., "Selection and characterization of HER2/neu-binding affibody ligands" Protein Eng Des Sel 17(5):455-462 (Jun. 18, 2004).
Wilcox, R., et al., "Cutting Edge: Expression of Functional CD137 Receptor by Dendritic Cells" J Immunol 168(9):4262-4267 (May 1, 2002).
Wilcox, R., et al., "Ligation of CD137 receptor prevents and reverses established anergy of CD8+ cytolytic T lymphocytes in vivo" Blood 103(1):177-184 (Jan. 1, 2004).
Wright, A., et al., "Effect of Glycosylation on Antibody Function: Implications for Genetic Engineering" Trends Biotechnol 15(1):26-32 (Jan. 1, 1997).
Yarden and Sliwkowski et al., "Untangling the ErbB signalling network" Nat Rev Mol Cell Biol. 2(2):127-37 (Feb. 2001).
Yazaki and Wu et al., "Expression of recombinant antibodies in mammalian cell lines" Methods Molec Biol 248:255-268 ( 2004).
Zahnd, C. et al., "A designed ankyrin repeat protein evolved to picomolar affinity to Her2" J Mol Biol 369(4):1015-1028 (Mar. 13, 2007).
Zhang, N. et al., "Targeted and untargeted CD137L fusion proteins for the immunotherapy of experimental solid tumors." Clin Cancer Res 13(9):2758-2767 (May 1, 2007).
Zhang, X., et al., "CD137 Promotes Proliferation and Survival of Human B Cells" J Immunol 184(2):787-795 (Jan. 15, 2010).
U.S. Appl. No. 10/072,079 B2, filed Sep. 11, 2018, Ehninger, A.
Kohrt et al., "Stimulation of natural killer cells with a CD137-specific antibody enhances trastuzumab efficacy in xenotransplant models of breast cancer" The Journal of Clinical Investigation 122(3):1066-1075 (2012).
Kuznetsova et al., "Structural Dynamics, Stability And Folding Of Proteins" 47(11):943-952 (2005).
Mariuzza et al., "The Structural Basis Of Antigen-Antibody Recognition" Annu.Rev. Biophys. Chem 16:139-159 (1987).
Rosano et al., "Recombinant protein expression in *Escherichia coli*: advances and challenges" Frontiers in Microbiology 5:1-17 (Apr. 2014).

* cited by examiner

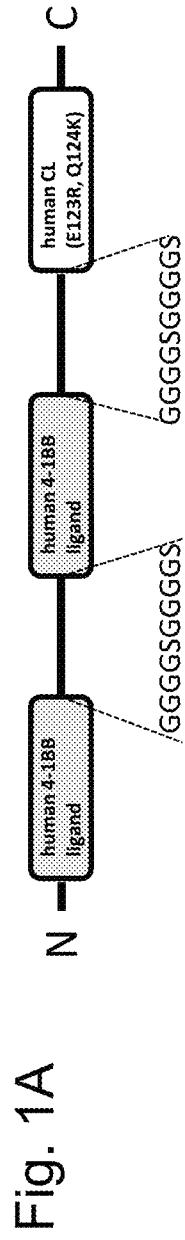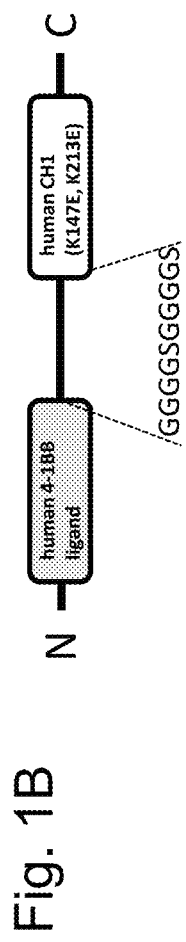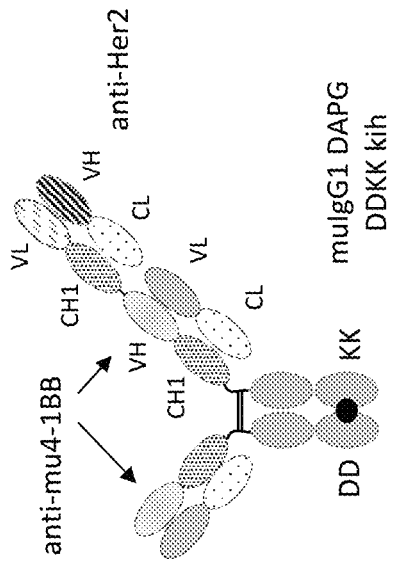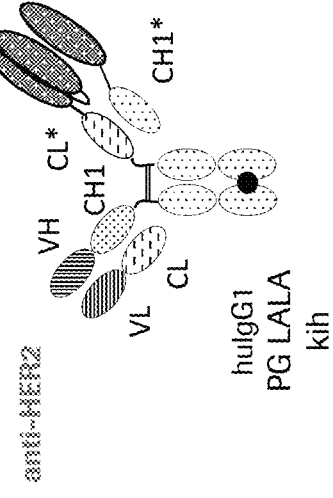
Fig. 1A
Fig. 1B
Fig. 2A
Fig. 2B

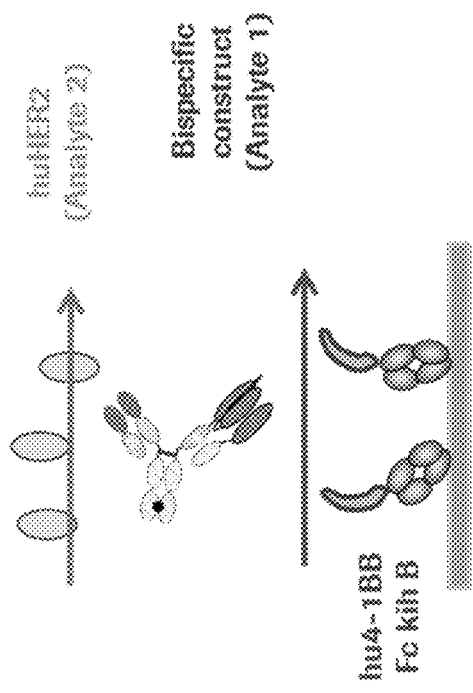
Fig. 3A
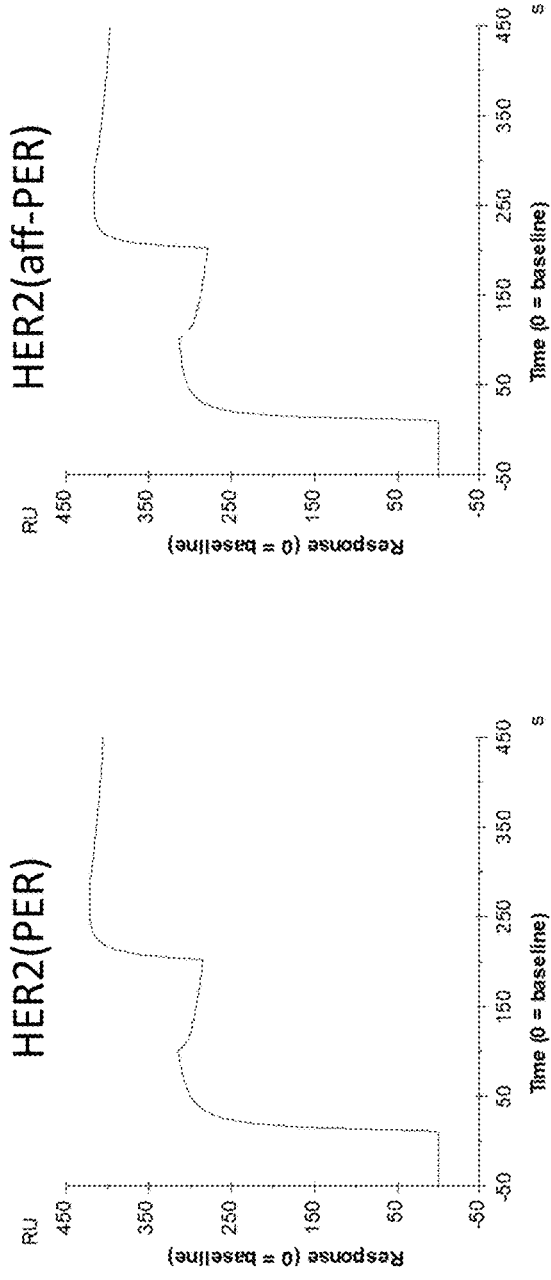
Fig. 3B
Fig. 3C

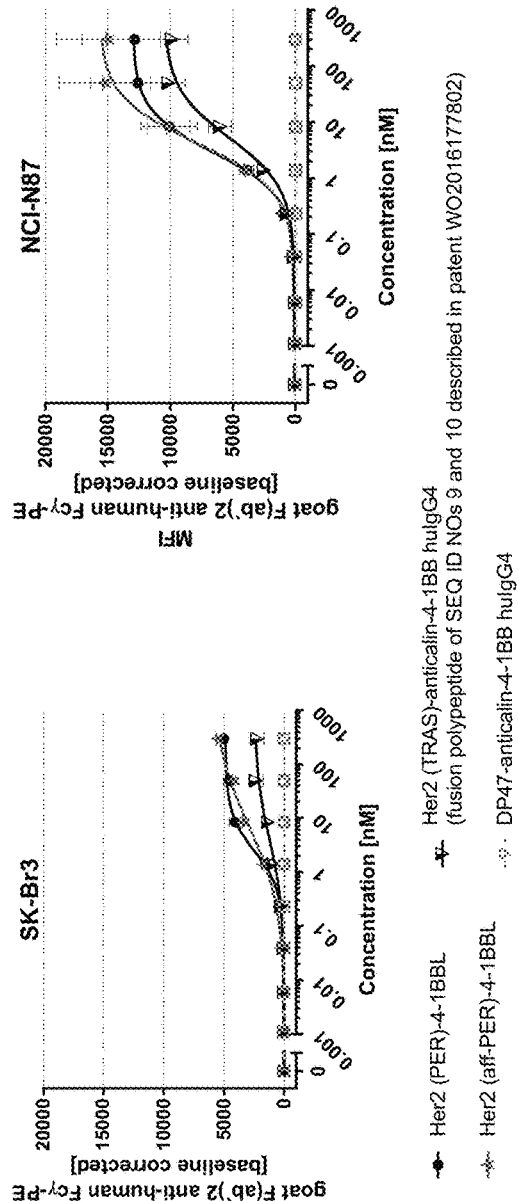
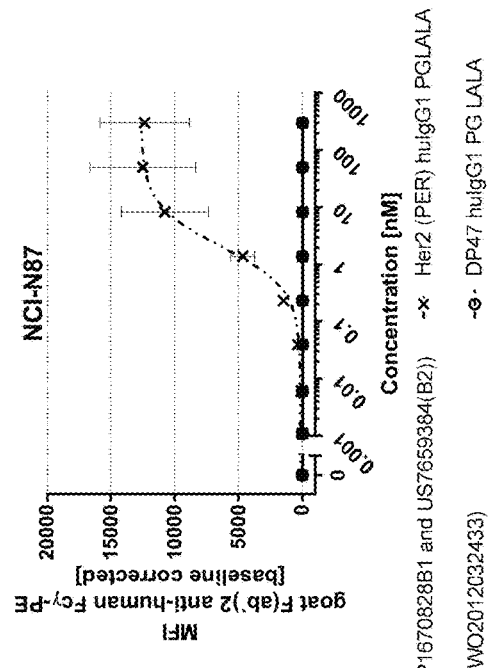
Fig. 4A, Fig. 4B, Fig. 4C, Fig. 4D

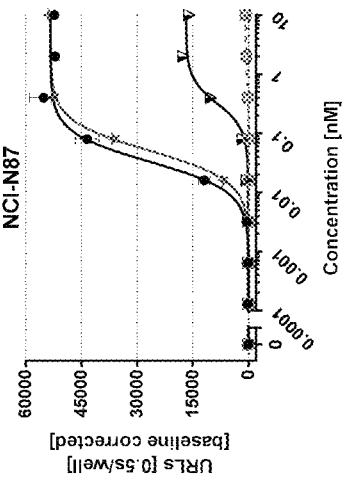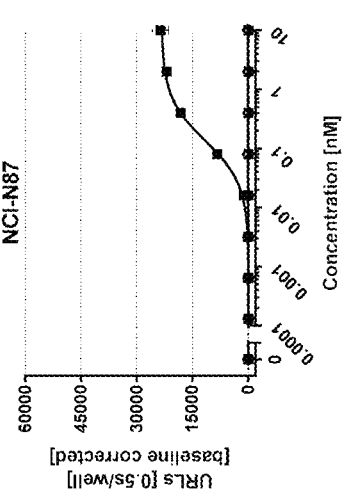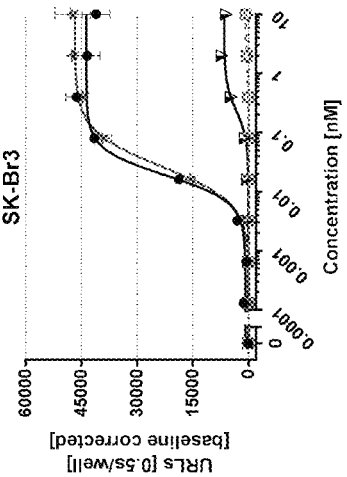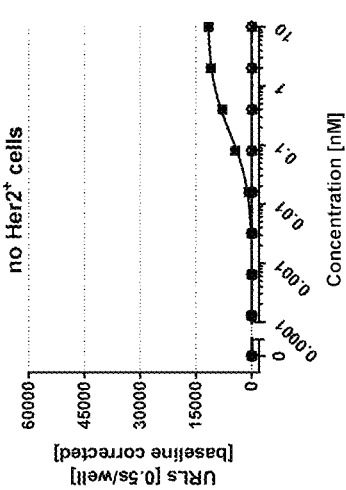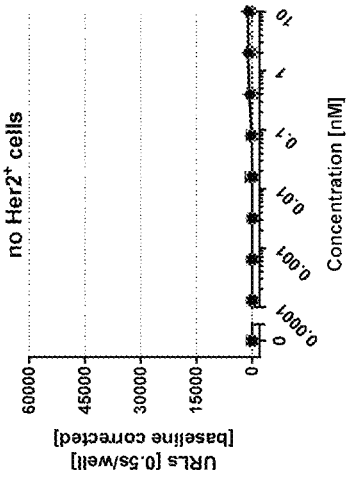
Fig. 7A Fig. 7B Fig. 7C Fig. 7D Fig. 7E Fig. 7F

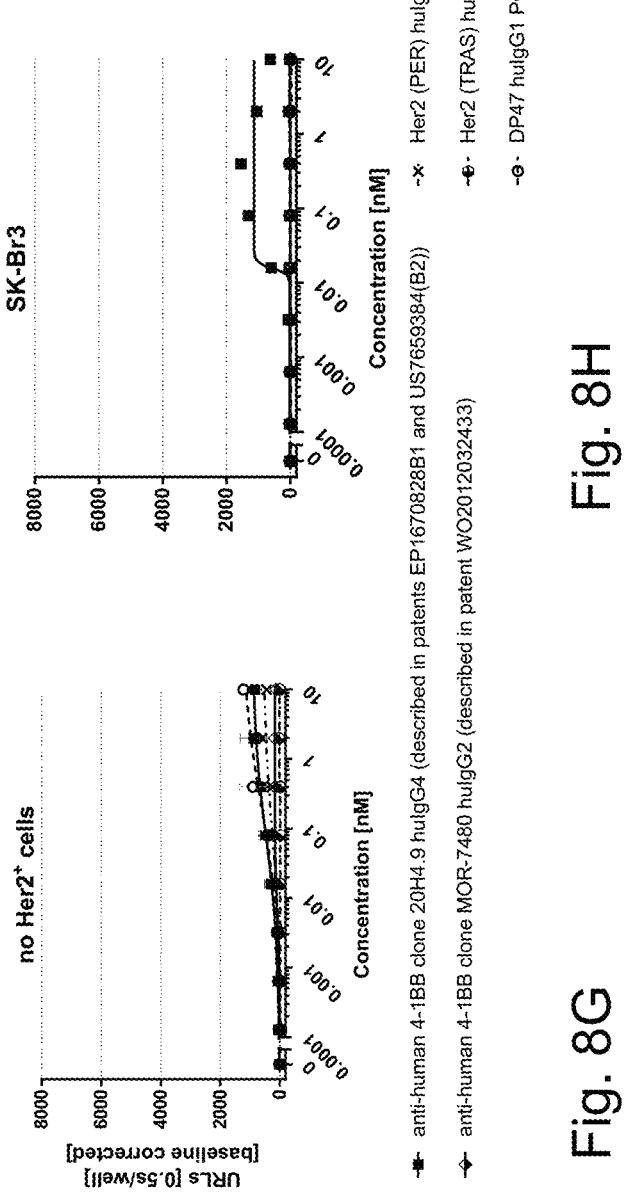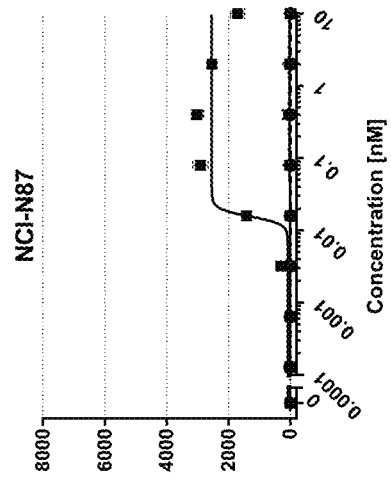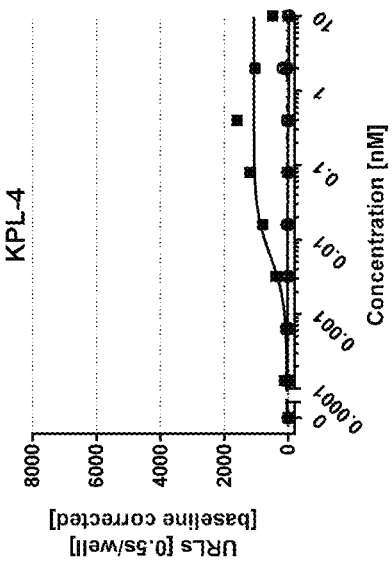

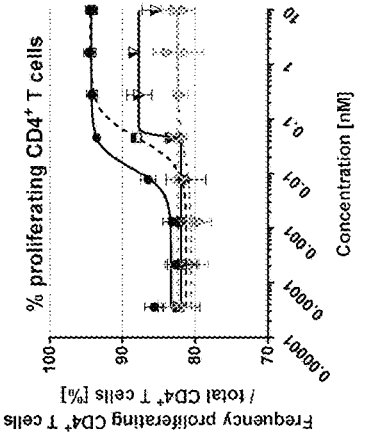 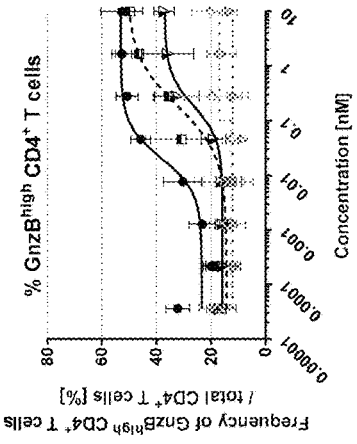 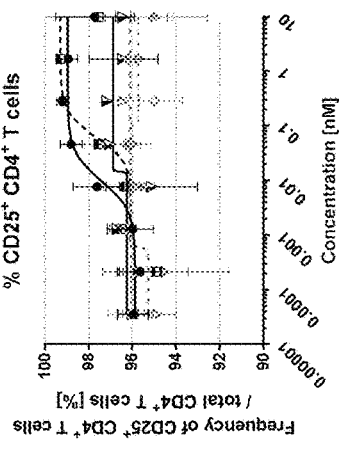 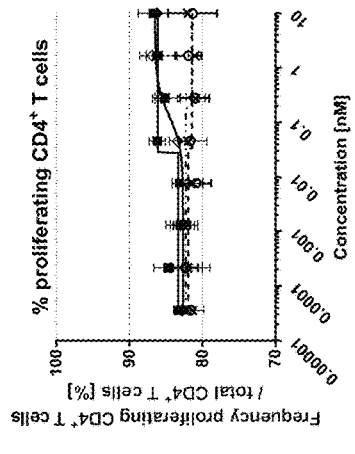 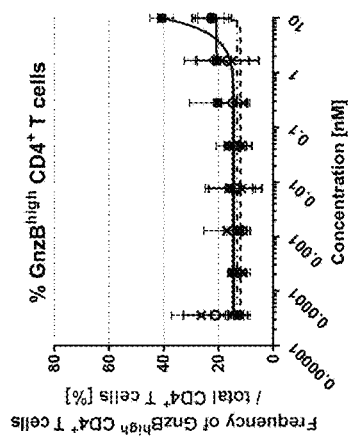 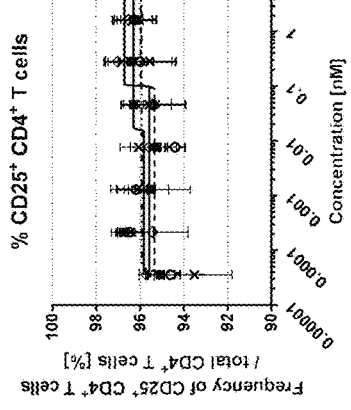 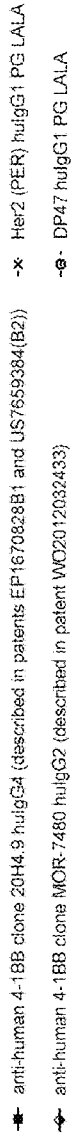
Fig. 11A Fig. 11B Fig. 11C Fig. 11D Fig. 11E Fig. 11F Fig. 15A
Her2(PER)-4-1BBL promotes CD8+ T cell proliferation
Fig. 15B
Her2(PER)-4-1BBL supports greater CD8+ T cell numbers
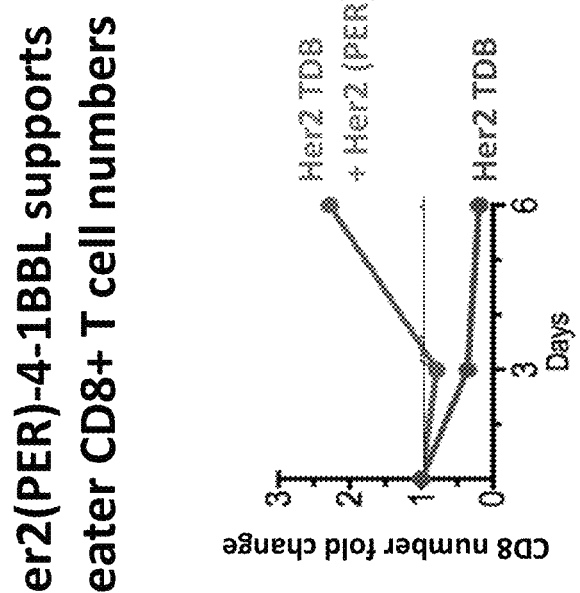
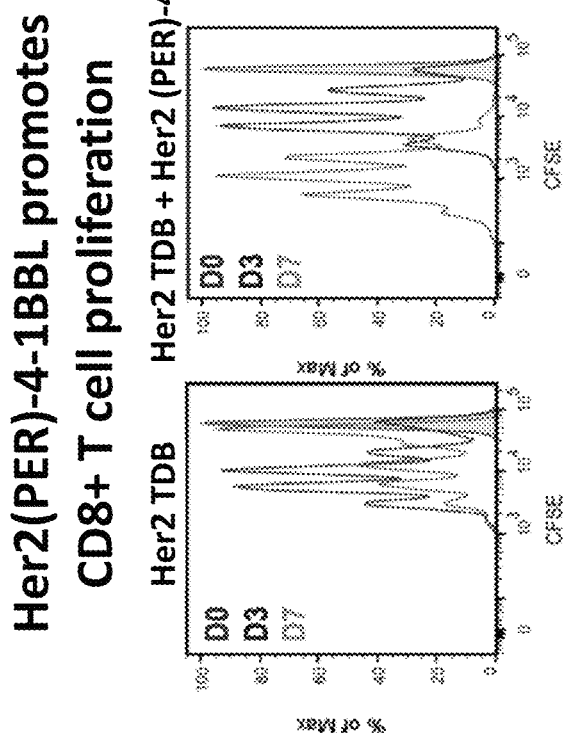

HER2-TARGETING ANTIGEN BINDING MOLECULES COMPRISING 4-1BBL

CROSS-REFERENCE TO RELATED APPLICATIONS

This application is a continuation of International Application No. PCT/EP2019/059391, filed Apr. 12, 2019, and published as International Publication No. WO 2019/197600, which claims priority to European Patent Application No. 18167147.0, filed Apr. 13, 2018, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Sep. 24, 2020 is named P34738-US_ST25 and is 184,255 bytes in size.

FIELD OF THE INVENTION

The invention relates to Her2 targeting 4-1BB agonists, in particular 4-1BBL trimer-containing antigen binding molecules comprising an antigen binding domain capable of specific binding to Her2 and their use in the treatment of cancer. The invention further relates to methods of producing these molecules and to methods of using the same.

BACKGROUND 4-1BB (CD137), a member of the TNF receptor superfamily, was first identified as an inducible molecule expressed by activated by T cells (Kwon and Weissman, 1989, Proc Natl Acad Sci USA 86, 1963-1967). Subsequent studies demonstrated that many other immune cells also express 4-1BB, including NK cells, B cells, NKT cells, monocytes, neutrophils, mast cells, dendritic cells (DCs) and cells of non-hematopoietic origin such as endothelial and smooth muscle cells (Vinay and Kwon, 2011, Cell Mol Immunol 8, 281-284). Expression of 4-1BB in different cell types is mostly inducible and driven by various stimulatory signals, such as T-cell receptor (TCR) or B-cell receptor triggering, as well as signaling induced through co-stimulatory molecules or receptors of pro-inflammatory cytokines (Diehl et al., 2002, J Immunol 168, 3755-3762; Zhang et al., 2010, Clin Cancer Res 13, 2758-2767).

4-1BB ligand (4-1BBL or CD137L) was identified in 1993 (Goodwin et al., 1993, Eur J Immunol 23, 2631-2641). It has been shown that expression of 4-1BBL was restricted on professional antigen presenting cells (APC) such as B-cells, DCs and macrophages. Inducible expression of 4-1BBL is characteristic for T-cells, including both φβ and γδ T-cell subsets, and endothelial cells (Shao and Schwarz, 2011, J Leukoc Biol 89, 21-29).

Co-stimulation through the 4-1BB receptor (for example by 4-1BBL ligation) activates multiple signaling cascades within the T cell (both $CD4^+$ and $CD8^+$ subsets), powerfully augmenting T cell activation (Bartkowiak and Curran, 2015). In combination with TCR triggering, agonistic 4-1BB-specific antibodies enhance proliferation of T-cells, stimulate lymphokine secretion and decrease sensitivity of T-lymphocytes to activation-induced cells death (Snell et al., 2011, Immunol Rev 244, 197-217). This mechanism was further advanced as the first proof of concept in cancer immunotherapy. In a preclinical model administration of an agonistic antibody against 4-1BB in tumor bearing mice led to potent anti-tumor effect (Melero et al., 1997, Nat Med 3, 682-685). Later, accumulating evidence indicated that 4-1BB usually exhibits its potency as an anti-tumor agent only when administered in combination with other immunomodulatory compounds, chemotherapeutic reagents, tumor-specific vaccination or radiotherapy (Bartkowiak and Curran, 2015, Front Oncol 5, 117).

Signaling of the TNFR-superfamily needs cross-linking of the trimerized ligands to engage with the receptors, so does the 4-1BB agonistic antibodies which require wild type Fc-binding (Li and Ravetch, 2011, Science 333, 1030-1034). However, systemic administration of 4-1BB-specific agonistic antibodies with the functionally active Fc domain resulted in influx of $CD8^+$ T-cells associated with liver toxicity (Dubrot et al., 2010, Cancer Immunol Immunother 59, 1223-1233) that is diminished or significantly ameliorated in the absence of functional Fc-receptors in mice. In the clinic, an Fc-competent 4-1BB agonistic Ab (BMS-663513) (NCT00612664) caused a grade 4 hepatitis leading to termination of the trial (Simeone and Ascierto, 2012, J Immunotoxicol 9, 241-247). Therefore, there is a need for effective and safer 4-1BB agonists.

The human epidermal growth factor receptor-2 (Her2; ErbB2) is a receptor tyrosine kinase and a member of the epidermal growth factor receptor (EGFR) family of transmembrane receptors. Her2 is overexpressed in a range of tumor types and it has been implicated in disease initiation and progression. It is associated with poor prognosis. For example, overexpression of Her2 is observed in approximately 30% of human breast cancers and it is implicated in the aggressive growth and poor clinical outcomes associated with these tumors (Slamon et al (1987) Science 235:177-182).

The humanized anti-Her2 monoclonal antibody trastuzumab (CAS 180288-69-1, HERCEPTIN®, huMAb4D5-8, rhuMAb Her2, Genentech) targets the extracellular domain of HER-2 (U.S. Pat. Nos. 5,677,171; 5,821,337; 6,054,297; 6,165,464; 6,339,142; 6,407,213; 6,639,055; 6,719,971; 6,800,738; 7,074,404; Coussens et al (1985) Science 230:1 132-9; Slamon et al (1989) Science 244:707-12; Slamon et al (2001) New Engl. J. Med. 344:783-792). Trastuzumab has been shown to inhibit the proliferation of human tumor cells that overexpress HER-2 and is a mediator of antibody-dependent cellular cytotoxicity, ADCC (Hudziak et al (1989) Mol Cell Biol 9:1 165-72; Lewis et al (1993) Cancer Immunol Immunother; 37:255-63; Baselga et al (1998) Cancer Res. 58:2825-2831; Hotaling et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137).

HERCEPTIN® (trastuzumab, Genentech Inc.) was approved in 1998 for the treatment of of patients with Her2-overexpressing metastatic breast cancers (Baselga et al, (1996) J. Clin. Oncol. 14:737-744). In 2006, the FDA approved HERCEPTIN® as part of a treatment regimen containing doxorubicin, cyclophosphamide and paclitaxel for the adjuvant treatment of patients with Her2-positive, node-positive breast cancer.

Pertuzumab (also known as recombinant humanized monoclonal antibody 2C4, rhuMAb 2C4, PERJETA®, Genentech, Inc, South San Francisco) is another antibody treatment targeting Her2. Pertuzumab is a Her dimerization inhibitor (HDI) and functions to inhibit the ability of Her2 to form active heterodimers or homodimers with other Her receptors (such as EGFR/Her 1, Her2, Her3 and Her4). See, for example, Harari and Yarden Oncogene 19:6102-14 (2000); Yarden and Sliwkowski. Nat Rev Mol Cell Biol 2:127-37 (2001); Sliwkowski, Nat Struct Biol 10:158-9 (2003); Cho et al. Nature 421:756-60 (2003); and Malik et al., Pro Am Soc Cancer Res 44:176-7 (2003); U.S. Pat. No. 7,560,111. PERJETA® was first approved in 2012 in combination with trastuzumab and docetaxel for the treatment of patients with advanced or late-stage (metastatic) Her2-positive breast cancer. The combination therapy using trastuzumab and pertuzumab is meanwhile also approved for the neoadjuvant (before surgery) treatment off Her2-positive, locally advanced, inflammatory, or early stage breast cancer and for adjuvant (after surgery) treatment of Her2-positive early breast cancer (EBC) at high risk of recurrence. The mechanisms of action of Perjeta and Herceptin are believed to complement each other, as both bind to the Her2 receptor, but to different places. The combination of Perjeta and Herceptin is thought to provide a more comprehensive, dual blockade of HER signaling pathways, thus preventing tumor cell growth and survival.

Bispecific, bivalent Her2 antibodies that are directed against domains II, III and IV of human ErbB2 are disclosed in WO 2012/143523. Bispecific HER-2 antibodies comprising optimized variants of the antibodies rhuMab 2C4 and hu4D5, called Herceptarg, have been described in WO 2015/091738.

Although the therapeutic efficacy of trastuzumab in breast carcinoma is well demonstrated, there are many patients who do not benefit from trastuzumab because of resistance. Given the lack of an effective anti-Her2 therapy in specific cancers expressing low levels of Her2, the resistance to the current therapies, and the prevalence of Her2 related cancers, new therapies are required to treat such cancers.

The new antigen binding molecules of the present invention combine an anti-Her2 antigen binding domain with a moiety that is capable of forming a costimulatory 4-1BB ligand timer and that is sufficiently stable to be pharmaceutically useful. Fusion proteins composed of a binding specificity for CD137 and a binding specificity for Her2/neu are disclosed in WO 2016/177802. These molecules are antibody-lipocalin mutein fusion polypeptides, meaning that a lipocalin mutein with binding specificity for CD137 is fused to an anti-Her2 antibody. Lipocalin muteins (anticalins) are non-antibody scaffolds and the conversion of such modalities into differentiated drugs has been challenging (Vazquez-Lombardi et al. 2015, Drug Discovery Today 20, 1271-1283). Compared to antibodies challenges could arise in view of different serum half-life, tissue penetration and immunogenicity. Thus, there is still a need for drug candidates with improved properties that are based on antibody technology or human-like proteins.

SUMMARY OF THE INVENTION

The new antigen binding molecules of the present invention combine an anti-Her2 antigen binding domain with a moiety that is capable of forming a costimulatory 4-1BBL trimer and that is sufficiently stable to be pharmaceutically useful. Surprisingly, antigen binding molecules of the invention provide a trimeric and thus biologically active human 4-1BB ligand, although one of the trimerizing 4-1BBL ectodomains is located on another polypeptide than the other two 4-1BBL ectodomains of the molecule. Targeted by the anti-Her2 antigen binding domain the antigen binding molecules of the present invention have an increased activity on the tumor site, comprise the natural human 4-1BB ligand and should thus impose less safety issues compared to conventional 4-1BB agonistic antibodies or more artificial fusion proteins.

In one aspect, the invention provides a 4-1BBL trimer-containing antigen binding molecule comprising
(a) an antigen binding domain capable of specific binding to Her2,
(b) a first and a second polypeptide that are linked to each other by a disulfide bond, wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and
(c) an Fc domain composed of a first and a second subunit capable of stable association.

In a particular aspect, the invention provides a 4-1BBL trimer-containing antigen binding molecule, wherein the ectodomain of 4-1BBL or a fragment thereof comprises the amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

In a further aspect, the invention provides a 4-1BBL trimer-containing antigen binding molecule, comprising
(a) an antigen binding domain capable of specific binding to Her2,
(b) a first and a second polypeptide that are linked to each other by a disulfide bond, wherein the antigen binding molecule is characterized in that the first polypeptide comprises the amino acid sequence selected from the group consisting of SEQ ID NO:9, SEQ ID NO:10, SEQ ID NO:11 and SEQ ID NO:12 and in that the second polypeptide comprises the amino acid sequence selected from the group consisting of SEQ ID NO:1, SEQ ID NO:5, SEQ ID NO:3 and SEQ ID NO:4, and
(c) an Fc domain composed of a first and a second subunit capable of stable association.

In one aspect, the Fc domain is an IgG, particularly an IgG1 Fc domain or an IgG4 Fc domain. More particularly, the Fc domain is an IgG1 Fc domain. In a particular aspect, the Fc domain comprises a modification promoting the association of the first and second subunit of the Fc domain. In a particular aspect, the invention provides a 4-1BBL trimer-containing antigen binding molecule, wherein the Fc domain comprises knob-into-hole modifications promoting association of the first and the second subunit of the Fc domain. In a specific aspect, the invention provides a 4-1BBL trimer-containing antigen binding molecule, wherein the first subunit of the Fc domain comprises the amino acid substitutions S354C and T366W (numbering according to Kabat EU index) and the second subunit of the Fc domain comprises the amino acid substitutions Y349C, T366S, L368A and Y407V (numbering according to Kabat EU index).

In another aspect, the invention is concerned with a 4-1BBL trimer-containing antigen binding molecule as defined herein before, comprising (c) an Fc domain composed of a first and a second subunit capable of stable association, wherein the Fc domain comprises one or more amino acid substitution that reduces binding to an Fc receptor, in particular towards Fcγ receptor. In particular, the Fc domain comprises amino acid substitutions at positions 234 and 235 (EU numbering according to Kabat) and/or 329 (EU numbering according to Kabat) of the IgG heavy chains. Particularly, provided is a 4-1BBL trimer-containing antigen binding molecule, wherein the Fc domain is an IgG1 Fc domain comprising the amino acid substitutions the amino acid substitutions L234A, L235A and P329G (numbering according to Kabat EU index).

In one aspect, the 4-1BBL trimer-containing antigen binding molecule is one, wherein wherein the antigen binding domain capable of specific binding to Her2 is a Fab molecule capable of specific binding to Her2. In another aspect, the antigen binding domain capable of specific binding to Her2 is a cross-over Fab molecule or a scFV molecule capable of specific binding to Her2.

In one aspect, the invention provides a 4-1BBL trimer-containing antigen binding molecule as described herein before, wherein the 4-1BBL trimer-containing antigen binding molecule comprises one Fab domain capable of specific binding to Her2, meaning that it comprises monovalent binding towards Her2.

In a further aspect, provided is a 4-1BBL trimer-containing antigen binding molecule, wherein wherein the antigen binding domain capable of specific binding to Her2 comprises (a) a VH domain comprising (i) CDR-H1 comprising the amino acid sequence of SEQ ID NO:13, (ii) CDR-H2 comprising the amino acid sequence of SEQ ID NO:14, and (iii) CDR-H3 comprising the amino acid sequence of SEQ ID NO:15, and a VL domain comprising (iv) CDR-L1 comprising the amino acid sequence of SEQ ID NO:16, (v) CDR-L2 comprising the amino acid sequence of SEQ ID NO:17, and (vi) CDR-L3 comprising the amino acid sequence of SEQ ID NO:18, or (b) a VH domain comprising (i) CDR-H1 comprising the amino acid sequence of SEQ ID NO:21, (ii) CDR-H2 comprising the amino acid sequence of SEQ ID NO:22, and (iii) CDR-H3 comprising the amino acid sequence of SEQ ID NO:23, and a VL domain comprising (iv) CDR-L1 comprising the amino acid sequence of SEQ ID NO:24, (v) CDR-L2 comprising the amino acid sequence of SEQ ID NO:25, and (vi) CDR-L3 comprising the amino acid sequence of SEQ ID NO:26, or (c) a VH domain comprising (i) CDR-H1 comprising the amino acid sequence of SEQ ID NO:29, (ii) CDR-H2 comprising the amino acid sequence of SEQ ID NO:30, and (iii) CDR-H3 comprising the amino acid sequence of SEQ ID NO:31, and a VL domain comprising (iv) CDR-L1 comprising the amino acid sequence of SEQ ID NO:32, (v) CDR-L2 comprising the amino acid sequence of SEQ ID NO:33, and (vi) CDR-L3 comprising the amino acid sequence of SEQ ID NO:34.

In a further aspect, the 4-1BBL trimer-containing antigen binding molecule of the invention comprises (a) a VH domain comprising an amino acid sequence of SEQ ID NO:19 and a VL domain comprising an amino acid sequence of SEQ ID NO:20, or (b) a VH domain comprising an amino acid sequence of SEQ ID NO:27 and a VL domain comprising an amino acid sequence of SEQ ID NO:28, or (c) a VH domain comprising an amino acid sequence of SEQ ID NO:35 and a VL domain comprising an amino acid sequence of SEQ ID NO:36.

In a further aspect, provided is a 4-1BBL trimer-containing antigen binding molecule, wherein the antigen binding molecule comprises a first heavy chain and a first light chain, both comprising a Fab molecule capable of specific binding to Her2, a second heavy chain comprising the constant domains and two ectodomains of a 4-1BBL or a fragment thereof connected to each other by a first peptide linker fused at its C-terminus by a second peptide linker to a second heavy or light chain, and a second light chain comprising a constant domain and one ectodomain of 4-1BBL or a fragment thereof fused at its C-terminus by a third peptide linker to a second light or heavy chain, respectively. More particularly, provided is a 4-1BBL trimer-containing antigen binding molecule, wherein the first peptide comprising two ectodomains of 4-1BBL or a fragment thereof connected to each other by a first peptide linker is fused at its C-terminus by a second peptide linker to a CL domain that is part of a heavy chain, and the second peptide comprising one ectodomain of said 4-1BBL or a fragment thereof is fused at its C-terminus by a third peptide linker to a CH1 domain that is part of a light chain.

In a particular aspect, the invention relates to a 4-1BBL trimer-containing antigen binding molecule as defined above, wherein the peptide linker is $(G4S)_2$, i.e. a peptide linker of SEQ ID NO:68. In one aspect, the peptide linker in all instances is $(G4S)_2$.

Provided is further a 4-1BBL trimer-containing antigen binding molecule, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E).

In another aspect, provided is a 4-1BBL trimer-containing antigen binding molecule, wherein the antigen binding molecule comprises (i) a first heavy chain comprising the VH domain comprising the amino acid sequence of SEQ ID NO:19 and a first light chain comprising the VL domain comprising the amino acid sequence of SEQ ID NO:20 or a first heavy chain comprising the VH domain comprising the amino acid sequence of SEQ ID NO:27 and a first light chain comprising the VL domain comprising the amino acid sequence of SEQ ID NO:28, or a first heavy chain comprising the VH domain comprising the amino acid sequence of SEQ ID NO:35 and a first light chain comprising the VL domain comprising the amino acid sequence of SEQ ID NO:36, (ii) a second heavy chain comprising the amino acid sequence selected from the group consisting of SEQ ID NO:37, SEQ ID NO:39, SEQ ID NO:41 and SEQ ID NO:43, and (iii) a second light chain comprising the amino acid sequence selected from the group consisting of SEQ ID NO:38, SEQ ID NO:40, SEQ ID NO:42 and SEQ ID NO:44

In a particular aspect, provided is a 4-1BBL trimer-containing antigen binding molecule comprising (a) a first heavy chain comprising the amino acid sequence of SEQ ID NO:45, a first light chain comprising the amino acid sequence of SEQ ID NO:46, a second heavy chain comprising the amino acid sequence of SEQ ID NO:37 and a second light chain comprising the amino acid sequence of SEQ ID NO:38, or (b) a first heavy chain comprising the amino acid sequence of SEQ ID NO:47, a first light chain comprising the amino acid sequence of SEQ ID NO:48, a second heavy chain comprising the amino acid sequence of SEQ ID NO:37 and a second light chain comprising the amino acid sequence of SEQ ID NO:38, or (c) a first heavy chain comprising the amino acid sequence of SEQ ID NO:49, a first light chain comprising the amino acid sequence of SEQ ID NO:50, a second heavy chain comprising the amino acid sequence of SEQ ID NO:37 and a second light chain comprising the amino acid sequence of SEQ ID NO:38.

According to another aspect of the invention, there is provided an isolated nucleic acid molecule encoding a 4-1BBL trimer-containing antigen binding molecule as defined herein before. The invention further provides a vector, particularly an expression vector, comprising the isolated nucleic acid molecule of the invention and a host cell comprising the isolated nucleic acid or the vector of the invention. In some embodiments the host cell is an eukaryotic cell, particularly a mammalian cell.

In another aspect, provided is a method for producing the 4-1BBL trimer-containing antigen binding molecule of the invention, comprising culturing the host cell of the invention under conditions suitable for expression of the 4-1BBL trimer-containing antigen binding molecule, and isolating the 4-1BBL trimer-containing antigen binding molecule. The invention also encompasses a 4-1BBL trimer-containing antigen binding molecule produced by the method of the invention.

The invention further provides a pharmaceutical composition comprising the 4-1BBL trimer-containing antigen binding molecule of the invention and at least one pharmaceutically acceptable excipient. In another aspect, a pharmaceutical composition is provided comprising the 4-1BBL trimer-containing antigen binding molecule of the invention and at least one pharmaceutically acceptable excipient, further comprising an additional therapeutic agent, e.g. a chemotherapeutic agent and/or other agents for use in cancer immunotherapy. In a further aspect, provided is a pharmaceutical composition further comprising a T-cell activating anti-CD3 bispecific antibody, in particular an anti-Her2/anti-CD3 bispecific antibody.

Also encompassed by the invention is the 4-1BBL trimer-containing antigen binding molecule of the invention, or the pharmaceutical composition of the invention, for use as a medicament. In one aspect is provided the 4-1BBL trimer-containing antigen binding molecule of the invention, or the pharmaceutical composition of the invention, for use in the treatment of a disease in an individual in need thereof. In a specific embodiment, provided is the 4-1BBL trimer-containing antigen binding molecule of the invention, or the pharmaceutical composition of the invention, for use in the treatment of cancer. In another aspect, provided is the 4-1BBL trimer-containing antigen binding molecule of the invention, or the pharmaceutical composition of the invention, for use in up-regulating or prolonging cytotoxic T cell activity. In another aspect, provided is the 4-1BBL trimer-containing antigen binding molecule of the invention, or the pharmaceutical composition of the invention, for use in the treatment of cancer, wherein the the 4-1BBL trimer-containing antigen binding molecule is used in combination with another therapeutic agent, in particular a T-cell activating anti-CD3 bispecific antibody. In one aspect, the T-cell activating anti-CD3 bispecific antibody is administered concurrently with, prior to, or subsequently to the 4-1BBL trimer-containing antigen binding molecule.

Also provided is the use of the 4-1BBL timer-containing antigen binding molecule of the invention for the manufacture of a medicament for the treatment of a disease in an individual in need thereof, in particular for the manufacture of a medicament for the treatment of cancer, as well as a method of treating a disease in an individual, comprising administering to said individual a therapeutically effective amount of a composition comprising the 4-1BBL trimer-containing antigen binding molecule as disclosed herein in a pharmaceutically acceptable form. In a specific aspect, the disease is cancer. Further provided is the use of the 4-1BBL trimer-containing antigen binding molecule of the invention for the manufacture of a medicament for the treatment of cancer, wherein the 4-1BBL timer-containing antigen binding molecule is used in combination with a T-cell activating anti-CD3 bispecific antibody, in particular an anti-Her2/anti-CD3 antibody. Furthermore, provided is a method for treating an individual having cancer comprising administering to the subject an effective amount of the 4-1BBL trimer-containing antigen binding molecule of the invention, or a pharmaceutical composition thereof, and an effective amount of a T-cell activating anti-CD3 bispecific antibody, in particular an anti-Her2/anti-CD3 antibody. Also provided is a method of up-regulating or prolonging cytotoxic T cell activity in an individual having cancer, comprising administering to the individual an effective amount of the 4-1BBL trimer-containing antigen binding molecule of the invention, or the pharmaceutical composition of the invention. In any of the above embodiments the individual is preferably a mammal, particularly a human.

BRIEF DESCRIPTION OF THE DRAWINGS

FIG. 1 shows the components for the assembly of the monovalent Her2-targeting split trimeric 4-1BB ligand Fc fusion antigen binding molecules. FIG. 1A shows the dimeric 4-1BB ligand that is fused at the C-terminus to a human IgG1-CL domain with mutations E123R and Q124K (charged variant) and FIG. 1B shows the monomeric 4-1BB ligand fused at its C-terminus to a human IgG1-CH1 domain with mutations K147E and K213E (charged variant).

FIG. 2A illustrates schematically the structure of the monovalent Her2-targeting split trimeric 4-1BB ligand Fc (kih) fusion antigen binding molecule comprising CH-CL cross with charged residues. The thick black point stands for the knob-into-hole modification. * symbolizes amino acid modifications in the CH1 and CL domain (so-called charged variant). FIG. 2B illustrates the mouse surrogate, i.e. a bispecific 4-1BB antibody with bivalent binding for mouse 4-1BB and monovalent binding for Her2 (anti-4-1BB/anti-Her2 moIgG1 DDKK DAPG, termed mu4-1BB-Her2). The thick black point stands for the DD/KK knob-into-hole modification. The DAPG mutations abolish the crosslinking of the fusion protein via mouse Fcγ receptors or the binding of complement but allow binding to FcRn, so that the molecule remains its antibody like pharmacokinetics.

FIG. 3A shows the setup of the SPR experiments for simultaneous binding of the Her2-targeting split trimeric 4-1BB ligand-containing antigen binding molecules of the invention. The simultaneous binding of Her2(PER)-4-1BBL (Analyte 1) to immobilized human 4-1BB and human Her2 (analyte 2) is shown in FIG. 3B. Simultaneous binding to human 4-1BB and human Her2 of Her2(aff PER)-4-1BBL is shown in FIG. 3C.

FIGS. 4A to 4D show the binding of Her2-targeting 4-1BB split trimeric ligand Fc fusion antigen binding molecules to Her2 expressed on the cell surface by human breast cancer cell line SK-Br3 (FIGS. 4A and 4C) or human gastric carcinoma cell line NCI-N87 (FIGS. 4B and 4D). Her2-targeting split 4-1BBL antigen binding molecules displaying the Her2 binders pertuzumab (PER) or affinity-matured pertuzumab (aff-PER) or the fusion protein Her2 (TRAS)-anticalin 4-1BB huIgG4 (as described in patent WO2016/177802) or previously described agonistic anti-human 4-1BB antibodies anti-human 4-1BB clone 20H4.9 huIgG4 (described in U.S. Pat. No. 7,659,384 B2) or anti-human 4-1BB clone MOR-7480 huIgG2 (described in WO 2012/032433) or control molecules as indicated in the legend were incubated with Her2 expressing cell lines SK-Br3 (FIGS. 4A and 4C) or NCI-N87 (FIGS. 4B and 4D) at different concentrations as indicated in the X-axis. Afterwards excessive and not bound molecules were washed of and bound molecules were detected with a secondary binding PE-conjugated anti-human Fc-fragment specific goat IgG F(ab')2 fragment. The median of fluorescence intensity (MFI) was measured by flow cytometry and indicates the affinity (monovalent binders) or avidity (bivalent binders) of the tested molecules in a dose dependent manner Values are baseline corrected by subtracting the blank control (e g staining with 2nd detection fragment only), shown is the mean+/−SEM.

The NFκB-mediated luciferase activity in a Jurkat-hu4-1BB-NFκB-luc2 reporter cell line is shown in FIGS. 7A to 7F. In 96-well plates Jurkat-hu4-1BB-NFκB-luc2 reporter cells were incubated with different concentrations (indicated in the x-axis) of Her2 (PER)-4-1BBL or Her2 (PER)-4-1BBL molecules or the fusion protein Her2 (TRAS)-anticalin 4-1BB huIgG4 or agonistic anti-human 4-1BB antibodies 20H4.9 huIgG4 or MOR-7480 huIgG2 or the control molecules as indicated in the legend. The results in the absence of Her2+ cells are shown in FIGS. 7A and 7D, in the presence of human Her2+ breast cancer cell line SK-Br3 in FIGS. 7B and 7E or in the presence of Her2+ human gastric cancer cell line NCI-N87 in FIGS. 7C and 7F. Reporter cells were incubated with the Her2-expressing tumor cells in an 1:5 ratio for 6 h. Afterwards cells were washed, lysed and incubated with Luciferin in a detection buffer. Luciferase-catalyzed oxidation of luciferin was detected via light emission as units of released light (y-axis). Shown is the mean+/−SEM. All values are baseline corrected by subtracting the baseline light emission.

The results of a second experiment comparing Her2 (PER)-4-1BBL with Her2 (TRAS)-4-1BBL are shown in FIGS. 8A to 8II. In 348-well plates Jurkat-hu4-1BB-NFκB-luc2 reporter cells were incubated with different concentrations (indicated in the x-axis) of Her2 (PER)-4-1BBL or Her2 (TRAS)-4-1BBL or the fusion protein Her2 (TRAS)-anticalin 4-1BB huIgG4 or agonistic anti-human 4-1BB antibodies 20H4.9 huIgG4 or MOR-7480 huIgG2 or control molecules as indicated in the legend. Shown is the NFκB-mediated luciferase expression in a Jurkat-hu4-1BB-NFκB-luc2 reporter cell line in the absence (FIGS. 8A and 8E) or the presence of human Her2+ breast cancer cell line SK-Br3 (FIGS. 8B and 8F), in the presence of human breast cancer cell line KPL-4 (FIGS. 8C and 8G) or Her2+ human gastric cancer cell line NCI-N87 (FIGS. 8D and 8H) when given in a reporter cell line to tumor cell line 1:5 ratio for 6 h. Cells were washed, lysed and incubated with Luciferin in a detection buffer. Luciferase-catalyzed oxidation of luciferin was detected via light emission as units of released light (y-axis). Shown is the mean+/−SEM. All values are baseline corrected by subtracting the baseline light emission.

Figure 9:
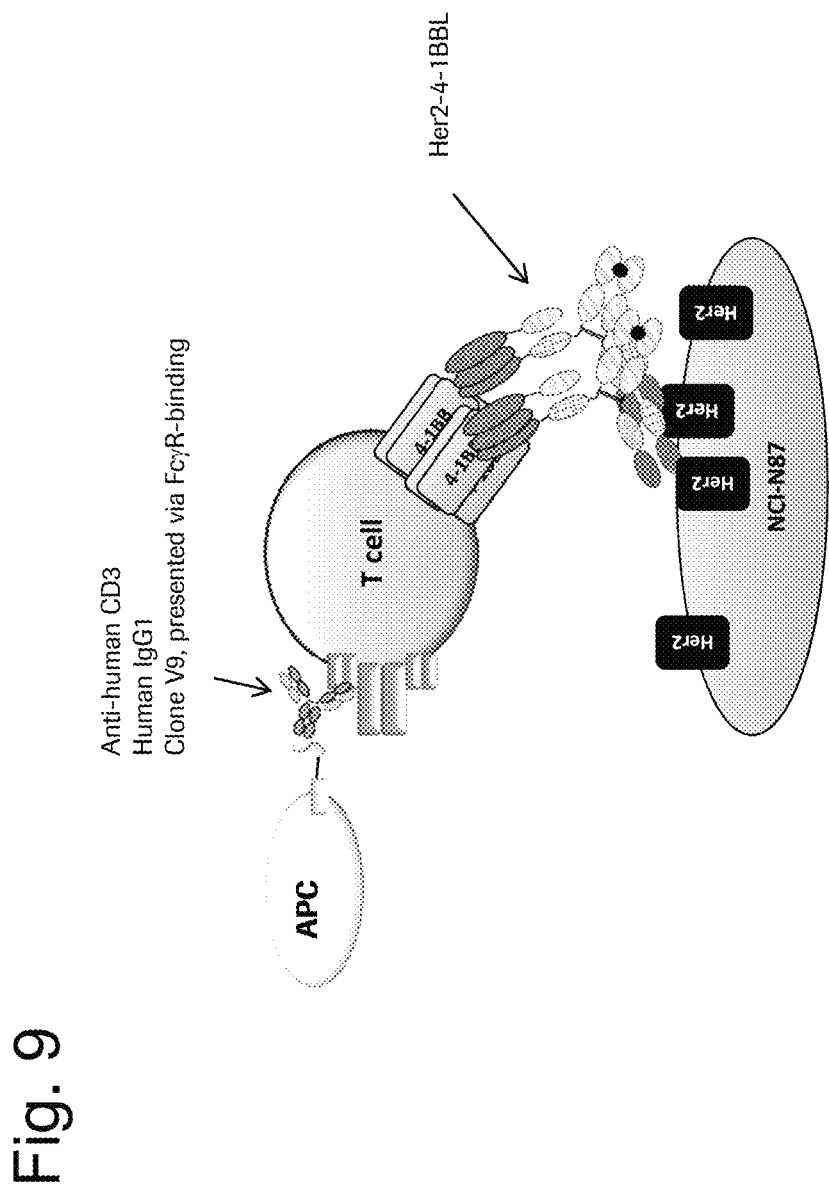

FIG. 9 shows a scheme that illustrates the general principal of the activation assay with human PBMCs as described in Example 3.2.2. T cells are activated by 2 nM agonistic CD3 antibody and co-stimulated with different concentrations of agonistic 4-1BB molecules in the presence of Her2-expressing gastric carcinoma NCI-N87 cells. The content/well comprised 50 Gy irradiated 2×10$^4$ NCI-N87 cells, 7.5×10$^4$ CFSE-labelled human PBMCs, 2 nM agonistic anti-human CD3 human IgG wt (clone V9) and different concentrations of Her2-targeting 4-1BB agonistic molecules (here shown as Her2-4-1BBL). Cells were incubated for 4 days and then T cell activation was determined my flow cytometry.

Figure 10A:
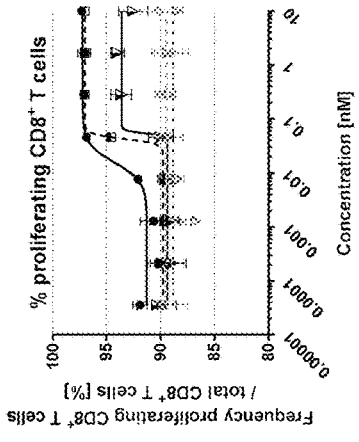
Figure 10B:
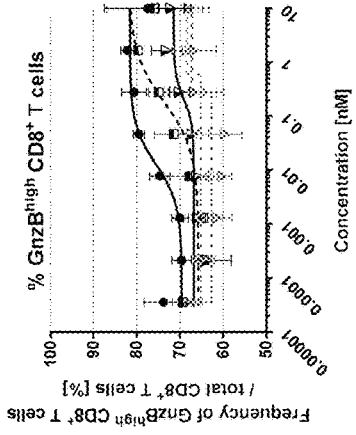
Figure 10C:
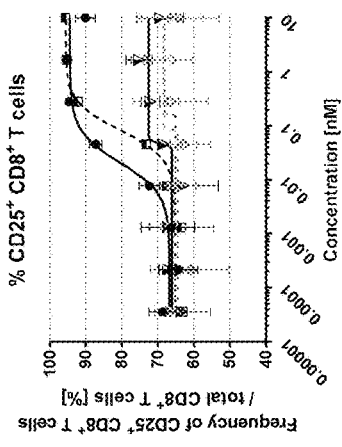
Figure 10D:
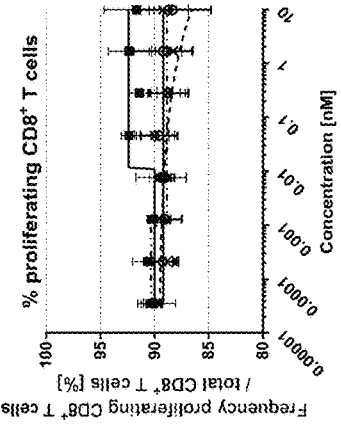
Figure 10E:
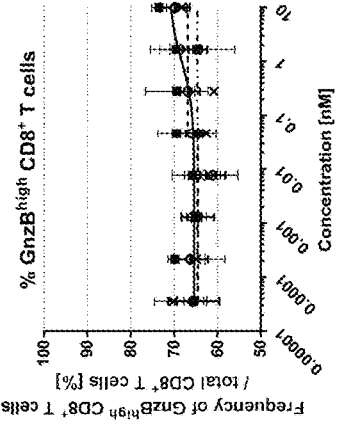
Figure 10F:
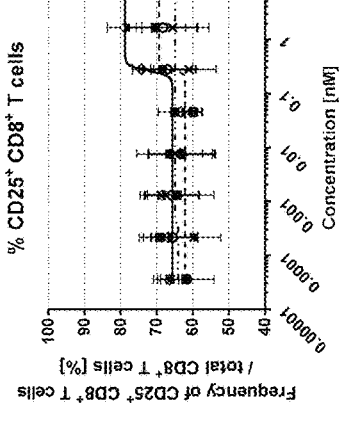

The results are shown as activation of CD8$^+$ T cells in FIGS. 10A to 10F. Resting PBMCs isolated from a buffy coat of a healthy donor were activated with 2 nM agonistic CD3 antibody and co-stimulated with different concentrations of agonistic 4-1BB molecules as indicated in the x-axis and in the legend in presence of Her2-expressing gastric carcinoma NCI-N87 cells for 4 days. Cells were gated on living CD8$^+$ T cells and analyzed for their frequency of CD25$^+$ (FIGS. 10A and 10D), Granzyme B$^{high}$ (FIGS. 10B and 10E) or proliferating (low CFSE MFI) CD8$^+$ T cells (FIGS. 10C and 10F). Shown is the mean+/−SD.

The activation of CD4$^+$ T cells is shown in FIGS. 11A to 11F. Resting PBMCs isolated from a buffy coat of a healthy donor were activated with 2 nM agonistic CD3 antibody and co-stimulated with different concentrations of agonistic 4-1BB molecules as indicated in the x-axis in the presence of Her2-expressing gastric carcinoma NCI-N87 cells for 4 days. Cells were gated on living CD4$^+$ T cells and analyzed for their frequency of CD25$^+$ (FIGS. 11A and 11D), Granzyme B$^{high}$ (FIGS. 11B and 11E) or proliferating (low CFSE MFI) CD4$^+$ T cells (FIGS. 11C and 11F). Shown is the mean+/−SD.

Figure 12:
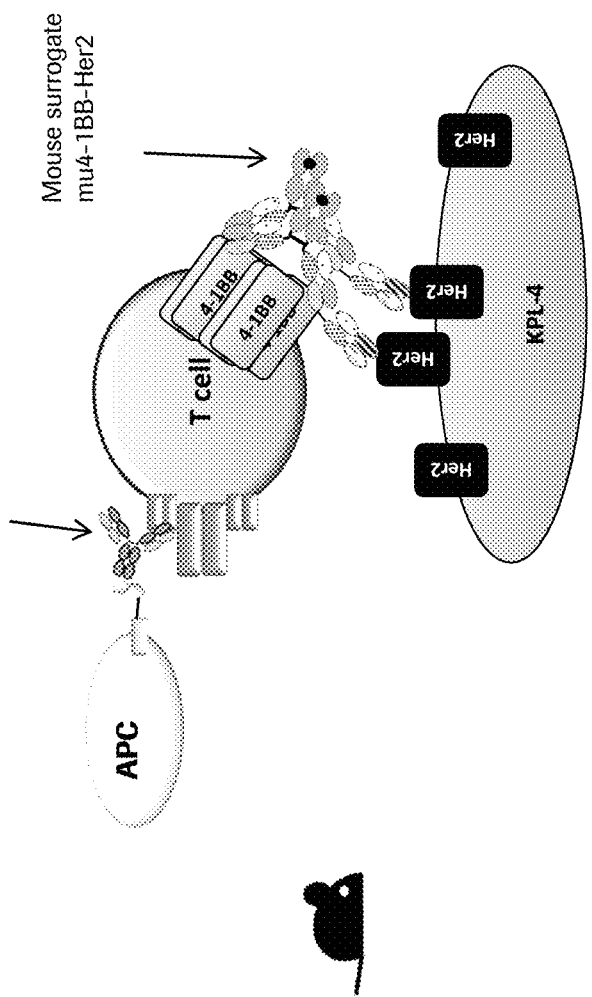

FIG. 12 shows a scheme that illustrates the general principal of the activation assay with mouse splenocytes as described in Example 3.2.3. T cells are activated by 0.5 µg/mL (~3.6 nM) agonistic anti-mouse CD3 Armenian hamster IgG antibody (clone 1452C11) and co-stimulated with different concentrations of agonistic mouse surrogate mu4-

1BB-Her2 in the presence of Her2-expressing human breast cancer cell line KPL-4. The content/well comprised 50 Gy irradiated 2×10$^4$ KPL-4 cells, 15×10$^4$ violet proliferation dye-labelled mouse splenocytes, 0.5 μg/mL (~3.6 nM) agonistic anti-mouse CD3 Armenian hamster IgG antibody (clone 1452C11) and different concentrations of mouse surrogate mu4-1BB-Her2 or an untargeted control mu4-1BB muIgG1 DAPG. Cells were incubated for 3 days and then T cell activation was determined my flow cytometry.

Figure 13A:
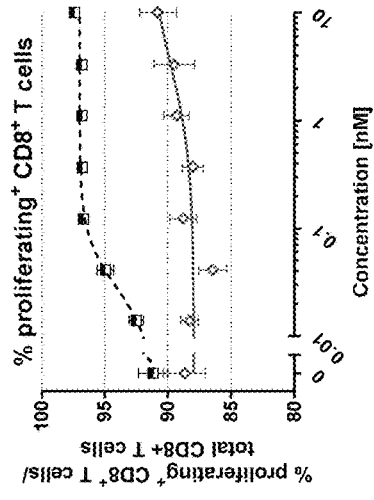
Figure 13B:
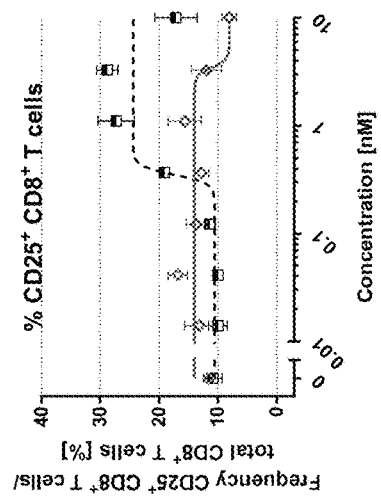
Figure 13C:
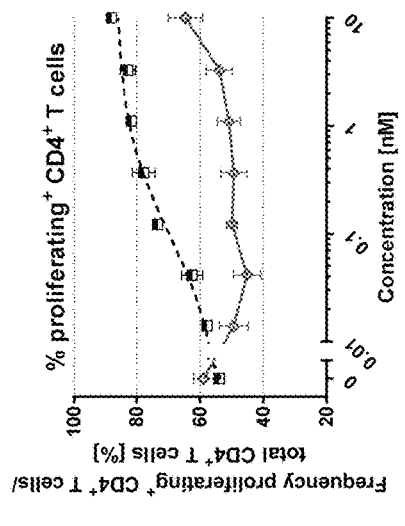
Figure 13D:
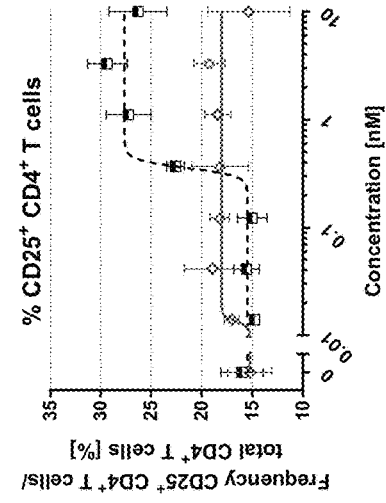

The results are shown as activation of mouse CD8$^+$ and CD4$^+$ T cells in FIGS. 13A to 13D. Resting mouse splenocytes isolated from C57BL/6 spleens were activated with 0.5 μg/mL (~3.6 nM) agonistic anti-mouse CD3 Armenian hamster IgG antibody (clone 1452C11) and co-stimulated with different concentrations of mouse surrogate mu4-1BB-Her2 or untargeted control as indicated in the x-axis and in the legend in presence of Her2-expressing human breast cancer KPL-4 cells for 3 days. Cells were gated on living CD8$^+$ or CD4$^+$ T cells and analyzed for their frequency of CD25$^+$ expression (FIGS. 13A and 13C) or proliferating (low violet proliferation dye MFI) (FIGS. 13B and 13D). Shown is the mean+/−SD of technical triplicates per point.

Figure 14A:
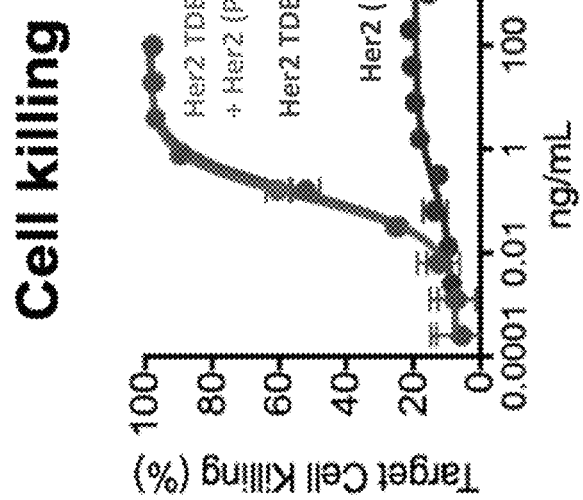
Figure 14B:
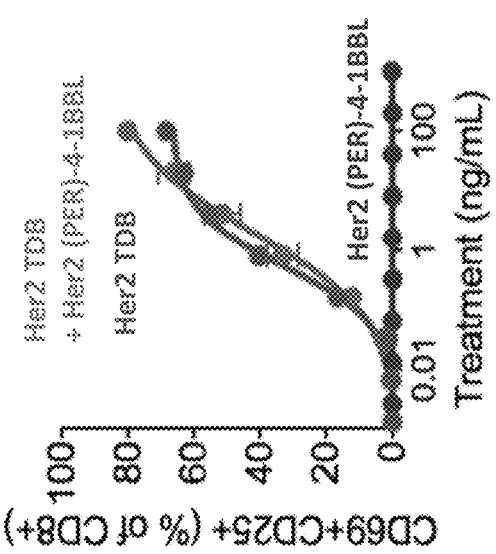

In FIG. 14A T cell activation of the combination of anti-Her2/anti-CD3 bispecific antibody (Her2 TDB) with Her2(PER)-4-1BBL and the T cell activation of the single agents is shown. A robust T cell activation was induced by Her2 TDB alone as well as by the combination of both agents. Target cell killing of the combination of anti-Her2/anti-CD3 bispecific antibody (Her2 TDB) with Her2(PER)-4-1BBL and the single agents is shown in FIG. 14B.

The results of the T cell proliferation assay for the combination of anti-Her2/anti-CD3 bispecific antibody (Her2 TDB) with Her2(PER)-4-1BBL are shown in FIGS. 15A and 15B. Addition of HER2-4-1BBL substantially enhanced anti-HER2/CD3-TDB induced T cell proliferation/survival in vitro.

FIGS. 16A to 16D show the tumor growth kinetics (linear scale) as observed in immune-competent mice that were implanted with human HER2 expressing Fo5 tumor allografts and treated with vehicle (FIG. 16A), Her2 TDB alone (FIG. 14B), mu 4-1BB-Her2 mouse surrogate alone (FIG. 14C) and the combination of Her2 TDB and mu 4-1BB-Her2 (FIG. 14D). The individual tumor growth kinetics of each animal for all treatment groups are shown. CR means no dectable tumor at the end of the study, PR means that at least 50% of tumor shrinkage is observed compared to day 0. Four of seven mice (57%) treated in combination with mu4-1BB-Her2 agonist demonstrated complete responses without detectable tumors in the end of study (CR=57%).

DETAILED DESCRIPTION OF THE INVENTION

Definitions

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigen binding domain capable of specific binding to Her2" or "moiety capable of specific binding to Her2" refers to a polypeptide molecule that specifically binds to Her2. In one aspect, the antigen binding domain is able to activate or inhibit signaling through Her2. In a particular aspect, the antigen binding domain is able to direct the entity to which it is attached (e.g. the 4-1BBL trimer) to a target site, for example to a specific type of tumor cell bearing Her2. Antigen binding domains capable of specific binding to Her2 include antibodies and fragments thereof as further defined herein. In relation to an antibody or fragment thereof, the term "moiety capable of specific binding to a target cell antigen" refers to the part of the molecule that comprises the area which specifically binds to and is complementary to part or all of an antigen. A moiety capable of specific antigen binding may be provided, for example, by one or more antibody variable domains (also called antibody variable regions). Particularly, a moiety capable of specific antigen binding comprises an antibody light chain variable region (VL) and an antibody heavy chain variable region (VH).

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used within the current application denotes the presence of a specified number of binding sites in an antigen binding molecule. As such, the terms "monovalent", "bivalent", "tetravalent", and "hexavalent" denote the presence of one binding site, two binding sites, four binding sites, and six binding sites, respectively, in an antigen binding molecule.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain Fab' fragments differ from Fab fragments by the addition of a few residues at the carboxy terminus of the heavy chain CH1 domain including one or more cysteins from the antibody hinge region. Fab'-SH are Fab' fragments in which the cysteine residue(s) of the constant domains bear a free thiol group. Pepsin treatment yields an F(ab')$_2$ fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin). CTLA-4 (Cytotoxic T Lymphocyte-associated Antigen 4) is a CD28-family receptor expressed on mainly CD4$^+$ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of Staphylococcus aureus which can be engineered to bind to antigen. The domain consists of a three-helical bundle of approximately 58 amino acids. Libraries have been generated by randomization of surface residues. For further details see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1. A single-domain antibody is an antibody fragment consisting of a single monomeric variable antibody domain. The first single domains were derived from the variable domain of the antibody heavy chain from camelids (nanobodies or $V_HH$ fragments). Furthermore, the term single-domain antibody includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can beengineered to include upto 25 amino acids without affecting the overall fold of the microprotein. For further details of engineered knottin domains, see WO2008098796.

Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), Biodrugs 19(5), 279-288 (2005), U.S. Pat. No. 7,250,297B1 and US20070224633.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

The term "capable of specific binding to Her2" refers to an antigen binding molecule that is capable of binding to Her2 with sufficient affinity such that the antigen binding molecule is useful as a diagnostic and/or therapeutic agent in targeting Her2. The antigen binding molecule includes but is not limited to, antibodies, Fab molecules, crossover Fab molecules, single chain Fab molecules, Fv molecules, scFv molecules, single domain antibodies, and VH and scaffold antigen binding protein. In one aspect, the extent of binding of an anti-Her2 antigen binding molecule to an unrelated, non-Her2 protein is less than about 10% of the binding of the antigen binding molecule to Her2 as measured, e.g., by surface plasmon resonance (SPR). In particular, an antigen binding molecule that is capable of specific binding to Her2 has a dissociation constant ($K_d$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{13}$ M, e.g., from $10^{-9}$ M to $10^{-13}$ M). In certain aspects, an anti-Her2 antigen binding molecule binds to Her2 from different species. In particular, the anti-Her2 antigen binding molecule binds to human and cynomolgus Her2.

The term "epitope" denotes the site on an antigen, either proteinaceous or non-proteinaceous, to which an anti-[[PRO]] antibody binds. Epitopes can be formed from contiguous amino acid stretches (linear epitope) or comprise non-contiguous amino acids (conformational epitope), e.g., coming in spatial proximity due to the folding of the antigen, i.e. by the tertiary folding of a proteinaceous antigen. Linear epitopes are typically still bound by an antibody after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 550 to about residue 610, inclusive, of human HER2 (SEQ ID NO: 54).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and pertuzumab bind to the extracellular domain of HER2 at the junction of domains I, II and III (Franklin et al. Cancer Cell 5:317-328 (2004)).

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

A "target cell antigen" as used herein refers to an antigenic determinant presented on the surface of a target cell, for example a T-cell or B-cell, a cell in a tumor such as a cancer cell or a cell of the tumor stroma. In certain aspects, the target cell antigen is an antigen on the surface of cancer cell. In one aspect, the target cell antigen is Her2.

The term "Her2", also known as "ErbB2", "ErbB2 receptor", or "c-Erb-B2", refers to any native, mature HER2 which results from processing of a HER2 precursor protein in a cell. The term includes HER2 from any vertebrate source, including mammals such as primates (e.g. humans and cynomolgus monkeys) and rodents (e.g., mice and rats), unless otherwise indicated. The term also includes naturally occurring variants of HER2, e.g., splice variants or allelic variants. The amino acid sequence of an exemplary human HER2 protein is shown in SEQ ID NO:54.

A "T-cell antigen" as used herein refers to an antigenic determinant presented on the surface of a T lymphocyte, particularly a cytotoxic T lymphocyte.

A "T cell activating therapeutic agent" as used herein refers to a therapeutic agent capable of inducing T cell activation in a subject, particularly a therapeutic agent designed for inducing T-cell activation in a subject. Examples of T cell activating therapeutic agents include bispecific antibodies that specifically bind an activating T cell antigen, such as CD3, and a target cell antigen, such as CEA or Folate Receptor.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3.

The term "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3E). The amino acid sequence of human CD3E is shown in UniProt (www.uniprot.org) accession no. P07766 (version 144), or NCBI (www.ncbi.nlm.nih.gov/) RefSeq NP_000724.1. See also SEQ ID NO: 85. The amino acid sequence of cynomolgus [*Macaca fascicularis*] CD3E is shown in NCBI GenBank no. BAB71849.1. See also SEQ ID NO: 86.

The term "variable domain" or "variable region" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR" as used herein refers to each of the regions of an antigen binding variable domain which are hypervariable in sequence and which determine antigen binding specificity, for example "complementarity determining regions" ("CDRs"). Generally, antigen binding domains comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262:732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature. Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain There are five major classes of antibodies: IgA, IgD, IgE, IgG, and IgM, and several of these may be further divided into subclasses (isotypes), e.g. IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ respectively.

The terms "constant region derived from human origin" or "human constant region" denote a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., et al., Sequences of Proteins of Immunological Interest, 5th ed., Public Health Service, National Institutes of Health, Bethesda, MD (1991)

(see also e.g. Johnson, G., and Wu, T. T., Nucleic Acids Res. 28 (2000) 214-218; Kabat, E. A., et al., Proc. Natl. Acad. Sci. USA 72 (1975) 2785-2788). Unless otherwise specified herein, numbering of amino acid residues in the constant region is according to the EU numbering system, also called the EU index of Kabat, as described in Kabat, E. A. et al., Sequences of Proteins of Immunological Interest, 5th ed., Public Health Service, National Institutes of Health, Bethesda, MD (1991), NIH Publication 91-3242.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain Therefore an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (Lys447), of the Fc region may or may not be present Amino acid sequences of heavy chains including an Fc region are denoted herein without C-terminal glycine-lysine dipeptide if not indicated otherwise. In one embodiment, a heavy chain including an Fc region as specified herein, comprised in an antibody according to the invention, comprises an additional C-terminal glycine-lysine dipeptide (G446 and K447, numbering according to EU index of Kabat). In one embodiment, a heavy chain including an Fc region as specified herein, comprised in an antibody according to the invention, comprises an additional C-terminal glycine residue (G446, numbering according to EU index of Kabat). Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)). The numbering is according to EU index of Kabat et al, Sequences of Proteins of Immunological Interest, 5th Ed. Public Health Service, National Institutes of Health, Bethesda, MD, 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The term "TNF ligand family member" or "TNF family ligand" refers to a proinflammatory cytokine. Cytokines in general, and in particular the members of the TNF ligand family, play a crucial role in the stimulation and coordination of the immune system. At present, nineteen cyctokines have been identified as members of the TNF (tumour necrosis factor) ligand superfamily on the basis of sequence, functional, and structural similarities. All these ligands are type II transmembrane proteins with a C-terminal extracellular domain (ectodomain), N-terminal intracellular domain and a single transmembrane domain. The C-terminal extracellular domain, known as TNF homology domain (THD), has 20-30% amino acid identity between the superfamily members and is responsible for binding to the receptor. The TNF ectodomain is also responsible for the TNF ligands to form trimeric complexes that are recognized by their specific receptors. Members of the TNF ligand family are selected from the group consisting of Lymphotoxin a (also known as LTA or TNFSF1), TNF (also known as TNFSF2), LTβ (also known as TNFSF3), OX40L (also known as TNFSF4), CD40L (also known as CD154 or TNFSF5), FasL (also known as CD95L, CD178 or TNFSF6), CD27L (also known as CD70 or TNFSF7), CD30L (also known as CD153 or TNFSF8), 4-1BBL (also known as TNFSF9), TRAIL (also known as APO2L, CD253 or TNFSF10), RANKL (also known as CD254 or TNFSF11), TWEAK (also known as TNFSF12), APRIL (also known as CD256 or TNFSF13), BAFF (also known as CD257 or TNFSF13B), LIGHT (also known as CD258 or TNFSF14), TL1A (also known as VEGI or TNFSF15), GITRL (also known as TNFSF18), EDA-A1 (also known as ectodysplasin A1) and EDA-A2 (also known as ectodysplasin A2). The term refers to any native TNF family ligand from any vertebrate source, including mammals such as primates (e.g. humans), non-human primates (e.g. cynomolgus monkeys) and rodents (e.g. mice and rats), unless otherwise indicated. The term "costimulatory TNF ligand family member" or "costimulatory TNF family ligand" refers to a subgroup of TNF ligand family members, which are able to costimulate proliferation and cytokine production of T-cells. These TNF family ligands can costimulate TCR signals upon interaction with their corresponding TNF receptors and the interaction with their receptors leads to recruitment of TNFR-associated factors (TRAF), which initiate signalling cascades that result in T-cell activation. Costimulatory TNF family ligands are selected from the group consisting of 4-1BBL, OX40L, GITRL, CD70, CD30L and LIGHT, more particularly the costimulatory TNF ligand family member is 4-1BBL.

As described herein before, 4-1BBL is a type II transmembrane protein and one member of the TNF ligand family. Complete or full length 4-1BBL having the amino acid sequence of SEQ ID NO:69 has been described to form trimers on the surface of cells. The formation of trimers is enabled by specific motives of the ectodomain of 4-1BBL. Said motives are designated herein as "trimerization region". The amino acids 50-254 of the human 4-1BBL sequence (SEQ ID NO:70) form the extracellular domain of 4-1BBL, but even fragments thereof are able to form the trimers. In specific embodiments of the invention, the term "ectodomain of 4-1BBL or a fragment thereof" refers to a polypeptide having an amino acid sequence selected from SEQ ID NO:4 (amino acids 52-254 of human 4-1BBL), SEQ ID NO:1 (amino acids 71-254 of human 4-1BBL), SEQ ID NO:3 (amino acids 80-254 of human 4-1BBL) and SEQ ID NO:2 (amino acids 85-254 of human 4-1BBL) or a polypeptide having an amino acid sequence selected from SEQ ID NO:5 (amino acids 71-248 of human 4-1BBL), SEQ ID NO:8 (amino acids 52-248 of human 4-1BBL), SEQ ID NO:7 (amino acids 80-248 of human 4-1BBL) and SEQ ID NO:6 (amino acids 85-248 of human 4-1BBL), but also other fragments of the ectodomain capable of trimerization are included herein.

An "ectodomain" is the domain of a membrane protein that extends into the extracellular space (i.e. the space outside the target cell). Ectodomains are usually the parts of proteins that initiate contact with surfaces, which leads to signal transduction. The ectodomain of TNF ligand family member as defined herein thus refers to the part of the TNF ligand protein that extends into the extracellular space (the extracellular domain), but also includes shorter parts or fragments thereof that are responsible for the trimerization and for the binding to the corresponding TNF receptor. The term "ectodomain of" a TNF ligand family member or a fragment thereof" thus refers to the extracellular domain of the TNF ligand family member that forms the extracellular domain or to parts thereof that are still able to bind to the receptor (receptor binding domain).

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 1 and 4, in particular 2, i.e. the peptides selected from the group consisting of GGGGS (SEQ ID NO:71), GGGGSGGGGS (SEQ ID NO:68), SGGGGSGGGG (SEQ ID NO:72), $(G4S)_3$ or GGGGSGGGGSGGGGS (SEQ ID NO:73), GGGGSGGGGSGGGG or $G4(SG4)_2$ (SEQ ID NO:74), and $(G_4S)_4$ or GGGGSGGGGSGGGGSGGGGS (SEQ ID NO:75), but also include the sequences GSPGSSSSGS (SEQ ID NO:76), GSGSGSGS (SEQ ID NO:77), GSGSGNGS (SEQ ID NO:78), GGSGSGSG (SEQ ID NO:79), GGSGSG (SEQ ID NO:80), GGSG (SEQ ID NO:81), GGSGNGSG (SEQ ID NO:82), GGNGSGSG (SEQ ID NO:83) and GGNGSG (SEQ ID NO:84). Peptide linkers of particular interest are $(G4S)_1$ or GGGGS (SEQ ID NO:71), $(G4S)_2$ or GGGGSGGGGS (SEQ ID NO:68) and $(G_4S)_3$ (SEQ ID NO:73).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A "fusion polypeptide" or "fusion protein" as used herein refers to a single chain polypeptide composed of an antibody fragment and a peptide that is not derived from an antibody. In one aspect, a fusion polypeptide is composed of one or two ectodomains of 4-1BBL or a fragment thereof fused to a part of antigen binding domain or Fc part. The fusion may occur by directly linking the N or C-terminal amino acid of the antigen binding moiety via a peptide linker to the C- or N-terminal amino acid of the ectodomain of said 4-1BBL or fragment thereof.

By "fused" or "connected" is meant that the components (e.g. a polypeptide and an ectodomain of said TNF ligand family member) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the TNF ligand trimer-containing antigen binding molecules provided herein are contemplated. For example, it may be desirable to improve the binding affinity and/or other biological properties of the TNF ligand trimer-containing antigen binding molecules Amino acid sequence variants of the TNF ligand trimer-containing antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

Her2-Targeting Antigen Binding Molecules Comprising 4-1Bbl

TABLE A

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more CDR residues are mutated and the variant antigen binding molecules displayed on phage and screened for a particular biological activity (e.g. binding affinity). In certain embodiments, substitutions, insertions, or deletions may occur within one or more CDRs so long as such alterations do not substantially reduce the ability of the antigen binding molecule to bind antigen. For example, conservative alterations (e.g., conservative substitutions as provided herein) that do not substantially reduce binding affinity may be made in CDRs. A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a 4-1BBL trimer-containing antigen binding molecule with an N-terminal methionyl residue. Other insertional variants of the molecule include the fusion to the N- or C-terminus to a polypeptide which increases the serum half-life of the 4-1BBL trimer-containing antigen binding molecule.

In certain embodiments, the 4-1BBL trimer-containing antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the 4-1BBL trimer-containing antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in 4-1BBL ligand trimer-containing antigen binding molecule may be made in order to create variants with certain improved properties. In one aspect, variants of 4-1BBL trimer-containing antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the 4-1BBL trimer-containing antigen binding molecules of the invention include those with bisected oligosaccharides, e.g., in which a biantennary oligosaccharide attached to the Fc region is bisected by GlcNAc. Such variants may have reduced fucosylation and/or improved ADCC function., see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the 4-1BBL trimer-containing antigen binding molecule of the invention, e.g., "thio-MAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antigen binding molecules may be generated as described, e.g., in U.S. Pat. No. 7,521,541.

In certain aspects, the 4-1BBL trimer-containing antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

In another aspect, immunoconjugates of the 4-1BBL trimer-containing antigen binding molecules provided herein maybe obtained. An "immunoconjugate" is an antibody conjugated to one or more heterologous molecule(s), including but not limited to a cytotoxic agent.

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi:10.1038/nm.4356 or EP 2 101 823 B1).

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e g mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, carcinoma, lymphoma, blastoma, sarcoma, leukemia, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colorectal cancer (CRC), pancreatic cancer, breast cancer, triple-negative breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, melanoma, multiple myeloma, B-cell cancer (lymphoma), chronic lymphocytic leukemia (CLL), acute lymphoblastic leukemia (ALL), hairy cell leukemia, chronic myeloblastic leukemia, including refractory versions of any of the above cancers, or a combination of one or more of the above cancers.

A "Her2-positive" cancer comprises cancer cells which have higher than normal levels of Her2. Examples of Her2-positive cancer include Her2-positive breast cancer and Her2-positive gastric cancer. Optionally, Her2-positive cancer has an immunohistochemistry (IHC) score of 2+ or 3+ and/or an in situ hybridization (ISH) amplification ratio >2.0.

The term "early stage breast cancer (EBC)" or "early breast cancer" is used herein to refer to breast cancer that has not spread beyond the breast or the axillary lymph nodes. This includes ductal carcinoma in situ and stage I, stage IIA, stage JIB, and stage MA breast cancers.

Reference to a tumor or cancer as a "Stage 0", "Stage I", "Stage II", "Stage III", or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor is known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

An "advanced" cancer is one which has spread outside the site or organ of origin, either by local invasion or metastasis. Accordingly, the term "advanced" cancer includes both locally advanced and metastatic disease.

A "recurrent" cancer is one which has regrown, either at the initial site or at a distant site, after a response to initial therapy, such as surgery. A "locally recurrent" cancer is cancer that returns after treatment in the same place as a previously treated cancer. An "operable" or "resectable" cancer is cancer which is confined to the primary organ and suitable for surgery (resection). A "non-resectable" or "unresectable" cancer is not able to be removed (resected) by surgery.

4-1BBL Trimer-Containing Antigen Binding Molecules of the Invention

The invention provides novel 4-1BBL trimer-containing antigen binding molecules with particularly advantageous properties such as producibility, stability, binding affinity, biological activity, targeting efficiency, reduced toxicity and reduced immunicity.

In a first aspect, the invention provides a 4-1BBL trimer-containing antigen binding molecule comprising (a) an antigen binding domain capable of specific binding to Her2,
(b) a first and a second polypeptide that are linked to each other by a disulfide bond, wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and
(c) an Fc domain composed of a first and a second subunit capable of stable association.

In a further aspect, provided is a 4-1BBL trimer-containing antigen binding molecule as defined herein before, comprising (a) an antigen binding domain capable of specific binding to Her2, and
(b) a first and a second polypeptide that are linked to each other by a disulfide bond, wherein the antigen binding molecule is characterized in that
  (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of a 4-1BBL or a fragment thereof that are connected to each other and to the CH1 or CL domain by a peptide linker and wherein the second polypeptide comprises one ectodomain of said 4-1BBL or a fragment thereof connected via a peptide linker to the CL or CH1 domain of said polypeptide, or
  (ii) the first polypeptide contains a CH3 domain and the second polypeptide contains a CH3 domain, respectively, and wherein the first polypeptide comprises two ectodomains of a 4-1BBL or a fragment thereof that are connected to each other and to the C-terminus of the CH3 domain by a peptide linker and wherein the second polypeptide comprises only one ectodomain of said 4-1BBL or a fragment thereof connected via a peptide linker to C-terminus of the CH3 domain of said polypeptide, or
  (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or a fragment thereof that are connected to each other and to to VH or VL by a peptide linker and wherein the second polypeptide comprises one ectodomain of said TNF ligand family member or a fragment thereof connected via a peptide linker to VL or VH of said polypeptide, and
(c) an Fc domain composed of a first and a second subunit capable of stable association.

In another aspect, provided is a 4-1BBL trimer-containing antigen binding molecule of as defined herein before, comprising (a) an antigen binding domain capable of specific binding to Her2, and
(b) a first and a second polypeptide that are linked to each other by a disulfide bond,
wherein the antigen binding molecule is characterized in that
  (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or a fragment thereof that are connected to each other and to the CH1 or CL domain by a peptide linker and wherein the second polypeptide comprises one ectodomain of said 4-1BBL or a fragment thereof connected via a peptide linker to the CL or CH1 domain of said polypeptide, or
  (ii) the first polypeptide contains a CH3 domain and the second polypeptide contains a CH3 domain, respectively, and wherein the first polypeptide comprises two ectodomains of 4-1BBL or a fragment thereof that are connected to each other and to the C-terminus of the CH3 domain by a peptide linker and wherein the second polypeptide comprises only one ectodomain of said 4-1BBL or a fragment thereof connected via a peptide linker to C-terminus of the CH3 domain of said polypeptide, and
(c) an Fc domain composed of a first and a second subunit capable of stable association.

In one aspect, the ectodomain of 4-1BBL comprises the amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5. More particularly, the ectodomain of 4-1BBL comprises the amino acid sequence of SEQ ID NO:1 or SEQ ID NO:5. Most particularly, the ectodomain of 4-1BBL comprises the amino acid sequence of SEQ ID NO:5. In particular, provided is a 4-1BBL trimer-containing antigen binding molecule of as defined herein before, wherein all three ectodomains of 4-1BBL or a fragment thereof are identical.

In a further aspect, the 4-1BBL trimer-containing antigen binding molecule of the invention comprises (a) an antigen binding domain capable of specific binding to Her2,
(b) a first and a second polypeptide that are linked to each other by a disulfide bond, wherein the antigen binding molecule is characterized in that the first polypeptide comprises the amino acid sequence selected from the group consisting of SEQ ID NO:9, SEQ ID NO:10, SEQ ID NO:11 and SEQ ID NO:12 and in that the second polypeptide comprises the amino acid sequence selected from the group consisting of SEQ ID NO:1, SEQ ID NO:5, SEQ ID NO:3 and SEQ ID NO:4, and
(c) an Fc domain composed of a first and a second subunit capable of stable association.

In one aspect, the 4-1BBL trimer-containing antigen binding molecule of the invention comprises (a) an antigen binding domain capable of specific binding to Her2,
(b) a first and a second polypeptide that are linked to each other by a disulfide bond,
wherein the antigen binding molecule is characterized in that the first polypeptide comprises the amino acid sequence of SEQ ID NO:10 and in that the second polypeptide comprises the amino acid sequence of SEQ ID NO:5, and (c) an Fc domain composed of a first and a second subunit capable of stable association.

In a further aspect, the 4-1BBL trimer-containing antigen binding molecule of the invention comprises
(a) an antigen binding domain capable of specific binding to Her2,
(b) a first and a second polypeptide that are linked to each other by a disulfide bond,
wherein the antigen binding molecule is characterized in that the first polypeptide comprises the amino acid sequence of SEQ ID NO:9 and in that the second polypeptide comprises the amino acid sequence of SEQ ID NO:1, and
(c) an Fc domain composed of a first and a second subunit capable of stable association.

In another aspect, the 4-1BBL trimer-containing antigen binding molecule of the invention comprises
(a) an antigen binding domain capable of specific binding to Her2,
(b) a first polypeptide containing a CH1 or CL domain and a second polypeptide containing a CL or CH1 domain, respectively, wherein the second polypeptide is linked to the first polypeptide by a disulfide bond between the CH1 and CL domain,
and wherein the antigen binding molecule is characterized in that the first polypeptide comprises two ectodomains of 4-1BBL or fragments thereof that are connected to each other and to the CH1 or CL domain by a peptide linker and in that the second polypeptide comprises only one ectodomain of 4-1BBL or a fragment thereof connected by a peptide linker to the CL or CH1 domain of said polypeptide.

In one aspect, provided is a 4-1BBL trimer-containing antigen binding molecule comprising
(a) an antigen binding domain capable of specific binding to Her2,
(b) a first polypeptide containing a CH1 domain and a second polypeptide containing a CL domain,
wherein the second polypeptide is linked to the first polypeptide by a disulfide bond between the CH1 and CL domain,
and wherein the antigen binding molecule is characterized in that the first polypeptide comprises two ectodomains of 4-1BBL or a fragment thereof that are connected to each other and to the CH1 domain by a peptide linker and in that the second polypeptide comprises one ectodomain of 4-1BBL or a fragment thereof connected via a peptide linker to the CL domain of said polypeptide.

In another aspect, the invention provides a 4-1BBL trimer-containing antigen binding molecule comprising
(a) one antigen binding domain capable of specific binding to Her2, and
(b) a first and a second polypeptide that are linked to each other by a disulfide bond,
wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and
(c) an Fc domain composed of a first and a second subunit capable of stable association In yet another aspect, the invention provides a 4-1BBL trimer-containing antigen binding molecule comprising
(a) more than one antigen binding domain capable of specific binding to Her2, and
(b) a first and a second polypeptide that are linked to each other by a disulfide bond,
wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and
(c) an Fc domain composed of a first and a second subunit capable of stable association.

In one aspect, the invention provides a 4-1BBL trimer-containing antigen binding molecule comprising
(a) two antigen binding domains capable of specific binding to Her2, and
(b) a first and a second polypeptide that are linked to each other by a disulfide bond,
wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and
(c) an Fc domain composed of a first and a second subunit capable of stable association.

In a further aspect, the invention provides a 4-1BBL trimer-containing antigen binding molecule as defined herein before, wherein antigen binding domain capable of specific binding to Her2 is selected from the group consisting of an antibody, an antibody fragment and a scaffold antigen binding protein.

In one aspect, provided is a 4-1BBL trimer-containing antigen binding molecule as described herein before, wherein the antigen binding domain capable of specific binding to Her2 is selected from the group consisting of an antibody fragment, a Fab molecule, a crossover Fab molecule, a single chain Fab molecule, a Fv molecule, a scFv molecule, a single domain antibody, or aVH and a scaffold antigen binding protein. In one aspect, the antigen binding domain capable of specific binding to Her2 is an aVH or a scaffold antigen binding protein.

In a particular aspect, provided is a 4-1BBL trimer-containing antigen binding molecule, wherein the antigen binding domain capable of specific binding to Her2 is a Fab molecule or a crossover Fab molecule capable of specific binding to Her2. In particular, the antigen binding domain capable of specific binding to Her2 is a Fab capable of specific binding to Her2.

In a further aspect, provided is a 4-1BBL trimer-containing antigen binding molecule according to the invention, wherein a peptide comprising two ectodomains of 4-1BBL or a fragment thereof connected to each other by a first peptide linker is fused at its C-terminus to the CH1 domain of a heavy chain by a second peptide linker and wherein one ectodomain of said 4-1BBL or a fragment thereof is fused at the its C-terminus to the CL domain on a light chain by a third peptide linker.

In another aspect, provided is a 4-1BBL trimer-containing antigen binding molecule according to the invention, wherein a peptide comprising two ectodomains of 4-1BBL or a fragment thereof connected to each other by a first peptide linker is fused at its C-terminus to the CL domain of a heavy chain by a second peptide linker and wherein one ectodomain of said 4-1BBL or a fragment thereof is fused at the its C-terminus to the CH1 domain on a light chain by a third peptide linker.

In a further aspect, the invention is concerned with a 4-1BBL trimer-containing antigen binding molecule according to the invention, wherein a peptide comprising two ectodomains of a 4-1BBL or a fragment thereof connected to each other by a first peptide linker is fused at its C-terminus to the CL domain of a light chain by a second peptide linker and wherein one ectodomain of said 4-1BBL or a fragment thereof is fused at the its C-terminus to the CH1 domain of the heavy chain by a third peptide linker.

In a particular aspect, the invention relates to a 4-1BBL trimer-containing antigen binding molecule as defined above, wherein the peptide linker is (G4S)$_2$. In one aspect, the first peptide linker is (G4S)$_2$ (SEQ ID NO:68), the second peptide linker is (G4S)$_2$ (SEQ ID NO:68) and the third peptide linker is (G4S)$_2$ (SEQ ID NO:68).

In another aspect, the 4-1BBL trimer-containing antigen binding molecule as defined herein before comprises an Fc domain composed of a first and a second subunit capable of stable association.

In particular, the 4-1BBL trimer-containing antigen binding molecule of the invention comprises (a) a Fab molecule capable of specific binding to Her2, wherein the Fab heavy chain is fused at the C-terminus to the N-terminus of a CH2 domain in the Fc domain and (c) an Fc domain composed of a first and a second subunit capable of stable association.

In a further aspect, the Fc domain is an IgG, particularly an IgG1 Fc domain or an IgG4 Fc domain. More particularly, the Fc domain is an IgG1 Fc domain. In a particular aspect, the Fc domain comprises a modification promoting the association of the first and second subunit of the Fc domain.

Fc Domain Modifications Reducing Fc Receptor Binding and/or Effector Function

The Fc domain of the 4-1BBL trimer-containing antigen binding molecules of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

The Fc domain confers favorable pharmacokinetic properties to the antigen binding molecules of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular aspects, the Fc domain of the 4-1BBL trimer-containing antigen binding molecule of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of a 4-1BBL trimer-containing antigen binding molecule provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In a particular aspect, the invention provides a 4-1BBL trimer-containing antigen binding molecule comprising
(a) an antigen binding domain capable of specific binding to Her2,
(b) a first and a second polypeptide that are linked to each other by a disulfide bond,
wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and
(c) an Fc domain composed of a first and a second subunit capable of stable association, wherein the Fc domain comprises one or more amino acid substitution that reduces binding to an Fc receptor, in particular towards Fcγ receptor.

In one aspect, the Fc domain of the 4-1BBL trimer-containing antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains More particularly, provided is a trimeric TNF family ligand-containing antigen binding molecule according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions. "EU numbering" refers to the numbering according to EU index of Kabat et al, Sequences of Proteins of Immunological Interest, 5th Ed. Public Health Service, National Institutes of Health, Bethesda, MD, 1991.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position 5228 (Kabat numbering), particularly the amino acid substitution S228P. In a more specific aspect, the Fc domain is an IgG4 Fc domain comprising amino acid substitutions L235E and S228P and P329G (EU numbering).

Such IgG4 Fc domain mutants and their Fcγ receptor binding properties are also described in WO 2012/130831.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or bispecific antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In a particular aspect, the Fc domain comprises a modification promoting the association of the first and second subunit of the Fc domain.

Fc Domain Modifications Promoting Heterodimerization

In one aspect, the 4-1BBL trimer-containing antigen binding molecules of the invention comprise
(a) an antigen binding domain capable of specific binding to Her2,
(b) a first and a second polypeptide that are linked to each other by a disulfide bond,
wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and (c) an Fc domain composed of a first and a second subunit capable of stable association. Thus, they comprise different moieties, fused to one or the other of the two subunits of the Fc domain that are typically comprised in two non-identical polypeptide chains ("heavy chains"). Recombinant co-expression of these polypeptides and subsequent dimerization leads to several possible combinations of the two polypeptides. To improve the yield and purity of the 4-1BBL trimer-containing antigen binding molecules in recombinant production, it will thus be advantageous to introduce in the Fc domain of the 4-1BBL trimer-containing antigen binding molecules of the invention a modification promoting the association of the desired polypeptides.

Accordingly, the Fc domain of the 4-1BBL trimer-containing antigen binding molecules of the invention comprises a modification promoting the association of the first and the second subunit of the Fc domain. The site of most extensive protein-protein interaction between the two subunits of a human IgG Fc domain is in the CH3 domain of the Fc domain. Thus, said modification is particularly in the CH3 domain of the Fc domain.

In a specific aspect, said modification is a so-called "knob-into-hole" modification, comprising a "knob" modification in one of the two subunits of the Fc domain and a "hole" modification in the other one of the two subunits of the Fc domain. Thus, in a particular aspect, the invention relates to a 4-1BBL trimer-containing antigen binding molecule as described herein before which comprises an IgG molecule, wherein the Fc part of the first heavy chain comprises a first dimerization module and the Fc part of the second heavy chain comprises a second dimerization module allowing a heterodimerization of the two heavy chains of the IgG molecule and the first dimerization module comprises knobs and the second dimerization module comprises holes according to the knob into hole technology.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular aspect, in the CH3 domain of the first subunit of the Fc domain of the 4-1BBL trimer-containing antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). More particularly, in the second subunit of the Fc domain additionally the threonine residue at position 366 is replaced with a serine residue (T366S) and the leucine residue at position 368 is replaced with an alanine residue (L368A). More particularly, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). The introduction of these two cysteine residues results in the formation of a disulfide bridge between the two subunits of the Fc domain. The disulfide bridge further stabilizes the dimer (Carter, J Immunol Methods 248, 7-15 (2001)).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Modifications in the CH1/CL Domains

To further improve correct pairing, the 4-1BBL trimer-containing antigen binding molecules can contain different charged amino acid substitutions (so-called "charged residues"). These modifications are introduced in the crossed or non-crossed CH1 and CL domains. In a particular aspect, the invention relates to a 4-1BBL trimer-containing antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the the amino acids at position 147 (EU numbering) and at position 213 (EU numbering) have been substituted by glutamic acid (E).

More particularly, the invention relates to a 4-1BBL trimer-containing antigen binding molecule, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E).

Thus, in a particular aspect, provided is a 4-1BBL trimer-containing antigen binding molecule comprising
(a) an antigen binding domain capable of specific binding to Her2,
(b) a first polypeptide containing a CL domain comprising the amino acid mutations E123R and Q124K and a second polypeptide containing a CH1 domain comprising the amino acid mutations K147E and K213E, wherein the second polypeptide is linked to the first polypeptide by a disulfide bond between the CH1 and CL domain,
and wherein the antigen binding molecule is characterized in that the first polypeptide comprises two ectodomains of 4-1BBL or a fragment thereof that are connected to each other and to the CL domain by a peptide linker and in that the second polypeptide comprises one 4-1BBL or a fragment thereof connected via a peptide linker to the CH1 domain of said polypeptide; and
(c) an Fc domain composed of a first and a second subunit capable of stable association.

In one aspect, the invention provides a 4-1BBL trimer-containing antigen binding molecule, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E). These modifications lead to so-called charged residues with advantageous properties that avoid undesired effects such as for example mispairing.

In particular, the CL domain comprises the amino acid mutations E123R and Q124K and the CH1 domain comprises the amino acid mutations K147E and K213E.

Particular 4-1BBL Trimer-Containing Antigen Binding Molecules

The invention provides a 4-1BBL trimer-containing antigen binding molecule that comprises an antigen binding domain capable of specific binding to Her2. In a particular aspect, the 4-1BBL trimer-containing antigen binding molecule comprises one moiety capable of specific binding to Her2, meaning the 4-1BBL trimer-containing antigen binding molecule is monovalent. In another aspect, the invention provides a 4-1BBL trimer-containing antigen binding molecule comprising two moieties capable of specific binding to Her2, meaning the 4-1BBL trimer-containing antigen binding molecule is bivalent.

In one aspect, the invention provides a 4-1BBL trimer-containing antigen binding molecule, wherein the antigen binding domain capable of specific binding to Her2 comprises
(a) a VH domain comprising (i) CDR-H1 comprising the amino acid sequence of SEQ ID NO:13, (ii) CDR-H2 comprising the amino acid sequence of SEQ ID NO:14, and (iii) CDR-H3 comprising the amino acid sequence of SEQ ID NO:15, and a VL domain comprising (iv) CDR-L1 comprising the amino acid sequence of SEQ ID NO:16, (v) CDR-L2 comprising the amino acid sequence of SEQ ID NO:17, and (vi) CDR-L3 comprising the amino acid sequence of SEQ ID NO:18, or
(b) a VH domain comprising (i) CDR-H1 comprising the amino acid sequence of SEQ ID NO:21, (ii) CDR-H2 comprising the amino acid sequence of SEQ ID NO:22, and (iii) CDR-H3 comprising the amino acid sequence of SEQ ID NO:23, and a VL domain comprising (iv) CDR-L1 comprising the amino acid sequence of SEQ ID NO:24, (v) CDR-L2 comprising the amino acid sequence of SEQ ID NO:25, and (vi) CDR-L3 comprising the amino acid sequence of SEQ ID NO:26, or
(c) a VH domain comprising (i) CDR-H1 comprising the amino acid sequence of SEQ ID NO:29, (ii) CDR-H2 comprising the amino acid sequence of SEQ ID NO:30, and (iii) CDR-H3 comprising the amino acid sequence of SEQ ID NO:31, and a VL domain comprising (iv) CDR-L1 comprising the amino acid sequence of SEQ ID NO:32, (v) CDR-L2 comprising the amino acid sequence of SEQ ID NO:33, and (vi) CDR-L3 comprising the amino acid sequence of SEQ ID NO:34.

In one aspect, the invention provides a 4-1BBL trimer-containing antigen binding molecule, wherein the antigen binding domain capable of specific binding to Her2 comprises a VH domain comprising (i) CDR-H1 comprising the amino acid sequence of SEQ ID NO:13, (ii) CDR-H2 comprising the amino acid sequence of SEQ ID NO:14, and (iii) CDR-H3 comprising the amino acid sequence of SEQ ID NO:15, and a VL domain comprising (iv) CDR-L1 comprising the amino acid sequence of SEQ ID NO:16, (v) CDR-L2 comprising the amino acid sequence of SEQ ID NO:17, and (vi) CDR-L3 comprising the amino acid sequence of SEQ ID NO:18.

In another aspect, provided is a 4-1BBL trimer-containing antigen binding molecule, wherein the antigen binding domain capable of specific binding to Her2 comprises a VH domain comprising (i) CDR-H1 comprising the amino acid sequence of SEQ ID NO:21, (ii) CDR-H2 comprising the amino acid sequence of SEQ ID NO:22, and (iii) CDR-H3 comprising the amino acid sequence of SEQ ID NO:23, and a VL domain comprising (iv) CDR-L1 comprising the amino acid sequence of SEQ ID NO:24, (v) CDR-L2 comprising the amino acid sequence of SEQ ID NO:25, and (vi) CDR-L3 comprising the amino acid sequence of SEQ ID NO:26.

In a further aspect, provided is a 4-1BBL trimer-containing antigen binding molecule, wherein the antigen binding domain capable of specific binding to Her2 comprises a VH domain comprising (i) CDR-H1 comprising the amino acid sequence of SEQ ID NO:29, (ii) CDR-H2 comprising the amino acid sequence of SEQ ID NO:30, and (iii) CDR-H3 comprising the amino acid sequence of SEQ ID NO:31, and a VL domain comprising (iv) CDR-L1 comprising the amino acid sequence of SEQ ID NO:32, (v) CDR-L2 comprising the amino acid sequence of SEQ ID NO:33, and (vi) CDR-L3 comprising the amino acid sequence of SEQ ID NO:34.

In a further aspect, the antigen binding domain capable of specific binding to Her2 comprises a heavy chain variable region comprising an amino acid sequence that is at least about 95%, 96%, 97%, 98%, 99% or 100% identical to the amino acid sequence of SEQ ID NO:19 and a light chain variable region comprising an amino acid sequence that is at least about 95%, 96%, 97%, 98%, 99% or 100% identical to the amino acid sequence of SEQ ID NO:20.

In another aspect, the antigen binding domain capable of specific binding to Her2 comprises a heavy chain variable region comprising an amino acid sequence that is at least about 95%, 96%, 97%, 98%, 99% or 100% identical to the amino acid sequence of SEQ ID NO:27 and a light chain variable region comprising an amino acid sequence that is at least about 95%, 96%, 97%, 98%, 99% or 100% identical to the amino acid sequence of SEQ ID NO:28.

In a further aspect, the antigen binding domain capable of specific binding to Her2 comprises a heavy chain variable region comprising an amino acid sequence that is at least about 95%, 96%, 97%, 98%, 99% or 100% identical to the amino acid sequence of SEQ ID NO:35 and a light chain variable region comprising an amino acid sequence that is at least about 95%, 96%, 97%, 98%, 99% or 100% identical to the amino acid sequence of SEQ ID NO:36.

In a further aspect, the invention provides a a 4-1BBL trimer-containing antigen binding molecule, wherein the antigen binding domain capable of specific binding to Her2 comprises
(a) a VH domain comprising an amino acid sequence of SEQ ID NO:19 and a VL domain comprising an amino acid sequence of SEQ ID NO:20, or
(b) a VH domain comprising an amino acid sequence of SEQ ID NO:27 and a VL domain comprising an amino acid sequence of SEQ ID NO:28, or
(c) a VH domain comprising an amino acid sequence of SEQ ID NO:35 and a VL domain comprising an amino acid sequence of SEQ ID NO:36.

In one aspect, provided is a 4-1BBL trimer-containing antigen binding molecule as defined herein before, wherein the antigen binding domain capable of specific binding to Her2 comprises a variable heavy chain comprising an amino acid sequence of SEQ ID NO:19 and a variable light chain comprising an amino acid sequence of SEQ ID NO:20 or wherein the antigen binding domain capable of specific binding to Her2 comprises a variable heavy chain comprising an amino acid sequence of SEQ ID NO:35 and a variable light chain comprising an amino acid sequence of SEQ ID NO:36.

In a particular aspect, the antigen binding domain capable of specific binding to Her2 comprises a heavy chain variable region comprising the amino acid sequence of SEQ ID NO:19 and a light chain variable region comprising the amino acid sequence of SEQ ID NO:20. In another particular aspect, the antigen binding domain capable of specific binding to Her2 comprises a heavy chain variable region comprising the amino acid sequence of SEQ ID NO:35 and a light chain variable region comprising the amino acid sequence of SEQ ID NO:36. In a specific aspect, the antigen binding domain capable of specific binding to Her2 comprises a VH domain consisting of amino acid sequence of SEQ ID NO:27 and a VL domain consisting of the amino acid sequence of SEQ ID NO:28.

In a further aspect, the 4-1BBL trimer-containing antigen binding molecule of the invention comprises
(i) a first heavy chain comprising the VH domain comprising the amino acid sequence of SEQ ID NO:19 and a first light chain comprising the VL domain comprising the amino acid sequence of SEQ ID NO:20 or
a first heavy chain comprising the VH domain comprising the amino acid sequence of SEQ ID NO:27 and
a first light chain comprising the VL domain comprising the amino acid sequence of SEQ ID NO:28, or
a first heavy chain comprising the VH domain comprising the amino acid sequence of SEQ ID NO:35 and
a first light chain comprising the VL domain comprising the amino acid sequence of SEQ ID NO:36,
(ii) a second heavy chain comprising the amino acid sequence selected from the group consisting of SEQ ID NO:37, SEQ ID NO:39, SEQ ID NO:41 and SEQ ID NO:43, and
(iii) a second light chain comprising the amino acid sequence selected from the group consisting of SEQ ID NO:38, SEQ ID NO:40, SEQ ID NO:42 and SEQ ID NO:44.

In a particular aspect, the 4-1BBL trimer-containing antigen binding molecule of the invention comprises
(a) an antigen binding domain of specific binding to Her2 comprising a heavy chain variable region comprising the amino acid sequence of SEQ ID NO:19 and a light chain variable region comprising the amino acid sequence of SEQ ID NO:20 or a heavy chain variable region comprising the amino acid sequence of SEQ ID NO:27 and a light chain variable region comprising the amino acid sequence of SEQ ID NO:28 or a heavy chain variable region comprising the amino acid sequence of SEQ ID NO:35 and a light chain variable region comprising the amino acid sequence of SEQ ID NO:36, and
(b) a first and a second polypeptide that are linked to each other by a disulfide bond, wherein the antigen binding molecule is characterized in that the first polypeptide comprises the the amino acid sequence of SEQ ID NO:10 and the second polypeptide comprises the amino acid sequence of SEQ ID NO:5.

In a particular aspect, provided is a 4-1BBL trimer-containing antigen binding molecule, wherein the antigen binding molecule comprises
(i) a first heavy chain comprising the VH domain comprising the amino acid sequence of SEQ ID NO:19 and a first light chain comprising the VL domain comprising the amino acid sequence of SEQ ID NO:20 or
a first heavy chain comprising the VH domain comprising the amino acid sequence of SEQ ID NO:27 and
a first light chain comprising the VL domain comprising the amino acid sequence of SEQ ID NO:28, or
a first heavy chain comprising the VH domain comprising the amino acid sequence of SEQ ID NO:35 and
a first light chain comprising the VL domain comprising the amino acid sequence of SEQ ID NO:36,
(ii) a second heavy chain comprising the amino acid sequence selected from the group consisting of SEQ ID NO:37, SEQ ID NO:39, SEQ ID NO:41 and SEQ ID NO:43, and
(iii) a second light chain comprising the amino acid sequence selected from the group consisting of SEQ ID NO:38, SEQ ID NO:40, SEQ ID NO:42 and SEQ ID NO:44.

In another aspect, the invention provides a 4-1BBL trimer-containing antigen binding molecule, wherein the antigen binding molecule comprises
(a) a first heavy chain comprising the amino acid sequence of SEQ ID NO:45, a first light chain comprising the amino acid sequence of SEQ ID NO:46, a second heavy chain comprising the amino acid sequence of SEQ ID NO:37 and a second light chain comprising the amino acid sequence of SEQ ID NO:38, or
(b) a first heavy chain comprising the amino acid sequence of SEQ ID NO:47, a first light chain comprising the amino acid sequence of SEQ ID NO:48, a second heavy chain comprising the amino acid sequence of SEQ ID NO:37 and a second light chain comprising the amino acid sequence of SEQ ID NO:38, or
(c) a first heavy chain comprising the amino acid sequence of SEQ ID NO:49, a first light chain comprising the amino acid sequence of SEQ ID NO:50, a second heavy chain comprising the amino acid sequence of SEQ ID NO:37 and a second light chain comprising the amino acid sequence of SEQ ID NO:38.

Polynucleotides

The invention further provides isolated nucleic acid molecules encoding a 4-1BBL trimer-containing antigen binding molecule as described herein or a fragment thereof.

The isolated polynucleotides encoding 4-1BBL trimer-containing antigen binding molecules of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated nucleic acid molecule encodes the entire 4-1BBL trimer-containing antigen binding molecule according to the invention as described herein. In particular, the isolated polynucleotide encodes a polypeptide comprised in the 4-1BBL trimer-containing antigen binding molecule according to the invention as described herein.

In one aspect, the present invention is directed to isolated nucleic acid molecules encoding a 4-1BBL trimer-containing antigen binding molecule, wherein the nucleic acid molecule comprises (a) a sequence that encodes an antigen binding domain capable of specific binding to a Her2, (b) a sequence that encodes a polypeptide comprising two ectodomains of 4-1BBL or a fragment thereof that are connected to each other by a peptide linker and (c) a sequence that encodes a polypeptide comprising one ectodomain of said 4-1BBL or a fragment thereof.

In another aspect, provided is an isolated polynucleotide encoding a 4-1BB ligand trimer-containing antigen binding molecule, wherein the polynucleotide comprises (a) a sequence that encodes a moiety capable of specific binding to Her2, (b) a sequence that encodes a polypeptide comprising two ectodomains of 4-1BBL or two fragments thereof that are connected to each other by a peptide linker and (c) a sequence that encodes a polypeptide comprising one ectodomain of 4-1BBL or a fragment thereof.

In certain aspects, the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods 4-1BBL trimer-containing antigen binding molecules of the invention may be obtained, for example, by solid-state peptide synthesis (e.g. Merrifield solid phase synthesis) or recombinant production. For recombinant production one or more polynucleotide encoding the 4-1BBL trimer-containing antigen binding molecule or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the 4-1BBL trimer-containing antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the 4-1BBL trimer-containing antigen binding molecule or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the 4-1BBL timer-containing antigen binding molecule of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the 4-1BBL trimer-containing antigen binding molecule or polypeptide fragments thereof is desired, DNA encoding a signal sequence may be placed upstream of the nucleic acid encoding a 4-1BBL trimer-containing antigen binding molecule of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding a 4-1BBL trimer-containing antigen binding molecule of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) a 4-1BBL trimer-containing antigen binding molecule of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040, 498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr− CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing a 4-1BBL trimer-containing antigen binding molecule of the invention or polypeptide fragments thereof is provided, wherein the method comprises culturing a host cell comprising polynucleotides encoding the 4-1BBL trimer-containing antigen binding molecule of the invention or polypeptide fragments thereof, as provided herein, under conditions suitable for expression of the 4-1BBL trimer-containing antigen binding molecule of the invention or polypeptide fragments thereof, and recovering the 4-1BBL trimer-containing antigen binding molecule of the invention or polypeptide fragments thereof from the host cell (or host cell culture medium).

In the 4-1BBL trimer-containing antigen binding molecule of the invention, the components (at least one moiety capable of specific binding to a target cell antigen, one polypeptide comprising two ectodomains of a TNF ligand family member or fragments thereof and a polypeptide comprising one ectodomain of said 4-1BBL family member or a fragment thereof) are not genetically fused to each other. The polypeptides are designed such that its components (two ectodomains of a TNF ligand family member or fragments thereof and other components such as CH or CL) are fused to each other directly or through a linker sequence. The composition and length of the linker may be determined in accordance with methods well known in the art and may be tested for efficacy. Examples of linker sequences between different components of the antigen binding molecules of the invention are found in the sequences provided herein. Additional sequences may also be included to incorporate a cleavage site to separate the individual components of the fusion protein if desired, for example an endopeptidase recognition sequence.

In certain embodiments the moieties capable of specific binding to a target cell antigen (e.g. Fab fragments) forming part of the antigen binding molecule comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human A humanized or fully human form of the immunoglobulin can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e g recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)) Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005) Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, NJ, 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the moieties capable of specific binding to a target cell antigen (e.g. Fab fragments) comprised in the antigen binding molecules of the present invention are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, NJ). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch.14 (Cold Spring Harbor Laboratory, Cold Spring Harbor, NY).

4-1BBL trimer-containing antigen binding molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the 4-1BBL trimer-containing antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the 4-1BBL trimer-containing antigen binding molecule or fragments thereof can be determined by any of a variety of well-known analytical methods including gel electrophoresis, high pressure liquid chromatography, and the like. For example, the 4-1BBL trimer-containing antigen binding molecules expressed as described in the Examples were shown to be intact and properly assembled as demonstrated by reducing and non-reducing SDS-PAGE.

Assays

The antigen binding molecules provided herein may be identified, screened for, or characterized for their physical/chemical properties and/or biological activities by various assays known in the art. Biological activity may include, e.g., the ability to enhance the activation and/or proliferation of different immune cells especially T-cells. E.g. they enhance secretion of immunomodulating cytokines. Other immunomodulating cytokines which are or can be enhanced are e.g IL2, Granzyme B etc. Biological activity may also include, cynomolgus binding crossreactivity, as well as binding to different cell types. Antigen binding molecules having such biological activity in vivo and/or in vitro are also provided.

1. Affinity Assays

The affinity of the 4-1BBL trimer-containing antigen binding molecule provided herein for 4-1BB (CD137) can be determined in accordance with the methods set forth in the Examples by surface plasmon resonance (SPR), using standard instrumentation such as a BIAcore instrument (GE Healthcare), and receptors or target proteins such as may be obtained by recombinant expression. The affinity of the 4-1BBL trimer-containing antigen binding molecule for HER2 can also be determined by surface plasmon resonance (SPR), using standard instrumentation such as a BIAcore instrument (GE Healthcare), and receptors or target proteins such as may be obtained by recombinant expression. A specific illustrative and exemplary embodiment for measuring binding affinity is described in Example 4. According to one aspect, $K_D$ is measured by surface plasmon resonance using a BIACORE® T100 machine (GE Healthcare) at 25° C.

2. Binding Assays and Other Assays

Binding of the 4-1BBL trimer-containing antigen binding molecule provided herein to the corresponding receptor expressing cells may be evaluated using cell lines expressing the particular receptor or target antigen, for example by flow cytometry (FACS). In one aspect, fresh peripheral blood mononuclear cells (PBMCs) expressing 4-1BB can be used in the binding assay. These cells are used directly after isolation (naïve PMBCs) or after stimulation (activated PMBCs). In another aspect, activated mouse splenocytes (expressing 4-1BB) can be used to demonstrate the binding of the 4-1BBL trimer-containing antigen binding molecule of the invention to 4-1BB expressing cells.

In a further aspect, cell lines expressing Her2 were used to demonstrate the binding of the antigen binding molecules to this target cell antigen.

In another aspect, competition assays may be used to identify an antigen binding molecule that competes with a specific antibody or antigen binding molecule for binding to Her2 or 4-1BB, respectively. In certain embodiments, such a competing antigen binding molecule binds to the same epitope (e.g., a linear or a conformational epitope) that is bound by a specific anti-Her2 antibody or a specific 4-1BB antibody. Detailed exemplary methods for mapping an epitope to which an antibody binds are provided in Morris (1996) "Epitope Mapping Protocols," in Methods in Molecular Biology vol. 66 (Humana Press, Totowa, NJ).

3. Activity Assays

In one aspect, assays are provided for identifying 4-1BBL trimer-containing antigen binding molecules that bind to Her2 and to 4-1BB having biological activity. Biological activity may include, e.g., agonistic signalling through 4-1BB on cancer cells expressing Her2. 4-1BBL trimer-containing antigen binding molecules identified by the assays as having such biological activity in vitro are also provided.

In certain aspects, a 4-1BBL trimer-containing antigen binding molecule of the invention is tested for such biological activity. Assays for detecting the biological activity of the molecules of the invention are those described in Example 3. Furthermore, assays for detecting cell lysis (e.g. by measurement of LDH release), induced apoptosis kinetics (e.g. by measurement of Caspase 3/7 activity) or apoptosis (e.g. using the TUNEL assay) are well known in the art. In addition, the biological activity of such complexes can be assessed by evaluating their effects on survival, proliferation and lymphokine secretion of various lymphocyte subsets such as NK cells, NKT-cells or γδ T-cells or assessing their capacity to modulate phenotype and function of antigen presenting cells such as dendritic cells, monocytes/macrophages or B-cells.

Pharmaceutical Compositions, Formulations and Routes of Administration

In a further aspect, the invention provides pharmaceutical compositions comprising any of the 4-1BBL trimer-containing antigen binding molecules provided herein, e.g., for use in any of the below therapeutic methods. In one embodiment, a pharmaceutical composition comprises any of the 4-1BBL trimer-containing antigen binding molecules provided herein and at least one pharmaceutically acceptable excipient. In another embodiment, a pharmaceutical composition comprises any of the 4-1BBL trimer-containing antigen binding molecules provided herein and at least one additional therapeutic agent, e.g., as described below.

Pharmaceutical compositions of the present invention comprise a therapeutically effective amount of one or more 4-1BBL trimer-containing antigen binding molecules dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one 4-1BBL trimer-containing antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the 4-1BBL trimer-containing antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the fusion proteins may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the fusion proteins of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The 4-1BBL trimer-containing antigen binding molecules may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

In one aspect, the pharmaceutical compositions may comprise any of the 4-1BBL trimer-containing antigen binding molecules provided herein and at least one additional therapeutic agent. In one aspect, the pharmaceutical compositions may comprise any of the 4-1BBL trimer-containing antigen binding molecules provided herein and a T-cell activating anti-CD3 bispecific antibody, in particular an anti-Her2/anti-CD3 antibody.

In one aspect, the anti-Her2/anti-CD3 antibody comprises a first antigen binding domain that binds to CD3, and a second antigen binding domain that binds to Her2. In a particular aspect the second binding domain binding to Her2 binds to a different epitope on Her2 than the 4-1BBL trimer-containing antigen binding molecule.

In one aspect, the anti-Her2/anti-CD3 bispecific antibody as used herein comprises a first antigen binding domain comprising a heavy chain variable region (VHCD3) comprising CDR-H1 sequence of SEQ ID NO:91, CDR-H2 sequence of SEQ ID NO:92, and CDR-H3 sequence of SEQ ID NO:93; and/or a light chain variable region (VLCD3) comprising CDR-L1 sequence of SEQ ID NO:94, CDR-L2 sequence of SEQ ID NO:95, and CDR-L3 sequence of SEQ ID NO:96. More particularly, the anti-Her2/anti-CD3 bispecific antibody comprises a first antigen binding domain comprising a heavy chain variable region (VHCD3) that is at least 90%, 95%, 96%, 97%, 98%, or 99% identical to the amino acid sequence of SEQ ID NO:97 and/or a light chain variable region (VLCD3) that is at least 90%, 95%, 96%, 97%, 98%, or 99% identical to the amino acid sequence of SEQ ID NO:98. In a further aspect, the anti-Her2/anti-CD3 bispecific antibody comprises a heavy chain variable region (VHCD3) comprising the amino acid sequence of SEQ ID NO:97 and/or a light chain variable region (VLCD3) comprising the amino acid sequence of SEQ ID NO:98.

In one aspect, the anti-Her2/anti-CD3 bispecific antibody comprises a second antigen binding domain that binds to the same epitope as the antibody 4D5 (humanized version thereof known as trastuzumab). In another aspect, the anti-Her2/anti-CD3 bispecific antibody comprises a second antigen binding domain that binds to the same epitope as the antibody 2C4 (humanized version thereof known as pertuzumab). In yet another aspect, anti-Her2/anti-CD3 bispecific antibody comprises a second antigen binding domain that binds to the same epitope as the antibody 7C2 (U.S. Pat. No. 9,518,118).

In another aspect, the anti-Her2/anti-CD3 bispecific antibody comprises a second antigen binding domain comprising (a) a heavy chain variable region ($V_H$Her2) comprising CDR-H1 sequence of SEQ ID NO:21, CDR-H2 sequence of SEQ ID NO:22, and CDR-H3 sequence of SEQ ID NO:23, and/or a light chain variable region ($V_L$Her2) comprising CDR-L1 sequence of SEQ ID NO:24, CDR-L2 sequence of SEQ ID NO:25, and CDR-L3 sequence of SEQ ID NO:26, or (b) a heavy chain variable region ($V_H$Her2) comprising CDR-H1 sequence of SEQ ID NO:13, CDR-H2 sequence of SEQ ID NO:14, and CDR-H3 sequence of SEQ ID NO:15, and/or a light chain variable region ($V_L$Her2) comprising CDR-L1 sequence of SEQ ID NO:16, CDR-L2 sequence of SEQ ID NO:17, and CDR-L3 sequence of SEQ ID NO:18, or (c) a heavy chain variable region ($V_H$Her2) comprising CDR-H1 sequence of SEQ ID NO:99, CDR-H2 sequence of SEQ ID NO:100, and CDR-H3 sequence of SEQ ID NO:101, and/or a light chain variable region ($V_L$Her2) comprising CDR-L1 sequence of SEQ ID NO:102, CDR-L2 sequence of SEQ ID NO:103, and CDR-L3 sequence of SEQ ID NO:104.

In one aspect, the anti-Her2/anti-CD3 bispecific comprises a second antigen binding domain comprising a heavy chain variable region ($V_H$Her2) that is at least 90%, 95%, 96%, 97%, 98%, or 99% identical to the amino acid sequence of SEQ ID NO:27 and/or a light chain variable region ($V_L$Her2) that is at least 90%, 95%, 96%, 97%, 98%, or 99% identical to the amino acid sequence of SEQ ID NO:28. In a further aspect, the anti-Her2/anti-CD3 bispecific comprises a second antigen binding domain comprising a heavy chain variable region ($V_H$Her2) comprising the amino acid sequence of SEQ ID NO:27 and/or a light chain variable region ($V_L$Her2) comprising the amino acid sequence of SEQ ID NO:28. In another aspect, the anti-Her2/anti-CD3 bispecific comprises a second antigen binding domain comprising a heavy chain variable region ($V_H$Her2) that is at least 90%, 95%, 96%, 97%, 98%, or 99% identical to the amino acid sequence of SEQ ID NO:19 and/or a light chain variable region ($V_L$Her2) that is at least 90%, 95%, 96%, 97%, 98%, or 99% identical to the amino acid sequence of SEQ ID NO:20. In a further aspect, the anti-Her2/anti-CD3 bispecific comprises a second antigen binding domain comprising a heavy chain variable region ($V_H$Her2) comprising the amino acid sequence of SEQ ID NO:19 and/or a light chain variable region ($V_L$CEA) comprising the amino acid sequence of SEQ ID NO:20. In another aspect, the anti-Her2/anti-CD3 bispecific comprises a second antigen binding domain comprising a heavy chain variable region ($V_H$Her2) that is at least 90%, 95%, 96%, 97%, 98%, or 99% identical to the amino acid sequence of SEQ ID NO:105 and/or a light chain variable region ($V_L$Her2) that is at least 90%, 95%, 96%, 97%, 98%, or 99% identical to the amino acid sequence of SEQ ID NO:106. In a further aspect, the anti-Her2/anti-CD3 bispecific comprises a second antigen binding domain comprising a heavy chain variable region ($V_H$Her2) comprising the amino acid sequence of SEQ ID NO:105 and/or a light chain variable region ($V_L$CEA) comprising the amino acid sequence of SEQ ID NO:106.

In one aspect, the anti-Her2/anti-CD3 bispecific antibody comprises a first antigen binding domain comprising a heavy chain variable region (VHCD3) comprising the amino acid sequence of SEQ ID NO:97 and/or a light chain variable region (VLCD3) comprising the amino acid sequence of SEQ ID NO:98 and a second antigen binding domain comprising a heavy chain variable region ($V_H$Her2) comprising the amino acid sequence of SEQ ID NO:27 and/or a light chain variable region ($V_L$Her2) comprising the amino acid sequence of SEQ ID NO:28.

The formulations to be used for in vivo administration are generally sterile. Sterility may be readily accomplished, e.g., by filtration through sterile filtration membranes.

Therapeutic Methods and Compositions

Any of the 4-1BBL trimer-containing antigen binding molecules provided herein may be used in therapeutic methods.

For use in therapeutic methods, 4-1BBL trimer-containing antigen binding molecules of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, 4-1BBL trimer-containing antigen binding molecules of the invention for use as a medicament are provided. In further aspects, 4-1BBL timer-containing antigen binding molecules of the invention for use in treating a disease, in particular for use in the treatment of cancer, are provided. In certain aspects, 4-1BBL trimer-containing antigen binding molecules of the invention for use in a method of treatment are provided. In one aspect, the invention provides a 4-1BBL timer-containing antigen binding molecule as described herein for use in the treatment of a disease in an individual in need thereof. In certain aspects, the invention provides a 4-1BBL timer-containing antigen binding molecule for use in a method of treating an individual having a disease comprising administering to the individual a therapeutically effective amount of the fusion protein. In certain aspects, the disease to be treated is Her2-positive cancer. Examples of Her2-positive cancers include breast cancer, ovarian cancer, gastric cancer, bladder cancer, salivary gland, endometrial cancer, pancreatic cancer and non-small-cell lung cancer (NSCLC). In one aspect, the Her2-positive cancer is Her2+ positive breast cancer, for instance early or locally advanced Her2+ positive breast cancer. Thus, a 4-1BBL trimer-containing antigen binding molecule as described herein for use in the treatment of these cancers is provided. The subject, patient, or "individual" in need of treatment is typically a mammal, more specifically a human.

In another aspect, provided is a 4-1BBL trimer-containing antigen binding molecule as described herein for use in the treatment of infectious diseases, in particular for the treatment of viral infections. In a further aspect, provided is a 4-1BBL timer-containing antigen binding molecule as described herein for use in the treatment of autoimmune diseases such as for example Lupus disease.

In a further aspect, the invention relates to the use of a 4-1BBL trimer-containing antigen binding molecule in the manufacture or preparation of a medicament for the treatment of a disease in an individual in need thereof. In one aspect, the medicament is for use in a method of treating a disease comprising administering to an individual having the disease a therapeutically effective amount of the medicament. In certain embodiments the disease to be treated is a proliferative disorder, particularly cancer. Thus, in one aspect, the invention relates to the use of a 4-1BBL trimer-containing antigen binding molecule of the invention in the manufacture or preparation of a medicament for the treatment of cancer, in particular Her2-positive cancers. Examples of Her2-positive cancers include breast cancer, ovarian cancer, gastric cancer, bladder cancer, salivary gland, endometrial cancer, pancreatic cancer and non-small-cell lung cancer (NSCLC). In certain aspect, cancers to be treated are Her2-positive breast cancer, in particular Her2-positive metastatic breast cancer. A skilled artisan may recognize that in some cases the 4-1BBL trimer-containing antigen binding molecule may not provide a cure but may only provide partial benefit. In some aspects, a physiological change having some benefit is also considered therapeutically beneficial. Thus, in some aspects, an amount of 4-1BBL trimer-containing antigen binding molecule that provides a physiological change is considered an "effective amount" or a "therapeutically effective amount".

In a further aspect, the invention provides a method for treating a disease in an individual, comprising administering to said individual a therapeutically effective amount of a 4-1BBL timer-containing antigen binding molecule of the invention. In one aspect a composition is administered to said individual, comprising a fusion protein of the invention in a pharmaceutically acceptable form. In certain aspects, the disease to be treated is a proliferative disorder. In a particular aspect, the disease is cancer. In certain aspects, the method further comprises administering to the individual a therapeutically effective amount of at least one additional therapeutic agent, e.g. an anti-cancer agent if the disease to be treated is cancer. An "individual" according to any of the above embodiments may be a mammal, preferably a human.

For the prevention or treatment of disease, the appropriate dosage of a 4-1BBL timer-containing antigen binding molecule of the invention (when used alone or in combination with one or more other additional therapeutic agents) will depend on the type of disease to be treated, the route of administration, the body weight of the patient, the type of antigen binding molecule, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The 4-1BBL trimer-containing antigen binding molecule is suitably administered to the patient at one time or over a series of treatments. Depending on the type and severity of the disease, about 1 µg/kg to 15 mg/kg (e.g. 0.1 mg/kg-10 mg/kg) of 4-1BBL timer-containing antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion protein would be in the range from about 0.005 mg/kg to about 10 mg/kg. In other examples, a dose may also comprise from about 1 µg/kg body weight, about 5 µg/kg body weight, about 10 µg/kg body weight, about 50 µg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 µg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful. The progress of this therapy is easily monitored by conventional techniques and assays.

The 4-1BBL trimer-containing antigen binding molecules of the invention will generally be used in an amount effective to achieve the intended purpose. For use to treat or prevent a disease condition, the 4-1BBL timer-containing antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the 4-1BBL timer-containing antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the 4-1BBL trimer-containing antigen binding molecule may not be related to plasma concentration. One skilled in the art will be able to optimize therapeutically effective local dosages without undue experimentation.

A therapeutically effective dose of the 4-1BBL trimer-containing antigen binding molecules described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. 4-1BBL timer-containing antigen binding molecules that exhibit large therapeutic indices are preferred. In one embodiment, the 4-1BBL timer-containing antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with fusion proteins of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The 4-1BBL trimer-containing antigen binding molecules of the invention may be administered in combination with one or more other agents in therapy. For instance, a fusion protein of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of 4-1BBL trimer-containing antigen binding molecule used, the type of disorder or treatment, and other factors discussed above. The 4-1BBL trimer-containing antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the 4-1BBL trimer-containing antigen binding molecule of the invention can occur prior to, simultaneously, and/or following, administration of the additional therapeutic agent and/or adjuvant.

Thus, in one aspect a 4-1BBL trimer-containing antigen binding molecule as described herein for use in the treatment of cancer, in particular Her2 positive cancer is provided, wherein the 4-1BBL trimer-containing antigen binding molecule is used in combination with a T-cell activating anti-CD3 bispecific antibody, in particular anti-Her2/anti-CD3 bispecific antibody.

In one aspect, the anti-Her2/anti-CD3 antibody comprises a first antigen binding domain that binds to CD3, and a second antigen binding domain that binds to Her2. In a particular aspect the second binding domain binding to Her2 binds to a different epitope on Her2 than the 4-1BBL trimer-containing antigen binding molecule.

In one aspect, the anti-Her2/anti-CD3 bispecific antibody as used herein comprises a first antigen binding domain comprising a heavy chain variable region (VHCD3) comprising CDR-H1 sequence of SEQ ID NO:91, CDR-H2 sequence of SEQ ID NO:92, and CDR-H3 sequence of SEQ ID NO:93; and/or a light chain variable region ($V_L$CD3) comprising CDR-L1 sequence of SEQ ID NO:94, CDR-L2 sequence of SEQ ID NO:95, and CDR-L3 sequence of SEQ ID NO:96. More particularly, the anti-Her2/anti-CD3 bispecific antibody comprises a first antigen binding domain comprising a heavy chain variable region (VHCD3) that is at least 90%, 95%, 96%, 97%, 98%, or 99% identical to the amino acid sequence of SEQ ID NO:97 and/or a light chain variable region (VLCD3) that is at least 90%, 95%, 96%, 97%, 98%, or 99% identical to the amino acid sequence of SEQ ID NO:98. In a further aspect, the anti-Her2/anti-CD3 bispecific antibody comprises a heavy chain variable region (VHCD3) comprising the amino acid sequence of SEQ ID NO:97 and/or a light chain variable region (VLCD3) comprising the amino acid sequence of SEQ ID NO:98.

In one aspect, the anti-Her2/anti-CD3 bispecific antibody comprises a second antigen binding domain that binds to the same epitope as the antibody 4D5 (humanized version thereof known as trastuzumab). In another aspect, the anti-Her2/anti-CD3 bispecific antibody comprises a second antigen binding domain that binds to the same epitope as the antibody 2C4 (humanized version thereof known as pertuzumab). In yet another aspect, anti-Her2/anti-CD3 bispecific antibody comprises a second antigen binding domain that binds to the same epitope as the antibody 7C2 (U.S. Pat. No. 9,518,118).

In another aspect, the anti-Her2/anti-CD3 bispecific antibody comprises a second antigen binding domain comprising (a) a heavy chain variable region ($V_H$Her2) comprising CDR-H1 sequence of SEQ ID NO:21, CDR-H2 sequence of SEQ ID NO:22, and CDR-H3 sequence of SEQ ID NO:23, and/or a light chain variable region ($V_L$Her2) comprising CDR-L1 sequence of SEQ ID NO:24, CDR-L2 sequence of SEQ ID NO:25, and CDR-L3 sequence of SEQ ID NO:26, or (b) a heavy chain variable region ($V_H$Her2) comprising CDR-H1 sequence of SEQ ID NO:13, CDR-H2 sequence of SEQ ID NO:14, and CDR-H3 sequence of SEQ ID NO:15, and/or a light chain variable region ($V_L$Her2) comprising CDR-L1 sequence of SEQ ID NO:16, CDR-L2 sequence of SEQ ID NO:17, and CDR-L3 sequence of SEQ ID NO:18, or (c) a heavy chain variable region ($V_H$Her2) comprising CDR-H1 sequence of SEQ ID NO:99, CDR-H2 sequence of SEQ ID NO:100, and CDR-H3 sequence of SEQ ID NO:101, and/or a light chain variable region ($V_L$Her2) comprising CDR-L1 sequence of SEQ ID NO:102, CDR-L2 sequence of SEQ ID NO:103, and CDR-L3 sequence of SEQ ID NO:104.

In one aspect, the anti-Her2/anti-CD3 bispecific comprises a second antigen binding domain comprising a heavy chain variable region ($V_H$Her2) that is at least 90%, 95%, 96%, 97%, 98%, or 99% identical to the amino acid sequence of SEQ ID NO:27 and/or a light chain variable region ($V_L$Her2) that is at least 90%, 95%, 96%, 97%, 98%, or 99% identical to the amino acid sequence of SEQ ID NO:28. In a further aspect, the anti-Her2/anti-CD3 bispecific comprises a second antigen binding domain comprising a heavy chain variable region ($V_H$Her2) comprising the amino acid sequence of SEQ ID NO:27 and/or a light chain variable region ($V_L$Her2) comprising the amino acid sequence of SEQ ID NO:28. In another aspect, the anti-Her2/anti-CD3 bispecific comprises a second antigen binding domain comprising a heavy chain variable region ($V_H$Her2) that is at least 90%, 95%, 96%, 97%, 98%, or 99% identical to the amino acid sequence of SEQ ID NO:19 and/or a light chain variable region ($V_L$Her2) that is at least 90%, 95%, 96%, 97%, 98%, or 99% identical to the amino acid sequence of SEQ ID NO:20. In a further aspect, the anti-Her2/anti-CD3 bispecific comprises a second antigen binding domain comprising a heavy chain variable region ($V_H$Her2) comprising the amino acid sequence of SEQ ID NO:19 and/or a light chain variable region ($V_L$CEA) comprising the amino acid sequence of SEQ ID NO:20. In another aspect, the anti-Her2/anti-CD3 bispecific comprises a second antigen binding domain comprising a heavy chain variable region ($V_H$Her2) that is at least 90%, 95%, 96%, 97%, 98%, or 99% identical to the amino acid sequence of SEQ ID NO:105 and/or a light chain variable region ($V_L$Her2) that is at least 90%, 95%, 96%, 97%, 98%, or 99% identical to the amino acid sequence of SEQ ID NO:106. In a further aspect, the anti-Her2/anti-CD3 bispecific comprises a second antigen binding domain comprising a heavy chain variable region ($V_H$Her2) comprising the amino acid sequence of SEQ ID NO:105 and/or a light chain variable region ($V_L$CEA) comprising the amino acid sequence of SEQ ID NO:106.

In one aspect, the anti-Her2/anti-CD3 bispecific antibody comprises a first antigen binding domain comprising a heavy chain variable region (VHCD3) comprising the amino acid sequence of SEQ ID NO:97 and/or a light chain variable region (VLCD3) comprising the amino acid sequence of SEQ ID NO:98 and a second antigen binding domain comprising a heavy chain variable region ($V_H$Her2) comprising the amino acid sequence of SEQ ID NO:27 and/or a light chain variable region ($V_L$Her2) comprising the amino acid sequence of SEQ ID NO:28.

In a further aspect, the 4-1BBL trimer-containing antigen binding molecule is used in combination with a T-cell activating anti-CD3 bispecific antibody and the T-cell activating anti-CD3 bispecific antibody is administered concurrently with, prior to, or subsequently to the 4-1BBL trimer-containing antigen binding molecule.

In a further aspect, provided is the use of the 4-1BBL trimer-containing antigen binding molecule for the manufacture of a medicament for the treatment of cancer, wherein the 4-1BBL trimer-containing antigen binding molecule is used in combination with a T-cell activating anti-CD3 bispecific antibody, in particular an anti-Her2/anti-CD3 bispecific antibody. In certain aspects, the disease to be treated is Her2-positive cancers. Examples of Her2-positive cancers include breast cancer, ovarian cancer, gastric cancer, bladder cancer, salivary gland, endometrial cancer, pancreatic cancer and non-small-cell lung cancer (NSCLC). In certain aspects, cancers to be treated are Her2-positive breast cancer, in particular Her2-positive metastatic breast cancer.

In a further aspect, the invention provides a method for treating cancer in an individual, comprising administering to said individual a therapeutically effective amount of a 4-1BBL trimer-containing antigen binding molecule of the invention and an effective amount a T-cell activating anti-CD3 bispecific antibody, in particular an anti-Her2/anti-CD3 bispecific antibody as defined above. In certain aspects, the method is for Her2-positive cancers. Examples of Her2-positive cancers include breast cancer, ovarian cancer, gastric cancer, bladder cancer, salivary gland, endometrial cancer, pancreatic cancer and non-small-cell lung cancer (NSCLC). In one aspect, the method is for treating Her2-positive metastatic breast cancer.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a 4-1BBL trimer-containing antigen binding molecule of the invention.

The label or package insert indicates that the composition is used for treating the condition of choice. Moreover, the article of manufacture may comprise (a) a first container with a composition contained therein, wherein the composition comprises a 4-1BBL trimer-containing antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE B (Sequences):

| SEQ ID NO: | Description | Sequence |
|---|---|---|
| 1 | Human (hu) 4-1BBL (71-254) | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD |

TABLE B-continued (Sequences):

| SEQ ID NO: | Description | Sequence |
|---|---|---|
| | | LPPASSEARNSAFGFQGRLLHLSAGQRLGVHLHTEARA RHAWQLTQGATVLGLFRVTPEIPAGLPSPRSE |
| 2 | hu 4-1BBL (85-254) | LDLRQGMFAQLVAQNVLLIDGPLSWYSDPGLAGVSLTG GLSYKEDTKELVVAKAGVYYVFFQLELRRVVAGEGSGS VSLALHLQPLRSAAGAAALALTVDLPPASSEARNSAFG FQGRLLHLSAGQRLGVHLHTEARARHAWQLTQGATVLG LFRVTPEIPAGLPSPRSE |
| 3 | hu 4-1BBL (80-254) | DPAGLLDLRQGMFAQLVAQNVLLIDGPLSWYSDPGLAG VSLTGGLSYKEDTKELVVAKAGVYYVFFQLELRRVVAG EGSGSVSLALHLQPLRSAAGAAALALTVDLPPASSEAR NSAFGFQGRLLHLSAGQRLGVHLHTEARARHAWQLTQG ATVLGLFRVTPEIPAGLPSPRSE |
| 4 | hu 4-1BBL (52-254) | PWAVSGARASPGSAASPRLREGPELSPDDPAGLLDLRQ GMFAQLVAQNVLLIDGPLSWYSDPGLAGVSLTGGLSYK EDTKELVVAKAGVYYVFFQLELRRVVAGEGSGSVSLAL HLQPLRSAAGAAALALTVDLPPASSEARNSAFGFQGRL LHLSAGQRLGVHLHTEARARHAWQLTQGATVLGLFRVT PEIPAGLPSPRSE |
| 5 | Human (hu) 4-1BBL (71-248) | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGL |
| 6 | hu 4-1BBL (85-248) | LDLRQGMFAQLVAQNVLLIDGPLSWYSDPGLAGVSLTG GLSYKEDTKELVVAKAGVYYVFFQLELRRVVAGEGSGS VSLALHLQPLRSAAGAAALALTVDLPPASSEARNSAFG FQGRLLHLSAGQRLGVHLHTEARARHAWQLTQGATVLG LFRVTPEIPAGL |
| 7 | hu 4-1BBL (80-248) | DPAGLLDLRQGMFAQLVAQNVLLIDGPLSWYSDPGLAG VSLTGGLSYKEDTKELVVAKAGVYYVFFQLELRRVVAG EGSGSVSLALHLQPLRSAAGAAALALTVDLPPASSEAR NSAFGFQGRLLHLSAGQRLGVHLHTEARARHAWQLTQG ATVLGLFRVTPEIPAGL |
| 8 | hu 4-1BBL (52-248) | PWAVSGARASPGSAASPRLREGPELSPDDPAGLLDLRQ GMFAQLVAQNVLLIDGPLSWYSDPGLAGVSLTGGLSYK EDTKELVVAKAGVYYVFFQLELRRVVAGEGSGSVSLAL HLQPLRSAAGAAALALTVDLPPASSEARNSAFGFQGRL LHLSAGQRLGVHLHTEARARHAWQLTQGATVLGLFRVT PEIPAGL |
| 9 | dimeric hu 4-1BBL (71-254) connected by (G4S)$_2$ linker | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLPSPRSEGGGGSG GGGSREGPELSPDDPAGLLDLRQGMFAQLVAQNVLLID GPLSWYSDPGLAGVSLTGGLSYKEDTKELVVAKAGVYY VFFQLELRRVVAGEGSGSVSLALHLQPLRSAAGAAALA LTVDLPPASSEARNSAFGFQGRLLHLSAGQRLGVHLHT EARARHAWQLTQGATVLGLFRVTPEIPAGLPSPRSE |
| 10 | dimeric hu 4-1BBL (71-248) connected by (G4S)$_2$ linker | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLGGGGSGGGGSRE GPELSPDDPAGLLDLRQGMFAQLVAQNVLLIDGPLSWY SDPGLAGVSLTGGLSYKEDTKELVVAKAGVYYVFFQLE LRRVVAGEGSGSVSLALHLQPLRSAAGAAALALTVDLP PASSEARNSAFGFQGRLLHLSAGQRLGVHLHTEARARH AWQLTQGATVLGLFRVTPEIPAGL |
| 11 | dimeric hu 4-1BBL (80-254) connected by (G4S)$_2$ linker | DPAGLLDLRQGMFAQLVAQNVLLIDGPLSWYSDPGLAG VSLTGGLSYKEDTKELVVAKAGVYYVFFQLELRRVVAG EGSGSVSLALHLQPLRSAAGAAALALTVDLPPASSEAR NSAFGFQGRLLHLSAGQRLGVHLHTEARARHAWQLTQG ATVLGLFRVTPEIPAGLPSPRSEGGGGSGGGGSDPAGL LDLRQGMFAQLVAQNVLLIDGPLSWYSDPGLAGVSLTG |

TABLE B-continued (Sequences):

| SEQ ID NO: | Description | Sequence |
|---|---|---|
|  |  | GLSYKEDTKELVVAKAGVYYVFFQLELRRVVAGEGSGS VSLALHLQPLRSAAGAAALALTVDLPPASSEARNSAFG FQGRLLHLSAGQRLGVHLHTEARARHAWQLTQGATVLG LFRVTPEIPAGLPSPRSE |
| 12 | dimeric hu 4-1BBL (52-254) connected by (G4S)$_2$ linker | PWAVSGARASPGSAASPRLREGPELSPDDPAGLLDLRQ GMFAQLVAQNVLLIDGPLSWYSDPGLAGVSLTGGLSYK EDTKELVVAKAGVYYVFFQLELRRVVAGEGSGSVSLAL HLQPLRSAAGAAALALTVDLPPASSEARNSAFGFQGRL LHLSAGQRLGVHLHTEARARHAWQLTQGATVLGLFRVT PEIPAGLPSPRSEGGGGSGGGGSPWAVSGARASPGSAA SPRLREGPELSPDDPAGLLDLRQGMFAQLVAQNVLLID GPLSWYSDPGLAGVSLTGGLSYKEDTKELVVAKAGVYY VFFQLELRRVVAGEGSGSVSLALHLQPLRSAAGAAALA LTVDLPPASSEARNSAFGFQGRLLHLSAGQRLGVHLHT EARARHAWQLTQGATVLGLFRVTPEIPAGLPSPRSE |
| 13 | heavy chain CDR-H1, pertuzumab | GFTFTDYTMD |
| 14 | heavy chain CDR-H2, pertuzumab | DVNPNSGGSIYNQRFKG |
| 15 | heavy chain CDR-H3, pertuzumab | NLGPSFYFDY |
| 16 | light chain CDR-L1, pertuzumab | KASQDVSIGVA |
| 17 | light chain CDR-L2, pertuzumab | SASYRYT |
| 18 | light chain CDR-L3, pertuzumab | QQYYIYPYT |
| 19 | heavy chain variable domain VH, pertuzumab | EVQLVESGGGLVQPGGSLRLSCAASGFTFTDYTMDWVR QAPGKGLEWVADVNPNSGGSIYNQRFKGRFTLSVDRSK NTLYLQMNSLRAEDTAVYYCARNLGPSFYFDYWGQGTL VTVSS |
| 20 | light chain variable domain VL, pertuzumab | DIQMTQSPSSLSASVGDRVTITCKASQDVSIGVAWYQQ KPGKAPKLLIYSASYRYTGVPSRFSGSGSGTDFTLTIS SLQPEDFATYYCQQYYIYPYTFGQGTKVEIK |
| 21 | heavy chain CDR-H1, trastuzumab | GFNIKDTYIH |
| 22 | heavy chain CDR-H2, trastuzumab | RIYPTNGYTRYADSVKG |
| 23 | heavy chain CDR-H3, trastuzumab | WGGDGFYAMDY |
| 24 | light chain CDR-L1, trastuzumab | RASQDVNTAVA |
| 25 | light chain CDR-L2, trastuzumab | SASFLYS |
| 26 | light chain CDR-L3, trastuzumab | QQHYTTPPT |
| 27 | heavy chain variable domain VH, trastuzumab | EVQLVESGGGLVQPGGSLRLSCAASGFNIKDTYIHWVR QAPGKGLEWVARIYPTNGYTRYADSVKGRFTISADTSK NTAYLQMNSLRAEDTAVYYCSRWGGDGFYAMDYWGQGT LVTVSS |
| 28 | light chain variable domain VL, trastuzumab | DIQMTQSPSSLSASVGDRVTITCRASQDVNTAVAWYQQ KPGKAPKLLIYSASFLYSGVPSRFSGSRSGTDFTLTIS SLQPEDFATYYCQQHYTTPPTFGQGTKVEIK |
| 29 | heavy chain CDR-H1, aff. pertuzumab | GFTFNDYTMD |
| 30 | heavy chain CDR-H2, aff. pertuzumab | DVNPNSGGSIVNRRFKG |
| 31 | heavy chain CDR-H3, aff pertuzumab | NLGPFFYFDY |
| 32 | light chain CDR-L1, aff. pertuzumab | KASQDVSTAVA |
| 33 | light chain CDR-L2, aff. pertuzumab | SASFRYT |
| 34 | light chain CDR-L3, aff. pertuzumab | QQHYTTPPT |
| 35 | heavy chain variable domain VH, aff. pertuzumab | EVQLVESGGGLVQPGGSLRLSCAASGFTFNDYTMDWVR QAPGKGLEWVADVNPNSGGSIVNRRFKGRFTLSVDRSK NTLYLQMNSLRAEDTAVYYCARNLGPFFYFDYWGQGTL VTVSS |

TABLE B-continued (Sequences):

| SEQ ID NO: | Description | Sequence |
|---|---|---|
| 36 | light chain variable domain VL, aff. pertuzumab | DIQMTQSPSSLSASVGDRVTITCKASQDVSTAVAWYQQ KPGKAPKLLIYSASFRYTGVPSRFSGSRSGTDFTLTIS SLQPEDFATYYCQQHYTTPPTFGQGTKVEIK |
| 37 | Dimeric 4-1BB ligand (71-248)-CL* Fc knob chain | see Table 1 |
| 38 | Monomeric 4-1BB ligand (71-248)-CH1* | see Table 1 |
| 39 | Dimeric 4-1BB ligand (71-248)-CL Fc knob chain | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLGGGGSGGGGSRE GPELSPDDPAGLLDLRQGMFAQLVAQNVLLIDGPLSWY SDPGLAGVSLTGGLSYKEDTKELVVAKAGVYYVFFQLE LRRVVAGEGSGSVSLALHLQPLRSAAGAAALALTVDLP PASSEARNSAFGFQGRLLHLSAGQRLGVHLHTEARARH AWQLTQGATVLGLFRVTPEIPAGLGGGGSGGGGSRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGECDKTHTCPPCPA PEAAGGPSVFLFPPKPKDTLMISRTPEVTCVVVDVSHE DPEVKFNWYVDGVEVHNAKTKPREEQYNSTYRVVSVLT VLHQDWLNGKEYKCKVSNKALGAPIEKTISKAKGQPRE PQVYTLPPCRDELTKNQVSLWCLVKGFYPSDIAVEWES NGQPENNYKTTPPVLDSDGSFFLYSKLTVDKSRWQQGN VFSCSVMHEALHNHYTQKSLSLSP |
| 40 | Monomeric 4-1BB ligand (71-248)-CH1 | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLGGGGSGGGGSAS TKGPSVFPLAPSSKSTSGGTAALGCLVKDYFPEPVTVS WNSGALTSGVHTFPAVLQSSGLYSLSSVVTVPSSSLGT QTYICNVNHKPSNTKVDKKVEPKSC |
| 41 | Dimeric 4-1BB ligand (71-254)-CL* Fc knob chain | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLPSPRSEGGGGSG GGGSREGPELSPDDPAGLLDLRQGMFAQLVAQNVLLID GPLSWYSDPGLAGVSLTGGLSYKEDTKELVVAKAGVYY VFFQLELRRVVAGEGSGSVSLALHLQPLRSAAGAAALA LTVDLPPASSEARNSAFGFQGRLLHLSAGQRLGVHLHT EARARHAWQLTQGATVLGLFRVTPEIPAGLPSPRSEGG GGSGGGGSRTVAAPSVFIFPPSDRKLKSGTASVVCLLN NFYPREAKVQWKVDNALQSGNSQESVTEQDSKDSTYSL SSTLTLSKADYEKHKVYACEVTHQGLSSPVTKSFNRGE CDKTHTCPPCPAPEAAGGPSVFLFPPKPKDTLMISRTP EVTCVVVDVSHEDPEVKFNWYVDGVEVHNAKTKPREEQ YNSTYRVVSVLTVLHQDWLNGKEYKCKVSNKALGAPIE KTISKAKGQPREPQVYTLPPCRDELTKNQVSLWCLVKG FYPSDIAVEWESNGQPENNYKTTPPVLDSDGSFFLYSK LTVDKSRWQQGNVFSCSVMHEALHNHYTQKSLSLSP |
| 42 | Monomeric 4-1BB ligand (71-254)-CH1* | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLPSPRSEGGGGSG GGSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSC |
| 43 | Dimeric 4-1BB ligand (71-254)-CL Fc knob chain | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLPSPRSEGGGGSG GGSREGPELSPDDPAGLLDLRQGMFAQLVAQNVLLID |

TABLE B-continued (Sequences):

| SEQ ID NO: | Description | Sequence |
|---|---|---|
| | | GPLSWYSDPGLAGVSLTGGLSYKEDTKELVVAKAGVYY VFFQLELRRVVAGEGSGSVSLALHLQPLRSAAGAAALA LTVDLPPASSEARNSAFGFQGRLLHLSAGQRLGVHLHT EARARHAWQLTQGATVLGLFRVTPEIPAGLPSPRSEGG GGSGGGGSRTVAAPSVFIFPPSDEQLKSGTASVVCLLN NFYPREAKVQWKVDNALQSGNSQESVTEQDSKDSTYSL SSTLTLSKADYEKHKVYACEVTHQGLSSPVTKSFNRGE CDKTHTCPPCPAPEAAGGPSVFLFPPKPKDTLMISRTP EVTCVVVDVSHEDPEVKFNWYVDGVEVHNAKTKPREEQ YNSTYRVVSVLTVLHQDWLNGKEYKCKVSNKALGAPIE KTISKAKGQPREPQVYTLPPCRDELTKNQVSLWCLVKG FYPSDIAVEWESNGQPENNYKTTPPVLDSDGSFFLYSK LTVDKSRWQQGNVFSCSVMHEALHNHYTQKSLSLSP |
| 44 | Monomeric 4-1BB ligand (71-254)-CH1 | REGPELSPDDPAGLLDLRQGMFAQLVAQNVLLIDGPLS WYSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLPSPRSEGGGGSG GGGSASTKGPSVFPLAPSSKSTSGGTAALGCLVKDYFP EPVTVSWNSGALTSGVHTFPAVLQSSGLYSLSSVVTVP SSSLGTQTYICNVNHKPSNTKVDKKVEPKSC |
| 45 | anti-Her2 (PER) Fc hole chain | see Table 1 |
| 46 | anti-Her2 (PER) light chain | see Table 1 |
| 47 | anti-Her2 (TRAS) Fc hole chain | see Table 2 |
| 48 | anti-Her2 (TRAS) light chain | see Table 2 |
| 49 | anti-Her2 (aff-PER) Fc hole chain | see Table 3 |
| 50 | anti-Her2 (aff-PER) light chain | see Table 3 |
| 51 | human 4-1BB ECD, aa 24-186 of Q07011 | LQDPCSNCPAGTFCDNNRNQICSPCPPNSFSSAGGQRT CDICRQCKGVFRTRKECSSTSNAECDCTPGFHCLGAGC SMCEQDCKQGQELTKKGCKDCCFGTFNDQKRGICRPWT NCSLDGKSVLVNGTKERDVVCGPSPADLSPGASSVTPP APAREPGHSPQ |
| 52 | Fc hole chain | see Table 5 |
| 53 | human 4-1BB antigen Fc knob chain | see Table 5 |
| 54 | human Her2, UniProt Acc. No. P04626-1 | MELAALCRWG LLLALLPPGA ASTQVCTGTD MKLRLPASPE THLDMLRHLY QGCQVVQGNL ELTYLPTNAS LSFLQDIQEV QGYVLIAHNQ VRQVPLQRLR IVRGTQLFED NYALAVLDNG DPLNNTTPVT GASPGGLREL QLRSLTEILK GGVLIQRNPQ LCYQDTILWK DIFHKNNQLA LTLIDTNRSR ACHPCSPMCK GSRCWGESSE DCQSLTRTVC AGGCARCKGP LPTDCCHEQC AAGCTGPKHS DCLACLHFNH SGICELHCPA LVTYNTDTFE SMPNPEGRYT FGASCVTACP YNYLSTDVGS CTLVCPLHNQ EVTAEDGTQR CEKCSKPCAR VCYGLGMEHL REVRAVTSAN IQEFAGCKKI FGSLAFLPES FDGDPASNTA ETLEEITGYL YISAWPDSLP DLSVFQNLQV IRGRILHNGA YSLTLQGLGI SWLGLRSLRE LGSGLALIHH NTHLCFVHTV PWDQLFRNPH QALLHTANRP EDECVGEGLA CHQLCARGHC WGPGPTQCVN CSQFLRGQEC VEECRVLQGL PREYVNARHC LPCHPECQPQ NGSVTCFGPE ADQCVACAHY KDPPFCVARC PSGVKPDLSY MPIWKFPDEE GACQPCPINC THSCVDLDDK GCPAEQRASP LTSIISAVVG ILLVVVLGVV FGILIKRRQQ KIRKYTMRRL LQETELVEPL TPSGAMPNQA QMRILKETEL RKVKVLGSGA FGTVYKGIWI PDGENVKIPV AIKVLRENTS PKANKEILDE AYVMAGVGSP YVSRLLGICL TSTVQLVTQL MPYGCLLDHV RENRGRLGSQ DLLNWCMQIA KGMSYLEDVR LVHRDLAARN VLVKSPNHVK ITDFGLARLL DIDETEYHAD GGKVPIKWMA LESILRRRFT HQSDVWSYGV |

TABLE B-continued (Sequences):

| SEQ ID NO: | Description | Sequence |
|---|---|---|
| | | TVWELMTFGA KPYDGIPARE IPDLLEKGER LPQPPICTID VYMIMVKCWM IDSECRPRFR ELVSEFSRMA RDPQRFVVIQ NEDLGPASPL DSTFYRSLLE DDDMGDLVDA EEYLVPQQGF FCPDPAPGAG GMVHHRHRSS STRSGGGDLT LGLEPSEEEA PRSPLAPSEG AGSDVFDGDL GMGAAKGLQS LPTHDPSPLQ RYSEDPTVPL PSETDGYVAP LTCSPQPEYV NQPDVRPQPP SPREGPLPAA RPAGATLERP KTLSPGKNGV VKDVFAFGGA VENPEYLTPQ GGAAPQPHPP PAFSPAFDNL YYWDQDPPER GAPPSTFKGT PTAENPEYLG LDVPV |
| 55 | 4-1BB antibody 20H4.9 IgG4, Heavy chain | MKHLWFFLLL VAAPRWVLSQ VQLQQWGAGL LKPSETLSLT CAVYGGSFSG YYWSWIRQSP EKGLEWIGEI NHGGYVTYNP SLESRVTISV DTSKNQFSLK LSSVTAADTA VYYCARDYGP GNYDWYFDLW GRGTLVTVSS ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKRVES KYGPPCPPCP APEFLGGPSV FLFPPKPKDT LMISRTPEVT CVVVDVSQED PEVQFNWYVD GVEVHNAKTK PREEQFNSTY RWSVLTVLHQ DWLNGKEYKC KVSNKGLPSS IEKTISKAKG QPREPQVYTL PPSQEEMTKN QVSLTCLVKG FYPSDIAVEW ESNGQPENNY KTTPPVLDSD GSFFLYSRLT VDKSRWQEGN VFSCSVMHEA LHNHYTQKSL SLSL |
| 56 | 4-1BB antibody 20H4.9 IgG4, Light chain | EIVLTQSPAT LSLSPGERAT LSCRASQSVS SYLAWYQQKP GQAPRLLIYD ASNRATGIPA RFSGSGSGTD FTLTISSLEP EDFAVYYCQQ RSNWPPALTF CGGTKVEIKR TVAAPSVFIF PPSDEQLKSG TASVVCLLNN FYPREAKVQW KVDNALQSGN SQESVTEQDS KDSTYSLSST LTLSKADYEK HKVYACEVTH QGLSSPVTKS FNRGEC |
| 57 | 4-1BB antibody MOR7480 IgG2, Heavy chain | EVQLVQSGAEVKKPGESLRISCKGSGYSFSTYWISWVR QMPGKGLEWMGKIYPGDSYTNYSPSFQGQVTISADKSI STAYLQWSSLKASDTAMYYCARGYGIFDYWGQGTLVTV SSASTKGPSVFPLAPCSRSTSESTAALGCLVKDYFPEP VTVSWNSGALTSGVHTFPAVLQSSGLYSLSSVVTVPSS NFGTQTYTCNVDHKPSNTKVDKTVERKCCVECPPCPAP PVAGPSVFLFPPKPKDTLMISRTPEVTCVVVDVSHEDP EVQFNWYVDGVEVHNAKTKPREEQFNSTFRVVSVLTVV HQDWLNGKEYKCKVSNKGLPAPIEKTISKTKGQPREPQ VYTLPPSREEMTKNQVSLTCLVKGFYPSDIAVEWESNG QPENNYKTTPPMLDSDGSFFLYSKLTVDKSRWQQGNVF SCSVMHEALHNHYTQKSLSLSP |
| 58 | 4-1BB antibody MOR7480 IgG2, Light chain | SYELTQPPSVSVSPGQTASITCSGDNIGDQYAHWYQQK PGQSPVLVIYQDKNRPSGIPERFSGSNSGNTATLTISG TQAMDEADYYCATYTGFGSLAVFGGGTKLTVLGQPKAA PSVTLFPPSSEELQANKATLYCLISDFYPGAVTVAWKA DSSPVKAGVETTTPSKQSNNKYAASSYLSLTPEQWKSH RSYSCQVTHEGSTVEKTVAPTECS |
| 59 | Her2 (TRAS)-anticalin-4-1BB human IgG4 heavy chain | EVQLVESGGGLVQPGGSLRLSCAASGFNIKDTYIHWVR QAPGKGLEWVARIYPTNGYTRYADSVKGRFTISADTSK NTAYLQMNSLRAEDTAVYYCSRWGGDGFYANDYWGQGT LVTVSSASTKGPSVFPLAPCSRSTSESTAALGCLVKDY FPEPVTVSWNSGALTSGVHTFPAVLQSSGLYSLSSVVT VPSSSLGTKTYTCNVDHKPSNTKVDKRVESKYGPPCPP CPAPEAAGGPSVFLFPPKPKDTLMISRTPEVTCVVVDV SQEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLTCLVKGFYPSDIAVE WESNGQPENNYKTTPPVLDSDGSFFLYSRLTVDKSRWQ EGNVESCSVMHEALHNHYTQKSLSLSLGKGGGGSGGGG SGGGGSQDSTSDLIPAPPLSKVPLQQNFQDNQFHGKWY VVGQAGNIRLREDKDPIKMMATIYELKEDKSYDVTMVK |

TABLE B-continued (Sequences):

| SEQ ID NO: | Description | Sequence |
|---|---|---|
| | | FDDKKCMYDIWTFVPGSQPGEFTLGKIKSFPGHTSSLV<br>RVVSTNYNQHAMVFFKFVFQNREEFYITLYGRTKELTS<br>ELKENFIRFSKSLGLPENHIVFPVPIDQCIDG |
| 60 | Her2 (TRAS)-anticalin-4-1BB human IgG4 light chain | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQHYTTPPTFGQGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC |
| 61 | DP47 Fc hole chain | EVQLLESGGGLVQPGGSLRLSCAASGFTFSSYAMSWVR<br>QAPGKGLEWVSAISGSGGSTYYADSVKGRFTISRDNSK<br>NTLYLQMNSLRAEDTAVYYCAKGSGEDYWGQGTLVTVS<br>SASTKGPSVFPLAPSSKSTSGGTAALGCLVKDYFPEPV<br>TVSWNSGALTSGVHTFPAVLQSSGLYSLSSVVTVPSSS<br>LGTQTYICNVNHKPSNTKVDKKVEPKSCDKTHTCPPCP<br>APEAAGGPSVFLFPPKPKDTLMISRTPEVTCVVVDVSH<br>EDPEVKFNWYVDGVEVHNAKTKPREEQYNSTYRVVSVL<br>TVLHQDWLNGKEYKCKVSNKALGAPIEKTISKAKGQPR<br>EPQVCTLPPSRDELTKNQVSLSCAVKGFYPSDIAVEWE<br>SNGQPENNYKTTPPVLDSDGSFFLVSKLTVDKSRWQQG<br>NVFSCSVMHEALHNHYTQKSLSLSP |
| 62 | DP47 light chain | EIVLTQSPGTLSLSPGERATLSCRASQSVSSSYLAWYQ<br>QKPGQAPRLLIYGASSRATGIPDRFSGSGSGTDFTLTI<br>SRLEPEDFAVYYCQQYGSSPLTFGQGTKVEIKRTVAAP<br>SVFIFPPSDEQLKSGTASVVCLLNNFYPREAKVQWKVD<br>NALQSGNSQESVTEQDSKDSTYSLSSTLTLSKADYEKH<br>KVYACEVTHQGLSSPVTKSFNRGEC |
| 63 | DP47-anticalin-4-1BB human IgG4 heavy chain | EVQLLESGGGLVQPGGSLRLSCAASGFTFSSYAMSWVR<br>QAPGKGLEWVSAISGSGGSTYYADSVKGRFTISRDNSK<br>NTLYLQMNSLRAEDTAVYYCAKGSGEDYWGQGTLVTVS<br>SASTKGPSVFPLAPCSRSTSESTAALGCLVKDYFPEPV<br>TVSWNSGALTSGVHTFPAVLQSSGLYSLSSVVTVPSSS<br>LGTKTYTCNVDHKPSNTKVDKRVESKYGPPCPPCPAPE<br>AAGGPSVFLEPPKPKDTLMISRTPEVTCVVVDVSQEDP<br>EVQFNWYVDGVEVHNAKTKPREEQFNSTYRVVSVLTVL<br>HQDWLNGKEYKCKVSNKGLPSSIEKTISKAKGQPREPQ<br>VYTLPPSQEEMTKNQVSLTCLVKGFYPSDIAVEWESNG<br>QPENNYKTTPPVLDSDGSFELYSRLTVDKSRWQEGNVF<br>SCSVMHEALHNHYTQKSLSLSLGKGGGGSGGGGSGGGG<br>SQDSTSDLIPAPPLSKVPLQQNFQDNQFHGKWYVVGQA<br>GNIRLREDKDPIKMMATIYELKEDKSYDVTMVKFDDKK<br>CMYDIWTFVPGSQPGEFTLGKIKSFPGHTSSLVRVVST<br>NYNQHAMVFFKFVFQNREEFYITLYGRTKELTSELKEN<br>FIRFSKSLGLPENHIVFPVPIDQCIDG |
| 64 | DP47-anticalin-4-1BB human IgG4 light chain | EIVLTQSPGTLSLSPGERATLSCRASQSVSSSYLAWYQ<br>QKPGQAPRLLIYGASSRATGIPDRFSGSGSGTDFTLTI<br>SRLEPEDFAVYYCQQYGSSPLTFGQGTKVEIKRTVAAP<br>SVFIFPPSDEQLKSGTASVVCLLNNFYPREAKVQWKVD<br>NALQSGNSQESVTEQDSKDSTYSLSSTLTLSKADYEKH<br>KVYACEVTHQGLSSPVTKSFNRGEC |
| 65 | Her2 (TRAS) human IgG1 P329G LALA, Heavy chain | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSCDKTHT<br>CPPCPAPEAAGGPSVFLFPPKPKDTLMISRTPEVTCVV<br>VDVSHEDPEVKFNWYVDGVEVHNAKTKPREEQYNSTYR<br>VVSVLTVLHQDWLNGKEYKCKVSNKALGAPIEKTISKA<br>KGQPREPQVYTLPPSRDELTKNQVSLTCLVKGFYPSDI<br>AVEWESNGQPENNYKTTPPVLDSDGSFFLYSKLTVDKS<br>RWQQGNVFSCSVMHEALHNHYTQKSLSLSP |
| 66 | Her2 (PER) human IgG1 P329G LALA, Heavy chain | EVQLVESGGGLVQPGGSLRLSCAASGFTFTDYTMDWVR<br>QAPGKGLEWVADVNPNSGGSIYNQRFKGRFTLSVDRSK<br>NTLYLQMNSLRAEDTAVYYCARNLGPSFYFDYWGQGTL<br>VTVSSASTKGPSVFPLAPSSKSTSGGTAALGCLVKDYF<br>PEPVTVSWNSGALTSGVHTFPAVLQSSGLYSLSSVVTV<br>PSSSLGTQTYICNVNHKPSNTKVDKKVEPKSCDKTHTC |

TABLE B-continued (Sequences):

| SEQ ID NO: | Description | Sequence |
|---|---|---|
| | | PPCPAPEAAGGPSVFLFPPKPKDTLMISRTPEVTCVVV DVSHEDPEVKFNWYVDGVEVHNAKTKPREEQYNSTYRV VSVLTVLHQDWLNGKEYKCKVSNKALGAPIEKTISKAK GQPREPQVYTLPPSRDELTKNQVSLTCLVKGFYPSDIA VEWESNGQPENNYKTTPPVLDSDGSFFLYSKLTVDKSR WQQGNVFSCSVMHEALHNHYTQKSLSLSP |
| 67 | DP47 human IgG1 P329G LALA, Heavy chain | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCAKGSGFDYWGQGTLVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKKVEPKSCDKTHTCPPCP APEAAGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALGAPIEKTISKAKGQPR EPQVYTLPPSRDELTKNQVSLTCLVKGFYPSDIAVEWE SNGQPENNYKTTPPVLDSDGSFFLYSKLTVDKSRWQQG NVFSCSVMHEALHNHYTQKSLSLSP |
| 68 | (G4S)2 peptide linker | GGGGSGGGGS |
| 69 | human4-1BBL (UniProt no. P41273) | MEYASDASLD PEAPWPPAPR ARACRVLPWA LVAGLLLLLL LAAACAVFLA CPWAVSGARA SPGSAASPRL REGPELSPDD PAGLLDLRQG MFAQLVAQNV LLIDGPLSWY SDPGLAGVSL TGGLSYKEDT KELVVAKAGV YVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE |
| 70 | human 4-1BBL(50-254) | ACPWAVSGARASPGSAASPRLREGPELSPDDPAGLLDL RQGMFAQLVAQNVLLIDGPLSWYSDPGLAGVSLTGGLS YKEDTKELVVAKAGVYYVFFQLELRRVVAGEGSGSVSL ALHLQPLRSAAGAAALALTVDLPPASSEARNSAFGFQG RLLHLSAGQRLGVHLHTEARARHAWQLTQGATVLGLFR VTPEIPAGLPSPRSE |
| 71 | Peptide linker G4S | GGGGS |
| 72 | Peptide linker (SG4)2 | SGGGGSGGGG |
| 73 | Peptide linker (G4S)3 | GGGGSGGGGSGGGGS |
| 74 | Peptide linker G4(SG4)2 | GGGGSGGGGSGGGG |
| 75 | Peptide linker (G4S)4 | GGGGSGGGGSGGGGSGGGGS |
| 76 | Peptide linker | GSPGSSSSGS |
| 77 | Peptide linker | GSGSGSGS |
| 78 | Peptide linker | GSGSGNGS |
| 79 | Peptide linker | GGSGSGSG |
| 80 | Peptide linker | GGSGSG |
| 81 | Peptide linker | GGSG |
| 82 | Peptide linker | GGSGNGSG |
| 83 | Peptide linker | GGNGSGSG |
| 84 | Peptide linker | GGNGSG |
| 85 | human CD3ε | UniProt No. P07766 |
| 86 | cynomolgus CD3ε | NCBI GenBank no. BAB71849.1 Uniprot Q05LI5 |
| 87 | VHCH1(EE) (MU137-1) Fc-KK (mu4-1BB-Her2) | See Table 4A |

TABLE B-continued (Sequences):

| SEQ ID NO: | Description | Sequence |
|---|---|---|
| 88 | VLCH1 (2C4) VHCH1(EE) (MU137-1) Fc-DD (mu4-1BB-Her2) | See Table 4A |
| 89 | VLCL(RK)-Light chain (MU137-1) (mu4-1BB-Her2) | See Table 4A |
| 90 | VHCL-Light chain (2C4) | See Table 4A |
| 91 | heavy chain CDR-H1, CD3 | NYYIH |
| 92 | heavy chain CDR-H2, CD3 | WIYPGDGNTK YNEKFKG |
| 93 | heavy chain CDR-H3, CD3 | DSYSNYYFDY |
| 94 | light chain CDR-L1, CD3 | KSSQSLLNSR TRKNYLA |
| 95 | light chain CDR-L2, CD3 | WASTRES |
| 96 | light chain CDR-L3, CD3 | TQSFILRT |
| 97 | heavy chain variable domain VH, CD3 | EVQLVQSGAE VKKPGASVKV SCKASGYTFT NYYIHWVRQA PGQGLEWIGW IYPGDGNTKY NEKFKGRATL TADTSTSTAY LELSSLRSED TAVYYCARDS YSNYYFDYWG QGTLVTVSS |
| 98 | light chain variable domain VL, CD3 | DIVMTQSPDS LAVSLGERAT INCKSSQSLL NSRTRKNYLA WYQQKPGQPP KLLIYWASTR ESGVPDRFSG SGSGTDFTLT ISSLQAEDVA VYYCTQSFIL RTFGQGTKVE IK |
| 99 | heavy chain CDR-H1, Her2 (7C2) | GYWMN |
| 100 | heavy chain CDR-H2, Her2 (7C2) | MIHPSDSEIR ANQKFRD |
| 101 | heavy chain CDR-H3, Her2 (7C2) | GTYDGGFEY |
| 102 | light chain CDR-L1, Her2 (7C2) | RASQSVSGSR FTYMH |
| 103 | light chain CDR-L2, Her2 (7C2) | YASILES |
| 104 | light chain CDR-L3, Her2 (7C2) | QHSWEIPPWT |
| 105 | heavy chain variable domain VH, Her2 (7C2) | QVQLQQPGAE LVRPGASVKL SCKASGYSFT GYWMNWLKQR PGQGLEWIGM IHPSDSEIRA NQKFRDKATL TVDKSSTTAY MQLSSPTSED SAVYYCARGT YDGGFEYWGQ GTTLTVSS |
| 106 | light chain variable domain VL, Her2 (7C2) | DIVLTQSPAS LVVSLGQRAT ISCRASQSVS GSRFTYMHWY QQKPGQPPKL LIKYASILES GVPARFSGGG SGTDFTLNIH PVEEDDTATY YCQHSWEIPP WTFGGGTKLE IK |

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991) Amino acids of antibody chains are numbered and referred to according to the EU numbering systems according to Kabat (Kabat, E. A., et al., Sequences of Proteins of Immunological Interest, 5th ed., Public Health Service, National Institutes of Health, Bethesda, MD (1991)) as defined above.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Example 1

Generation and Production of Her2-Targeting 4-1BB Agonistic Antigen Binding Molecules 1.1. Generation and Production of Her2-Targeting 4-1BB Ligand Trimer-Containing Fc Fusion Antigen Binding Molecules The Her2 binders used to target the trimeric 4-1BB ligand were pertuzumab (termed in the text below PER), trastuzumab (TRAS) and affinity matured pertuzumab (aff-PER) as described in WO 2015/091738.

The variable region of heavy and light chain DNA sequences encoding a binder specific for Her2, were subcloned in frame with either the constant heavy chain of the hole or the constant light chain of human IgG1.

The DNA sequence encoding part of the ectodomain (amino acid 71-248) of human 4-1BB ligand was synthetized according to the P41273 sequence of Uniprot database.

A polypeptide containing two ectodomains of 4-1BB ligand, separated by (G4S)2 linkers, and fused to the human IgG1-CL domain, was cloned as depicted in FIG. 1A: human 4-1BB ligand, (G4S)2 connector, human 4-1BB ligand, (G4S)2 connector, human CL.

A polypeptide containing one ectodomain of 4-1BB ligand and fused to the human IgG1-CH domain, was cloned as described in FIG. 1B: human 4-1BB ligand, (G4S)2 connector, human CH.

To improve correct pairing the following mutations were introduced in the crossed CH-CL. In the dimeric 4-1BB ligand fused to human CL the mutations E123R and Q124K were introduced. In the monomeric 4-1BB ligand fused to human CH1, the mutations K147E and K213E were cloned into the human CH1 domain as described in International Patent Appl. Publ. No. WO 2015/150447.

The variable region of heavy and light chain DNA sequences encoding the binders specific for Her2 (PER, TRAS and aff-PER) were subcloned in frame with either the constant heavy chain of the hole or the constant light chain of human IgG1.

In the Fc domain the P329G, L234A and L235A mutations were introduced in the constant region of the knob and hole heavy chains to abrogate binding to Fc gamma receptors according to the method described in International Patent Appl. Publ. No. WO 2012/130831. Combination of the dimeric ligand-Fc knob chain containing the S354C/T366W mutations, the monomeric CH1 fusion, the targeted anti-Her2-Fc hole chain containing the Y349C/T366S/L368A/Y407V mutations and the anti-Her2 light chain allowed the generation of a heterodimer, which includes an assembled trimeric 4-1BB ligand and a Her2 binding Fab (FIG. 2A).

Table 1 shows the amino acid sequences of the monovalent anti-Her2(PER) split trimeric 4-1BB ligand Fc (kih) fusion antigen binding molecule containing CH1-CL crossover and charged residues. The molecule is called Her2(PER)-4-1BBL.

Table 2 shows the amino acid sequences of the monovalent anti-Her2(TRAS) split trimeric 4-1BB ligand Fc (kih) fusion antigen binding molecule containing CH1-CL crossover and charged residues. The molecule is called Her2(TRAS)-4-1BBL Table 3 shows the amino acid sequences of the monovalent Her2(aff-PER) split trimeric 4-1BB ligand Fc (kih) fusion antigen binding molecule containing CH1-CL crossover and charged residues. The molecule is called Her2(aff-PER)-4-1BBL

TABLE 1

Amino acid sequences of Her2(PER)-4-1BBL containing CH1-CL crossover and charged residues (*for charged residues)

| SEQ ID NO: | Description | Sequences |
|---|---|---|
| 37 | Dimeric hu 4-1BBL (71-248)-CL* Fc knob chain | REGPELSPDDPAGLLDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGLGGGGSGGGGSREGPELSPDDPAGLLDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLERVTPEIPAGLGGGGSGGGGSRTVAAPSVFIFPPSDRKLKSGTASVVCLLNNFYPREAKVQWKVDNALQSGNSQESVTEQDSKDSTYSLSSTLTLSKADYEKHKVYACEVTHQGLSSPVTKSFNRGECDKTHTCPPCPAPEAAGGPSVFLEPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSP |
| 38 | Monomeric hu 4-1BBL (71-248)-CH1* | REGPELSPDDPAGLLDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGLGGGGSGGGGSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSC |
| 45 | anti-Her2 (PER) Fc hole chain | EVQLVESGGGLVQPGGSLRLSCAASGFTFTDYTMDWVRQAPGKGLEWVADVNPNSGGSTYNQRFKGRFTLSVDRSKNTLYLQMNSLRAEDTAVYYCARNLGPSFYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLEPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSP |
| 46 | anti-Her2 (PER) light chain | DIQMTQSPSSLSASVGDRVTITCKASQDVSIGVAWYQQKPGKAPKLLIYSASYRYTGVPSRFSGSGSGTDFTLTISSLQPEDFATYYCQQYYTYPYTEGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 2

Amino acid sequences of Her2(TRAS)-4-1BBL containing CH1-CL crossover and charged residues (*for charged residues)

| SEQ ID NO: | Description | Sequences |
|---|---|---|
| 37 | Dimeric hu 4-1BBL (71-248)-CL* Fc knob chain | see Table 1 |
| 38 | Monomeric hu 4-1BBL (71-248)-CH1* | see Table 1 |
| 47 | anti-Her2 (TRAS) Fc hole chain | EVQLVESGGGLVQPGGSLRLSCAASGFNIKDTYTHWVRQAPGKGLEWVARTYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKT |

TABLE 2-continued

Amino acid sequences of Her2 (TRAS)-4-1BBL containing CH1-CL crossover and charged residues (*for charged residues)

| SEQ ID NO: | Description | Sequences |
|---|---|---|
| | | TPPVLDSDGSFFLVSKLTVDKSRWQQGNVESCSVMHEALHNHYTQKSLSLSP |
| 48 | anti-Her2 (TRAS) light chain | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 3

Amino acid sequences of Her2 (aff-PER)-4-1BBL containing CH1-CL crossover and charged residues (*for charged residues)

| SEQ ID NO: | Description | Sequences |
|---|---|---|
| 37 | Dimeric hu 4-1BBL (71-248)-CL* Fc knob chain | see Table 1 |
| 38 | Monomeric hu 4-1BBL (71-248)-CH1* | see Table 1 |
| 49 | anti-Her2 (aff-PER) Fc hole chain | EVQLVESGGGLVQPGGSLRLSCAASGFTFNDYTMDWVRQAPGKGLEWVADVNPNSGGSIVNRRFKGRFTLSVDRSKNTLYLQMNSLRAEDTAVYYCARNLGPFFYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLEPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSP |
| 50 | anti-Her2 (aff-PER) light chain | DIQMTQSPSSLSASVGDRVTITCKASQDVSTAVAWYQQKPGKAPKLLIYSASFRYTGVPSRFSGSRSGTDFTLTISSLQPEDFATYYCQQHYTTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

The bispecific constructs were produced by co-transfecting HEK293-EBNA cells with the mammalian expression vectors using polyethylenimine. The cells were transfected with the corresponding expression vectors in a 1:1:1:1 ("vector 4-1BBL Fc-knob chain": "vector 4-1BBL light chain":"vector Fc-hole chain": "vector light chain").

Production was performed in shake flasks using HEK293 EBNA cells. For transfection, cells were centrifuged and medium replaced by pre-warmed CD CHO medium. Expression vectors were mixed in CD CHO medium, PEI was added, the solution vortexed and incubated for 10 minutes at room temperature. Afterwards, cells were mixed with the DNA/PEI solution, transferred to shake flask and incubated for 3 hours at 37° C. in an incubator with a 5% CO₂ atmosphere. After the incubation, Excell medium with supplements was added. One day after transfection 12% Feed was added. After culturing for 7 days, the cell supernatant was collected by centrifugation. The solution was sterile filtered, supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a Protein A MabSelect SuRe column (GE Healthcare) equilibrated with 20 mM sodium phosphate, 20 mM sodium citrate pH 7.5. Unbound protein was removed by washing with equilibration buffer. The bound protein was eluted using a step elution created with 20 mM sodium citrate, 100 mM sodium chloride, 100 mM glycine, pH 3.0. The pH of collected fractions was adjusted by adding 1/10 (v/v) of 0.5 M sodium phosphate pH8.0. The protein was concentrated and filtered prior to loading on a HiLoad Superdex 200 column (GE Healthcare) equilibrated with 20 mM histidine, 140 mM sodium chloride, pH 6.0.

The protein concentration of purified constructs was determined by measuring the OD at 280 nm, using the molar extinction coefficient calculated on the basis of the amino acid sequence. Purity and molecular weight of the bispecific constructs were analyzed by CE-SDS in the presence and absence of a reducing agent (Invitrogen, USA) using a LabChipGXII (Caliper). The aggregate content of bispecific constructs was analyzed using a TSKgel G3000 SW XL analytical size-exclusion column (Tosoh) equilibrated in a 25 mM K2HPO$_4$, 125 mM NaCl, 200 mM L-Arginine Monohydrocloride, 0.02% (w/v) NaN$_3$, pH 6.7 running buffer at 25° C.

Table 4 summarizes the yield and final monomer content of the HER2 targeted and untargeted 4-1BB ligand timer-containing Fc (kih) fusion antigen binding molecules and control molecules.

TABLE 4

Biochemical analysis of Her2 targeted 4-1BB ligand trimer-containing Fc (kih) fusion antigen binding molecules

| Molecule | Monomer [%] (SEC) | Yield [mg/l] | CE-SDS (non-red) |
|---|---|---|---|
| Her2 (PER) 4-1-BBL | 98 | 3.5 | 89 |
| Her2 (TRAS) 4-1BBL | 100 | 2.8 | 97 |
| Her2 (aff-PER) 4-1BBL | 98 | 16.4 | 93 |

1.2. Generation and Production of Her2-Targeting 4-1BB Agonistic Antigen Binding Molecule as Mouse Surrogate (mu4-1BB-Her2)

As the mu 4-1BBL naturally forms a dimer (A. Brita et al. 2018) and not a timer as in humans, a bispecific agonistic 4-1BB antibody with bivalent binding for mouse 4-1BB and monovalent binding for Her2, also termed 2+1, has been prepared as illustrated in FIG. 2B.

In this example the HC1 of the construct was comprised of the following components, VHCH1 of an anti-mouse 4-1BB (clone MU137-1) followed by CH2 and CH3. HC2 was comprised of VLCH1 of anti-Her2 (clone 2C4, Adams C W et al, Cancer Immunol Immunother, 55(6), 2006, pp. 717-727, cross Fab) followed by VHCH1 of an anti-mouse 4-1BB (clone MU137-1) and CH2 and CH3. The mutations promoting heterodimerization described by Gunasekaran et al., J. Biol. Chem. 2010, 19637-19646, namely E356K and D399K (termed KK) and K392D and K409D (termed DD), were introduced in HC1 and HC2, respectively.

Furthermore, DAPG mutations were introduced in the constant regions of the heavy chains to abrogate binding to mouse Fc gamma receptors according to the method described e.g. in Baudino et al. J. Immunol. (2008), 181, 6664-6669, or in WO 2016/030350 A1. Briefly, the D265A and P329G mutations have been introduced in the constant region of the Fc-DD and Fc-KK heavy chains to abrogate binding to Fc gamma receptors (numbering according to Kabat EU index; i.e. D265A, P329G).

Combination of the Fc-DD with the Fc-KK chain allowed generation of a heterodimer, which includes one Her2 binding Fab and two 4-1BB binding Fabs. To improve correct pairing, the following mutations were introduced in the CH-CL of the anti-4-1BB Fab: E123R and Q124K in CL and K147E and K213E in CH1.

The amino acid sequences for the 2+1 anti-4-1BB (MU137-1), anti-Her2 (2C4) antibody can be found in Table 4A.

TABLE 4A

Amino acid sequences of 2+1 anti-mu 4-1BB anti-Her2 (2C4) antibody DAPG DDKK (mu4-1BB-Her2)

| SEQ ID NO: | Description | Sequences |
|---|---|---|
| 87 | VHCH1(EE) (MU137-1) Fc-KK | DVQLVESGGGLVQPGRSLKLSCAASGFIFSYFDMAWVRQAPTKG LEWVASISPSGDIPYYRDSVKGRFTVSRENAKSSLYLQMDSLRS EDTATYYCARRSYGGYSELDYWGQGVMVTSSAKTTPPSVYPLA PGSAAQTNSMVTLGCLVEGYFPEPVTVTWNSGSLSSGVHTFPAV LQSDLYTLSSSVTVPSSTWPSQTVTCNVAHPASSTKVDEKIVPR DCGCKPCICTVPEVSSVFIFPPKPKDVLTITLTPKVTCVVVAIS KDDPEVQFSWFVDDVEVHTAQTKPREEQINSTERSVSELPIMHQ DWLNGKEFKCRVNSAAFGAPIEKTISKTKGRPKAPQVYTIPPPK KQMAKDKVSLTCMITNFFPEDITVEWQWNGQPAENYKNTQPIMK TDGSYFVYSKLNVQKSNWEAGNTFTCSVLHEGLHNHHTEKSLSH SP |
| 88 | VLCH1 (2C4) VHCH1(EE) (MU137-1) Fc-DD | DTVMTQSHKIMSTSVGDRVSITCKASQDVSIGVAWYQQRPGQSP KLLIYSASYRYTGVPDRFTGSGSGTDFTFTISSVQAEDLAVYYC QQYYTYPYTFGGGTKLEIKSSAKTTPPSVYPLAPGSAAQTNSMV TLGCLVKGYFPEPVTVTWNSGSLSSGVHTFPAVLQSDLYTLSSS VTVPSSTWPSQTVTCNVAHPASSTKVDKKIVPRDCGGGGSGGGG SDVQLVESGGGLVQPGRSLKLSCAASGFIFSYFDMAWVRQAPTK GLEWVASISPSGDIPYYRDSVKGRFTVSRENAKSSLYLQMDSLR SEDTATYYCARRSYGGYSELDYWGQGVMVTVSSAKTTPPSVYPL APGSAAQTNSMVTLGCLVEGYFPEPVTVTWNSGSLSSGVHTFPA VLQSDLYTLSSSVTVPSSTWPSQTVTCNVAHPASSTKVDEKIVP RDCGCKPCICTVPEVSSVFIFPPKPKDVLTITLTPKVTCVVVAI SKDDPEVQFSWFVDDVEVHTAQTKPREEQINSTFRSVSELPIMH QDWLNGKEFKCRVNSAAFGAPIEKTISKTKGRPKAPQVYTIPPP KEQMAKDKVSLTCMITNFFPEDITVEWQWNGQPAENYDNTQPIM DTDGSYFVYSDLNVQKSNWEAGNTFTCSVLHEGLHNHHTEKSLS HSP |
| 89 | VLCL(RK)-Light chain (MU137-1) | DIQMTQSPASLSASLEEIVTITCQASQDIGNWLAWYHQKPGKSP QLLIYGTSSLADGVPSRFSGSSSGSQYSLKISRLQVEDIGIYYC LQAYGAPWTFGGGTKLELKRADAAPTVSIFPPSSRKLTSGGASV VCFLNNFYPKDINVKWKIDGSERQNGVLNSWTDQDSKDSTYSMS STLTLTKDEYERHNSYTCEATHKTSTSPIVKSFNRNEC |

TABLE 4A-continued

Amino acid sequences of 2+1 anti-mu 4-1BB anti-Her2
(2C4) antibody DAPG DDKK (mu4-1BB-Her2)

| SEQ ID NO: | Description | Sequences |
|---|---|---|
| 90 | VHCL-Light chain (2C4) | EVQLQQSGPELVKPGTSVKISCKASGFTFTDYTMDWVKQSHGKS LEWIGDVNPNSGGSTYNQRFKGKASLTVDRSSRIVYMELRSLTF EDTAVYYCARNLGPSFYFDYWGQGTTLTVSSASDAAPTVSIFPP SSEQLTSGGASVVCFLNNEYPKDINVKWKIDGSERQNGVLNSWT DQDSKDSTYSMSSTLTLTKDEYERHNSYTCEATHKTSTSPIVKS FNRNEC |

TABLE 4B

Biochemical analysis of 2 + 1 anti-mu 4-1BB anti-Her2 (2C4) antibody

| Molecule | Monomer [%] (SEC) | Yield [mg/l] | CE-SDS (non-red) |
|---|---|---|---|
| 2 + 1 H2H anti-mu 4-1BB anti-Her2 (2C4) muIgG1 DAPG DDKK (mu4-1BB-Her2) | 100 | 2.5 | 100 |

Example 2

Functional Characterization of Her2-Targeting Split Trimeric 4-1BB Ligand Fc Fusion Antigen Binding Molecules by Surface Plasmon Resonance Preparation of 4-1BB Fc (Kih) Fusion Molecule A DNA sequence encoding the ectodomain of human 4-1BB (amino acids 24 to 186 of human 4-1BB according to Q07011, SEQ ID NO:51) were subcloned in frame with the human IgG1 heavy chain CH2 and CH3 domains on the knob. An AcTEV protease cleavage site was introduced between an antigen ectodomain and the Fc of human IgG1. An Avi tag for directed biotinylation was introduced at the C-terminus of the antigen-Fc knob. Combination of the antigen-Fc knob chain containing the S354C/T366W mutations, with a Fc hole chain containing the Y349C/T366S/L368A/Y407V mutations allows generation of a heterodimer which includes a single copy of 4-1BB ectodomain containing chain, thus creating a monomeric form of Fc-linked antigen. Table 5 shows the amino acid sequences of the antigen Fc-fusion construct.

All 4-1BB-Fc-fusion molecule encoding sequences were cloned into a plasmid vector, which drives expression of the insert from an MPSV promoter and contains a synthetic polyA signal sequence located at the 3' end of the CDS. In addition, the vector contains an EBV OriP sequence for episomal maintenance of the plasmid.

For preparation of the biotinylated monomeric antigen/Fc fusion molecule, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 2:1:0.05 ratio ("antigen ECD-AcTEV-Fc knob": "Fc hole": "BirA").

For protein production in 500 ml shake flasks, 400 million HEK293 EBNA cells were seeded 24 hours before transfection. For transfection cells were centrifuged for 5 minutes at 210 g, and the supernatant was replaced by pre-warmed CD CHO medium. Expression vectors were resuspended in 20 mL of CD CHO medium containing 200 µg of vector DNA. After addition of 540 µL of polyethylenimine (PEI), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection, 1 mM valproic acid and 7% Feed 1 with supplements were added to the culture. After 7 days of culturing, the cell supernatant was collected

TABLE 5

Amino acid sequences of monomeric human 4-1BB Fc(kih) fusion molecule

| SEQ ID NO: | Antigen | Sequence |
|---|---|---|
| 52 | Fc hole chain | DKTHTCPPCPAPELLGGPSVFLFPPKPKDTLMISRTPEVTCVVV DVSHEDPEVKFNWYVDGVEVHNAKTKPREEQYNSTYRVVSVLTV LHQDWLNGKEYKCKVSNKALPAPIEKTISKAKGQPREPQVCTLP PSRDELTKNQVSLSCAVKGFYPSDIAVEWESNGQPENNYKTTPP VLDSDGSFFLVSKLTVDKSRWQQGNVFSCSVMHEALHNHYTQKS LSLSP |
| 53 | human 4-1BB antigen Fc knob chain | LQDPCSNCPAGTFCDNNRNQICSPCPPNSFSSAGGQRTCDICRQ CKGVFRTRKECSSTSNAECDCTPGFHCLGAGCSMCEQDCKQGQE LTKKGCKDCCFGTFNDQKRGICRPWTNCSLDGKSVLVNGTKERD VVCGPSPADLSPGASSVTPPAPAREPGHSPQVDEQLYFQGGSPK SADKTHTCPPCPAPELLGGPSVFLFPPKPKDTLMISRTPEVTCV VVDVSHEDPEVKFNWYVDGVEVHNAKTKPREEQYNSTYRVVSVL TVLHQDWLNGKEYKCKVSNKALPAPIEKTISKAKGQPREPQVYT LPPCRDELTKNQVSLWCLVKGFYPSDIAVEWESNGQPENNYKTT PPVLDSDGSFFLYSKLTVDKSRWQQGNVFSCSVMHEALHNHYTQ KSLSLSPGKSGGLNDIFEAQKIEWHE | by spinning down cells for 15 min at 210 g. The solution was sterile filtered (0.22 μm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HiTrap ProteinA HP column (CV=5 mL, GE Healthcare) equilibrated with 40 mL 20 mM sodium phosphate, 20 mM sodium citrate pH 7.5. Unbound protein was removed by washing with at least 10 column volumes of 20 mM sodium phosphate, 20 mM sodium citrate, 0.5 M sodium chloride containing buffer (pH 7.5). The bound protein was eluted using a linear pH-gradient of sodium chloride (from 0 to 500 mM) created over 20 column volumes of 20 mM sodium citrate, 0.01% (v/v) Tween-20, pH 3.0. The column was then washed with 10 column volumes of 20 mM sodium citrate, 500 mM sodium chloride, 0.01% (v/v) Tween-20, pH 3.0.

The pH of collected fractions was adjusted by adding 1/40 (v/v) of 2M Tris, pH8.0. The protein was concentrated and filtered prior to loading on a HiLoad Superdex 200 column (GE Healthcare) equilibrated with 2 mM MOPS, 150 mM sodium chloride, 0.02% (w/v) sodium azide solution of pH 7.4.

Recombinant human Her2 (ECD of ErbB2 protein, amino acids 23 to 652 of SEQ ID NO:54, UniProt Acc. No. P04626-1) is commercially available (e.g. from abcam, Cat No. ab168896) and was used for the determination of binding to Her2.

Determination of simultaneous binding of Her2-targeting split trimeric 4-1BB ligand Fc fusion antigen binding molecules The capacity of binding simultaneously human 4-1BB Fc(kih) and human Her2 was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). Biotinylated human 4-1BB Fc(kih) was directly coupled to a flow cell of a streptavidin (SA) sensor chip. Immobilization levels up to 450 resonance units (RU) were used.

The Her2-targeting split trimeric 4-1BB ligand Fc fusion constructs were passed at a concentration range of 200 nM with a flow of 30 μL/minute through the flow cells over 90 seconds and dissociation was set to zero sec. Human Her2 was injected as second analyte with a flow of 30 μL/minute through the flow cells over 90 seconds at a concentration of 500 nM (FIG. 3A). The dissociation was monitored for 120 sec. Bulk refractive index differences were corrected for by subtracting the response obtained in a reference flow cell, where no protein was immobilized.

As can be seen in the graphs of FIGS. 3B and 3C, the bispecific constructs could bind simultaneously human 4-1BB and human Her2.

Example 3

Functional Characterization of the Her2-Targeting Split Trimeric 4-1BB Ligand Fc Fusion Antigen Binding Molecules For the functional assays we tested the above described monovalent Her2-targeting split trimeric 4-1BB ligand Fc fusion antigen binding molecules, namely Her2 (PER)-4-1BBL, Her2 (aff-PER)-4-1BBL and Her2 (TRAS)-4-1BBL against two previously described agonistic anti-human 4-1BB antibodies, i.e. anti-human 4-1BB clone 20H4.9 human IgG4 (described in patents EP1670828B1 and U.S. Pat. No. 7,659,384(B2), antibody with heavy chains of SEQ ID NO:55 and light chains of SEQ ID NO:56) and anti-human 4-1BB clone MOR7480 human IgG2 (described in patent application WO2012/032433, antibody with heavy chains of SEQ ID NO:57 and light chains of SEQ ID NO:58), and a previously described fusion polypeptide Her2 (TRAS)-anticalin-4-1BB human IgG4 (fusion polypeptide of SEQ ID Nos 59 and 60 as described in patent application WO2016/177802).

Furthermore, different control molecules like untargeted DP47-4-1BBL (molecule comprising the amino acid sequences of SEQ ID Nos:37, 28, 61 and 62 and described as Control D in WO 2016/075278 A1, a germline control, termed DP47, not binding to the antigen was used to replace the antigen binding domain), DP47-anticalin-4-1BB human IgG4 (fusion polypeptide of SEQ ID NO:63 and 64 prepared in analogy to the molecules described in WO2016/17780), Her2 (TRAS) human IgG1 P329G LALA (antibody with heavy chains of SEQ ID NO:65 and light chains of SEQ ID NO:48), Her2 (PER) human IgG1 P329G LALA (antibody with heavy chains of SEQ ID NO:66 and light chains of SEQ ID NO:46) and a non-targeted DP47 human IgG1 P329G LALA (antibody with heavy chains of SEQ ID NO:67 and light chains of SEQ ID NO:62) were used. These IgG1 antibodies comprise the Pro329Gly, Leu234Ala and Leu235Ala mutations, to abrogate binding to Fc gamma receptors.

3.1. Binding to Her2-Expressing Tumor Cells

To test binding to cell surfaced expressed Her2, different human Her2-expressing tumor cells were used: human breast cancer cell line SK-Br3 (ATCC HTB-30), human breast cancer cell line KPL-4 (Kawasaki Medical School) and human gastric cancer cell line NCI-N87 (ATCC CRL-5822).

$0.2 \times 10^6$ tumor cells resuspended in DPBS (Gibco by Life Technologies, Cat. No. 14190-326) were added to each well of a round-bottom suspension cell 96-well plates (greiner bio-one, cellstar, Cat.-No. 650185). Cells were washed once with 200 μL DPBS and pellets were resuspended. 100 μL/well of 4° C. cold DPBS buffer containing 1:5000 diluted Fixable Viability Dye eFluor 450 (eBioscience, Cat.-No. 65-0863-18) were added and plates were incubated for 30 minutes at 4° C. Cells were washed once with 200 μL 4° C. cold DPBS buffer and resuspended in 50 μL/well of 4° C. cold FACS buffer (DPBS supplied with 2% FBS, 5 mM EDTA pH8 (Amresco, Cat.-No. E177) and 7.5 mM Sodium azide (Sigma-Aldrich 52002) containing titrated concentrations of the human split 4-1BB ligand molecules called Her2 (PER)-4-1BBL or Her2 (aff-PER)-4-1BBL or Her2 (TRAS)-4-1BBL as well as the control molecule, i.e. non-targeted DP47-4-1BBL, or anti-human 4-1BB antibodies called anti-human 4-1BB clone 20H4.9 huIgG4 or anti-human 4-1BB clone MOR-7480 huIgG2 or fusion proteins Her2 (TRAS)-anticalin-4-1BB huIgG4 or its untargeted control DP47-anticalin-4-1BB huIgG4 or Her2 (TRAS) huIgG1 P329G LALA or Her2 (PER) huIgG1 P329G LALA or DP47 huIgG1 P329G LALA. The cells were incubated for 1 hour at 4° C. and afterwards washed several times with cold FACS buffer to remove non bound antibodies. Cells were further stained with 50 μL/well of 4° C. cold FACS buffer 5 μg/mL PE-conjugated AffiniPure anti-human IgG F(ab')2-fragment-specific goat F(ab')2 fragment (Jackson ImmunoResearch, Cat. No. 109 116 097) for 30 minutes at 4° C. Cells were washed twice with 200 μL 4 C FACS buffer and cells were fixed in 50 DPBS containing 1% Formaldehyde (Sigma, HT501320-9.5L) for at least 10 min. Afterwards cells were resuspended in 100 µL 4° C. FACS buffer and acquired using the MACS Quant Analyzer 10 flow cytometer (Miltenyi Biotech) coupled to a Cytomat (ThermoFisher). Data was analyzed using FlowJo Version 10 (FLowJo LLC), Microsoft Excel and Graph Pad Prism Version 6 (Graph Pad Software Inc.).

As shown in FIGS. 4A to 4D, Her2 (PER)-4-1BBL and Her2 (aff-PER)-4-1BBL show a similar binding to human Her2 expressed by the human tumor cells SK-Br3 or NCI-N87, whereby the Her2 (aff-PER)-4-1BBL molecule shows slightly higher $EC_{50}$ values as listed in Table 6. The antibody Her2 (PER) huIgG P329G LALA binds—different to Her2 (PER)-4-1BBL—bivalent instead of monovalent. This is reflected by a slightly lower MFI (less antibodies/cell surface as the antibody can occupy two instead of one Her2 molecule) as shown in FIG. 4 and a slighter lower $EC_{50}$ value reflecting the avidity effect as listed in Table 6. The bivalent trastuzumab binding fusion protein Her2 (TRAS)-anticalin-4-1BB huIgG4 reflects a lower MFI than the bivalent binding Her2 (PER) huIgG P329G LALA and higher $EC_{50}$ values (shown in FIG. 4 and Table 6). This reflects the lower affinity and avidity of the trastuzumab (TRAS) binder compared to the pertuzumab (PER) binder.

TABLE 6

$EC_{50}$ values of binding curves to Her2+ tumor cell lines shown in FIG. 4

|  | Her2 (aff-PER)-4-1BBL | Her2 (PER)-4-1BBL | Her2 (PER) huIgG1 PGLALA | Her2 (TRAS)-anticalin 4-1BB huIgG4 |
|---|---|---|---|---|
| $EC_{50}$ [nM] on SK-Br3 cells | 7.3 | 2.4 | 1.3 | 4.1 |
| $EC_{50}$ [nM] on NCI-N87 cells | 4.3 | 2.9 | 2.1 | 5.3 |

Figure 5A:
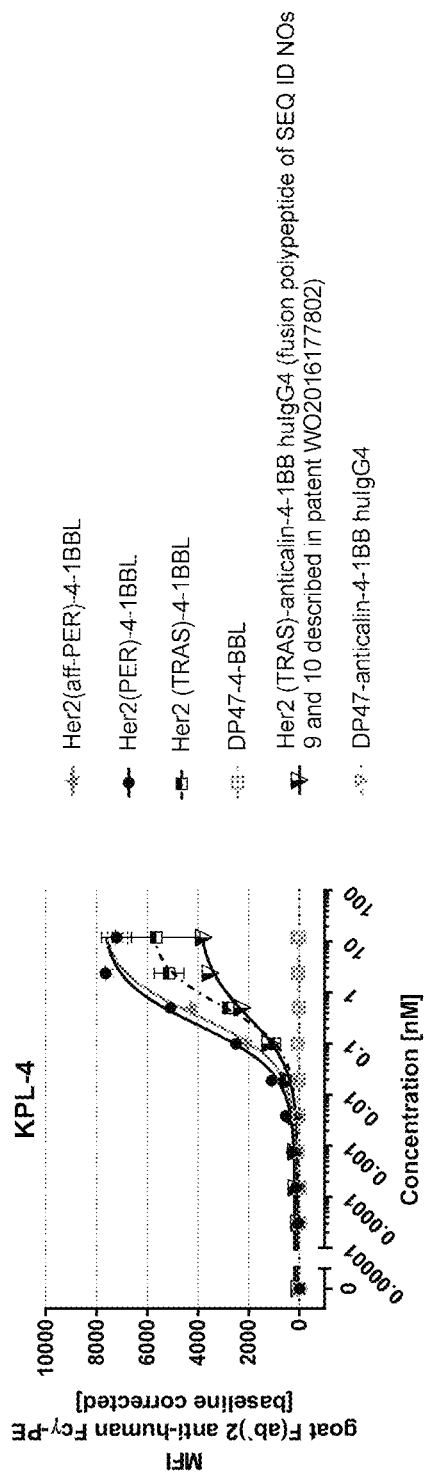
FIGS. 5A and 5B illustrate the binding of Her2-targeting split trimeric 4-1BB ligand Fc fusion antigen binding molecules to Her2 expressed by human breast cancer cell line KPL-4 the cell surface. Her2-targeting split 4-1BBL antigen binding molecules comprising the Her2 binders PER, aff-PER or trastuzumab (TRAS), the fusion protein Her2 (TRAS)-anticalin 4-1BB huIgG4 (as described in patent WO2016/177802) or previously described agonistic anti-human 4-1BB antibodies 20H4.9 huIgG4 or MOR-7480 huIgG2 or control molecules as indicated in the legend were incubated with Her2 expressing cell lines KL-4 at different concentrations as indicated in the X-axis. Afterwards excessive and not bound molecules were washed of and bound molecules were detected with a secondary binding PE-conjugated anti-human Fc-fragment specific goat IgG F(ab')2 fragment. The median of fluorescence intensity (MFI) was measured by flow cytometry and indicates the affinity (monovalent binders) or avidity (bivalent binders) of the tested molecules in a dose dependent manner. Values are baseline corrected by subtracting the blank control (e g staining with 2nd detection fragment only), shown is the mean+/−SEM.
Figure 5B:
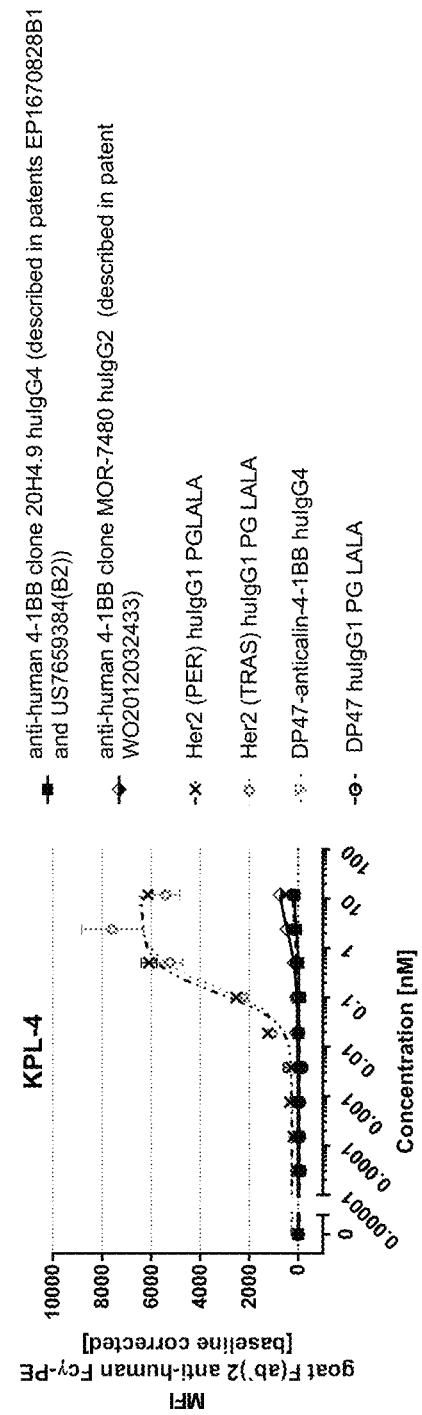

As shown in FIGS. 5A and 5B, Her2 (PER)-4-1BBL and Her2 (aff-PER)-4-1BBL show a similar binding to human Her2 expressed by the human breast cancer cell line KPL-4. Her2 (Tras)-4-1BBL has a lower MFI (FIG. 5A) and a lightly higher $EC_{50}$ value (Table 7) than Her2 (PER)-4-1BBL and Her2 (aff-PER)-4-1BBL, reflecting the lower affinity of trastuzumab (TRAS) compared to pertuzumab (PER). This is only shown for the monovalent Her2 binding constructs as the bivalent Her2-binding Her2 (TRAS) huIgG1 PG LALA and Her2 (PER) huIgG1 PG LALA molecules (displaying avidity) binding similar (FIG. 5B and Table 7). The bivalent Her2-binding molecule Her2 (TRAS)-anticalin-4-1BB huIgG4 showed a lower MFI than Her2 (Tras)-4-1BBL (FIG. 5A) but lower $EC_{50}$ (Table 6)—this reflects the difference between affinity (monovalent binding) and avidity (bivalent binding) of the two Her2 (TRAS)-targeted molecules.

TABLE 7

$EC_{50}$ values of binding curves to Her2+ tumor cell line KPL-4 shown in FIG. 5

|  | $EC_{50}$ [nM] on KPL-4 cells |
|---|---|
| Her2 (PER)-4-1BBL | 0.23 |
| Her2 (aff-PER)-4-1BBL | 0.35 |
| Her2 (TRAS)-4-1BBL | 0.54 |
| Her2 (TRAS)-anticalin 4-1BB huIgG4 | 0.34 |
| Her2 (PER) huIgG1 PGLALA | 0.12 |
| Her2 (TRAS) huIgG1 PGLALA | 0.16 |

3.2 Biological Activity Assays 3.2.1 NFκB Activation in Jurkat Cells Expressing Human 4-1BB and a NFκB-Luc Reporter Cassette Jurkat-hu4-1BB-NFκB-luc2 reporter cell line was ordered and received from Promega (CS196004) and cultured in RPMI 1640 (GIBCO by Life Technologies, Cat.-No. 42401-042) supplied with 10% FCS (GIBCO by Life Technologies, Cat.-No. 16000-044), 2 mM GlutaMAX-I (GIBCO by Life Technologies, Cat.-No. 35050-038), 1 mM Sodium-Pyruvate (SIGMA-Aldrich, Cat.-No. S8636), 0.1 mM MEM-non essential amino acid solution (SIGMA-Aldrich, Cat.-No. M7145), 25 mM HEPES (Sigma Life Science, Cat.-No. H0887), 600 µg/ml G-418 (Roche, Cat.-No. 04727894001) and 400 m/ml Hygromycin B (Roche, Cat.-No. 10843555001). To set up the activation assay, Jurkat-hu4-1BB-NFκB-luc2 were resuspended in RPMI 1640 supplied with 10% FCS and 2 mM GlutaMAX-I (further referred as assay medium) and 20'000 cells in 100 µL were seeded in each well of a tissue-culture treated flat bottom white 96-well plate (Huber lab, greiner bio-one Cat.-No. 655083) or T 000 cells in 10 µL were seeded in each well of a tissue-culture treated flat bottom white 384-well plate (Corning, Cat.-No. 3826). Afterwards 50 jut (96-well plate) or 10 µL (384-well plate) of either assay medium or Her2-expressing tumor cells (either SK-Br3, KLP-4 or NCI-N87, 100'000 cells/well in 96-well plate or 10'000 cells/well in 384-well plate) were added. Finally 50 µL (96-well plate) or 10 µL (384-well plate) assay medium containing different titrated concentrations of monovalent Her2-targeting split trimeric 4-1BB ligand Fc fusion antigen binding molecules called Her2 (PER)-4-1BBL, Her2(aff-PER)-4-1BBL or Her2 (TRAS)-4-1BBL or non-targeted control DP47-4-1BBL or anti-human 4-1BB antibodies 20H4.9 huIgG4 or MOR-7480 huIgG2 or the fusion proteins Her2 (TRAS)-anticalin-4-1BB huIgG4 or its untargeted control DP47-anticalin-4-1BB huIgG4 or the control antibodies Her2 (TRAS) huIgG1 P329G LALA or Her2 (PER) huIgG1 P329G LALA or DP47 huIgG1 P329G LALA were added. Plates were incubated for 6 h at 37° C. and 5% $CO_2$ in a cell culture incubator.

To detect luciferase activity using 96-well plates, plates were washed twice with 200 µL/well DPBS. 40 µl fresh prepared Reporter Lysis Buffer (Promega, Cat-No: E3971) were added to each well and the plate were stored over night at −20° C. The next day frozen plates and detection buffer (Luciferase 1000 Assay System, Promega, Cat. No. E4550) were thawed to room temperature. 100 µl of detection buffer were added to each well and plates were measured as fast as possible using a Tecan microplate reader (Tecan) with 500 ms integration time, no filter, collecting all wave length and top reading.

To detect luciferase activity using 384-well plates, to each well freshly to RT thawed 64 One-Glo Luciferase (Promega, Cat.-No. E6110) were added and plates were measured as fast as possible using a Tecan microplate reader (Tecan) with 500 ms integration time, no filter, collecting all wave length and top reading. Light emission emitting due to luciferase-mediated Luciferin oxidation was detected as units of released light (URLs). Data was analyzed using Microsoft Excel and Graph Pad Prism Version 6 (Graph Pad Software Inc.).

Figure 6:
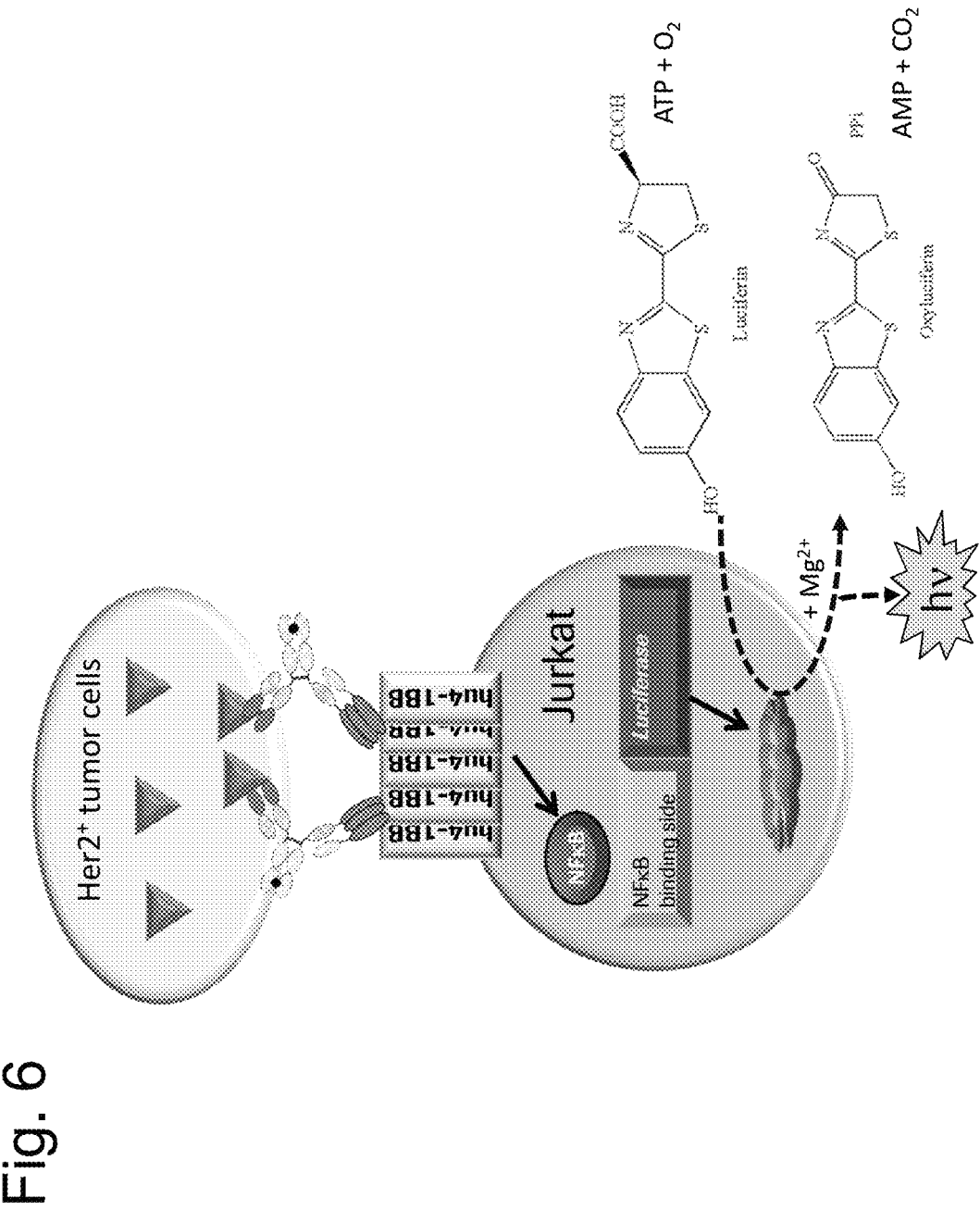
FIG. 6 shows a scheme that illustrates the general principal of the NFκB activation assay with human 4-1BB expressing Jurkat reporter cell line. Crosslinking of human 4-1BB, expressed on the reporter cells, induces NFκB activation and NFκB-mediated Luciferase expression. After lysis of the cells, luciferase can catalyze the oxidation of Luciferin to Oxyluciferin. This chemical reaction correlates positively with the strength of NFκB-mediated luciferase expression and can be measured by the strength of light emission (units of released light).

In FIG. 6, the setup of the Jurkat-hu4-1BB-NFκB-luc2 activation assay is illustrated. As shown in FIGS. 7A to 7F, Her2 (PER)-4-1BBL and Her2 (aff-PER)-4-1BBL display a similar activity in the presence of Her2-expressing tumor cells (FIGS. 7B and 7C), whereas the fusion protein Her2 (TRAS)-anticalin 4-1BB huIgG1 shows less activity potential—displayed in less area under the curve as well as a higher $EC_{50}$ value listed in Table 8. All three Her2 targeted 4-1BB agonistic molecules do not induce any activation of the reporter cell line Jurkat-hu4-1BB-NFκB-luc2 in the absence of Her2-expressing cells (FIG. 7A). Only the agonistic anti-human 4-1BB clone 20H4.9 huIgG4 was able to induce Jurkat-hu4-1BB-NFκB-luc2 activation—independent of the presence or absence of Her2-expressing tumor cells (FIGS. 7D, 7E and 7F).

TABLE 8

$EC_{50}$ values of NFκB-activation-induced Luciferase activity-curves shown in FIG. 7

| | Her2(PER)-4-1BBL | Her2 (aff-PER)-4-1BBL | Her2 (TRAS)-anticalin-4-1BB huIgG4 | Anti-hu 4-1BB clone 20H4.9 huIgG4 |
|---|---|---|---|---|
| $EC_{50}$ [nM] with no Her2+ cells | n.d. | n.d. | n.d. | 0.16 |
| $EC_{50}$ [nM] on SK-Br3 cells | 0.02 | 0.03 | 0.23 | 0.20 |
| $EC_{50}$ [nM] on NCI-N87 cells | 0.03 | 0.05 | 0.32 | 0.14 |

Figure 8A:
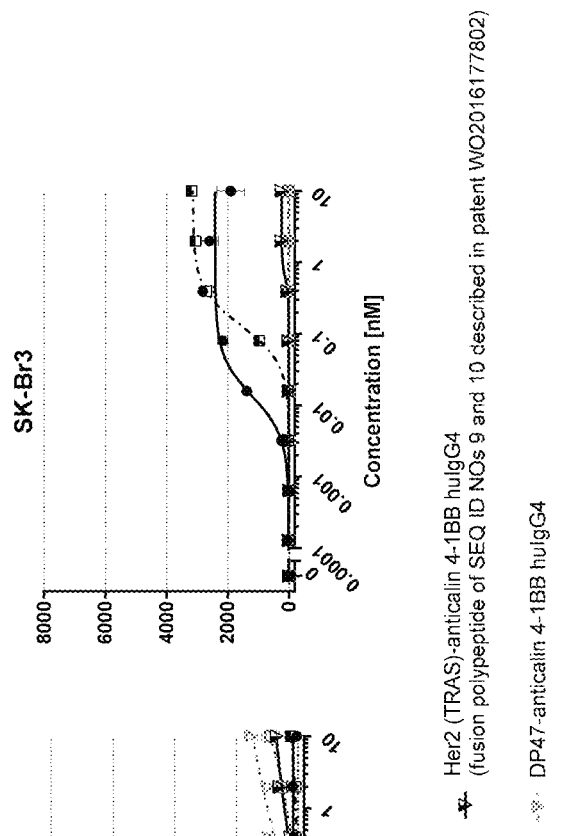
Figure 8B:
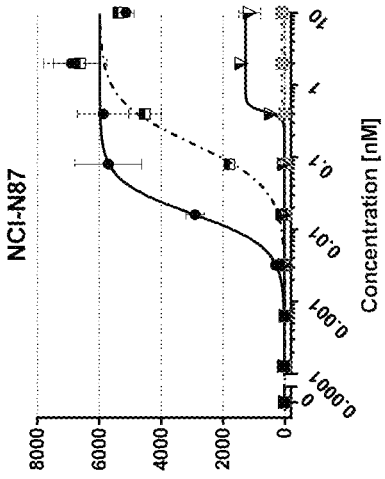
Figure 8C:
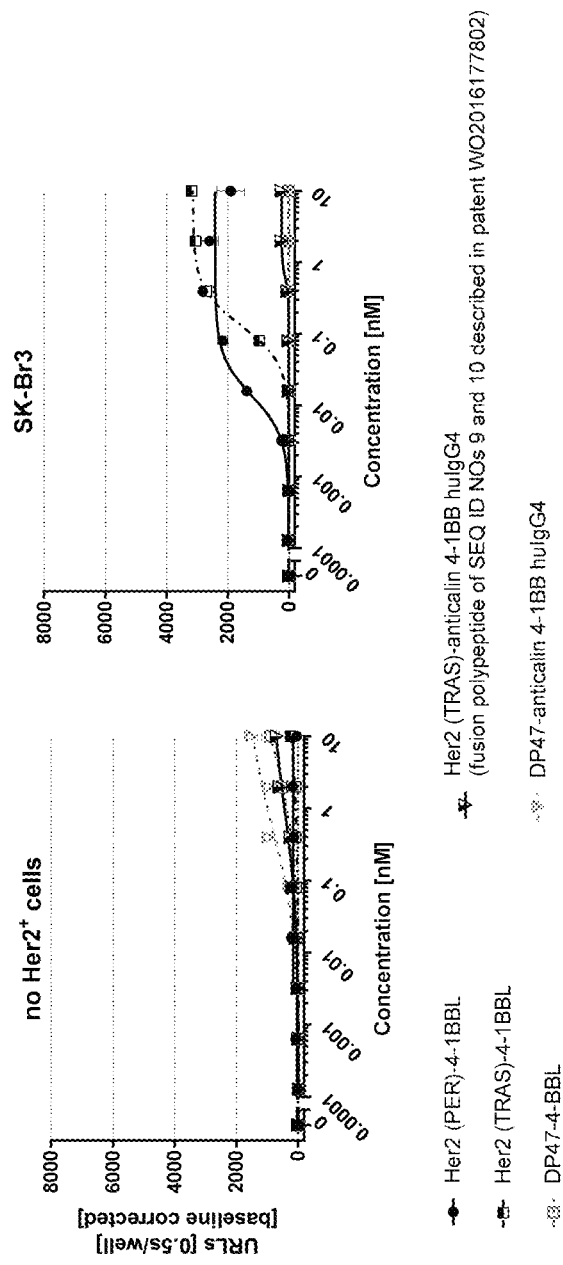
Figure 8D:
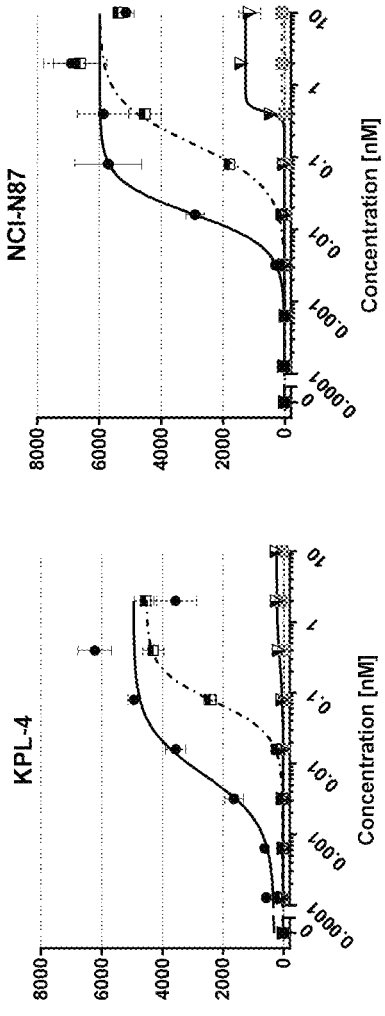

In FIGS. 8A to 8D, Her2 (PER)-4-1BBL is compared with Her2 (TRAS)-4-1BBL. Due to the lower affinity binder trastuzumab (TRAS) the Her2 (TRAS)-4-1BBL displays less activity than Her2 (PER)-4-1BBL (FIGS. 8B, 8C and 8D). This is displayed in a lower area under the curve and a higher $EC_{50}$ value as displayed in Table 9. In the absence of Her2+ tumor cells both molecules did not activate the reporter cell line Jurkat-hu4-1BB-NFκB-luc2 (FIG. 8A). Again the fusion protein Her2 (TRAS)-anticalin 4-1BB huIgG1 shows less activity than Her2 (PER)-4-1BBL or Her2 (TRAS)-4-1BBL shown by lower area under the curve, lower plateau values and a higher $EC_{50}$ (shown in FIGS. 8B-8D and Table 9) Similar as in FIG. 7, also in this experiment only the agonistic anti-human 4-1BB clone 20H4.9 huIgG4 was able to induce Jurkat-hu4-1BB-NFκB-luc2 activation—independent of the presence or absence of Her2-expressing tumor cells (FIGS. 8E-8Il).

TABLE 9

$EC_{50}$ values of NFκB-activation-induced Luciferase activity-curves shown in FIG 8

| $EC_{50}$ [nM] | Her2(PER)-4-1BBL | Her2 (TRAS)-4-1BBL | Her2 (TRAS)-anticalin-4-1BB huIgG4 | Anti-hu 4-1BB clone 20H4.9 huIgG4 |
|---|---|---|---|---|
| no Her-2+ cells | n.d. | 0.02 | 0.02 | 0.07 |
| SK-Br3 | 0.01 | 0.07 | 0.28 | 0.01 |
| KPL-4 | 0.01 | 0.13 | 0.62 | 0.02 |
| NCI-N87 | 0.02 | 0.16 | 0.43 | 0.02 |

3.2.2 Activation Assay of Human PBMCs in the Presence of Her2-Expressing Tumor Cell Line NCI-N87

For Her2-binding-mediated crosslinking the Her2-expressing adherent human gastric carcinoma cell line NCI-N87 was used. NCI-N87 cells were washed with DPBS (Gibco by Life Technologies, Cat. No. 14190 326) and treated with enzyme-free, PBS-based Cell Dissociation Buffer (Gibco by Life Technologies, Cat.-No. 13151-014) for 15 minutes at 37° C. Cells were harvested and resuspended in T cell medium consisting of RPMI 1640 supplied with 10% FCS, 2 mM GlutaMAX-I, 1 mM Sodium-Pyruvate (SIGMA-Aldrich, Cat.-No. S8636), 1% MEM-non essential Aminoacid Solution (SIGMA-Aldrich, Cat.-No. M7145) and 50 uM β-Mercaptoethanol (Sigma-Aldrich, Cyt.-No. M3148) and irradiated with 50 Gy (X-Ray Irradiator RS 2000, Rad source).

$2\times10^4$ NCI-N87 cells in 50 μL T cell medium were seeded to each well of a round bottom tissue culture 96-well plate (TTP, Cat.-No. 92697). 50 μL of T cell medium containing different titrated concentrations of human monovalent Her2-targeting split trimeric 4-1BB ligand Fc fusion antigen binding molecules Her2 (PER)-4-1BBL, Her2(aff-PER)-4-1BBL or Her2 (TRAS)-4-1BBL or non-targeted control molecule DP47-4-1BBL or agonistic anti-human 4-1BB antibodies anti-human 4-1BB clone 20H4.9 huIgG4 or anti-human 4-1BB clone MOR-7480 huIgG2 or fusion proteins Her2 (TRAS)-anticalin-4-1BB huIgG4 or its untargeted control DP47-anticalin-4-1BB huIgG4 or the control antibodies Her2 (TRAS) huIgG1 P329G LALA, Her2 (PER) huIgG1 P329G LALA or DP47 huIgG1 P329G LALA were added. Human PBMCs isolated from a buffy coat of a healthy donor were labeled in 37° C. warm DPBS containing 40 nM CFDA-SE (SIGMA-Aldrich, Cat.-No. 21888-25MG-F) for 15 min at 37° C. CFSE-labeling was stopped by adding fetal bovine serum (FBS), PBMCs were washed twice and resuspended in T cell medium to a final concentration of $1.5\times10^6$ cells/mL. 50 μL of this PBMC cell solution were seeded to each well to add $7.5\times10^4$ CFSE-labeled PBMCs well. Finally a stock solution of T cell medium containing 8 nM agonistic anti-human CD3 human IgG1 clone V9 was prepared and 50 μL/well were added to each well giving a final concentration of 2 nM anti-human CD3 human IgG1 clone V9.

Plates were incubated for 4 days at 37° C. and 5% $CO_2$ in a cell incubator. Cells were washed with DPBS and stained with 100 μL/well DPBS containing 1:1000 diluted LIVE/DEAD Fixable Aqua Dead Cell Stain Kit (Molecular Probes by Life Technology, Cat.-No. L34957) for 30 min at 4° C. Cells were washed once with 200 μL/well DPBS and stained with 50 μL FACS buffer (DPBS supplied with 2% FBS, 5 mM EDTA pH8 (Amresco, Cat. No. E177) and 7.5 mM Sodium azide (Sigma-Aldrich S2002)) containing 0.1 μg/mL PerCP-Cy5.5-conjugated anti-human CD137 mouse IgG1 κ (clone 4B4-1, BioLegend, Cat.-No. 309814), 0.1 μg/mL PE/Cy7-conjugated anti-human PD-1 mouse IgG1 κ (clone EH12.2H7, BioLegend, Cat.-No. 329918), 0.03 μg/mL APC-conjugated anti-human CD25 mouse IgG1 (clone BC96, BioLegend, Cat.-No. 302610), 0.06 μg/mL APC/Cy7-conjugated anti-human CD8 Mouse IgG1 κ (clone RPA-T8, BioLegend, Cat.-No. 3301016), BV421-conjugated anti-human CD4 Mouse IgG1 κ (clone RPA-T4, BioLegend, Cat.-No. 300532) for 30 min at 4° C. Cells were washed twice with 200 μL/well DPBS and incubated for 30 min at 4° C. with 50 μL/well freshly prepared FoxP3 Perm/Fix buffer (eBioscience Cat.-No. 00-5123). Cells were washed twice with 200 μL/well DPBS, resuspended in 50 μL/well freshly prepared Perm-buffer (eBioscience Cat.-No 00-8333) supplied with PE-conjugated 1:250 diluted anti-human Granzyme B mouse IgG1 κ (clone GB11, Lot 4269803, BD Pharmingen, Cat.-No. 561142) and incubated for 1 h at 4° C. Plates were washed twice with 200 μL/well DPBS and cells were fixed for 15 min with DPBS containing 1% Formaldehyde (Sigma, HT501320-9.5L). Cells were resuspended in 100 μL/well FACS-buffer and acquired using the MACS Quant Analyzer X (Miltenyi Biotech). Data was analyzed using FlowJo V10 (FlowJo, LLC), Microsoft Excel and GraphPad Prism 6 (GraphPad Software, Inc).

In FIG. 9, the setup of the PBMC activation assay is illustrated. As shown in FIGS. 10A to 10F and FIGS. 11A to 11F, Her2 (PER)-4-1BBL induced the strongest activation of CD8 and CD4 T cells indicated by the upregulation of IL-2Rα (CD25) (FIGS. 10A and 11A), intracellular increase of granzyme B (FIGS. 10B and 11B) and increased proliferation (FIGS. 10C and 11C). Her2 (TRAS)-4-1BBL induced as well a strong activation of CD8 (FIGS. 10A-10C) and CD4 T cells (FIGS. 11A-11C), however with higher $EC_{50}$ values. The fusion polypeptide Her2(TRAS)-anticalin 4-1BB huIgG4 mediated less T cell activation displayed mainly in much lower frequency of $CD25^+$, Granzyme $B^{high}$ and proliferating CD8 (FIGS. 10A-10C) and CD4 T cells (FIGS. 11A-11C). The agonistic anti-human 4-1BB clone 20H4.9 huIgG4 antibody displays again some activation potential, however not as potent as the Her2-targeted 4-1BB agonist polypeptides (FIGS. 10D-10F and FIGS. 11D-11F). $EC_{50}$ values and area under the curve values above background are listed in Table 10 and Table 11.

TABLE 10

$EC_{50}$ values of CD8 and CD4 T cell activation curves shown in FIG. 10 and 11

| $EC_{50}$ [nM] PBMC activation assay | Her2(PER)-4-1BBL | Her2 (TRAS)-4-1BBL | Her2 (TRAS)-anticalin-4-1BB huIgG4 | Anti-hu 4-1BB clone 20H4.9 huIgG4 | Anti-hu 4-1BB clone MOR-7480 hu IgG2 |
|---|---|---|---|---|---|
| % $CD25^+$ CD8 | 0.01 | 0.06 | n.d. | n.d. | n.d. |
| % $GnzB^{high}$ CD8 | 0.02 | 0.19 | 0.19 | n.d. | n.d. |
| % proliferating CD8 | 0.01 | 0.04 | 0.05 | ~0.03 | n.d. |
| % $CD25^+$ CD4 | 0.02 | 0.08 | n.d. | n.d. | n.d. |
| % $GnzB^{high}$ CD4 | 0.01 | 0.19 | 0.21 | n.d. | n.d. |
| % proliferating CD4 | 0.02 | 0.04 | 0.05 | 0.01 | 0.13 |

TABLE 11

Area under the curve above background values of CD8 and CD4 T cell activation curves shown in FIG. 10 and 11

| AUC above background | Her2(PER)-4-1BBL | Her2 (TRAS)-4-1BBL | Her2 (TRAS)-anticalin-4-1BB huIgG4 | Anti-hu 4-1BB clone 20H4.9 huIgG4 | Anti-hu 4-1BB clone MOR-7480 hu IgG2 |
|---|---|---|---|---|---|
| % $CD25^+$ CD8 | 10 | 8 | 4 | n.d. | n.d. |
| % $GnzB^{high}$ CD8 | 122 | 63 | 58 | n.d. | n.d. |
| % proliferating CD8 | 38 | 27 | 13 | 16 | 0.1 |
| % $CD25^+$ CD4 | 81 | 64 | 15 | n.d. | n.d. |
| % $GnzB^{high}$ CD4 | 55 | 27 | 23 | n.d. | n.d. |
| % proliferating CD4 | 25 | 20 | 12 | 10 | 12 |

3.2.3 Activation Assay of of Mouse Splenocytes in the Presence of Her2-Expressing Tumor Cell Line KPL-4

For Her2-binding-mediated crosslinking the Her2-expressing adherent human breast cancer cell line KPL-4 was used. KPL-4 cells were washed with DPBS (Gibco by Life Technologies, Cat. No. 14190 326) and treated with enzyme-free, PBS-based Cell Dissociation Buffer (Gibco by Life Technologies, Cat.-No. 13151-014) for 15 minutes at 37° C. Cells were harvested and resuspended in T cell medium consisting of RPMI 1640 supplied with 10% FCS, 2 mM GlutaMAX-I, 1 mM Sodium-Pyruvate (SIGMA-Aldrich, Cat.-No. S8636), 1% MEM-non essential Aminoacid Solution (SIGMA-Aldrich, Cat.-No. M7145) and 50 uM β-Mercaptoethanol (Sigma-Aldrich, Cyt.-No. M3148) and irradiated with 50 Gy (X-Ray Irradiator RS 2000, Rad source).

$2 \times 10^4$ irradiated KPL-4 cells in 50 µl T cell medium were seeded to each well of a round bottom tissue culture 96-well plate (TTP, Cat.-No. 92697). 50 µL, of T cell medium containing different titrated concentrations of mouse surrogate mu4-1BB-Her2 or the untargeted control mu4-1BB muIgG1 DAPG were added. Mouse splenocytes were isolated from freshly collected spleens of C57BL/6 mice (Octo Dissociator, Miltenyi Biotech following manufacture's protocol). Afterwards erythrocytes were lysed by an incubation for 10 min at room temperature in ACK lysis buffer (0.15M $NH_4CL$, 10 mM $KHCO_3$, 0.1 mM EDTA in $ddH_2O$, pH 7.2). Lysis was stopped by adding T cell medium and cells were washed with DPBS. Mouse splenocytes were labeled by incubation in 37° C. warm DPBS containing 0.5 µM CellTrace violet proliferation dye (Molecular Probes by Life Technologies, Cat.-No. C34557) for 15 min at 37° C. Labeling was stopped by adding fetal bovine serum (FBS), mouse splenocytes were washed twice and resuspended in T cell medium to a final concentration of $3 \times 10^6$ cells/mL. 50 µl of this mouse splenocyte cell solution were seeded to each well to add $15 \times 10^4$ violet proliferation dye-labeled mouse splenocytes per well. Finally a stock solution of T cell medium containing 2 µg/mL agonistic anti-mouse CD3ε armenian hamster IgG1 clone 1452C11 (BioLegend Cat.-No. 100331) was prepared and 50 µL/well were added to each well giving a final concentration of 0.5 µg/mL agonistic anti-mouse CDR armenian hamster IgG1 clone 1452C11.

Plates were incubated for 3 days at 37° C. and 5% $CO_2$ in a cell incubator. Cells were washed with DPBS and stained with 100 µL/well DPBS containing 1:1000 diluted LIVE/DEAD Fixable Aqua Dead Cell Stain Kit (Molecular Probes by Life Technology, Cat.-No. L34957) for 30 min at 4° C. Cells were washed once with 200 µL/well DPBS and stained with 50 µl FACS buffer (DPBS supplied with 2% FBS, 5 mM EDTA pH8 (Amresco, Cat. No. E177) and 7.5 mM Sodium azide (Sigma-Aldrich S2002)) containing 0.67 µg/mL anti-mouse CD8a-APC-Cy7 (BioLegend, Cat.-No. 100714, clone 53-6.7, rat IgG2a κ), 0.67 µg/mL anti-mouse CD4-APC (BioLegend, Cat.-No. 100412 clone GK1.5, rat IgG2b, 0.67 µg/mL anti-mouse CD137-PE (BioLegend, Cat.-No. 106106, clone 17B5, Syrian Hamster IgG), 0.67 µg/mL anti-mouse CD25-PerCP-Cy5.5 (BioLegend, Cat.-No. 101912, clone 3C7, Rat IgG2b, κ) for 30 min at 4° C. Cells were washed twice with 200 µL/well DPBS and incubated for 30 min at 4° C. with 50 µL/well freshly prepared FoxP3 Perm/Fix buffer (eBioscience Cat.-No. 00-5123). Cells were washed twice with 200 µL/well DPBS, resuspended in 50 µL/well freshly prepared Perm-buffer (eBioscience Cat.-No 00-8333) supplied with 10 µg/mL anti-mouse Eomes-AlexaFluor 488 (eBioscience, Cat.-No. 53-4875-82, clone Dan11mag, ratIgG2a) and incubated for 1 h at 4° C. Plates were washed twice with 200 µL/well DPBS and cells were fixed for 15 min with DPBS containing 1% Formaldehyde (Sigma, HT501320-9.5L). Cells were resuspended in 100 µL/well FACS-buffer and acquired using the MACS Quant Analyzer X (Miltenyi Biotech). Data was analyzed using FlowJo V10 (FlowJo, LLC), Microsoft Excel and GraphPad Prism 6 (GraphPad Software, Inc).

In FIG. 12, the setup of the mouse splenocyte activation assay is illustrated. As shown in FIGS. 13A to 13D mouse surrogate mu4-1BB-Her2 induced activation of CD8 and CD4 T cells indicated by the upregulation of IL-2Rα (CD25) (FIGS. 13A and 13C) and increased proliferation (FIGS. 13B and 13D). In contrast, non-targeted agonistic mu4-1BB muIgG1 DAPG did not induce such an activation. Therefore, this synergistic costimulatory effect is strongly dependent on Her2-crosslinking $EC_{50}$ values and area under the curve values above background are listed in Table 12 and Table 13.

TABLE 12

$EC_{50}$ values of mouse CD8 and CD4 T cell activation curves shown in FIG. 13

| $EC_{50}$ [nM] Mouse splenocyte activation assay | mu4-1BB-Her2 |
|---|---|
| % $CD25^+$ CD8 | 0.35 |
| % proliferating CD8 | ~0.03 |
| % $CD25^+$ CD4 | 0.36 |
| % proliferating CD4 | ~0.1 |

TABLE 13

Area under the curve of mouse CD8 and CD4 T cell activation curves shown in FIG. 14

| AUC Mouse splenocyte activation assay | mu4-1BB muIgG1 DAPG | mu4-1BB-Her2 |
|---|---|---|
| % $CD25^+$ CD8 | 53 | 64 |
| % proliferating CD8 | 354 | 380 |
| % $CD25^+$ CD4 | 70 | 80 |
| % proliferating CD4 | 208 | 279 |

Example 4

In Vitro Testing of the Combination of Her2(PER)-4-1BBL and Her2/CD3 Bispecific Antibody To test the combination of Her2(PER)-4-1BBL and Her2/CD3 bispecific antibody (Her2 TDB, Junttila et al., 2014), we generated a 4-1BBL bispecific molecule that binds to Her2 using pertuzumab (2C4) derived Fab (FIG. 2A). Trastuzumab based Her2/CD3 bispecific antibody (Her2-TDB) binds to domain IV of Her2 (Cho et al., 2003), whereas Her2(PER)-4-1BBL binds to domain II of HER2 (Franklin et al., 2004) non-competitively. Her2 TDB was produced as described in WO 2015/095392 A1. The mouse surrogate is a muIgG2a HER2 TDB with the "knob" arm being murine anti-HER2(hu4D5) and the "hole" arm being chimeric anti-murine CD3(2C11) (Leo et al. Proc Natl Acad Sci USA. 84: 1374-1378, 1987).

Human Peripheral Blood Mononuclear Cells (PBMC) and $CD8^+$ T Cell Isolation:

Human PBMC were separated from the blood of healthy volunteers using Lymphoprep medium (STEMCELL Technologies). $CD8^+$ cells were extracted from PBMC using human $CD8^+$ Isolation Kit from Miltenyi Biotec (#130-094-156) by negative selection.

In Vitro T Cell Activation:

All antibodies for flow cytometry cell staining were from BD Biosciences (San Jose, CA). Human CD8+ cells and human breast cancer cell line SKBR3 cells (in 3:1 ratio) were incubated in the presence of test article for 24 hours in flat-bottom 96 well plate (BD). After incubation, cells were transferred to a new V-bottom 96 well plate. Cells were stained with anti CD8-FITC, anti CD69-PE, and anti CD25-APC. CD69 and CD25 surface expression was detected on $CD8^+$ T cells by flow cytometry. The percentage of $CD8^+$ $CD69^+$ $CD25^+$ was reported as T cell activation.

In Vitro Target Cell Killing:

Effector cells (human $CD8^+$ cells) and target cells (SKBR3, at density of 20,000 cells per well) were incubated in 3:1 ratio in the presence of test article for 48 hours in black, clear-bottomed 96 well plates. In the end of incubation, cell supernatant was discarded and plates were washed 2× with PBS. 100 uL Cell Titer-Glow Luminescent Cell Viability reagent (Promega cat #G7570) was added and plates were read on luminometer as described in the instructions.

In Vitro T Cell Proliferation & Survival:

$CD8^+$ T cell proliferation response was detected by measuring carboxyfluorescein succinimidyl ester (CFSE) fluorescence intensity dilution. In brief, Human $CD8^+$ T cells were labeled with CFSE and co-cocultured with SKBR3 target cells and tested articles. HER2 TDB was used at 100 ng/ml and 4-1BB agonist was used at 1000 ng/ml. An aliquot of the cells from day 0 (fresh isolated and labeled $CD8^+$), day 3 and day 7 were analyzed by flow cytometry for CFSE fluorescence intensity. The survival of $CD8^+$ T cells were measured by number of live $CD8^+$ T cells in day 0, day 3 and day 7.

As expected, single agent Her2(PER)-4-1BBL did not induce T cell activation or target cell killing in vitro (FIGS. 14A and 14B, respectively). Anti-HER2/CD3-TDB induced robust T cell activation and tumor cell killing, but this was not substantially enhanced by co-treatment with Her2(PER)-4-1BBL. In contrast, addition of Her2(PER)-4-1BBL substantially enhanced anti-HER2/CD3-TDB induced T cell proliferation/survival in vitro (FIGS. 15A and 15B).

Example 5

Figure 16A:
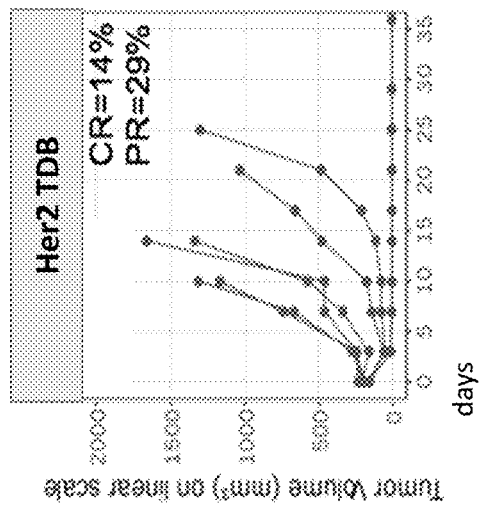
Figure 16B:
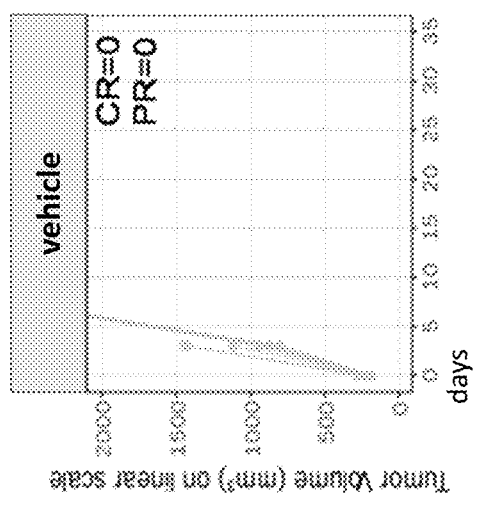
Figure 16C:
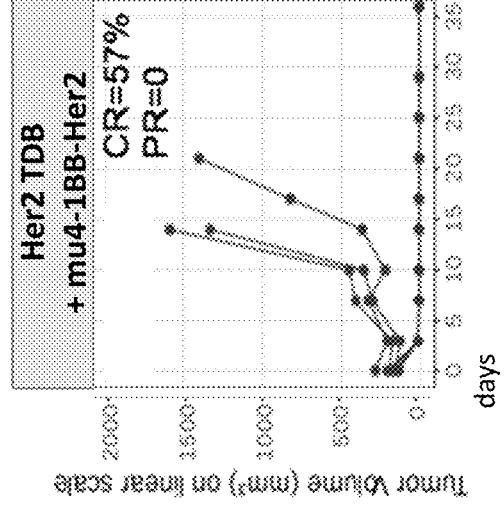
Figure 16D:
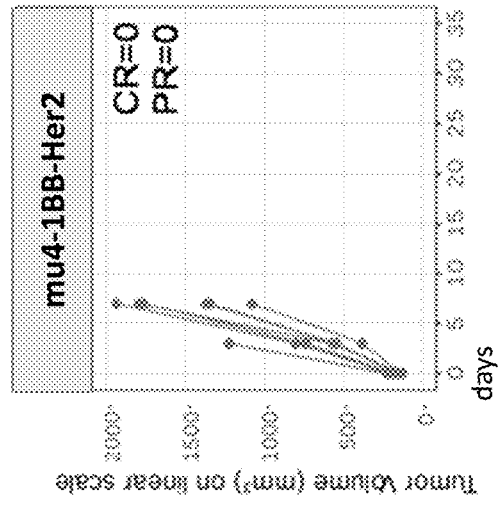

In Vivo Anti-Tumor Efficacy of of the Combination of Mouse Surrogate Her2(2C4)-4-1BB and Her2/CD3 Bispecific Antibody Anti-tumor activity of the murine 4-1BB agonists was tested in immune-competent mice that were implanted with human HER2 expressing Fo5 tumor allografts (Lewis Phillips et al., 2008). Single agent HER2 TDB treatment typically results in transient responses in treatment of this model and complete responses are rare even with high dose levels (Li et al., 2018). TDB co-treatment with mu4-1BB Her2 did not result in significant improvement of responses, but four of seven mice (57%) treated with the combination of Her2 TDB and mu4-1BB-Her2 demonstrated complete responses without detectable tumors in the end of study (FIG. 16D).

Anti-Tumor Efficacy—Fo5 Tumor Allograft Model:

A 1 cm incision was made in the skin just rostral to the third mammary fat pad on female FVB WT mice. A pocket for the tumor was made into the No. 2/3 mammary fat pad and a 2×2 mm MMTV-Her2-transgenic Founder #5 (Fo5) tumor section (Lewis Phillips et al., 2008) was placed into the pocket. The skin was closed using wound clips. Wound clips were removed at 7-10 days post-surgery and mice were monitored for appearance of palpable tumors. When tumor volumes grew to an average of ~190 $mm^3$, they were placed into treatment cohorts with an equivalent tumor volume average size.

Tumor-bearing mice were divided in groups of 7 animals per group (N=7). One group was treated with 0.5 mg/kg i.v.

doses of HER2 TDB twice weekly (qwx2) on days 0, 7 and 14. Another group was treated with 10 mg/kg doses of mu4-1-BB-Her(2C4) (mouse surrogate) twice weekly (qwx2) injected i.v. on day 0 and i.p. on day 7 and a further group was treated with 0.5 mg/kg i.v. doses of Her2 TDB twice weekly (qwx2) on days 0, 7 and 14 and 10 mg/kg doses of mu4-1-BB Her2(2C4) (mouse surrogate) twice weekly (qwx2) injected i.v. on day 0 and i.p. on day 7. The control group was only treated with vehicle.

CITATIONS

Ascierto, P. A., E. Simeone, M. Sznol, Y. X. Fu, and I. Melero (2010), Clinical experiences with anti-CD137 and anti-HER2 therapeutic antibodies. Semin Oncol 37:508-516.

Aggarwal B. B. (2003), Signalling pathways of the TNF superfamily: a double-edged sword. Nat. Rev. Immunol. 3(9), 745-56.

Banner D. et al (1993), Crystal structure of the soluble human 55 kd TNF receptor-human TNF beta complex: implications for TNF receptor activation. Cell 73, 431-445.

Bodmer J., Schneider P. and Tschopp, J. (2002), The molecular architecture of the TNF superfamily. Trends in Biochemical Sciences 27(1), 19-26.

Broll, K., Richter, G., Pauly, S., Hofstaedter, F., and Schwarz, H. (2001). CD137 expression in tumor vessel walls. High correlation with malignant tumors. Am J Clin Pathol 115, 543-549.

Buechele, C., Baessler, T., Schmiedel, B. J., Schumacher, C. E., Grosse-Hovest, L., Rittig, K., and Salih, H. R. (2012). 4-1BB ligand modulates direct and Rituximab-induced NK-cell reactivity in chronic lymphocytic leukemia. Eur J Immunol 42, 737-748.

Chen S., Lee L., Fisher T., Jessen B., Elliott M., Evering W., Logronio K., Tu K. H., Tsaparikos K., Li X., Wang H., Ying C., Xiong M., Van Arsdale T., and. Lin J. C. (2015), Combination of 4-1BB Agonist and PD-1 Antagonist Promotes Antitumor Effector/Memory CD8 T Cells in a Poorly Immunogenic Tumor Model. Cancer Immunology Research 3(2), 149-160. Published online 11 Nov. 2014.

Cho, H. S., Mason, K., Ramyar, K. X., Stanley, A. M., Gabelli, S. B., Denney, D. W., Jr., and Leahy, D. J. (2003). Structure of the extracellular region of HER2 alone and in complex with the Herceptin Fab. Nature 421, 756-760

Choi, B. K., Kim, Y. H., Kwon, P. M., Lee, S. C., Kang, S. W., Kim, M. S., Lee, M. J., and Kwon, B. S. (2009). 4-1BB functions as a survival factor in dendritic cells. J Immunol 182, 4107-4115.

Cuadros, C., Dominguez, A. L., Lollini, P. L., Croft, M., Mittler, R. S., Borgstrom, P., and Lustgarten, J. (2005). Vaccination with dendritic cells pulsed with apoptotic tumors in combination with anti-OX40 and anti-4-1BB monoclonal antibodies induces T cell-mediated protective immunity in Her-2/neu transgenic mice. Int J Cancer 116, 934-943.

Curran, M. A., Kim, M., Montalvo, W., Al-Shamkhani, A, and Allison, J. P. (2011). Combination CTLA-4 blockade and 4-1BB activation enhances tumor rejection by increasing T-cell infiltration, proliferation, and cytokine production. PLoS One 6, e19490.

Diehl, L., van Mierlo, G. J., den Boer, A. T., van der Voort, E., Fransen, M., van Bostelen, L., Krimpenfort, P., Melief, C. J., Mittler, R., Toes, R. E., and Offringa, R. (2002). In vivo triggering through 4-1BB enables Th-independent priming of CTL in the presence of an intact CD28 costimulatory pathway. J Immunol 168, 3755-3762.

Dubrot, J., Milheiro, F., Alfaro, C., Palazon, A., Martinez-Forero, I., Perez-Gracia, J. L., Morales-Kastresana, A., Romero-Trevejo, J. L., Ochoa, M. C., Hervas-Stubbs, S., et al. (2010). Treatment with anti-CD137 mAbs causes intense accumulations of liver T cells without selective antitumor immunotherapeutic effects in this organ. Cancer Immunol Immunother 59, 1223-1233.

Franklin, M. C., Carey, K. D., Vajdos, F. F., Leahy, D. J., de Vos, A. M., and Sliwkowski, M. X. (2004). Insights into ErbB signaling from the structure of the ErbB2-pertuzumab complex. Cancer Cell 5, 317-328.

Futagawa, T., Akiba, H., Kodama, T., Takeda, K., Hosoda, Y., Yagita, H., and Okumura, K. (2002). Expression and function of 4-1BB and 4-1BB ligand on murine dendritic cells. Int Immunol 14, 275-286.

Guo, Z., Cheng, D., Xia, Z., Luan, M., Wu, L., Wang, G., and Zhang, S. (2013). Combined TIM-3 blockade and CD137 activation affords the long-term protection in a murine model of ovarian cancer. J Transl Med 11, 215.

Heinisch, I. V., Daigle, I., Knopfli, B., and Simon, H. U. (2000). CD137 activation abrogates granulocyte-macrophage colony-stimulating factor-mediated anti-apoptosis in neutrophils. Eur J Immunol 30, 3441-3446.

Hornig, N., Kermer, V., Frey, K., Diebolder, P., Kontermann, R. E., Mueller, D. (2012), Combination of a bispecific antibody and costimulatory antibody-ligand fusion proteins for targeted cancer immunotherapy. J. Immunother. 35, 418-429.

Ju, S. A., Cheon, S. H., Park, S. M., Tam, N. Q., Kim, Y. M., An, W. G., and Kim, B. S. (2008). Eradication of established renal cell carcinoma by a combination of 5-fluorouracil and anti-4-1BB monoclonal antibody in mice. Int J Cancer 122, 2784-2790.

Junttila, T. T., Li, J., Johnston, J., Hristopoulos, M., Clark, R., Ellerman, D, Wang, B. E., Li, Y., Mathieu, M., Li, G., et al. (2014). Antitumor efficacy of a bispecific antibody that targets HER2 and activates T cells. Cancer Res 74, 5561-5571.

Kienzle, G., and von Kempis, J. (2000). CD137 (ILA/4-1BB), expressed by primary human monocytes, induces monocyte activation and apoptosis of B lymphocytes. Int Immunol 12, 73-82.

Kim, D. H., Chang, W. S., Lee, Y. S., Lee, K. A., Kim, Y. K., Kwon, B. S., and Kang, C. Y. (2008). 4-1BB engagement costimulates NKT cell activation and exacerbates NKT cell ligand-induced airway hyperresponsiveness and inflammation. J Immunol 180, 2062-2068.

Kim, Y. H., Choi, B. K., Oh, H. S., Kang, W. J., Mittler, R. S., and Kwon, B. S. (2009). Mechanisms involved in synergistic anticancer effects of anti-4-1BB and cyclophosphamide therapy. Mol Cancer Ther 8, 469-478.

Kwon, B. S., and Weissman, S. M. (1989). cDNA sequences of two inducible T-cell genes. Proc Natl Acad Sci USA 86, 1963-1967.

Lee, H., Park, H. J., Sohn, H. J., Kim, J. M., and Kim, S. J. (2011). Combinatorial therapy for liver metastatic colon cancer: dendritic cell vaccine and low-dose agonistic anti-4-1BB antibody co-stimulatory signal. J Surg Res 169, e43-50.

Levitsky, V., de Campos-Lima, P. O., Frisan, T., and Masucci, M. G. (1998). The clonal composition of a peptide-specific oligoclonal CTL repertoire selected in response to persistent EBV infection is stable over time. J Immunol 161, 594-601.

Lewis Phillips, G. D., Li, G., Dugger, D. L., Crocker, L. M., Parsons, K. L., Mai, E., Blattler, W. A., Lambert, J. M., Chari, R. V., Lutz, R. J., et al. (2008). Targeting HER2-positive breast cancer with trastuzumab-DM1, an antibody-cytotoxic drug conjugate. Cancer Res 68, 9280-9290.

Li, F., and Ravetch, J. V. (2011). Inhibitory Fcgamma receptor engagement drives adjuvant and anti-tumor activities of agonistic CD40 antibodies. Science 333, 1030-1034.

Li, J., Ybarra, R., Mak, J., Herault, A., De Almeida, P., Arrazate, A., Ziai, J., Totpal, K., Junttila, M. R., Walsh, K. B., and Junttila, T. T. (2018). IFNgamma-induced Chemokines Are Required for CXCR3-mediated T-Cell Recruitment and Antitumor Efficacy of Anti-HER2/CD3 Bispecific Antibody. Clinical Cancer Research 24, 6447-6458.

Lin, W., Voskens, C. J., Zhang, X., Schindler, D. G., Wood, A., Burch, E., Wei, Y., Chen, L., Tian, G., Tamada, K., et al. (2008). Fc-dependent expression of CD137 on human NK cells: insights into "agonistic" effects of anti-CD137 monoclonal antibodies. Blood 112, 699-707.

Melero, I., Johnston, J. V., Shufford, W. W., Mittler, R. S., and Chen, L. (1998). NK1.1 cells express 4-1BB (CDw137) costimulatory molecule and are required for tumor immunity elicited by anti-4-1BB monoclonal antibodies. Cell Immunol 190, 167-172.

Melero, I., Shuford, W. W., Newby, S. A., Aruffo, A., Ledbetter, J. A., Hellstrom, K. E., Mittler, R. S., and Chen, L. (1997). Monoclonal antibodies against the 4-1BB T-cell activation molecule eradicate established tumors. Nat Med 3, 682-685.

Merchant, A. M., Zhu, Z., Yuan, J. Q., Goddard, A., Adams, C. W., Presta, L. G., and Carter, P. (1998). An efficient route to human bispecific IgG. Nat Biotechnol 16, 677-681.

Morales-Kastresana, A., Sanmamed, M. F., Rodriguez, I., Palazon, A., Martinez-Forero, I., Labiano, S., Hervas-Stubbs, S., Sangro, B., Ochoa, C., Rouzaut, A., et al. (2013). Combined immunostimulatory monoclonal antibodies extend survival in an aggressive transgenic hepatocellular carcinoma mouse model. Clin Cancer Res 19, 6151-6162.

Mueller, D., Frey, K., Kontermann, R. E. (2008), A novel antibody-4-1BB1 fusion protein for targeted costimulation in cancer immunotherapy, J. Immunother. 31, 714-722.

Murillo, O., Dubrot, J., Palazon, A., Anna, A., Azpilikueta, A., Alfaro, C., Solano, S., Ochoa, M. C., Berasain, C., Gabari, I., et al. (2009). In vivo depletion of DC impairs the anti-tumor effect of agonistic anti-CD137 mAb. Eur J Immunol 39, 2424-2436.

Narazaki, H., Zhu, Y., Luo, L., Zhu, G., and Chen, L. (2010). CD137 agonist antibody prevents cancer recurrence: contribution of CD137 on both hematopoietic and nonhematopoietic cells. Blood 115, 1941-1948.

Nishimoto, H., Lee, S. W., Hong, H., Potter, K. G., Maeda-Yamamoto, M., Kinoshita, T., Kawakami, Y., Mittler, R. S., Kwon, B. S., Ware, C. F., et al. (2005). Costimulation of mast cells by 4-1BB, a member of the tumor necrosis factor receptor superfamily, with the high-affinity IgE receptor. Blood 106, 4241-4248.

Olofsson, P. S., Soderstrom, L. A., Wagsater, D., Sheikine, Y., Ocaya, P., Lang, F., Rabu, C., Chen, L., Rudling, M., Aukrust, P., et al. (2008). CD137 is expressed in human atherosclerosis and promotes development of plaque inflammation in hypercholesterolemic mice. Circulation 117, 1292-1301.

Palazon, A., Teijeira, A., Martinez-Forero, I., Hervas-Stubbs, S., Roncal, C., Penuelas, I., Dubrot, J., Morales-Kastresana, A., Perez-Gracia, J. L., Ochoa, M. C., et al. (2011). Agonist anti-CD137 mAb act on tumor endothelial cells to enhance recruitment of activated T lymphocytes. Cancer Res 71, 801-811.

Taraban, V. Y., Rowley, T. F., O'Brien, L., Chan, H. T., Haswell, L. E., Green, M. H., Tutt, A. L., Glennie, M. J., and Al-Shamkhani, A (2002). Expression and costimulatory effects of the TNF receptor superfamily members CD134 (OX40) and CD137 (4-1BB), and their role in the generation of anti-tumor immune responses. Eur J Immunol 32, 3617-3627.

Schwarz, H., Valbracht, J., Tuckwell, J., von Kempis, J., and Lotz, M. (1995). ILA, the human 4-1BB homologue, is inducible in lymphoid and other cell lineages. Blood 85, 1043-1052.

Shao, Z., and Schwarz, H. (2011). CD137 ligand, a member of the tumor necrosis factor family, regulates immune responses via reverse signal transduction. J Leukoc Biol 89, 21-29.

Shi, W., and Siemann, D. W. (2006). Augmented antitumor effects of radiation therapy by 4-1BB antibody (BMS-469492) treatment. Anticancer Res 26, 3445-3453.

Shindo Y., Yoshimura K., Kuramasu A., Watanabe Y., Ito H.; Kondo T., et al. (2015). Combination Immunotherapy with 4-1BB activation and PD-1 blockade enhances antitumor efficacy in a mouse model of subcutaneous tumor. Anticancer Res. 35(1), 129-136.

Simeone, E., and Ascierto, P. A. (2012) Immunomodulating antibodies in the treatment of metastatic melanoma: the experience with anti-CTLA-4, anti-CD137, and anti-HER2 J Immunotoxicol 9, 241-247.

Snell, L. M., Lin, G. H., McPherson, A. J., Moraes, T. J., and Watts, T. H. (2011). T-cell intrinsic effects of GITR and 4-1BB during viral infection and cancer immunotherapy Immunol Rev 244, 197-217.

Stagg, J., Loi, S., Divisekera, U., Ngiow, S. F., Duret, H., Yagita, H., Teng, M. W., and Smyth, M. J. (2011). Anti-ErbB-2 mAb therapy requires type I and II interferons and synergizes with anti-PD-1 or anti-CD137 mAb therapy. Proc Natl Acad Sci USA 108, 7142-7147.

Teng, M. W., Sharkey, J., McLaughlin, N. M., Exley, M. A., and Smyth, M. J. (2009). CD1d-based combination therapy eradicates established tumors in mice. J Immunol 183, 1911-1920.

von Kempis, J., Schwarz, H., and Lotz, M. (1997). Differentiation-dependent and stimulus-specific expression of ILA, the human 4-1BB-homologue, in cells of mesenchymal origin. Osteoarthritis Cartilage 5, 394-406.

Wei, H., Zhao, L., Li, W., Fan, K., Qian, W., Hou, S., Wang, H., Dai, M., Hellstrom, I., Hellstrom, K. E., and Guo, Y. (2013). Combinatorial PD-1 blockade and CD137 activation has therapeutic efficacy in murine cancer models and synergizes with cisplatin. PLoS One 8, e84927.

Wei H., Zhao L., Hellstrom I., Hellstrom K. E. and Guo Y. (2014). Dual targeting of CD137 co-stimulatory and PD-1 co-inhibitory molecules for ovarian cancer immunotherapy, OncoImmunology, 3:4, e28248, DOI: 10.4161/onci.28248.

Wilcox, R. A., Chapoval, A. I., Gorski, K. S., Otsuji, M., Shin, T., Flies, D. B., Tamada, K., Mittler, R. S., Tsuchiya, H., Pardoll, D. M., and Chen, L. (2002). Cutting edge: Expression of functional CD137 receptor by dendritic cells. J Immunol 168, 4262-4267.

Wilcox, R. A., Tamada, K., Flies, D. B., Zhu, G., Chapoval, A. I., Blazar, B. R., Kast, W. M., and Chen, L. (2004). Ligation of CD137 receptor prevents and reverses established anergy of CD8+ cytolytic T lymphocytes in vivo. Blood 103, 177-184.

Zhang, N., Sadun, R. E., Arias, R. S., Flanagan, M. L., Sachsman, S. M., Nien, Y, Khawli, L. A., Hu, P., Epstein, A. L. (2007). Targeted and untargeted CD137L fusion proteins for the immunotherapy of experimental solid tumors. Clin. Cancer Res. 13, 2758-2767.

Zhang, X., Voskens, C. J., Sallin, M., Maniar, A., Montes, C. L., Zhang, Y., Lin, W., Li, G., Burch, E., Tan, M., et al. (2010). CD137 promotes proliferation and survival of human B cells J Immunol 184, 787-795.

The invention claimed is:

1. A 4-1BBL trimer-containing antigen binding molecule, wherein the antigen binding molecule comprises
a first heavy chain comprising the amino acid sequence of SEQ ID NO:45, a first light chain comprising the amino acid sequence of SEQ ID NO:46, a second heavy chain comprising the amino acid sequence of SEQ ID NO:37 and a second light chain comprising the amino acid sequence of SEQ ID NO:38.

2. Isolated nucleic acid molecule encoding the 4-1BBL trimer-containing antigen binding molecule of claim 1.

3. A vector comprising the isolated nucleic acid molecule of claim 2.

4. The vector of claim 3, wherein the vector is an expression vector.

5. A host cell comprising the expression vector of claim 4.

6. A method of producing a 4-1BBL trimer-containing antigen binding molecule, comprising culturing the host cell of claim 5 under conditions suitable for expression of the 4-1BBL trimer-containing antigen binding molecule.

7. The method of claim 6, further comprising recovering the 4-1BBL trimer-containing antigen binding molecule from the host cell.

8. 4-1BBL trimer-containing antigen binding molecule produced by the method of claim 7.

9. A method of making a pharmaceutical composition comprising the 4-1BBL trimer-containing antigen binding molecule of claim 1 comprising combining the 4-1BBL trimer-containing antigen binding molecule with at least one pharmaceutically acceptable excipient.

10. The method of claim 9, further comprising combining a T-cell activating anti-CD3 bispecific antibody with the 4-1BBL trimer-containing antigen binding molecule and the at least one excipient.

11. The method of claim 10, wherein the T-cell activating anti-CD3 bispecific antibody is an anti-Her2/anti-CD3 bispecific antibody.

* * * * *

UNITED STATES PATENT AND TRADEMARK OFFICE
CERTIFICATE OF CORRECTION

Page 1 of 3

PATENT NO. : 12,065,478 B2
APPLICATION NO. : 17/066711
DATED : August 20, 2024
INVENTOR(S) : Claudia Ferrara Koller et al.

It is certified that error appears in the above-identified patent and that said Letters Patent is hereby corrected as shown below:

On the Title Page

Item (30), under Foreign Application Priority Data, Line 1, delete "18167147" and insert -- 18167147.0 --, therefor.

In the Specification

In Column 1, Line 55, delete "ϕβ" and insert -- αβ --, therefor.
In Column 2, Line 57, delete "of of" and insert -- of --, therefor.
In Column 5, Line 8, delete "wherein wherein" and insert -- wherein --, therefor.
In Column 5, Line 22, delete "wherein wherein" and insert -- wherein --, therefor.
In Column 7, Line 58, delete "the the" and insert -- the --, therefor.
In Column 7, Lines 58-59, delete "timer-containing" and insert -- trimer-containing --, therefor.
In Column 7, Line 65, delete "timer-containing" and insert -- trimer-containing --, therefor.
In Column 8, Line 11, delete "timer-containing" and insert -- trimer-containing --, therefor.
In Column 9, Line 19, delete "(e g" and insert -- (e.g. --, therefor.
In Column 9, Line 40, delete "(e g" and insert -- (e.g. --, therefor.
In Column 10, Line 8, delete "8A to 811." and insert -- 8A to 8H. --, therefor.
In Column 11, Line 42, delete "(FIG. 14B)," and insert -- (FIG. 16B), --, therefor.
In Column 11, Lines 42-43, delete "(FIG. 14C)," and insert -- (FIG. 16C), --, therefor.
In Column 11, Line 44, delete "(FIG. 14D)." and insert -- (FIG. 16D). --, therefor.
In Column 11, Line 46, delete "dectable" and insert -- detectable --, therefor.
In Column 14, Line 5, delete "cysteins" and insert -- cysteines --, therefor.
In Column 16, Line 44, delete "beengineered" and insert -- be engineered --, therefor.
In Column 17, Line 35, delete "1013" and insert -- 10-13 --, therefor.
In Column 19, Line 24, delete "(CD3E)." and insert -- (CD3ε). --, therefor.
In Column 19, Line 25, delete "CD3E" and insert -- CD3ε --, therefor.
In Column 19, Line 29, delete "CD3E" and insert -- CD3ε --, therefor.
In Column 23, Line 26, delete "cyctokines" and insert -- cytokines --, therefor.
In Column 23, Line 39, delete "a" and insert -- α --, therefor.

Signed and Sealed this
Twenty-second Day of July, 2025

Coke Morgan Stewart
*Acting Director of the United States Patent and Trademark Office*

CERTIFICATE OF CORRECTION (continued)
U.S. Pat. No. 12,065,478 B2

In Column 24, Line 37, delete "of'" and insert -- of --, therefor.
In Column 24, Line 51, delete "(G4S)₃" and insert -- (G$_4$S)$_3$ --, therefor.
In Column 28, Lines 51-52, delete "polyaminoacids" and insert -- polyamino acids --, therefor.
In Column 28, Line 54, delete "propropylene glycol" and insert -- polypropylene glycol --, therefor.
In Column 28, Line 54, delete "prolypropylene" and insert -- polypropylene --, therefor.
In Column 31, Line 7, delete "e g" and insert -- e.g. --, therefor.
In Column 31, Line 64, delete "bronchioloalviolar" and insert -- bronchioloalveolar --, therefor.
In Column 32, Line 17, delete "ependymonas," and insert -- ependymoma, --, therefor.
In Column 33, Line 58, delete "to to" and insert -- to --, therefor.
In Column 35, Line 59, delete "association" and insert -- association. --, therefor.
In Column 36, Line 32, delete "aVH" and insert -- a VH --, therefor.
In Column 36, Line 34, delete "aVH" and insert -- a VH --, therefor.
In Column 39, Line 38, delete "in a" and insert -- in an --, therefor.
In Column 41, Line 41, delete "the the" and insert -- the --, therefor.
In Column 43, Line 58, delete "a a" and insert -- a --, therefor.
In Column 45, Line 1, delete "the the" and insert -- the --, therefor.
In Column 47, Line 12, delete "timer-containing" and insert -- trimer-containing --, therefor.
In Column 47, Line 54, delete "tetracyclins)." and insert -- tetracyclines). --, therefor.
In Column 50, Line 41, delete "(e g" and insert -- (e.g. --, therefor.
In Column 52, Line 37, delete "e.g" and insert -- e.g. --, therefor.
In Column 54, Line 47, delete "less that" and insert -- less than --, therefor.
In Column 55, Line 31, delete "insterstitial" and insert -- interstitial --, therefor.
In Column 55, Line 39, delete "glycosaminoglycanases" and insert -- glycosaminoglycans --, therefor.
In Column 58, Line 22, delete "timer-containing" and insert -- trimer-containing --, therefor.
In Column 58, Line 28, delete "timer-containing" and insert -- trimer-containing --, therefor.
In Column 58, Line 31, delete "timer-containing" and insert -- trimer-containing --, therefor.
In Column 58, Line 46, delete "timer-containing" and insert -- trimer-containing --, therefor.
In Column 58, Line 50, delete "timer-containing" and insert -- trimer-containing --, therefor.
In Column 59, Line 16, delete "timer-containing" and insert -- trimer-containing --, therefor.
In Column 59, Line 28, delete "timer-containing" and insert -- trimer-containing --, therefor.
In Column 59, Line 49, delete "timer-containing" and insert -- trimer-containing --, therefor.
In Column 60, Line 21, delete "timer-containing" and insert -- trimer-containing --, therefor.
In Column 60, Line 40, delete "timer-containing" and insert -- trimer-containing --, therefor.
In Column 60, Line 65, delete "timer-containing" and insert -- trimer-containing --, therefor.
In Column 60, Line 67, delete "timer-containing" and insert -- trimer-containing --, therefor.
In Column 64, Line 11, delete "timer-containing" and insert -- trimer-containing --, therefor.
In Columns 75-76, Table B, under "Sequence", Line 38, delete "FE" and insert -- FF --, therefor.
In Columns 83-84, Table 1, under "Sequence", Line 12, delete "LE" and insert -- LF --, therefor.
In Columns 83-84, Table 1, under "Sequence", Line 26, delete "TY" and insert -- IY --, therefor.
In Columns 83-84, Table 1, under "Sequence", Line 30, delete "LE" and insert -- LF --, therefor.
In Columns 83-84, Table 1, under "Sequence", Line 38, delete "TYPYTE" and insert -- IYPYTF --, therefor.
In Columns 83-84, Table 2, under "Sequence", Line 3, delete "TH" and insert -- IH --, therefor.
In Columns 83-84, Table 2, under "Sequence", Line 4, delete "TY" and insert -- IY --, therefor.
In Columns 85-86, Table 2, under "Sequence", Line 1, delete "VE" and insert -- VF --, therefor.
In Columns 85-86, Table 3, under "Sequence", Line 8, delete "LE" and insert -- LF --, therefor.

CERTIFICATE OF CORRECTION (continued)
U.S. Pat. No. 12,065,478 B2

In Column 87, Line 1, delete "K2HPO$_4$," and insert -- K2HPO4, --, therefor.
In Column 87, Line 2, delete "Monohydrocloride," and insert -- Monohydrochloride, --, therefor.
In Column 87, Line 5, delete "timer-" and insert -- trimer- --, therefor.
In Columns 87-88, Table 4A, under "Sequence", Line 14, delete "TY" and insert -- IY --, therefor.
In Columns 89-90, Table 4A, under "Sequence", Line 2, delete "ST" and insert -- SI --, therefor.
In Column 92, Line 67, delete "50" and insert -- 50 µl/well --, therefor.
In Column 93, Line 4, delete "Biotech)" and insert -- Biotec) --, therefor.
In Column 94, Line 18, delete "20'000" and insert -- 20,000 --, therefor.
In Column 94, Line 21, delete "T 000 cells" and insert -- 2,000 cells --, therefor.
In Column 94, Line 23, delete "jut" and insert -- µL --, therefor.
In Column 94, Line 26, delete "100'000" and insert -- 100,000 --, therefor.
In Column 94, Line 27, delete "10'000" and insert -- 10,000 --, therefor.
In Column 94, Line 53, delete "64" and insert -- 6 µL --, therefor.
In Column 95, Line 42, delete "8E to 811" and insert -- 8E to 8H --, therefor.
In Column 96, Line 2, delete "Aminoacid" and insert -- Amino acid --, therefor.
In Column 96, Line 65, delete "Biotech)." and insert -- Biotec). --, therefor.
In Column 97, Line 59, delete "of of" and insert -- of --, therefor.
In Column 98, Line 3, delete "Aminoacid" and insert -- Amino acid --, therefor.
In Column 98, Line 14, delete "Biotech" and insert -- Biotec --, therefor.
In Column 98, Lines 25-26, delete "50 µl" and insert -- 50 µL --, therefor.
In Column 98, Line 40, delete "50 µl" and insert -- 50 µL --, therefor.
In Column 98, Line 62, delete "Biotech)." and insert -- Biotec). --, therefor.
In Column 100, Line 12, delete "Titer-Glow" and insert -- Titer-Glo --, therefor.
In Column 100, Line 39, delete "of of" and insert -- of --, therefor.

In the Claims

In Column 229, Claim 1, Line 57, delete "comprises" and insert -- comprises: --, therefor.

SEQUENCE LISTING

<160> NUMBER OF SEQ ID NOS: 106

<210> SEQ ID NO 1
<211> LENGTH: 184
<212> TYPE: PRT
<213> ORGANISM: Homo sapiens

<400> SEQUENCE: 1

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180
```

<210> SEQ ID NO 2
<211> LENGTH: 170
<212> TYPE: PRT
<213> ORGANISM: Homo sapiens

<400> SEQUENCE: 2

```
Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60
```

```
Leu Arg Arg Val Val Ala Gly Glu Gly Ser Gly Ser Val Ser Leu Ala
 65                  70                  75                  80

Leu His Leu Gln Pro Leu Arg Ser Ala Ala Gly Ala Ala Ala Leu Ala
                 85                  90                  95

Leu Thr Val Asp Leu Pro Pro Ala Ser Ser Glu Ala Arg Asn Ser Ala
                100                 105                 110

Phe Gly Phe Gln Gly Arg Leu Leu His Leu Ser Ala Gly Gln Arg Leu
                115                 120                 125

Gly Val His Leu His Thr Glu Ala Arg Ala Arg His Ala Trp Gln Leu
            130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170

<210> SEQ ID NO 3
<211> LENGTH: 175
<212> TYPE: PRT
<213> ORGANISM: Homo sapiens

<400> SEQUENCE: 3

Asp Pro Ala Gly Leu Asp Leu Arg Gln Gly Met Phe Ala Gln Leu
 1               5                  10                  15

Val Ala Gln Asn Val Leu Leu Ile Asp Gly Pro Leu Ser Trp Tyr Ser
                 20                  25                  30

Asp Pro Gly Leu Ala Gly Val Ser Leu Thr Gly Gly Leu Ser Tyr Lys
                 35                  40                  45

Glu Asp Thr Lys Glu Leu Val Val Ala Lys Ala Gly Val Tyr Tyr Val
 50                  55                  60

Phe Phe Gln Leu Glu Leu Arg Arg Val Val Ala Gly Glu Gly Ser Gly
 65                  70                  75                  80

Ser Val Ser Leu Ala Leu His Leu Gln Pro Leu Arg Ser Ala Ala Gly
                 85                  90                  95

Ala Ala Ala Leu Ala Leu Thr Val Asp Leu Pro Pro Ala Ser Ser Glu
                100                 105                 110

Ala Arg Asn Ser Ala Phe Gly Phe Gln Gly Arg Leu Leu His Leu Ser
                115                 120                 125

Ala Gly Gln Arg Leu Gly Val His Leu His Thr Glu Ala Arg Ala Arg
            130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175

<210> SEQ ID NO 4
<211> LENGTH: 203
<212> TYPE: PRT
<213> ORGANISM: Homo sapiens

<400> SEQUENCE: 4

Pro Trp Ala Val Ser Gly Ala Arg Ala Ser Pro Gly Ser Ala Ala Ser
 1               5                  10                  15

Pro Arg Leu Arg Glu Gly Pro Glu Leu Ser Pro Asp Asp Pro Ala Gly
                 20                  25                  30

Leu Leu Asp Leu Arg Gln Gly Met Phe Ala Gln Leu Val Ala Gln Asn
                 35                  40                  45
```

Val Leu Leu Ile Asp Gly Pro Leu Ser Trp Tyr Ser Asp Pro Gly Leu
 50                  55                  60

Ala Gly Val Ser Leu Thr Gly Gly Leu Ser Tyr Lys Glu Asp Thr Lys
 65                  70                  75                  80

Glu Leu Val Val Ala Lys Ala Gly Val Tyr Tyr Val Phe Phe Gln Leu
                 85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
            115                 120                 125

Ala Leu Thr Val Asp Leu Pro Pro Ala Ser Ser Glu Ala Arg Asn Ser
        130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu
            195                 200

<210> SEQ ID NO 5
<211> LENGTH: 178
<212> TYPE: PRT
<213> ORGANISM: Homo sapiens

<400> SEQUENCE: 5

Arg Glu Gly Pro Glu Leu Ser Pro Asp Asp Pro Ala Gly Leu Leu Asp
 1                   5                  10                  15

Leu Arg Gln Gly Met Phe Ala Gln Leu Val Ala Gln Asn Val Leu Leu
                 20                  25                  30

Ile Asp Gly Pro Leu Ser Trp Tyr Ser Asp Pro Gly Leu Ala Gly Val
             35                  40                  45

Ser Leu Thr Gly Gly Leu Ser Tyr Lys Glu Asp Thr Lys Glu Leu Val
 50                  55                  60

Val Ala Lys Ala Gly Val Tyr Tyr Val Phe Phe Gln Leu Glu Leu Arg
 65                  70                  75                  80

Arg Val Val Ala Gly Glu Gly Ser Gly Ser Val Ser Leu Ala Leu His
                 85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu

<210> SEQ ID NO 6
<211> LENGTH: 164
<212> TYPE: PRT
<213> ORGANISM: Homo sapiens

```
<400> SEQUENCE: 6

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
                115                 120                 125

Gly Val His Leu His Thr Glu Ala Arg Ala Arg His Ala Trp Gln Leu
        130                 135                 140

Thr Gln Gly Ala Thr Val Leu Gly Leu Phe Arg Val Thr Pro Glu Ile
145                 150                 155                 160

Pro Ala Gly Leu

<210> SEQ ID NO 7
<211> LENGTH: 169
<212> TYPE: PRT
<213> ORGANISM: Homo sapiens

<400> SEQUENCE: 7

Asp Pro Ala Gly Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
                20                  25                  30

Asp Pro Gly Leu Ala Gly Val Ser Leu Thr Gly Gly Leu Ser Tyr Lys
            35                  40                  45

Glu Asp Thr Lys Glu Leu Val Val Ala Lys Ala Gly Val Tyr Tyr Val
50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
        130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu
                165

<210> SEQ ID NO 8
<211> LENGTH: 197
<212> TYPE: PRT
```

<213> ORGANISM: Homo sapiens

<400> SEQUENCE: 8

Pro Trp Ala Val Ser Gly Ala Arg Ala Ser Pro Gly Ser Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu
            195

<210> SEQ ID NO 9
<211> LENGTH: 378
<212> TYPE: PRT
<213> ORGANISM: Artificial Sequence
<220> FEATURE:
<223> OTHER INFORMATION: dimeric hu 4-1BBL (71-254) connected by (G4S)2
      linker

<400> SEQUENCE: 9

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val

```
                130                 135                 140
His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Arg Glu Gly Pro Glu Leu Ser Pro Asp Asp Pro Ala Gly Leu
            195                 200                 205

Leu Asp Leu Arg Gln Gly Met Phe Ala Gln Leu Val Ala Gln Asn Val
        210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Ala Leu Ala
        290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
            355                 360                 365

Pro Ala Gly Leu Pro Ser Pro Arg Ser Glu
        370                 375

<210> SEQ ID NO 10
<211> LENGTH: 366
<212> TYPE: PRT
<213> ORGANISM: Artificial Sequence
<220> FEATURE:
<223> OTHER INFORMATION: dimeric hu 4-1BBL (71-248) connected by (G4S)2
      linker

<400> SEQUENCE: 10

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110
```

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
        130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Ser Gly Gly Gly Ser Arg Glu Gly Pro
                180                 185                 190

Glu Leu Ser Pro Asp Asp Pro Ala Gly Leu Leu Asp Leu Arg Gln Gly
                195                 200                 205

Met Phe Ala Gln Leu Val Ala Gln Asn Val Leu Leu Ile Asp Gly Pro
        210                 215                 220

Leu Ser Trp Tyr Ser Asp Pro Gly Leu Ala Gly Val Ser Leu Thr Gly
225                 230                 235                 240

Gly Leu Ser Tyr Lys Glu Asp Thr Lys Glu Leu Val Val Ala Lys Ala
                245                 250                 255

Gly Val Tyr Tyr Val Phe Phe Gln Leu Glu Leu Arg Arg Val Val Ala
                260                 265                 270

Gly Glu Gly Ser Gly Ser Val Ser Leu Ala Leu His Leu Gln Pro Leu
        275                 280                 285

Arg Ser Ala Ala Gly Ala Ala Ala Leu Ala Leu Thr Val Asp Leu Pro
        290                 295                 300

Pro Ala Ser Ser Glu Ala Arg Asn Ser Ala Phe Gly Phe Gln Gly Arg
305                 310                 315                 320

Leu Leu His Leu Ser Ala Gly Gln Arg Leu Gly Val His Leu His Thr
                325                 330                 335

Glu Ala Arg Ala Arg His Ala Trp Gln Leu Thr Gln Gly Ala Thr Val
                340                 345                 350

Leu Gly Leu Phe Arg Val Thr Pro Glu Ile Pro Ala Gly Leu
        355                 360                 365

<210> SEQ ID NO 11
<211> LENGTH: 360
<212> TYPE: PRT
<213> ORGANISM: Artificial Sequence
<220> FEATURE:
<223> OTHER INFORMATION: dimeric hu 4-1BBL (80-254) connected by (G4S)2
      linker

<400> SEQUENCE: 11

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

```
Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu Gly
                165                 170                 175

Gly Gly Gly Ser Gly Gly Gly Ser Asp Pro Ala Gly Leu Leu Asp
            180                 185                 190

Leu Arg Gln Gly Met Phe Ala Gln Leu Val Ala Gln Asn Val Leu Leu
    195                 200                 205

Ile Asp Gly Pro Leu Ser Trp Tyr Ser Asp Pro Gly Leu Ala Gly Val
    210                 215                 220

Ser Leu Thr Gly Gly Leu Ser Tyr Lys Glu Asp Thr Lys Glu Leu Val
225                 230                 235                 240

Val Ala Lys Ala Gly Val Tyr Tyr Val Phe Phe Gln Leu Glu Leu Arg
                245                 250                 255

Arg Val Val Ala Gly Glu Gly Ser Gly Ser Val Ser Leu Ala Leu His
            260                 265                 270

Leu Gln Pro Leu Arg Ser Ala Ala Gly Ala Ala Leu Ala Leu Thr
    275                 280                 285

Val Asp Leu Pro Pro Ala Ser Ser Glu Ala Arg Asn Ser Ala Phe Gly
    290                 295                 300

Phe Gln Gly Arg Leu Leu His Leu Ser Ala Gly Gln Arg Leu Gly Val
305                 310                 315                 320

His Leu His Thr Glu Ala Arg Ala Arg His Ala Trp Gln Leu Thr Gln
                325                 330                 335

Gly Ala Thr Val Leu Gly Leu Phe Arg Val Thr Pro Glu Ile Pro Ala
            340                 345                 350

Gly Leu Pro Ser Pro Arg Ser Glu
    355                 360

<210> SEQ ID NO 12
<211> LENGTH: 416
<212> TYPE: PRT
<213> ORGANISM: Artificial Sequence
<220> FEATURE:
<223> OTHER INFORMATION: dimeric hu 4-1BBL (52-254) connected by (G4S)2
      linker

<400> SEQUENCE: 12

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
```

```
            100                 105                 110
Ala Leu His Leu Gln Pro Leu Arg Ser Ala Gly Ala Ala Leu
            115                 120                 125

Ala Leu Thr Val Asp Leu Pro Pro Ala Ser Ser Glu Ala Arg Asn Ser
130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu Gly Gly Gly Gly Ser
            195                 200                 205

Gly Gly Gly Gly Ser Pro Trp Ala Val Ser Gly Ala Arg Ala Ser Pro
210                 215                 220

Gly Ser Ala Ala Ser Pro Arg Leu Arg Glu Gly Pro Glu Leu Ser Pro
225                 230                 235                 240

Asp Asp Pro Ala Gly Leu Leu Asp Leu Arg Gln Gly Met Phe Ala Gln
                245                 250                 255

Leu Val Ala Gln Asn Val Leu Leu Ile Asp Gly Pro Leu Ser Trp Tyr
            260                 265                 270

Ser Asp Pro Gly Leu Ala Gly Val Ser Leu Thr Gly Gly Leu Ser Tyr
            275                 280                 285

Lys Glu Asp Thr Lys Glu Leu Val Val Ala Lys Ala Gly Val Tyr Tyr
        290                 295                 300

Val Phe Phe Gln Leu Glu Leu Arg Arg Val Val Ala Gly Glu Gly Ser
305                 310                 315                 320

Gly Ser Val Ser Leu Ala Leu His Leu Gln Pro Leu Arg Ser Ala Ala
                325                 330                 335

Gly Ala Ala Ala Leu Ala Leu Thr Val Asp Leu Pro Pro Ala Ser Ser
            340                 345                 350

Glu Ala Arg Asn Ser Ala Phe Gly Phe Gln Gly Arg Leu Leu His Leu
        355                 360                 365

Ser Ala Gly Gln Arg Leu Gly Val His Leu His Thr Glu Ala Arg Ala
        370                 375                 380

Arg His Ala Trp Gln Leu Thr Gln Gly Ala Thr Val Leu Gly Leu Phe
385                 390                 395                 400

Arg Val Thr Pro Glu Ile Pro Ala Gly Leu Pro Ser Pro Arg Ser Glu
                405                 410                 415

<210> SEQ ID NO 13
<211> LENGTH: 10
<212> TYPE: PRT
<213> ORGANISM: Artificial Sequence
<220> FEATURE:
<223> OTHER INFORMATION: heavy chain CDR-H1, pertuzumab

<400> SEQUENCE: 13

Gly Phe Thr Phe Thr Asp Tyr Thr Met Asp
1               5                   10

<210> SEQ ID NO 14
<211> LENGTH: 17
<212> TYPE: PRT
<213> ORGANISM: Artificial Sequence
<220> FEATURE:
<223> OTHER INFORMATION: heavy chain CDR-H2, pertuzumab
```

```
<400> SEQUENCE: 14

Asp Val Asn Pro Asn Ser Gly Gly Ser Ile Tyr Asn Gln Arg Phe Lys
1               5                   10                  15

Gly

<210> SEQ ID NO 15
<211> LENGTH: 10
<212> TYPE: PRT
<213> ORGANISM: Artificial Sequence
<220> FEATURE:
<223> OTHER INFORMATION: heavy chain CDR-H3, pertuzumab

<400> SEQUENCE: 15

Asn Leu Gly Pro Ser Phe Tyr Phe Asp Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: light chain CDR-L1, pertuzumab

<400> SEQUENCE: 16

Lys Ala Ser Gln Asp Val Ser Ile Gly Val Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: light chain CDR-L2, pertuzumab

<400> SEQUENCE: 17

Ser Ala Ser Tyr Arg Tyr Thr
1               5

<210> SEQ ID NO 18
<211> LENGTH: 9
<212> TYPE: PRT
<213> ORGANISM: Artificial Sequence
<220> FEATURE:
<223> OTHER INFORMATION: light chain CDR-L3, pertuzumab

<400> SEQUENCE: 18

Gln Gln Tyr Tyr Ile Tyr Pro Tyr Thr
1               5

<210> SEQ ID NO 19
<211> LENGTH: 119
<212> TYPE: PRT
<213> ORGANISM: Artificial Sequence
<220> FEATURE:
<223> OTHER INFORMATION: heavy chain variable domain VH, pertuzumab

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Thr Met Asp Trp Val Arg Gln Ala Pro Gly Lys Gly Leu Glu Trp Val
            35                  40                  45
```

```
Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115
```

<210> SEQ ID NO 20
<211> LENGTH: 107
<212> TYPE: PRT
<213> ORGANISM: Artificial Sequence
<220> FEATURE:
<223> OTHER INFORMATION: light chain variable domain VL, pertuzumab

<400> SEQUENCE: 20

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Val Ser Ile Gly
             20                  25                  30

Val Ala Trp Tyr Gln Gln Lys Pro Gly Lys Ala Pro Lys Leu Leu Ile
         35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys
            100                 105
```

<210> SEQ ID NO 21
<211> LENGTH: 10
<212> TYPE: PRT
<213> ORGANISM: Artificial Sequence
<220> FEATURE:
<223> OTHER INFORMATION: heavy chain CDR-H1, trastuzumab

<400> SEQUENCE: 21

```
Gly Phe Asn Ile Lys Asp Thr Tyr Ile His
  1               5                  10
```

<210> SEQ ID NO 22
<211> LENGTH: 17
<212> TYPE: PRT
<213> ORGANISM: Artificial Sequence
<220> FEATURE:
<223> OTHER INFORMATION: heavy chain CDR-H2, trastuzumab

<400> SEQUENCE: 22

```
Arg Ile Tyr Pro Thr Asn Gly Tyr Thr Arg Tyr Ala Asp Ser Val Lys
  1               5                  10                  15

Gly
```

<210> SEQ ID NO 23
<211> LENGTH: 11
<212> TYPE: PRT
<213> ORGANISM: Artificial Sequence

```
<220> FEATURE:
<223> OTHER INFORMATION: heavy chain CDR-H3, trastuzumab

<400> SEQUENCE: 23

Trp Gly Gly Asp Gly Phe Tyr Ala Met Asp Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: light chain CDR-L1, trastuzumab

<400> SEQUENCE: 24

Arg Ala Ser Gln Asp Val Asn Thr Ala Val Ala
1               5                   10

<210> SEQ ID NO 25
<211> LENGTH: 7
<212> TYPE: PRT
<213> ORGANISM: Artificial Sequence
<220> FEATURE:
<223> OTHER INFORMATION: light chain CDR-L2, trastuzumab

<400> SEQUENCE: 25

Ser Ala Ser Phe Leu Tyr Ser
1               5

<210> SEQ ID NO 26
<211> LENGTH: 9
<212> TYPE: PRT
<213> ORGANISM: Artificial Sequence
<220> FEATURE:
<223> OTHER INFORMATION: light chain CDR-L3, trastuzumab

<400> SEQUENCE: 26

Gln Gln His Tyr Thr Thr Pro Pro Thr
1               5

<210> SEQ ID NO 27
<211> LENGTH: 120
<212> TYPE: PRT
<213> ORGANISM: Artificial Sequence
<220> FEATURE:
<223> OTHER INFORMATION: heavy chain variable domain VH, trastuzumab

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 28
<211> LENGTH: 107
<212> TYPE: PRT
<213> ORGANISM: Artificial Sequence
<220> FEATURE:
<223> OTHER INFORMATION: light chain variable domain VL, trastuzumab

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 29
<211> LENGTH: 10
<212> TYPE: PRT
<213> ORGANISM: Artificial Sequence
<220> FEATURE:
<223> OTHER INFORMATION: heavy chain CDR-H1, aff. pertuzumab

<400> SEQUENCE: 29

```
Gly Phe Thr Phe Asn Asp Tyr Thr Met Asp
1               5                   10
```

<210> SEQ ID NO 30
<211> LENGTH: 17
<212> TYPE: PRT
<213> ORGANISM: Artificial Sequence
<220> FEATURE:
<223> OTHER INFORMATION: heavy chain CDR-H2, aff. pertuzumab

<400> SEQUENCE: 30

```
Asp Val Asn Pro Asn Ser Gly Gly Ser Ile Val Asn Arg Arg Phe Lys
1               5                   10                  15

Gly
```

<210> SEQ ID NO 31
<211> LENGTH: 10
<212> TYPE: PRT
<213> ORGANISM: Artificial Sequence
<220> FEATURE:
<223> OTHER INFORMATION: heavy chain CDR-H3,aff  pertuzumab

<400> SEQUENCE: 31

```
Asn Leu Gly Pro Phe Phe Tyr Phe Asp Tyr
1               5                   10
```

<210> SEQ ID NO 32
<211> LENGTH: 11
<212> TYPE: PRT
<213> ORGANISM: Artificial Sequence

```
<220> FEATURE:
<223> OTHER INFORMATION: light chain CDR-L1,aff. pertuzumab

<400> SEQUENCE: 32

Lys Ala Ser Gln Asp Val Ser Thr Ala Val Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: light chain CDR-L2, aff. pertuzumab

<400> SEQUENCE: 33

Ser Ala Ser Phe Arg Tyr Thr
1               5

<210> SEQ ID NO 34
<211> LENGTH: 9
<212> TYPE: PRT
<213> ORGANISM: Artificial Sequence
<220> FEATURE:
<223> OTHER INFORMATION: light chain CDR-L3, aff. pertuzumab

<400> SEQUENCE: 34

Gln Gln His Tyr Thr Thr Pro Pro Thr
1               5

<210> SEQ ID NO 35
<211> LENGTH: 119
<212> TYPE: PRT
<213> ORGANISM: Artificial Sequence
<220> FEATURE:
<223> OTHER INFORMATION: heavy chain variable domain VH, aff. pertuzumab

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser
        115

<210> SEQ ID NO 36
<211> LENGTH: 107
<212> TYPE: PRT
<213> ORGANISM: Artificial Sequence
<220> FEATURE:
<223> OTHER INFORMATION: light chain variable domain VL, aff. pertuzumab

<400> SEQUENCE: 36

Asp Ile Gln Met Thr Gln Ser Pro Ser Ser Leu Ser Ala Ser Val Gly
```

```
                1               5                   10                  15
            Asp Arg Val Thr Ile Thr Cys Lys Ala Ser Gln Asp Val Ser Thr Ala
                                20                  25                  30

Val Ala Trp Tyr Gln Gln Lys Pro Gly Lys Ala Pro Lys Leu Leu Ile
                        35                  40                  45

Tyr Ser Ala Ser Phe Arg Tyr Thr Gly Val Pro Ser Arg Phe Ser Gly
                    50                  55                  60

Ser Arg Ser Gly Thr Asp Phe Thr Leu Thr Ile Ser Ser Leu Gln Pro
            65                  70                  75                  80

Glu Asp Phe Ala Thr Tyr Tyr Cys Gln Gln His Tyr Thr Thr Pro Pro
                            85                  90                  95

Thr Phe Gly Gln Gly Thr Lys Val Glu Ile Lys
                            100                 105

<210> SEQ ID NO 37
<211> LENGTH: 708
<212> TYPE: PRT
<213> ORGANISM: Artificial Sequence
<220> FEATURE:
<223> OTHER INFORMATION: Dimeric 4-1BB ligand (71-248) - CL* Fc knob
      chain

<400> SEQUENCE: 37

Arg Glu Gly Pro Glu Leu Ser Pro Asp Asp Pro Ala Gly Leu Leu Asp
            1               5                   10                  15

Leu Arg Gln Gly Met Phe Ala Gln Leu Val Ala Gln Asn Val Leu Leu
                            20                  25                  30

Ile Asp Gly Pro Leu Ser Trp Tyr Ser Asp Pro Gly Leu Ala Gly Val
                        35                  40                  45

Ser Leu Thr Gly Gly Leu Ser Tyr Lys Glu Asp Thr Lys Glu Leu Val
                    50                  55                  60

Val Ala Lys Ala Gly Val Tyr Tyr Val Phe Phe Gln Leu Glu Leu Arg
            65                  70                  75                  80

Arg Val Val Ala Gly Glu Gly Ser Gly Ser Val Ser Leu Ala Leu His
                            85                  90                  95

Leu Gln Pro Leu Arg Ser Ala Ala Gly Ala Ala Ala Leu Ala Leu Thr
                            100                 105                 110

Val Asp Leu Pro Pro Ala Ser Ser Glu Ala Arg Asn Ser Ala Phe Gly
                        115                 120                 125

Phe Gln Gly Arg Leu Leu His Leu Ser Ala Gly Gln Arg Leu Gly Val
                    130                 135                 140

His Leu His Thr Glu Ala Arg Ala Arg His Ala Trp Gln Leu Thr Gln
            145                 150                 155                 160

Gly Ala Thr Val Leu Gly Leu Phe Arg Val Thr Pro Glu Ile Pro Ala
                            165                 170                 175

Gly Leu Gly Gly Gly Gly Ser Gly Gly Gly Gly Ser Arg Glu Gly Pro
                            180                 185                 190

Glu Leu Ser Pro Asp Asp Pro Ala Gly Leu Leu Asp Leu Arg Gln Gly
                        195                 200                 205

Met Phe Ala Gln Leu Val Ala Gln Asn Val Leu Leu Ile Asp Gly Pro
                    210                 215                 220

Leu Ser Trp Tyr Ser Asp Pro Gly Leu Ala Gly Val Ser Leu Thr Gly
            225                 230                 235                 240

Gly Leu Ser Tyr Lys Glu Asp Thr Lys Glu Leu Val Val Ala Lys Ala
                            245                 250                 255
```

```
Gly Val Tyr Tyr Val Phe Phe Gln Leu Glu Leu Arg Arg Val Val Ala
                260                 265                 270

Gly Glu Gly Ser Gly Ser Val Ser Leu Ala Leu His Leu Gln Pro Leu
            275                 280                 285

Arg Ser Ala Ala Gly Ala Ala Ala Leu Ala Leu Thr Val Asp Leu Pro
        290                 295                 300

Pro Ala Ser Ser Glu Ala Arg Asn Ser Ala Phe Gly Phe Gln Gly Arg
305                 310                 315                 320

Leu Leu His Leu Ser Ala Gly Gln Arg Leu Gly Val His Leu His Thr
                325                 330                 335

Glu Ala Arg Ala Arg His Ala Trp Gln Leu Thr Gln Gly Ala Thr Val
            340                 345                 350

Leu Gly Leu Phe Arg Val Thr Pro Glu Ile Pro Ala Gly Leu Gly Gly
        355                 360                 365

Gly Gly Ser Gly Gly Gly Ser Arg Thr Val Ala Ala Pro Ser Val
    370                 375                 380

Phe Ile Phe Pro Pro Ser Asp Arg Lys Leu Lys Ser Gly Thr Ala Ser
385                 390                 395                 400

Val Val Cys Leu Leu Asn Asn Phe Tyr Pro Arg Glu Ala Lys Val Gln
                405                 410                 415

Trp Lys Val Asp Asn Ala Leu Gln Ser Gly Asn Ser Gln Glu Ser Val
            420                 425                 430

Thr Glu Gln Asp Ser Lys Asp Ser Thr Tyr Ser Leu Ser Ser Thr Leu
        435                 440                 445

Thr Leu Ser Lys Ala Asp Tyr Glu Lys His Lys Val Tyr Ala Cys Glu
450                 455                 460

Val Thr His Gln Gly Leu Ser Ser Pro Val Thr Lys Ser Phe Asn Arg
465                 470                 475                 480

Gly Glu Cys Asp Lys Thr His Thr Cys Pro Pro Cys Pro Ala Pro Glu
                485                 490                 495

Ala Ala Gly Gly Pro Ser Val Phe Leu Phe Pro Pro Lys Pro Lys Asp
            500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Gly
            580                 585                 590

Ala Pro Ile Glu Lys Thr Ile Ser Lys Ala Lys Gly Gln Pro Arg Glu
        595                 600                 605

Pro Gln Val Tyr Thr Leu Pro Pro Cys Arg Asp Glu Leu Thr Lys Asn
            610                 615                 620

Gln Val Ser Leu Trp Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
```

```
                675                 680                 685
Ser Val Met His Glu Ala Leu His Asn His Tyr Thr Gln Lys Ser Leu
    690                 695                 700
Ser Leu Ser Pro
705

<210> SEQ ID NO 38
<211> LENGTH: 291
<212> TYPE: PRT
<213> ORGANISM: Artificial Sequence
<220> FEATURE:
<223> OTHER INFORMATION: Monomeric 4-1BB ligand (71-248)-CH1*

<400> SEQUENCE: 38

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Gly Ser Gly Gly Gly Gly Ser Ala Ser Thr Lys
            180                 185                 190

Gly Pro Ser Val Phe Pro Leu Ala Pro Ser Ser Lys Ser Thr Ser Gly
        195                 200                 205

Gly Thr Ala Ala Leu Gly Cys Leu Val Glu Asp Tyr Phe Pro Glu Pro
    210                 215                 220

Val Thr Val Ser Trp Asn Ser Gly Ala Leu Thr Ser Gly Val His Thr
225                 230                 235                 240

Phe Pro Ala Val Leu Gln Ser Ser Gly Leu Tyr Ser Leu Ser Ser Val
                245                 250                 255

Val Thr Val Pro Ser Ser Ser Leu Gly Thr Gln Thr Tyr Ile Cys Asn
            260                 265                 270

Val Asn His Lys Pro Ser Asn Thr Lys Val Asp Glu Lys Val Glu Pro
        275                 280                 285

Lys Ser Cys
    290

<210> SEQ ID NO 39
<211> LENGTH: 708
<212> TYPE: PRT
```

<213> ORGANISM: Artificial Sequence
<220> FEATURE:
<223> OTHER INFORMATION: Dimeric 4-1BB ligand (71-248) - CL Fc knob chain

<400> SEQUENCE: 39

```
Arg Glu Gly Pro Glu Leu Ser Pro Asp Asp Pro Ala Gly Leu Leu Asp
1               5                   10                  15
Leu Arg Gln Gly Met Phe Ala Gln Leu Val Ala Gln Asn Val Leu Leu
                20                  25                  30
Ile Asp Gly Pro Leu Ser Trp Tyr Ser Asp Pro Gly Leu Ala Gly Val
            35                  40                  45
Ser Leu Thr Gly Gly Leu Ser Tyr Lys Glu Asp Thr Lys Glu Leu Val
50                  55                  60
Val Ala Lys Ala Gly Val Tyr Tyr Val Phe Phe Gln Leu Glu Leu Arg
65                  70                  75                  80
Arg Val Val Ala Gly Glu Gly Ser Gly Ser Val Ser Leu Ala Leu His
                85                  90                  95
Leu Gln Pro Leu Arg Ser Ala Ala Gly Ala Ala Ala Leu Ala Leu Thr
                100                 105                 110
Val Asp Leu Pro Pro Ala Ser Ser Glu Ala Arg Asn Ser Ala Phe Gly
            115                 120                 125
Phe Gln Gly Arg Leu Leu His Leu Ser Ala Gly Gln Arg Leu Gly Val
130                 135                 140
His Leu His Thr Glu Ala Arg Ala Arg His Ala Trp Gln Leu Thr Gln
145                 150                 155                 160
Gly Ala Thr Val Leu Gly Leu Phe Arg Val Thr Pro Glu Ile Pro Ala
                165                 170                 175
Gly Leu Gly Gly Gly Gly Ser Gly Gly Gly Gly Ser Arg Glu Gly Pro
                180                 185                 190
Glu Leu Ser Pro Asp Asp Pro Ala Gly Leu Leu Asp Leu Arg Gln Gly
            195                 200                 205
Met Phe Ala Gln Leu Val Ala Gln Asn Val Leu Leu Ile Asp Gly Pro
210                 215                 220
Leu Ser Trp Tyr Ser Asp Pro Gly Leu Ala Gly Val Ser Leu Thr Gly
225                 230                 235                 240
Gly Leu Ser Tyr Lys Glu Asp Thr Lys Glu Leu Val Val Ala Lys Ala
                245                 250                 255
Gly Val Tyr Tyr Val Phe Phe Gln Leu Glu Leu Arg Arg Val Val Ala
                260                 265                 270
Gly Glu Gly Ser Gly Ser Val Ser Leu Ala Leu His Leu Gln Pro Leu
            275                 280                 285
Arg Ser Ala Ala Gly Ala Ala Ala Leu Ala Leu Thr Val Asp Leu Pro
290                 295                 300
Pro Ala Ser Ser Glu Ala Arg Asn Ser Ala Phe Gly Phe Gln Gly Arg
305                 310                 315                 320
Leu Leu His Leu Ser Ala Gly Gln Arg Leu Gly Val His Leu His Thr
                325                 330                 335
Glu Ala Arg Ala Arg His Ala Trp Gln Leu Thr Gln Gly Ala Thr Val
                340                 345                 350
Leu Gly Leu Phe Arg Val Thr Pro Glu Ile Pro Ala Gly Leu Gly Gly
            355                 360                 365
Gly Gly Ser Gly Gly Gly Gly Ser Arg Thr Val Ala Ala Pro Ser Val
370                 375                 380
```

-continued

```
Phe Ile Phe Pro Pro Ser Asp Glu Gln Leu Lys Ser Gly Thr Ala Ser
385                 390                 395                 400

Val Val Cys Leu Leu Asn Asn Phe Tyr Pro Arg Glu Ala Lys Val Gln
                405                 410                 415

Trp Lys Val Asp Asn Ala Leu Gln Ser Gly Asn Ser Gln Glu Ser Val
            420                 425                 430

Thr Glu Gln Asp Ser Lys Asp Ser Thr Tyr Ser Leu Ser Ser Thr Leu
        435                 440                 445

Thr Leu Ser Lys Ala Asp Tyr Glu Lys His Lys Val Tyr Ala Cys Glu
    450                 455                 460

Val Thr His Gln Gly Leu Ser Ser Pro Val Thr Lys Ser Phe Asn Arg
465                 470                 475                 480

Gly Glu Cys Asp Lys Thr His Thr Cys Pro Pro Cys Pro Ala Pro Glu
                485                 490                 495

Ala Ala Gly Gly Pro Ser Val Phe Leu Phe Pro Pro Lys Pro Lys Asp
            500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Gly
            580                 585                 590

Ala Pro Ile Glu Lys Thr Ile Ser Lys Ala Lys Gly Gln Pro Arg Glu
        595                 600                 605

Pro Gln Val Tyr Thr Leu Pro Pro Cys Arg Asp Glu Leu Thr Lys Asn
    610                 615                 620

Gln Val Ser Leu Trp Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
    690                 695                 700

Ser Leu Ser Pro
705

<210> SEQ ID NO 40
<211> LENGTH: 291
<212> TYPE: PRT
<213> ORGANISM: Artificial Sequence
<220> FEATURE:
<223> OTHER INFORMATION: Monomeric 4-1BB ligand (71-248)-CH1

<400> SEQUENCE: 40

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30
```

```
Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
 50                  55                  60

Val Ala Lys Ala Gly Val Tyr Tyr Val Phe Phe Gln Leu Glu Leu Arg
 65                  70                  75                  80

Arg Val Val Ala Gly Glu Gly Ser Gly Ser Val Ser Leu Ala Leu His
                 85                  90                  95

Leu Gln Pro Leu Arg Ser Ala Ala Gly Ala Ala Ala Leu Ala Leu Thr
                100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Gly Ser Gly Gly Gly Ser Ala Ser Thr Lys
                180                 185                 190

Gly Pro Ser Val Phe Pro Leu Ala Pro Ser Ser Lys Ser Thr Ser Gly
            195                 200                 205

Gly Thr Ala Ala Leu Gly Cys Leu Val Lys Asp Tyr Phe Pro Glu Pro
210                 215                 220

Val Thr Val Ser Trp Asn Ser Gly Ala Leu Thr Ser Gly Val His Thr
225                 230                 235                 240

Phe Pro Ala Val Leu Gln Ser Ser Gly Leu Tyr Ser Leu Ser Ser Val
                245                 250                 255

Val Thr Val Pro Ser Ser Ser Leu Gly Thr Gln Thr Tyr Ile Cys Asn
            260                 265                 270

Val Asn His Lys Pro Ser Asn Thr Lys Val Asp Lys Lys Val Glu Pro
        275                 280                 285

Lys Ser Cys
    290

<210> SEQ ID NO 41
<211> LENGTH: 720
<212> TYPE: PRT
<213> ORGANISM: Artificial Sequence
<220> FEATURE:
<223> OTHER INFORMATION: Dimeric 4-1BB ligand (71-254) - CL* Fc knob
      chain

<400> SEQUENCE: 41

Arg Glu Gly Pro Glu Leu Ser Pro Asp Asp Pro Ala Gly Leu Leu Asp
 1               5                  10                  15

Leu Arg Gln Gly Met Phe Ala Gln Leu Val Ala Gln Asn Val Leu Leu
                 20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
 50                  55                  60

Val Ala Lys Ala Gly Val Tyr Tyr Val Phe Phe Gln Leu Glu Leu Arg
 65                  70                  75                  80

Arg Val Val Ala Gly Glu Gly Ser Gly Ser Val Ser Leu Ala Leu His
                 85                  90                  95
```

-continued

```
Leu Gln Pro Leu Arg Ser Ala Ala Gly Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Arg Glu Gly Pro Glu Leu Ser Pro Asp Asp Pro Ala Gly Leu
        195                 200                 205

Leu Asp Leu Arg Gln Gly Met Phe Ala Gln Leu Val Ala Gln Asn Val
    210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Leu Ala
    290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
        355                 360                 365

Pro Ala Gly Leu Pro Ser Pro Arg Ser Glu Gly Gly Gly Ser Gly
    370                 375                 380

Gly Gly Gly Ser Arg Thr Val Ala Ala Pro Ser Val Phe Ile Phe Pro
385                 390                 395                 400

Pro Ser Asp Arg Lys Leu Lys Ser Gly Thr Ala Ser Val Val Cys Leu
                405                 410                 415

Leu Asn Asn Phe Tyr Pro Arg Glu Ala Lys Val Gln Trp Lys Val Asp
            420                 425                 430

Asn Ala Leu Gln Ser Gly Asn Ser Gln Glu Ser Val Thr Glu Gln Asp
        435                 440                 445

Ser Lys Asp Ser Thr Tyr Ser Leu Ser Ser Thr Leu Thr Leu Ser Lys
    450                 455                 460

Ala Asp Tyr Glu Lys His Lys Val Tyr Ala Cys Glu Val Thr His Gln
465                 470                 475                 480

Gly Leu Ser Ser Pro Val Thr Lys Ser Phe Asn Arg Gly Glu Cys Asp
                485                 490                 495

Lys Thr His Thr Cys Pro Pro Cys Pro Ala Pro Glu Ala Ala Gly Gly
            500                 505                 510
```

```
Pro Ser Val Phe Leu Phe Pro Pro Lys Pro Lys Asp Thr Leu Met Ile
            515                 520                 525
Ser Arg Thr Pro Glu Val Thr Cys Val Val Asp Val Ser His Glu
530                 535                 540
Asp Pro Glu Val Lys Phe Asn Trp Tyr Val Asp Gly Val Glu Val His
545                 550                 555                 560
Asn Ala Lys Thr Lys Pro Arg Glu Glu Gln Tyr Asn Ser Thr Tyr Arg
            565                 570                 575
Val Val Ser Val Leu Thr Val Leu His Gln Asp Trp Leu Asn Gly Lys
            580                 585                 590
Glu Tyr Lys Cys Lys Val Ser Asn Lys Ala Leu Gly Ala Pro Ile Glu
            595                 600                 605
Lys Thr Ile Ser Lys Ala Lys Gly Gln Pro Arg Glu Pro Gln Val Tyr
            610                 615                 620
Thr Leu Pro Pro Cys Arg Asp Glu Leu Thr Lys Asn Gln Val Ser Leu
625                 630                 635                 640
Trp Cys Leu Val Lys Gly Phe Tyr Pro Ser Asp Ile Ala Val Glu Trp
            645                 650                 655
Glu Ser Asn Gly Gln Pro Glu Asn Asn Tyr Lys Thr Thr Pro Pro Val
            660                 665                 670
Leu Asp Ser Asp Gly Ser Phe Phe Leu Tyr Ser Lys Leu Thr Val Asp
            675                 680                 685
Lys Ser Arg Trp Gln Gln Gly Asn Val Phe Ser Cys Ser Val Met His
            690                 695                 700
Glu Ala Leu His Asn His Tyr Thr Gln Lys Ser Leu Ser Leu Ser Pro
705                 710                 715                 720

<210> SEQ ID NO 42
<211> LENGTH: 297
<212> TYPE: PRT
<213> ORGANISM: Artificial Sequence
<220> FEATURE:
<223> OTHER INFORMATION: Monomeric 4-1BB ligand (71-254)-CH1*

<400> SEQUENCE: 42

Arg Glu Gly Pro Glu Leu Ser Pro Asp Asp Pro Ala Gly Leu Leu Asp
1               5                   10                  15
Leu Arg Gln Gly Met Phe Ala Gln Leu Val Ala Gln Asn Val Leu Leu
            20                  25                  30
Ile Asp Gly Pro Leu Ser Trp Tyr Ser Asp Pro Gly Leu Ala Gly Val
            35                  40                  45
Ser Leu Thr Gly Gly Leu Ser Tyr Lys Glu Asp Thr Lys Glu Leu Val
50                  55                  60
Val Ala Lys Ala Gly Val Tyr Tyr Val Phe Phe Gln Leu Glu Leu Arg
65                  70                  75                  80
Arg Val Val Ala Gly Glu Gly Ser Gly Ser Val Ser Leu Ala Leu His
            85                  90                  95
Leu Gln Pro Leu Arg Ser Ala Ala Gly Ala Ala Ala Leu Ala Leu Thr
            100                 105                 110
Val Asp Leu Pro Pro Ala Ser Ser Glu Ala Arg Asn Ser Ala Phe Gly
            115                 120                 125
Phe Gln Gly Arg Leu Leu His Leu Ser Ala Gly Gln Arg Leu Gly Val
            130                 135                 140
His Leu His Thr Glu Ala Arg Ala Arg His Ala Trp Gln Leu Thr Gln
145                 150                 155                 160
```

```
Gly Ala Thr Val Leu Gly Leu Phe Arg Val Thr Pro Glu Ile Pro Ala
            165                 170                 175

Gly Leu Pro Ser Pro Arg Ser Glu Gly Gly Gly Ser Gly Gly Gly
        180                 185                 190

Gly Ser Ala Ser Thr Lys Gly Pro Ser Val Phe Pro Leu Ala Pro Ser
        195                 200                 205

Ser Lys Ser Thr Ser Gly Gly Thr Ala Ala Leu Gly Cys Leu Val Glu
    210                 215                 220

Asp Tyr Phe Pro Glu Pro Val Thr Val Ser Trp Asn Ser Gly Ala Leu
225                 230                 235                 240

Thr Ser Gly Val His Thr Phe Pro Ala Val Leu Gln Ser Ser Gly Leu
                245                 250                 255

Tyr Ser Leu Ser Ser Val Val Thr Val Pro Ser Ser Ser Leu Gly Thr
            260                 265                 270

Gln Thr Tyr Ile Cys Asn Val Asn His Lys Pro Ser Asn Thr Lys Val
        275                 280                 285

Asp Glu Lys Val Glu Pro Lys Ser Cys
    290                 295

<210> SEQ ID NO 43
<211> LENGTH: 720
<212> TYPE: PRT
<213> ORGANISM: Artificial Sequence
<220> FEATURE:
<223> OTHER INFORMATION: Dimeric 4-1BB ligand (71-254) - CL Fc knob
      chain

<400> SEQUENCE: 43

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly Gly
            180                 185                 190

Gly Ser Arg Glu Gly Pro Glu Leu Ser Pro Asp Asp Pro Ala Gly Leu
        195                 200                 205

Leu Asp Leu Arg Gln Gly Met Phe Ala Gln Leu Val Ala Gln Asn Val
    210                 215                 220
```

```
Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
            245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
            275                 280                 285

Leu His Leu Gln Pro Leu Arg Ser Ala Ala Gly Ala Ala Ala Leu Ala
            290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
            355                 360                 365

Pro Ala Gly Leu Pro Ser Pro Arg Ser Glu Gly Gly Gly Ser Gly
            370                 375                 380

Gly Gly Gly Ser Arg Thr Val Ala Ala Pro Ser Val Phe Ile Phe Pro
385                 390                 395                 400

Pro Ser Asp Glu Gln Leu Lys Ser Gly Thr Ala Ser Val Val Cys Leu
                405                 410                 415

Leu Asn Asn Phe Tyr Pro Arg Glu Ala Lys Val Gln Trp Lys Val Asp
            420                 425                 430

Asn Ala Leu Gln Ser Gly Asn Ser Gln Glu Ser Val Thr Glu Gln Asp
            435                 440                 445

Ser Lys Asp Ser Thr Tyr Ser Leu Ser Ser Thr Leu Thr Leu Ser Lys
            450                 455                 460

Ala Asp Tyr Glu Lys His Lys Val Tyr Ala Cys Glu Val Thr His Gln
465                 470                 475                 480

Gly Leu Ser Ser Pro Val Thr Lys Ser Phe Asn Arg Gly Glu Cys Asp
                485                 490                 495

Lys Thr His Thr Cys Pro Pro Cys Pro Ala Pro Glu Ala Ala Gly Gly
            500                 505                 510

Pro Ser Val Phe Leu Phe Pro Pro Lys Pro Lys Asp Thr Leu Met Ile
            515                 520                 525

Ser Arg Thr Pro Glu Val Thr Cys Val Val Val Asp Val Ser His Glu
            530                 535                 540

Asp Pro Glu Val Lys Phe Asn Trp Tyr Val Asp Gly Val Glu Val His
545                 550                 555                 560

Asn Ala Lys Thr Lys Pro Arg Glu Glu Gln Tyr Asn Ser Thr Tyr Arg
                565                 570                 575

Val Val Ser Val Leu Thr Val Leu His Gln Asp Trp Leu Asn Gly Lys
            580                 585                 590

Glu Tyr Lys Cys Lys Val Ser Asn Lys Ala Leu Gly Ala Pro Ile Glu
            595                 600                 605

Lys Thr Ile Ser Lys Ala Lys Gly Gln Pro Arg Glu Pro Gln Val Tyr
            610                 615                 620

Thr Leu Pro Pro Cys Arg Asp Glu Leu Thr Lys Asn Gln Val Ser Leu
625                 630                 635                 640
```

```
Trp Cys Leu Val Lys Gly Phe Tyr Pro Ser Asp Ile Ala Val Glu Trp
                645                 650                 655

Glu Ser Asn Gly Gln Pro Glu Asn Asn Tyr Lys Thr Thr Pro Pro Val
            660                 665                 670

Leu Asp Ser Asp Gly Ser Phe Phe Leu Tyr Ser Lys Leu Thr Val Asp
            675                 680                 685

Lys Ser Arg Trp Gln Gln Gly Asn Val Phe Ser Cys Ser Val Met His
690                 695                 700

Glu Ala Leu His Asn His Tyr Thr Gln Lys Ser Leu Ser Leu Ser Pro
705                 710                 715                 720
```

<210> SEQ ID NO 44
<211> LENGTH: 297
<212> TYPE: PRT
<213> ORGANISM: Artificial Sequence
<220> FEATURE:
<223> OTHER INFORMATION: Monomeric 4-1BB ligand (71-254)-CH1

<400> SEQUENCE: 44

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Ala Ser Thr Lys Gly Pro Ser Val Phe Pro Leu Ala Pro Ser
        195                 200                 205

Ser Lys Ser Thr Ser Gly Gly Thr Ala Ala Leu Gly Cys Leu Val Lys
    210                 215                 220

Asp Tyr Phe Pro Glu Pro Val Thr Val Ser Trp Asn Ser Gly Ala Leu
225                 230                 235                 240

Thr Ser Gly Val His Thr Phe Pro Ala Val Leu Gln Ser Ser Gly Leu
                245                 250                 255

Tyr Ser Leu Ser Ser Val Val Thr Val Pro Ser Ser Ser Leu Gly Thr
            260                 265                 270

Gln Thr Tyr Ile Cys Asn Val Asn His Lys Pro Ser Asn Thr Lys Val
        275                 280                 285
```

```
Asp Lys Lys Val Glu Pro Lys Ser Cys
    290                 295
```

<210> SEQ ID NO 45
<211> LENGTH: 447
<212> TYPE: PRT
<213> ORGANISM: Artificial Sequence
<220> FEATURE:
<223> OTHER INFORMATION: anti-Her2 (PER) Fc hole chain

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350
```

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 46
<211> LENGTH: 214
<212> TYPE: PRT
<213> ORGANISM: Artificial Sequence
<220> FEATURE:
<223> OTHER INFORMATION: anti-Her2 (PER) light chain

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 448
<212> TYPE: PRT
<213> ORGANISM: Artificial Sequence
<220> FEATURE:
<223> OTHER INFORMATION: anti-Her2 (TRAS) Fc hole chain

<400> SEQUENCE: 47

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
            325                 330                 335

Lys Thr Ile Ser Lys Ala Lys Gly Gln Pro Arg Glu Pro Gln Val Cys
        340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
            405                 410                 415
```

-continued

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

<210> SEQ ID NO 48
<211> LENGTH: 214
<212> TYPE: PRT
<213> ORGANISM: Artificial Sequence
<220> FEATURE:
<223> OTHER INFORMATION: anti-Her2 (TRAS) light chain

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 447
<212> TYPE: PRT
<213> ORGANISM: Artificial Sequence
<220> FEATURE:
<223> OTHER INFORMATION: anti-Her2 (aff-PER) Fc hole chain

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 50
<211> LENGTH: 214
<212> TYPE: PRT
<213> ORGANISM: Artificial Sequence
<220> FEATURE:

<223> OTHER INFORMATION: anti-Her2 (aff-PER) light chain

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Arg Tyr Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 163
<212> TYPE: PRT
<213> ORGANISM: Homo sapiens

<400> SEQUENCE: 51

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro 130                 135                 140
Gly Ala Ser Ser Val Thr Pro Pro Ala Pro Ala Arg Glu Pro Gly His
145                 150                 155                 160

Ser Pro Gln

<210> SEQ ID NO 52
<211> LENGTH: 225
<212> TYPE: PRT
<213> ORGANISM: Artificial Sequence
<220> FEATURE:
<223> OTHER INFORMATION: Fc hole chain

<400> SEQUENCE: 52

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro
225

<210> SEQ ID NO 53
<211> LENGTH: 422
<212> TYPE: PRT
<213> ORGANISM: Artificial Sequence
<220> FEATURE:
<223> OTHER INFORMATION: human 4-1BB antigen Fc knob chain

<400> SEQUENCE: 53

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
                20                  25                  30

Ala Gly Gly Gln Arg Thr Cys Asp Ile Cys Arg Gln Cys Lys Gly Val

```
                35                  40                  45
Phe Arg Thr Arg Lys Glu Cys Ser Ser Thr Ser Asn Ala Glu Cys Asp
 50                  55                  60

Cys Thr Pro Gly Phe His Cys Leu Gly Ala Gly Cys Ser Met Cys Glu
 65                  70                  75                  80

Gln Asp Cys Lys Gln Gly Gln Glu Leu Thr Lys Lys Gly Cys Lys Asp
                 85                  90                  95

Cys Cys Phe Gly Thr Phe Asn Asp Gln Lys Arg Gly Ile Cys Arg Pro
                100                 105                 110

Trp Thr Asn Cys Ser Leu Asp Gly Lys Ser Val Leu Val Asn Gly Thr
                115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln Val Asp Glu Gln Leu Tyr Phe Gln Gly Gly Ser Pro Lys
                165                 170                 175

Ser Ala Asp Lys Thr His Thr Cys Pro Pro Cys Pro Ala Pro Glu Leu
                180                 185                 190

Leu Gly Gly Pro Ser Val Phe Leu Phe Pro Pro Lys Pro Lys Asp Thr
                195                 200                 205

Leu Met Ile Ser Arg Thr Pro Glu Val Thr Cys Val Val Val Asp Val
210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
                260                 265                 270

Asn Gly Lys Glu Tyr Lys Cys Lys Val Ser Asn Lys Ala Leu Pro Ala
                275                 280                 285

Pro Ile Glu Lys Thr Ile Ser Lys Ala Lys Gly Gln Pro Arg Glu Pro
290                 295                 300

Gln Val Tyr Thr Leu Pro Pro Cys Arg Asp Glu Leu Thr Lys Asn Gln
305                 310                 315                 320

Val Ser Leu Trp Cys Leu Val Lys Gly Phe Tyr Pro Ser Asp Ile Ala
                325                 330                 335

Val Glu Trp Glu Ser Asn Gly Gln Pro Glu Asn Asn Tyr Lys Thr Thr
                340                 345                 350

Pro Pro Val Leu Asp Ser Asp Gly Ser Phe Phe Leu Tyr Ser Lys Leu
                355                 360                 365

Thr Val Asp Lys Ser Arg Trp Gln Gln Gly Asn Val Phe Ser Cys Ser
                370                 375                 380

Val Met His Glu Ala Leu His Asn His Tyr Thr Gln Lys Ser Leu Ser
385                 390                 395                 400

Leu Ser Pro Gly Lys Ser Gly Gly Leu Asn Asp Ile Phe Glu Ala Gln
                405                 410                 415

Lys Ile Glu Trp His Glu
                420

<210> SEQ ID NO 54
<211> LENGTH: 1245
<212> TYPE: PRT
<213> ORGANISM: Homo sapiens
```

<400> SEQUENCE: 54

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Glu Thr Leu Glu Glu Ile Thr Gly Tyr Leu
385                 390                 395                 400

Tyr Ile Ser Ala Trp Pro Asp Ser Leu Pro Asp Leu Ser Val Phe Gln
```

```
                    405                 410                 415
Asn Leu Gln Val Ile Arg Gly Arg Ile Leu His Asn Gly Ala Tyr Ser
                420                 425                 430

Leu Thr Leu Gln Gly Leu Gly Ile Ser Trp Leu Gly Leu Arg Ser Leu
            435                 440                 445

Arg Glu Leu Gly Ser Gly Leu Ala Leu Ile His His Asn Thr His Leu
        450                 455                 460

Cys Phe Val His Thr Val Pro Trp Asp Gln Leu Phe Arg Asn Pro His
465                 470                 475                 480

Gln Ala Leu Leu His Thr Ala Asn Arg Pro Glu Asp Glu Cys Val Gly
                485                 490                 495

Glu Gly Leu Ala Cys His Gln Leu Cys Ala Arg Gly His Cys Trp Gly
            500                 505                 510

Pro Gly Pro Thr Gln Cys Val Asn Cys Ser Gln Phe Leu Arg Gly Gln
        515                 520                 525

Glu Cys Val Glu Glu Cys Arg Val Leu Gln Gly Leu Pro Arg Glu Tyr
    530                 535                 540

Val Asn Ala Arg His Cys Leu Pro Cys His Pro Glu Cys Gln Pro Gln
545                 550                 555                 560

Asn Gly Ser Val Thr Cys Phe Gly Pro Glu Ala Asp Gln Cys Val Ala
                565                 570                 575

Cys Ala His Tyr Lys Asp Pro Pro Phe Cys Val Ala Arg Cys Pro Ser
            580                 585                 590

Gly Val Lys Pro Asp Leu Ser Tyr Met Pro Ile Trp Lys Phe Pro Asp
        595                 600                 605

Glu Glu Gly Ala Cys Gln Pro Cys Pro Ile Asn Cys Thr His Ser Cys
    610                 615                 620

Val Asp Leu Asp Asp Lys Gly Cys Pro Ala Glu Gln Arg Ala Ser Pro
625                 630                 635                 640

Leu Thr Ser Ile Ile Ser Ala Val Val Gly Ile Leu Leu Val Val Val
                645                 650                 655

Leu Gly Val Val Phe Gly Ile Leu Ile Lys Arg Arg Gln Gln Lys Ile
            660                 665                 670

Arg Lys Tyr Thr Met Arg Arg Leu Leu Gln Glu Thr Glu Leu Val Glu
        675                 680                 685

Pro Leu Thr Pro Ser Gly Ala Met Pro Asn Gln Ala Gln Met Arg Ile
    690                 695                 700

Leu Lys Glu Thr Glu Leu Arg Lys Val Lys Val Leu Gly Ser Gly Ala
705                 710                 715                 720

Phe Gly Thr Val Tyr Lys Gly Ile Trp Ile Pro Asp Gly Glu Asn Val
                725                 730                 735

Lys Ile Pro Val Ala Ile Lys Val Leu Arg Glu Asn Thr Ser Pro Lys
            740                 745                 750

Ala Asn Lys Glu Ile Leu Asp Glu Ala Tyr Val Met Ala Gly Val Gly
        755                 760                 765

Ser Pro Tyr Val Ser Arg Leu Leu Gly Ile Cys Leu Thr Ser Thr Val
    770                 775                 780

Gln Leu Val Thr Gln Leu Met Pro Tyr Gly Cys Leu Leu Asp His Val
785                 790                 795                 800

Arg Glu Asn Arg Gly Arg Leu Gly Ser Gln Asp Leu Leu Asn Trp Cys
                805                 810                 815

Met Gln Ile Ala Lys Gly Met Ser Tyr Leu Glu Asp Val Arg Leu Val
            820                 825                 830
```

-continued

His Arg Asp Leu Ala Ala Arg Asn Val Leu Val Lys Ser Pro Asn His
    835                 840                 845

Val Lys Ile Thr Asp Phe Gly Leu Ala Arg Leu Leu Asp Ile Asp Glu
850                 855                 860

Thr Glu Tyr His Ala Asp Gly Gly Lys Val Pro Ile Lys Trp Met Ala
865                 870                 875                 880

Leu Glu Ser Ile Leu Arg Arg Arg Phe Thr His Gln Ser Asp Val Trp
            885                 890                 895

Ser Tyr Gly Val Thr Val Trp Glu Leu Met Thr Phe Gly Ala Lys Pro
            900                 905                 910

Tyr Asp Gly Ile Pro Ala Arg Glu Ile Pro Asp Leu Leu Glu Lys Gly
            915                 920                 925

Glu Arg Leu Pro Gln Pro Pro Ile Cys Thr Ile Asp Val Tyr Met Ile
    930                 935                 940

Met Val Lys Cys Trp Met Ile Asp Ser Glu Cys Arg Pro Arg Phe Arg
945                 950                 955                 960

Glu Leu Val Ser Glu Phe Ser Arg Met Ala Arg Asp Pro Gln Arg Phe
                965                 970                 975

Val Val Ile Gln Asn Glu Asp Leu Gly Pro Ala Ser Pro Leu Asp Ser
            980                 985                 990

Thr Phe Tyr Arg Ser Leu Leu Glu Asp Asp Asp Met Gly Asp Leu Val
        995                 1000                1005

Asp Ala Glu Glu Tyr Leu Val Pro Gln Gln Gly Phe Phe Cys Pro
    1010                1015                1020

Asp Pro Ala Pro Gly Ala Gly Gly Met Val His His Arg His Arg
    1025                1030                1035

Ser Ser Ser Thr Arg Ser Gly Gly Gly Asp Leu Thr Leu Gly Leu
    1040                1045                1050

Glu Pro Ser Glu Glu Glu Ala Pro Arg Ser Pro Leu Ala Pro Ser
    1055                1060                1065

Glu Gly Ala Gly Ser Asp Val Phe Asp Gly Asp Leu Gly Met Gly
    1070                1075                1080

Ala Ala Lys Gly Leu Gln Ser Leu Pro Thr His Asp Pro Ser Pro
    1085                1090                1095

Leu Gln Arg Tyr Ser Glu Asp Pro Thr Val Pro Leu Pro Ser Glu
    1100                1105                1110

Thr Asp Gly Tyr Val Ala Pro Leu Thr Cys Ser Pro Gln Pro Glu
    1115                1120                1125

Tyr Val Asn Gln Pro Asp Val Arg Pro Gln Pro Pro Ser Pro Arg
    1130                1135                1140

Glu Gly Pro Leu Pro Ala Ala Arg Pro Ala Gly Ala Thr Leu Glu
    1145                1150                1155

Arg Pro Lys Thr Leu Ser Pro Gly Lys Asn Gly Val Val Lys Asp
    1160                1165                1170

Val Phe Ala Phe Gly Gly Ala Val Glu Asn Pro Glu Tyr Leu Thr
    1175                1180                1185

Pro Gln Gly Gly Ala Ala Pro Gln Pro His Pro Pro Ala Phe
    1190                1195                1200

Ser Pro Ala Phe Asp Asn Leu Tyr Tyr Trp Asp Gln Asp Pro Pro
    1205                1210                1215

Glu Arg Gly Ala Pro Pro Ser Thr Phe Lys Gly Thr Pro Thr Ala
    1220                1225                1230

```
Glu Asn  Pro Glu Tyr Leu Gly  Leu Asp Val Pro Val
   1235             1240                1245
```

<210> SEQ ID NO 55
<211> LENGTH: 464
<212> TYPE: PRT
<213> ORGANISM: Artificial Sequence
<220> FEATURE:
<223> OTHER INFORMATION: 4-1BB antibody 20H4.9 IgG4, Heavy chain

<400> SEQUENCE: 55

```
Met Lys His Leu Trp Phe Phe Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro Gly Asn Tyr Asp Trp Tyr Phe Asp
            115                 120                 125

Leu Trp Gly Arg Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
            275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Trp Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350
```

-continued

```
Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460
```

<210> SEQ ID NO 56
<211> LENGTH: 216
<212> TYPE: PRT
<213> ORGANISM: Artificial Sequence
<220> FEATURE:
<223> OTHER INFORMATION: 4-1BB antibody 20H4.9 IgG4, Light chain

<400> SEQUENCE: 56

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Cys Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 57
<211> LENGTH: 440
<212> TYPE: PRT
<213> ORGANISM: Artificial Sequence
<220> FEATURE:

<223> OTHER INFORMATION: 4-1BB antibody MOR7480 IgG2, Heavy chain

<400> SEQUENCE: 57

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400
```

-continued

```
Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro
        435                 440

<210> SEQ ID NO 58
<211> LENGTH: 214
<212> TYPE: PRT
<213> ORGANISM: Artificial Sequence
<220> FEATURE:
<223> OTHER INFORMATION: 4-1BB antibody MOR7480 IgG2, Light chain

<400> SEQUENCE: 58

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Tyr Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 59
<211> LENGTH: 640
<212> TYPE: PRT
<213> ORGANISM: Artificial Sequence
<220> FEATURE:
<223> OTHER INFORMATION: Her2 (TRAS)-anticalin-4-1BB human IgG4 heavy
      chain

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
                35                  40                  45
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Gly
        435                 440                 445

Gly Gly Gly Ser Gly Gly Gly Gly Ser Gly Gly Gly Gly Ser Gln Asp
    450                 455                 460
```

```
Ser Thr Ser Asp Leu Ile Pro Ala Pro Leu Ser Lys Val Pro Leu
465                 470                 475                 480

Gln Gln Asn Phe Gln Asp Asn Gln Phe His Gly Lys Trp Tyr Val Val
                485                 490                 495

Gly Gln Ala Gly Asn Ile Arg Leu Arg Glu Asp Lys Asp Pro Ile Lys
            500                 505                 510

Met Met Ala Thr Ile Tyr Glu Leu Lys Glu Asp Lys Ser Tyr Asp Val
        515                 520                 525

Thr Met Val Lys Phe Asp Asp Lys Lys Cys Met Tyr Asp Ile Trp Thr
    530                 535                 540

Phe Val Pro Gly Ser Gln Pro Gly Glu Phe Thr Leu Gly Lys Ile Lys
545                 550                 555                 560

Ser Phe Pro Gly His Thr Ser Ser Leu Val Arg Val Val Ser Thr Asn
                565                 570                 575

Tyr Asn Gln His Ala Met Val Phe Phe Lys Phe Val Phe Gln Asn Arg
            580                 585                 590

Glu Glu Phe Tyr Ile Thr Leu Tyr Gly Arg Thr Lys Glu Leu Thr Ser
        595                 600                 605

Glu Leu Lys Glu Asn Phe Ile Arg Phe Ser Lys Ser Leu Gly Leu Pro
    610                 615                 620

Glu Asn His Ile Val Phe Pro Val Pro Ile Asp Gln Cys Ile Asp Gly
625                 630                 635                 640

<210> SEQ ID NO 60
<211> LENGTH: 214
<212> TYPE: PRT
<213> ORGANISM: Artificial Sequence
<220> FEATURE:
<223> OTHER INFORMATION: Her2 (TRAS)-anticalin-4-1BB human IgG4 light
      chain

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                180               185               190
Ala Cys Glu Val Thr His Gln Gly Leu Ser Ser Pro Val Thr Lys Ser
            195                 200                 205

Phe Asn Arg Gly Glu Cys
    210

<210> SEQ ID NO 61
<211> LENGTH: 443
<212> TYPE: PRT
<213> ORGANISM: Artificial Sequence
<220> FEATURE:
<223> OTHER INFORMATION: DP47 Fc hole chain

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
```

```
                 325                 330                 335
Ala Lys Gly Gln Pro Arg Glu Pro Gln Val Cys Thr Leu Pro Pro Ser
                340                 345                 350

Arg Asp Glu Leu Thr Lys Asn Gln Val Ser Leu Ser Cys Ala Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro
                435                 440

<210> SEQ ID NO 62
<211> LENGTH: 215
<212> TYPE: PRT
<213> ORGANISM: Artificial Sequence
<220> FEATURE:
<223> OTHER INFORMATION: DP47 light chain

<400> SEQUENCE: 62

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 63
<211> LENGTH: 635
<212> TYPE: PRT
```

<213> ORGANISM: Artificial Sequence
<220> FEATURE:
<223> OTHER INFORMATION: DP47-anticalin-4-1BB human IgG4 heavy chain

<400> SEQUENCE: 63

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
```

```
                385                 390                 395                 400
Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
                420                 425                 430

Gln Lys Ser Leu Ser Leu Ser Leu Gly Lys Gly Gly Gly Gly Ser Gly
                435                 440                 445

Gly Gly Gly Ser Gly Gly Gly Ser Gln Asp Ser Thr Ser Asp Leu
                450                 455                 460

Ile Pro Ala Pro Pro Leu Ser Lys Val Pro Leu Gln Gln Asn Phe Gln
465                 470                 475                 480

Asp Asn Gln Phe His Gly Lys Trp Tyr Val Val Gly Gln Ala Gly Asn
                    485                 490                 495

Ile Arg Leu Arg Glu Asp Lys Asp Pro Ile Lys Met Met Ala Thr Ile
                500                 505                 510

Tyr Glu Leu Lys Glu Asp Lys Ser Tyr Asp Val Thr Met Val Lys Phe
                515                 520                 525

Asp Asp Lys Lys Cys Met Tyr Asp Ile Trp Thr Phe Val Pro Gly Ser
530                 535                 540

Gln Pro Gly Glu Phe Thr Leu Gly Lys Ile Lys Ser Phe Pro Gly His
545                 550                 555                 560

Thr Ser Ser Leu Val Arg Val Val Ser Thr Asn Tyr Asn Gln His Ala
                565                 570                 575

Met Val Phe Phe Lys Phe Val Phe Gln Asn Arg Glu Glu Phe Tyr Ile
                580                 585                 590

Thr Leu Tyr Gly Arg Thr Lys Glu Leu Thr Ser Glu Leu Lys Glu Asn
                595                 600                 605

Phe Ile Arg Phe Ser Lys Ser Leu Gly Leu Pro Glu Asn His Ile Val
                610                 615                 620

Phe Pro Val Pro Ile Asp Gln Cys Ile Asp Gly
625                 630                 635

<210> SEQ ID NO 64
<211> LENGTH: 215
<212> TYPE: PRT
<213> ORGANISM: Artificial Sequence
<220> FEATURE:
<223> OTHER INFORMATION: DP47-anticalin-4-1BB human IgG4 light chain

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
```

```
                115                 120                 125
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 65
<211> LENGTH: 448
<212> TYPE: PRT
<213> ORGANISM: Artificial Sequence
<220> FEATURE:
<223> OTHER INFORMATION: Her2 (TRAS) human IgG1 P329G LALA, Heavy chain

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
            260                 265                 270
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445
```

<210> SEQ ID NO 66
<211> LENGTH: 447
<212> TYPE: PRT
<213> ORGANISM: Artificial Sequence
<220> FEATURE:
<223> OTHER INFORMATION: Her2 (PER) human IgG1 P329G LALA, Heavy chain

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180             185             190
Ser Ser Leu Gly Thr Gln Thr Tyr Ile Cys Asn Val Asn His Lys Pro
        195             200             205
Ser Asn Thr Lys Val Asp Lys Lys Val Glu Pro Lys Ser Cys Asp Lys
        210             215             220
Thr His Thr Cys Pro Pro Cys Pro Ala Pro Glu Ala Ala Gly Gly Pro
225             230             235             240
Ser Val Phe Leu Phe Pro Pro Lys Pro Lys Asp Thr Leu Met Ile Ser
            245             250             255
Arg Thr Pro Glu Val Thr Cys Val Val Val Asp Val Ser His Glu Asp
            260             265             270
Pro Glu Val Lys Phe Asn Trp Tyr Val Asp Gly Val Glu Val His Asn
        275             280             285
Ala Lys Thr Lys Pro Arg Glu Glu Gln Tyr Asn Ser Thr Tyr Arg Val
        290             295             300
Val Ser Val Leu Thr Val Leu His Gln Asp Trp Leu Asn Gly Lys Glu
305             310             315             320
Tyr Lys Cys Lys Val Ser Asn Lys Ala Leu Gly Ala Pro Ile Glu Lys
            325             330             335
Thr Ile Ser Lys Ala Lys Gly Gln Pro Arg Glu Pro Gln Val Tyr Thr
            340             345             350
Leu Pro Pro Ser Arg Asp Glu Leu Thr Lys Asn Gln Val Ser Leu Thr
            355             360             365
Cys Leu Val Lys Gly Phe Tyr Pro Ser Asp Ile Ala Val Glu Trp Glu
        370             375             380
Ser Asn Gly Gln Pro Glu Asn Asn Tyr Lys Thr Thr Pro Pro Val Leu
385             390             395             400
Asp Ser Asp Gly Ser Phe Phe Leu Tyr Ser Lys Leu Thr Val Asp Lys
            405             410             415
Ser Arg Trp Gln Gln Gly Asn Val Phe Ser Cys Ser Val Met His Glu
            420             425             430
Ala Leu His Asn His Tyr Thr Gln Lys Ser Leu Ser Leu Ser Pro
        435             440             445

<210> SEQ ID NO 67
<211> LENGTH: 443
<212> TYPE: PRT
<213> ORGANISM: Artificial Sequence
<220> FEATURE:
<223> OTHER INFORMATION: DP47 human IgG1 P329G LALA, Heavy chain

<400> SEQUENCE: 67

Glu Val Gln Leu Leu Glu Ser Gly Gly Gly Leu Val Gln Pro Gly Gly
1               5               10              15
Ser Leu Arg Leu Ser Cys Ala Ala Ser Gly Phe Thr Phe Ser Ser Tyr
            20              25              30
Ala Met Ser Trp Val Arg Gln Ala Pro Gly Lys Gly Leu Glu Trp Val
        35              40              45
Ser Ala Ile Ser Gly Ser Gly Gly Ser Thr Tyr Tyr Ala Asp Ser Val
    50              55              60
Lys Gly Arg Phe Thr Ile Ser Arg Asp Asn Ser Lys Asn Thr Leu Tyr
65              70              75              80
Leu Gln Met Asn Ser Leu Arg Ala Glu Asp Thr Ala Val Tyr Tyr Cys
            85              90              95
Ala Lys Gly Ser Gly Phe Asp Tyr Trp Gly Gln Gly Thr Leu Val Thr
```

```
            100                 105                 110
Val Ser Ser Ala Ser Thr Lys Gly Pro Ser Val Phe Pro Leu Ala Pro
    115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 68
<211> LENGTH: 10
<212> TYPE: PRT
<213> ORGANISM: Artificial Sequence
<220> FEATURE:
<223> OTHER INFORMATION: (G4S)2 peptide linker

<400> SEQUENCE: 68

Gly Gly Gly Gly Ser Gly Gly Gly Gly Ser
1               5                   10
```

```
<210> SEQ ID NO 69
<211> LENGTH: 254
<212> TYPE: PRT
<213> ORGANISM: Homo sapiens

<400> SEQUENCE: 69

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Cys Ala Val Phe
            35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
                115                 120                 125

Asp Thr Lys Glu Leu Val Val Ala Lys Ala Gly Val Tyr Tyr Val Phe
            130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
        210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 70
<211> LENGTH: 205
<212> TYPE: PRT
<213> ORGANISM: Homo sapiens

<400> SEQUENCE: 70

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
                20                  25                  30

Ala Gly Leu Leu Asp Leu Arg Gln Gly Met Phe Ala Gln Leu Val Ala
            35                  40                  45

Gln Asn Val Leu Leu Ile Asp Gly Pro Leu Ser Trp Tyr Ser Asp Pro
        50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
```

```
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
    130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205

<210> SEQ ID NO 71
<211> LENGTH: 5
<212> TYPE: PRT
<213> ORGANISM: Artificial Sequence
<220> FEATURE:
<223> OTHER INFORMATION: Peptide linker G4S

<400> SEQUENCE: 71

Gly Gly Gly Gly Ser
1               5

<210> SEQ ID NO 72
<211> LENGTH: 10
<212> TYPE: PRT
<213> ORGANISM: Artificial Sequence
<220> FEATURE:
<223> OTHER INFORMATION: Peptide linker (SG4)2

<400> SEQUENCE: 72

Ser Gly Gly Gly Gly Ser Gly Gly Gly Gly
1               5                   10

<210> SEQ ID NO 73
<211> LENGTH: 15
<212> TYPE: PRT
<213> ORGANISM: Artificial Sequence
<220> FEATURE:
<223> OTHER INFORMATION: Peptide linker (G4S)3

<400> SEQUENCE: 73

Gly Gly Gly Gly Ser Gly Gly Gly Gly Ser Gly Gly Gly Gly Ser
1               5                   10                  15

<210> SEQ ID NO 74
<211> LENGTH: 14
<212> TYPE: PRT
<213> ORGANISM: Artificial Sequence
<220> FEATURE:
<223> OTHER INFORMATION: Peptide linker G4(SG4)2

<400> SEQUENCE: 74

Gly Gly Gly Gly Ser Gly Gly Gly Gly Ser Gly Gly Gly Gly
1               5                   10

<210> SEQ ID NO 75
<211> LENGTH: 20
<212> TYPE: PRT
```

```
<213> ORGANISM: Artificial Sequence
<220> FEATURE:
<223> OTHER INFORMATION: Peptide linker (G4S)4

<400> SEQUENCE: 75

Gly Gly Gly Gly Ser Gly Gly Gly Gly Ser Gly Gly Gly Gly Ser Gly
1               5                   10                  15

Gly Gly Gly Ser
            20

<210> SEQ ID NO 76
<211> LENGTH: 10
<212> TYPE: PRT
<213> ORGANISM: Artificial Sequence
<220> FEATURE:
<223> OTHER INFORMATION: Peptide linker GSPGSSSSGS

<400> SEQUENCE: 76

Gly Ser Pro Gly Ser Ser Ser Ser Gly Ser
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Peptide linker GSGSGSGS

<400> SEQUENCE: 77

Gly Ser Gly Ser Gly Ser Gly Ser
1               5

<210> SEQ ID NO 78
<211> LENGTH: 8
<212> TYPE: PRT
<213> ORGANISM: Artificial Sequence
<220> FEATURE:
<223> OTHER INFORMATION: Peptide linker GSGSGNGS

<400> SEQUENCE: 78

Gly Ser Gly Ser Gly Asn Gly Ser
1               5

<210> SEQ ID NO 79
<211> LENGTH: 8
<212> TYPE: PRT
<213> ORGANISM: Artificial Sequence
<220> FEATURE:
<223> OTHER INFORMATION: Peptide linker GGSGSGSG

<400> SEQUENCE: 79

Gly Gly Ser Gly Ser Gly Ser Gly
1               5

<210> SEQ ID NO 80
<211> LENGTH: 6
<212> TYPE: PRT
<213> ORGANISM: Artificial Sequence
<220> FEATURE:
<223> OTHER INFORMATION: Peptide linker GGSGSG

<400> SEQUENCE: 80

Gly Gly Ser Gly Ser Gly
1               5

<210> SEQ ID NO 81
```

```
<211> LENGTH: 4
<212> TYPE: PRT
<213> ORGANISM: Artificial Sequence
<220> FEATURE:
<223> OTHER INFORMATION: Peptide linker GGSG

<400> SEQUENCE: 81

Gly Gly Ser Gly
1

<210> SEQ ID NO 82
<211> LENGTH: 8
<212> TYPE: PRT
<213> ORGANISM: Artificial Sequence
<220> FEATURE:
<223> OTHER INFORMATION: GGSGNGSG

<400> SEQUENCE: 82

Gly Gly Ser Gly Asn Gly Ser Gly
1               5

<210> SEQ ID NO 83
<211> LENGTH: 8
<212> TYPE: PRT
<213> ORGANISM: Artificial Sequence
<220> FEATURE:
<223> OTHER INFORMATION: Peptide inker GGNGSGSG

<400> SEQUENCE: 83

Gly Gly Asn Gly Ser Gly Ser Gly
1               5

<210> SEQ ID NO 84
<211> LENGTH: 6
<212> TYPE: PRT
<213> ORGANISM: Artificial Sequence
<220> FEATURE:
<223> OTHER INFORMATION: Peptide linker GGNGSG

<400> SEQUENCE: 84

Gly Gly Asn Gly Ser Gly
1               5

<210> SEQ ID NO 85
<211> LENGTH: 207
<212> TYPE: PRT
<213> ORGANISM: Homo sapiens

<400> SEQUENCE: 85

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110
```

```
Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
                195                 200                 205
```

<210> SEQ ID NO 86
<211> LENGTH: 198
<212> TYPE: PRT
<213> ORGANISM: Macacis fascularis

<400> SEQUENCE: 86

```
Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
                20                  25                  30

Gln Thr Pro Tyr Gln Val Ser Ile Ser Gly Thr Thr Val Ile Leu Thr
            35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Val Tyr Tyr Trp Ser Lys
        130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
                180                 185                 190

Leu Asn Gln Arg Arg Ile
        195
```

<210> SEQ ID NO 87
<211> LENGTH: 442
<212> TYPE: PRT
<213> ORGANISM: Artificial Sequence
<220> FEATURE:
<223> OTHER INFORMATION: VHCH1(EE) (MU137-1) Fc-KK (mu4-1BB-Her2)

<400> SEQUENCE: 87

```
Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Ile Phe Ser Tyr Phe
```

```
                20                  25                  30
Asp Met Ala Trp Val Arg Gln Ala Pro Thr Lys Gly Leu Glu Trp Val
            35                  40                  45
Ala Ser Ile Ser Pro Ser Gly Asp Ile Pro Tyr Tyr Arg Asp Ser Val
            50                  55                  60
Lys Gly Arg Phe Thr Val Ser Arg Glu Asn Ala Lys Ser Ser Leu Tyr
65                  70                  75                  80
Leu Gln Met Asp Ser Leu Arg Ser Glu Asp Thr Ala Thr Tyr Tyr Cys
                85                  90                  95
Ala Arg Arg Ser Tyr Gly Gly Tyr Ser Glu Leu Asp Tyr Trp Gly Gln
            100                 105                 110
Gly Val Met Val Thr Val Ser Ser Ala Lys Thr Thr Pro Pro Ser Val
            115                 120                 125
Tyr Pro Leu Ala Pro Gly Ser Ala Ala Gln Thr Asn Ser Met Val Thr
            130                 135                 140
Leu Gly Cys Leu Val Glu Gly Tyr Phe Pro Glu Pro Val Thr Val Thr
145                 150                 155                 160
Trp Asn Ser Gly Ser Leu Ser Ser Gly Val His Thr Phe Pro Ala Val
            165                 170                 175
Leu Gln Ser Asp Leu Tyr Thr Leu Ser Ser Ser Val Thr Val Pro Ser
            180                 185                 190
Ser Thr Trp Pro Ser Gln Thr Val Thr Cys Asn Val Ala His Pro Ala
            195                 200                 205
Ser Ser Thr Lys Val Asp Glu Lys Ile Val Pro Arg Asp Cys Gly Cys
            210                 215                 220
Lys Pro Cys Ile Cys Thr Val Pro Glu Val Ser Ser Val Phe Ile Phe
225                 230                 235                 240
Pro Pro Lys Pro Lys Asp Val Leu Thr Ile Thr Leu Thr Pro Lys Val
            245                 250                 255
Thr Cys Val Val Val Ala Ile Ser Lys Asp Asp Pro Glu Val Gln Phe
            260                 265                 270
Ser Trp Phe Val Asp Asp Val Glu Val His Thr Ala Gln Thr Lys Pro
            275                 280                 285
Arg Glu Glu Gln Ile Asn Ser Thr Phe Arg Ser Val Ser Glu Leu Pro
            290                 295                 300
Ile Met His Gln Asp Trp Leu Asn Gly Lys Glu Phe Lys Cys Arg Val
305                 310                 315                 320
Asn Ser Ala Ala Phe Gly Ala Pro Ile Glu Lys Thr Ile Ser Lys Thr
            325                 330                 335
Lys Gly Arg Pro Lys Ala Pro Gln Val Tyr Thr Ile Pro Pro Pro Lys
            340                 345                 350
Lys Gln Met Ala Lys Asp Lys Val Ser Leu Thr Cys Met Ile Thr Asn
            355                 360                 365
Phe Phe Pro Glu Asp Ile Thr Val Glu Trp Gln Trp Asn Gly Gln Pro
            370                 375                 380
Ala Glu Asn Tyr Lys Asn Thr Gln Pro Ile Met Lys Thr Asp Gly Ser
385                 390                 395                 400
Tyr Phe Val Tyr Ser Lys Leu Asn Val Gln Lys Ser Asn Trp Glu Ala
            405                 410                 415
Gly Asn Thr Phe Thr Cys Ser Val Leu His Glu Gly Leu His Asn His
            420                 425                 430
His Thr Glu Lys Ser Leu Ser His Ser Pro
            435                 440
```

-continued

<210> SEQ ID NO 88
<211> LENGTH: 663
<212> TYPE: PRT
<213> ORGANISM: Artificial Sequence
<220> FEATURE:
<223> OTHER INFORMATION: VLCH1 (2C4) VHCH1(EE) (MU137-1) Fc-DD
      (mu4-1BB-Her2)

<400> SEQUENCE: 88

Asp Thr Val Met Thr Gln Ser His Lys Ile Met Ser Thr Ser Val Gly
1               5                   10                  15

Asp Arg Val Ser Ile Thr Cys Lys Ala Ser Gln Asp Val Ser Ile Gly
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ile Tyr Pro Tyr
                85                  90                  95

Thr Phe Gly Gly Gly Thr Lys Leu Glu Ile Lys Ser Ser Ala Lys Thr
            100                 105                 110

Thr Pro Pro Ser Val Tyr Pro Leu Ala Pro Gly Ser Ala Ala Gln Thr
        115                 120                 125

Asn Ser Met Val Thr Leu Gly Cys Leu Val Lys Gly Tyr Phe Pro Glu
130                 135                 140

Pro Val Thr Val Thr Trp Asn Ser Gly Ser Leu Ser Ser Gly Val His
145                 150                 155                 160

Thr Phe Pro Ala Val Leu Gln Ser Asp Leu Tyr Thr Leu Ser Ser Ser
                165                 170                 175

Val Thr Val Pro Ser Ser Thr Trp Pro Ser Gln Thr Val Thr Cys Asn
            180                 185                 190

Val Ala His Pro Ala Ser Ser Thr Lys Val Asp Lys Lys Ile Val Pro
        195                 200                 205

Arg Asp Cys Gly Gly Gly Ser Gly Gly Gly Ser Asp Val Gln
    210                 215                 220

Leu Val Glu Ser Gly Gly Gly Leu Val Gln Pro Gly Arg Ser Leu Lys
225                 230                 235                 240

Leu Ser Cys Ala Ala Ser Gly Phe Ile Phe Ser Tyr Phe Asp Met Ala
                245                 250                 255

Trp Val Arg Gln Ala Pro Thr Lys Gly Leu Glu Trp Val Ala Ser Ile
            260                 265                 270

Ser Pro Ser Gly Asp Ile Pro Tyr Tyr Arg Asp Ser Val Lys Gly Arg
        275                 280                 285

Phe Thr Val Ser Arg Glu Asn Ala Lys Ser Ser Leu Tyr Leu Gln Met
    290                 295                 300

Asp Ser Leu Arg Ser Glu Asp Thr Ala Thr Tyr Tyr Cys Ala Arg Arg
305                 310                 315                 320

Ser Tyr Gly Gly Tyr Ser Glu Leu Asp Tyr Trp Gly Gln Gly Val Met
                325                 330                 335

Val Thr Val Ser Ser Ala Lys Thr Thr Pro Pro Ser Val Tyr Pro Leu
            340                 345                 350

Ala Pro Gly Ser Ala Ala Gln Thr Asn Ser Met Val Thr Leu Gly Cys

```
                    355                 360                 365
Leu Val Glu Gly Tyr Phe Pro Glu Pro Val Thr Val Thr Trp Asn Ser
        370                 375                 380

Gly Ser Leu Ser Ser Gly Val His Thr Phe Pro Ala Val Leu Gln Ser
385                 390                 395                 400

Asp Leu Tyr Thr Leu Ser Ser Ser Val Thr Val Pro Ser Ser Thr Trp
                405                 410                 415

Pro Ser Gln Thr Val Thr Cys Asn Val Ala His Pro Ala Ser Ser Thr
            420                 425                 430

Lys Val Asp Glu Lys Ile Val Pro Arg Asp Cys Gly Cys Lys Pro Cys
        435                 440                 445

Ile Cys Thr Val Pro Glu Val Ser Ser Val Phe Ile Phe Pro Pro Lys
    450                 455                 460

Pro Lys Asp Val Leu Thr Ile Thr Leu Thr Pro Lys Val Thr Cys Val
465                 470                 475                 480

Val Val Ala Ile Ser Lys Asp Asp Pro Glu Val Gln Phe Ser Trp Phe
                485                 490                 495

Val Asp Asp Val Glu Val His Thr Ala Gln Thr Lys Pro Arg Glu Glu
            500                 505                 510

Gln Ile Asn Ser Thr Phe Arg Ser Val Ser Glu Leu Pro Ile Met His
        515                 520                 525

Gln Asp Trp Leu Asn Gly Lys Glu Phe Lys Cys Arg Val Asn Ser Ala
    530                 535                 540

Ala Phe Gly Ala Pro Ile Glu Lys Thr Ile Ser Lys Thr Lys Gly Arg
545                 550                 555                 560

Pro Lys Ala Pro Gln Val Tyr Thr Ile Pro Pro Lys Glu Gln Met
                565                 570                 575

Ala Lys Asp Lys Val Ser Leu Thr Cys Met Ile Thr Asn Phe Phe Pro
            580                 585                 590

Glu Asp Ile Thr Val Glu Trp Gln Trp Asn Gly Gln Pro Ala Glu Asn
        595                 600                 605

Tyr Asp Asn Thr Gln Pro Ile Met Asp Thr Asp Gly Ser Tyr Phe Val
    610                 615                 620

Tyr Ser Asp Leu Asn Val Gln Lys Ser Asn Trp Glu Ala Gly Asn Thr
625                 630                 635                 640

Phe Thr Cys Ser Val Leu His Glu Gly Leu His Asn His His Thr Glu
                645                 650                 655

Lys Ser Leu Ser His Ser Pro
            660

<210> SEQ ID NO 89
<211> LENGTH: 214
<212> TYPE: PRT
<213> ORGANISM: Artificial Sequence
<220> FEATURE:
<223> OTHER INFORMATION: VLCL(RK)-Light chain (MU137-1) (mu4-1BB-Her2)

<400> SEQUENCE: 89

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr His Gln Lys Pro Gly Lys Ser Pro Gln Leu Leu Ile
        35                  40                  45

Tyr Gly Thr Ser Ser Leu Ala Asp Gly Val Pro Ser Arg Phe Ser Gly
```

```
        50                  55                  60
Ser Ser Ser Gly Ser Gln Tyr Ser Leu Lys Ile Ser Arg Leu Gln Val
 65                  70                  75                  80

Glu Asp Ile Gly Ile Tyr Tyr Cys Leu Gln Ala Tyr Gly Ala Pro Trp
                     85                  90                  95

Thr Phe Gly Gly Gly Thr Lys Leu Glu Leu Lys Arg Ala Asp Ala Ala
                100                 105                 110

Pro Thr Val Ser Ile Phe Pro Pro Ser Arg Lys Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
        210
```

<210> SEQ ID NO 90
<211> LENGTH: 226
<212> TYPE: PRT
<213> ORGANISM: Artificial Sequence
<220> FEATURE:
<223> OTHER INFORMATION: VHCL-Light chain (2C4)

<400> SEQUENCE: 90

```
Glu Val Gln Leu Gln Gln Ser Gly Pro Glu Leu Val Lys Pro Gly Thr
  1               5                  10                  15

Ser Val Lys Ile Ser Cys Lys Ala Ser Gly Phe Thr Phe Thr Asp Tyr
                 20                  25                  30

Thr Met Asp Trp Val Lys Gln Ser His Gly Lys Ser Leu Glu Trp Ile
                 35                  40                  45

Gly Asp Val Asn Pro Asn Ser Gly Ser Ile Tyr Asn Gln Arg Phe
 50                  55                  60

Lys Gly Lys Ala Ser Leu Thr Val Asp Arg Ser Ser Arg Ile Val Tyr
 65                  70                  75                  80

Met Glu Leu Arg Ser Leu Thr Phe Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110

Thr Thr Leu Thr Val Ser Ser Ala Ser Asp Ala Ala Pro Thr Val Ser
            115                 120                 125

Ile Phe Pro Pro Ser Ser Glu Gln Leu Thr Ser Gly Gly Ala Ser Val
        130                 135                 140

Val Cys Phe Leu Asn Asn Phe Tyr Pro Lys Asp Ile Asn Val Lys Trp
145                 150                 155                 160

Lys Ile Asp Gly Ser Glu Arg Gln Asn Gly Val Leu Asn Ser Trp Thr
                165                 170                 175

Asp Gln Asp Ser Lys Asp Ser Thr Tyr Ser Met Ser Ser Thr Leu Thr
                180                 185                 190

Leu Thr Lys Asp Glu Tyr Glu Arg His Asn Ser Tyr Thr Cys Glu Ala
```

-continued

```
                195                 200                 205
Thr His Lys Thr Ser Thr Ser Pro Ile Val Lys Ser Phe Asn Arg Asn
    210                 215                 220

Glu Cys
225

<210> SEQ ID NO 91
<211> LENGTH: 5
<212> TYPE: PRT
<213> ORGANISM: Artificial Sequence
<220> FEATURE:
<223> OTHER INFORMATION: heavy chain CDR-H1, CD3

<400> SEQUENCE: 91

Asn Tyr Tyr Ile His
1               5

<210> SEQ ID NO 92
<211> LENGTH: 17
<212> TYPE: PRT
<213> ORGANISM: Artificial Sequence
<220> FEATURE:
<223> OTHER INFORMATION: heavy chain CDR-H2, CD3

<400> SEQUENCE: 92

Trp Ile Tyr Pro Gly Asp Gly Asn Thr Lys Tyr Asn Glu Lys Phe Lys
1               5                   10                  15

Gly

<210> SEQ ID NO 93
<211> LENGTH: 10
<212> TYPE: PRT
<213> ORGANISM: Artificial Sequence
<220> FEATURE:
<223> OTHER INFORMATION: heavy chain CDR-H3, CD3

<400> SEQUENCE: 93

Asp Ser Tyr Ser Asn Tyr Tyr Phe Asp Tyr
1               5                   10

<210> SEQ ID NO 94
<211> LENGTH: 17
<212> TYPE: PRT
<213> ORGANISM: Artificial Sequence
<220> FEATURE:
<223> OTHER INFORMATION: light chain CDR-L1, CD3

<400> SEQUENCE: 94

Lys Ser Ser Gln Ser Leu Leu Asn Ser Arg Thr Arg Lys Asn Tyr Leu
1               5                   10                  15

Ala

<210> SEQ ID NO 95
<211> LENGTH: 7
<212> TYPE: PRT
<213> ORGANISM: Artificial Sequence
<220> FEATURE:
<223> OTHER INFORMATION: light chain CDR-L2, CD3

<400> SEQUENCE: 95

Trp Ala Ser Thr Arg Glu Ser
1               5

<210> SEQ ID NO 96
```

```
<211> LENGTH: 8
<212> TYPE: PRT
<213> ORGANISM: Artificial Sequence
<220> FEATURE:
<223> OTHER INFORMATION: light chain CDR-L3, CD3

<400> SEQUENCE: 96

Thr Gln Ser Phe Ile Leu Arg Thr
1               5

<210> SEQ ID NO 97
<211> LENGTH: 119
<212> TYPE: PRT
<213> ORGANISM: Artificial Sequence
<220> FEATURE:
<223> OTHER INFORMATION: heavy chain variable domain VH, CD3

<400> SEQUENCE: 97

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Ile
            35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 98
<211> LENGTH: 112
<212> TYPE: PRT
<213> ORGANISM: Artificial Sequence
<220> FEATURE:
<223> OTHER INFORMATION: light chain variable domain VL, CD3

<400> SEQUENCE: 98

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 99
<211> LENGTH: 5
```

```
<212> TYPE: PRT
<213> ORGANISM: Artificial Sequence
<220> FEATURE:
<223> OTHER INFORMATION: heavy chain CDR-H1, Her2 (7C2)

<400> SEQUENCE: 99

Gly Tyr Trp Met Asn
1               5

<210> SEQ ID NO 100
<211> LENGTH: 17
<212> TYPE: PRT
<213> ORGANISM: Artificial Sequence
<220> FEATURE:
<223> OTHER INFORMATION: heavy chain CDR-H2, Her2 (7C2)

<400> SEQUENCE: 100

Met Ile His Pro Ser Asp Ser Glu Ile Arg Ala Asn Gln Lys Phe Arg
1               5                   10                  15

Asp

<210> SEQ ID NO 101
<211> LENGTH: 9
<212> TYPE: PRT
<213> ORGANISM: Artificial Sequence
<220> FEATURE:
<223> OTHER INFORMATION: heavy chain CDR-H3, Her2 (7C2)

<400> SEQUENCE: 101

Gly Thr Tyr Asp Gly Gly Phe Glu Tyr
1               5

<210> SEQ ID NO 102
<211> LENGTH: 15
<212> TYPE: PRT
<213> ORGANISM: Artificial Sequence
<220> FEATURE:
<223> OTHER INFORMATION: light chain CDR-L1, Her2 (7C2)

<400> SEQUENCE: 102

Arg Ala Ser Gln Ser Val Ser Gly Ser Arg Phe Thr Tyr Met His
1               5                   10                  15

<210> SEQ ID NO 103
<211> LENGTH: 7
<212> TYPE: PRT
<213> ORGANISM: Artificial Sequence
<220> FEATURE:
<223> OTHER INFORMATION: light chain CDR-L2, Her2 (7C2)

<400> SEQUENCE: 103

Tyr Ala Ser Ile Leu Glu Ser
1               5

<210> SEQ ID NO 104
<211> LENGTH: 10
<212> TYPE: PRT
<213> ORGANISM: Artificial Sequence
<220> FEATURE:
<223> OTHER INFORMATION: light chain CDR-L3, Her2 (7C2)

<400> SEQUENCE: 104

Gln His Ser Trp Glu Ile Pro Pro Trp Thr
1               5                   10

<210> SEQ ID NO 105
```

```
<211> LENGTH: 118
<212> TYPE: PRT
<213> ORGANISM: Artificial Sequence
<220> FEATURE:
<223> OTHER INFORMATION: heavy chain variable domain VH, Her2 (7C2)

<400> SEQUENCE: 105

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Gly Tyr
            20                  25                  30

Trp Met Asn Trp Leu Lys Gln Arg Pro Gly Gln Gly Leu Glu Trp Ile
        35                  40                  45

Gly Met Ile His Pro Ser Asp Ser Glu Ile Arg Ala Asn Gln Lys Phe
    50                  55                  60

Arg Asp Lys Ala Thr Leu Thr Val Asp Lys Ser Ser Thr Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Thr Tyr Asp Gly Gly Phe Glu Tyr Trp Gly Gln Gly Thr
            100                 105                 110

Thr Leu Thr Val Ser Ser
        115

<210> SEQ ID NO 106
<211> LENGTH: 112
<212> TYPE: PRT
<213> ORGANISM: Artificial Sequence
<220> FEATURE:
<223> OTHER INFORMATION: light chain variable domain VL, Her2 (7C2)

<400> SEQUENCE: 106

Asp Ile Val Leu Thr Gln Ser Pro Ala Ser Leu Val Val Ser Leu Gly
1               5                   10                  15

Gln Arg Ala Thr Ile Ser Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Ala
    50                  55                  60

Arg Phe Ser Gly Gly Gly Ser Gly Thr Asp Phe Thr Leu Asn Ile His
65                  70                  75                  80

Pro Val Glu Glu Asp Asp Thr Ala Thr Tyr Tyr Cys Gln His Ser Trp
                85                  90                  95

Glu Ile Pro Pro Trp Thr Phe Gly Gly Gly Thr Lys Leu Glu Ile Lys
            100                 105                 110
```